US012359196B2

(12) United States Patent
Izhar et al.

(10) Patent No.: US 12,359,196 B2
(45) Date of Patent: Jul. 15, 2025

(54) DIFFERENTIAL KNOCKOUT OF AN ALLELE OF A HETEROZYGOUS FIBRINOGEN ALPHA CHAIN (FGA) GENE

(71) Applicant: EmendoBio Inc., Wilmington, DE (US)

(72) Inventors: Lior Izhar, Tel-aviv (IL); David Baram, Nir Zvi (IL); Joseph Georgeson, Rehovot (IL); Michal Golan-Mashiach, Ness-ziona (IL); Asael Herman, Ness-ziona (IL); Rafi Emmanuel, Ramlaa (IL)

(73) Assignee: EmendoBio Inc., Wilmington, DE (US)

( * ) Notice: Subject to any disclaimer, the term of this patent is extended or adjusted under 35 U.S.C. 154(b) by 685 days.

(21) Appl. No.: 16/767,506

(22) PCT Filed: Nov. 28, 2018

(86) PCT No.: PCT/US2018/062871
§ 371 (c)(1),
(2) Date: May 27, 2020

(87) PCT Pub. No.: WO2019/108670
PCT Pub. Date: Jun. 6, 2019

(65) Prior Publication Data
US 2020/0332287 A1    Oct. 22, 2020

Related U.S. Application Data

(60) Provisional application No. 62/651,630, filed on Apr. 2, 2018, provisional application No. 62/591,350, filed on Nov. 28, 2017.

(51) Int. Cl.
| | |
|---|---|
| *A61K 48/00* | (2006.01) |
| *A61P 13/12* | (2006.01) |
| *C12N 9/22* | (2006.01) |
| *C12N 15/10* | (2006.01) |
| *C12N 15/11* | (2006.01) |
| *C12N 15/85* | (2006.01) |
| *C12N 15/90* | (2006.01) |
| *A61K 38/00* | (2006.01) |

(52) U.S. Cl.
CPC ............ *C12N 15/11* (2013.01); *A61K 48/005* (2013.01); *A61P 13/12* (2018.01); *C12N 9/22* (2013.01); *C12N 15/102* (2013.01); *C12N 15/111* (2013.01); *C12N 15/85* (2013.01); *C12N 15/90* (2013.01); *A61K 38/00* (2013.01); *C12N 2310/20* (2017.05); *C12N 2320/34* (2013.01); *C12N 2800/80* (2013.01)

(58) Field of Classification Search
CPC ........ C12N 15/11; C12N 9/22; C12N 15/102; C12N 15/111; C12N 15/85; C12N 15/90; C12N 2310/20; C12N 2320/34; C12N 2800/80; A61P 13/12; A61K 48/005; A61K 38/00
See application file for complete search history.

(56) References Cited

U.S. PATENT DOCUMENTS

2016/0208243 A1*  7/2016  Zhang ................ C12N 9/22

FOREIGN PATENT DOCUMENTS

| WO | WO-2005071114 A1 * | 8/2005 | ........... C12Q 1/6883 |
| WO | WO-2013130868 A1 * | 9/2013 | ........... A61K 31/713 |
| WO | WO 2017/053713 A1 | 3/2017 | |

OTHER PUBLICATIONS

Islam et al in "Therapeutic Suppression of Nonsense Mutation: An Emerging Target in Multiple Diseases and Thrombotic Disorders" (Current Pharmaceutical Design, 2007, vol. 23, No. 11: pp. 1598-1609). (Year: 2017).*
Zhao et al SEQ ID No. 1 for WO-2013130868-A1 (Year: 2013).*
Score report for SEQ ID No. 132 for WO-2005071114-A1 to Dogolu et al (Year: 2005).*
International Search Report issued Mar. 26, 2019 in connection with PCT International Application No. PCT/US2018/062871.
Written Opinion (form PCT/ISA/237) issued Mar. 26, 2019 in connection with PCT International Application No. PCT/US2018/062871.
International Preliminary Report on Patentability issued Jun. 2, 2020 in connection with PCT/US2018/062871.

* cited by examiner

*Primary Examiner* — Catherine S Hibbert
(74) *Attorney, Agent, or Firm* — Potomac Law Group, PLLC; Jamaica Potts Szeliga

(57) ABSTRACT

RNA molecules comprising a guide sequence portion having 17-20 nucleotides in the sequence of 17-20 contiguous nucleotides set forth in any one of SEQ ID NOs: 1-1990 and compositions, methods, and uses thereof.

3 Claims, 14 Drawing Sheets
Specification includes a Sequence Listing.

DIFFERENTIAL KNOCKOUT OF AN ALLELE OF A HETEROZYGOUS FIBRINOGEN ALPHA CHAIN (FGA) GENE

CROSS-REFERENCE TO RELATED APPLICATIONS

This application is a § 371 national stage of PCT International Application No. PCT/US2018/062871, filed Nov. 28, 2018, claiming the benefit of U.S. Provisional Application No. 62/651,630, filed Apr. 2, 2018, and U.S. Provisional Application No. 62/591,350, filed Nov. 28, 2017, the contents of which are hereby incorporated by reference into the application.

Throughout this application, various publications are referenced, including referenced in parenthesis. The disclosures of all publications mentioned in this application in their entireties are hereby incorporated by reference into this application in order to provide additional description of the art to which this invention pertains and of the features in the art which can be employed with this invention.

REFERENCE TO SEQUENCE LISTING

This application incorporates-by-reference nucleotide sequences which are present in the filed named "181128_90239-A-PCT_SequenceListing_ADR.txt", which is 365 kilobytes in size, and which was created on Nov. 27, 2018 in the IBM-PC machine format, having an operating system compatibility with MS-Windows, which is contained in the text file filed Nov. 28, 2018 as part of this application.

BACKGROUND OF INVENTION

There are several classes of DNA variation in the human genome, including insertions and deletions, differences in the copy number of repeated sequences, and single nucleotide polymorphisms (SNPs). A SNP is a DNA sequence variation occurring when a single nucleotide (adenine (A), thymine (T), cytosine (C), or guanine (G)) in the genome differs between human subjects or paired chromosomes in an individual. Over the years, the different types of DNA variations have been the focus of the research community either as markers in studies to pinpoint traits or disease causation or as potential causes of genetic disorders.

A genetic disorder is caused by one or more abnormalities in the genome. Genetic disorders may be regarded as either "dominant" or "recessive." Recessive genetic disorders are those which require two copies (i.e., two alleles) of the abnormal/defective gene to be present. In contrast, a dominant genetic disorder involves a gene or genes which exhibit(s) dominance over a normal (functional/healthy) gene or genes. As such, in dominant genetic disorders only a single copy (i.e., allele) of an abnormal gene is required to cause or contribute to the symptoms of a particular genetic disorder. Such mutations include, for example, gain-of-function mutations in which the altered gene product possesses a new molecular function or a new pattern of gene expression. Other examples include dominant negative mutations, which have a gene product that acts antagonistically to the wild-type allele.

Renal Amyloidosis

Amyloidosis is a protein mis-folding disorder, in which normally soluble proteins undergo conformational changes and are deposited in the extracellular space as abnormal insoluble fibrils that progressively disrupt tissue structure and function. Fibrinogen A alpha chain (also known as fibrinogen A alpha chain (FGA)) gene encodes the alpha subunit of the coagulation factor fibrinogen, which is a blood clot component, produced and secreted by liver hepatocyte cells. Mutations in FGA gene were shown to be associated with Fibrinogen A alpha chain amyloidosis (AFib) which is an autosomal dominant disease that causes hereditary renal amyloidosis.

SUMMARY OF THE INVENTION

Disclosed is an approach for knocking out the expression of a dominant-mutated allele by disrupting the dominant-mutated allele or degrading the resulting mRNA.

The present disclosure provides a method for utilizing at least one naturally occurring nucleotide difference or polymorphism (e.g., single nucleotide polymorphism (SNP)) for distinguishing/discriminating between two alleles of a gene, one allele bearing a mutation such that it encodes a mutated protein causing a disease phenotype ("mutated allele"), and the other allele encoding for a functional protein ("functional allele"). In some embodiments, the method further comprises the step of knocking out expression of the mutated protein and allowing expression of the functional protein.

According to embodiments of the present invention, there is provided a first RNA molecule comprising a guide sequence portion having 17-20 nucleotides in the sequence of 17-20 contiguous nucleotides set forth in any one of SEQ ID NOs: 1-1990.

According to embodiments of the present invention, there is provided a first RNA molecule comprising a guide sequence portion having 17-20 contiguous nucleotides set forth in any one of SEQ ID NOs: 1-1990.

According to some embodiments of the present invention, there is provided a composition comprising an RNA molecule comprising a guide sequence portion having 17-20 nucleotides in the sequence of 17-20 contiguous nucleotides set forth in any one of SEQ ID NOs: 1-1990 and a CRISPR nuclease.

According to some embodiments of the present invention, there is provided a method for inactivating a mutant FGA allele in a cell, the method comprising delivering to the cell a composition comprising an RNA molecule comprising a guide sequence portion having 17-20 nucleotides in the sequence of 17-20 contiguous nucleotides set forth in any one of SEQ ID NOs: 1-1990 and a CRISPR nuclease.

According to some embodiments of the present invention, there is provided a method for treating AFib amyloidosis, the method comprising delivering to a subject having AFib amyloidosis a composition comprising an RNA molecule comprising a guide sequence portion having 17-20 nucleotides in the sequence of 17-20 contiguous nucleotides set forth in any one of SEQ ID NOs: 1-1990 and a CRISPR nuclease.

According to some embodiments of the present invention, there is provided use of a composition comprising an RNA molecule comprising a guide sequence portion having 17-20 nucleotides in the sequence of 17-20 contiguous nucleotides set forth in any one of SEQ ID NOs: 1-1990 and a CRISPR nuclease for inactivating a mutant FGA allele in a cell, comprising delivering to the cell the composition comprising an RNA molecule comprising a guide sequence portion having 17-20 nucleotides in the sequence of 17-20 contiguous nucleotides set forth in any one of SEQ ID NOs: 1-1990 and a CRISPR nuclease.

According to embodiments of the present invention, there is provided a medicament comprising an RNA molecule comprising a guide sequence portion having 17-20 nucleotides in the sequence of 17-20 contiguous nucleotides set forth in any one of SEQ ID NOs: 1-1990 and a CRISPR nuclease for use in inactivating a mutant FGA allele in a cell, wherein the medicament is administered by delivering to the cell the composition comprising an RNA molecule comprising a guide sequence portion having 17-20 nucleotides in the sequence of 17-20 contiguous nucleotides set forth in any one of SEQ ID NOs: 1-1990 and a CRISPR nuclease.

According to some embodiments of the present invention, there is provided use of a composition comprising an RNA molecule comprising a guide sequence portion having 17-20 nucleotides in the sequence of 17-20 contiguous nucleotides set forth in any one of SEQ ID NOs: 1-1990 and a CRISPR nuclease for treating ameliorating or preventing AFib amyloidosis, comprising delivering to a subject having or at risk of having AFib amyloidosis the composition of comprising an RNA molecule comprising a guide sequence portion having 17-20 nucleotides in the sequence of 17-20 contiguous nucleotides set forth in any one of SEQ ID NOs: 1-1990 and a CRISPR nuclease.

According to some embodiments of the present invention, there is provided a medicament comprising the composition comprising an RNA molecule comprising a guide sequence portion having 17-20 nucleotides in the sequence of 17-20 contiguous nucleotides set forth in any one of SEQ ID NOs: 1-1990 and a CRISPR nuclease for use in treating ameliorating or preventing AFib amyloidosis, wherein the medicament is administered by delivering to a subject having or at risk of having AFib amyloidosis the composition comprising an RNA molecule comprising a guide sequence portion having 17-20 nucleotides in the sequence of 17-20 contiguous nucleotides set forth in any one of SEQ ID NOs: 1-1990 and a CRISPR nuclease.

According to some embodiments of the present invention, there is provided a kit for inactivating a mutant FGA allele in a cell, comprising an RNA molecule comprising a guide sequence portion having 17-20 nucleotides in the sequence of 17-20 contiguous nucleotides set forth in any one of SEQ ID NOs: 1-1990, a CRISPR nuclease, and/or a tracrRNA molecule; and instructions for delivering the RNA molecule; CRISPR nuclease, and/or the tracrRNA to the cell.

According to some embodiments of the present invention, there is provided a kit for treating AFib amyloidosis in a subject, comprising an RNA molecule comprising a guide sequence portion having 17-20 nucleotides in the sequence of 17-20 contiguous nucleotides set forth in any one of SEQ ID NOs: 1-1990, a CRISPR nuclease, and/or a tracrRNA molecule; and instructions for delivering the RNA molecule; CRISPR nuclease, and/or the tracrRNA to a subject having or at risk of having AFib amyloidosis.

BRIEF DESCRIPTION OF THE DRAWINGS

In FIG. 2A-2D, exon 5 of the FGA gene bears an FGA mutation and encodes for the putative amyloid forming region suggested to effect formation of aggregates. Removal of, inter alia, exon 5 results in production of a fibrinogen alpha subunit that may be secreted without forming aggregates.

In FIG. 4A and FIG. 4B, each of exons 2, 3, and 4 encode a portion of the coiled coil region essential for the assembly of fibrinogen, necessary to produce a fibrinogen alpha subunit which may be assembled into a Fibrinogen hexamer and secreted from the cell.

In FIG. 5A-5C exon 4 of the FGA gene encodes a portion of the coiled coil region required for the assembly of the protein into fibrinogen required to produce a protein that assembles into a Fibrinogen hexamer secreted from the cell. In FIG. 5A and FIG. 5B, exon 5 bears the FGA mutation, removal of which results in the formation of a truncated fibrinogen alpha subunit which may be secreted without forming aggregates or alternatively RNA decay may be triggered resulting in knockout of the expression of the mutated allele.

In FIG. 6A and FIG. 6B exon 1 is removed to prevent the secretion of the fibrinogen hexamer carrying an FGA gene mutation.

In FIG. 10A indels are introduced on rs6050 SNP resulting with truncated protein without the putative amyloid forming region. In FIG. 10B exclusion of the coiled-coil domain or FGA Exon 5 by knock-out is generated with two RNA molecules. One guide targets a SNP and the second guide a sequence common to both alleles. The first guide targets a SNP/SEQ in either Intron 4, Intron2, 5'UTR, or promoter region while a second guide targets a sequence in Intron 5, a common region to both transcripts.

FIG. 11A represents the average±standard deviation of two independent experiments. FIG. 11B, Exon 5 excision rate was tested using gFGA 12 and gFGA 22. FIG. 11C, on target activity was determined by DNA Capillary Electrophoresis. FIG. 11D, the data shows a decrease of approximately 60% in Exon 5 levels of treated cells, while no significant change was detected in Exon 6 levels. FIG. 11C and FIG. 11D represent the average standard deviation of 4 independent experiments.

DETAILED DESCRIPTION

Definitions

Figure 1:
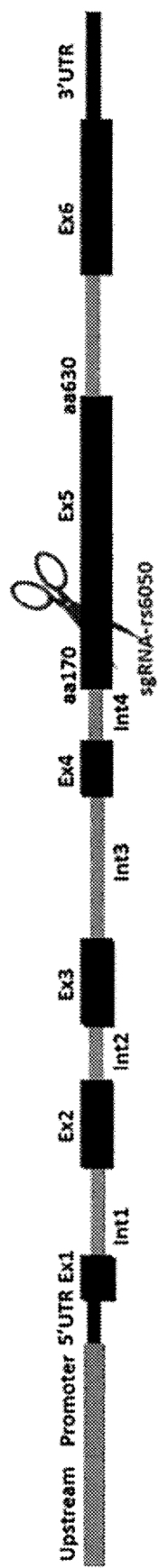
FIG. 1: Utilization of one RNA molecule to direct a CRISPR nuclease to a Single Nucleotide Polymorphism or Wild Type (SNP/WT) sequence located upstream to the mutation site in the mutated FGA allele and not in the functional allele to create a double-strand break (DSB) leading to formation of a frameshift mutation in an exon of the mutated FGA allele to produce a truncated fibrinogen alpha subunit lacking the FGA mutation and lacking the putative amyloid forming region suggested to effect formation of aggregates. The resultant truncated fibrinogen alpha subunit may be secreted without forming aggregates or alternatively RNA decay may be triggered resulting in knockout of the expression of the mutated allele.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

It should be understood that the terms "a" and "an" as used above and elsewhere herein refer to "one or more" of the enumerated components. It will be clear to one of ordinary skill in the art that the use of the singular includes the plural unless specifically stated otherwise. Therefore, the terms "a," "an" and "at least one" are used interchangeably in this application.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

Unless otherwise stated, adjectives such as "substantially" and "about" modifying a condition or relationship characteristic of a feature or features of an embodiment of the invention, are understood to mean that the condition or characteristic is defined to within tolerances that are acceptable for operation of the embodiment for an application for which it is intended. Unless otherwise indicated, the word "or" in the specification and claims is considered to be the inclusive "or" rather than the exclusive or, and indicates at least one of, or any combination of items it conjoins.

In the description and claims of the present application, each of the verbs, "comprise," "include" and "have" and conjugates thereof, are used to indicate that the object or objects of the verb are not necessarily a complete listing of components, elements or parts of the subject or subjects of the verb. Other terms as used herein are meant to be defined by their well-known meanings in the art.

The "guide sequence portion" of an RNA molecule refers to a nucleotide sequence that is capable of hybridizing to a specific target DNA sequence, e.g., the guide sequence portion has a nucleotide sequence which is fully complementary to said target DNA sequence. In some embodiments, the guide sequence portion is 17, 18, 19, 20, 21, 22, 23, or 24 nucleotides in length, or approximately 17-24, 18-22, 19-22, 18-20, or 17-20 nucleotides in length. The guide sequence portion may be part of an RNA molecule that can form a complex with a CRISPR nuclease with the guide sequence portion serving as the DNA targeting portion of the CRISPR complex. When the DNA molecule having the guide sequence portion is present contemporaneously with the CRISPR molecule the RNA molecule is capable of targeting the CRISPR nuclease to the specific target DNA sequence. Each possibility represents a separate embodiment. An RNA molecule can be custom designed to target any desired sequence.

In embodiments of the present invention, an RNA molecule comprises a guide sequence portion having 17-20 nucleotides in the sequence of 17-20 contiguous nucleotides set forth in any one of SEQ ID NOs: 1-1990, 1-409, or 410-1990.

As used herein, "contiguous nucleotides" set forth in a SEQ ID NO refers to nucleotides in a sequence of nucleotides in the order set forth in the SEQ ID NO without any intervening nucleotides.

In embodiments of the present invention, the guide sequence portion may be 20 nucleotides in length and consists of 20 nucleotides in the sequence of 20 contiguous nucleotides set forth in any one of SEQ ID NOs: 1-1990. In embodiments of the present invention, the guide sequence portion may be less than 20 nucleotides in length. For example, in embodiments of the present invention the guide sequence portion may be 17, 18, or 19 nucleotides in length. In such embodiments the guide sequence portion may consist of 17, 18, or 19 nucleotides, respectively, in the sequence of 17-20 contiguous nucleotides set forth in any one of SEQ ID NOs: 1-1990. For example, a guide sequence portion having 17 nucleotides in the sequence of 17 contiguous nucleotides set forth in SEQ ID NO: 1 may consist of any one of the following nucleotide sequences (nucleotides excluded from the contiguous sequence are marked in strike-through):

```
                                          SEQ ID NO: 1
AUUGACUCUGCUUGGUUUUU 17 nucleotide guide sequence 1:
AUUGACUCUGCUUGGUUUUU 17 nucleotide guide sequence 2:
AUUGACUCUGCUUGGUUUUU 17 nucleotide guide sequence 3:
AUUGACUCUGCUUGGUUUUU 17 nucleotide guide sequence 4:
AUUGACUCUGCUUGGUUUUU
```

In embodiments of the present invention, the guide sequence portion may be greater than 20 nucleotides in length. For example, in embodiments of the present invention the guide sequence portion may be 21, 22, 23, or 24 nucleotides in length. In such embodiments the guide sequence portion comprises 20 nucleotides in the sequence of 20 contiguous nucleotides set forth in any one of SEQ ID NOs: 1-1990 and additional nucleotides fully complimentary to a nucleotide or sequence of nucleotides adjacent to the 3' end of the target sequence, 5' end of the target sequence, or both.

In embodiments of the present invention a CRISPR nuclease and an RNA molecule comprising a guide sequence portion form a CRISPR complex that binds to a target DNA sequence to effect cleavage of the target DNA sequence. CRISPR nucleases, e.g. Cpf1, may form a CRISPR complex comprising a CRISPR nuclease and RNA molecule without a further tracrRNA molecule. Alternatively, CRISPR nucleases, e.g. Cas9, may form a CRISPR complex between the CRISPR nuclease, an RNA molecule, and atracrRNA molecule.

In embodiments of the present invention, the RNA molecule may further comprise the sequence of a tracrRNA molecule. Such embodiments may be designed as a synthetic fusion of the guide portion of the RNA molecule and the trans-activating crRNA (tracrRNA). (See Jinek (2012) Science). Embodiments of the present invention may also form CRISPR complexes utilizing a separate tracrRNA molecule and a separate RNA molecule comprising a guide sequence portion. In such embodiments the tracrRNA molecule may hybridize with the RNA molecule via basepairing and may be advantageous in certain applications of the invention described herein.

The term "tracr mate sequence" refers to a sequence sufficiently complementary to a tracrRNA molecule so as to hybridize to the tracrRNA via basepairing and promote the formation of a CRISPR complex. (See U.S. Pat. No. 8,906, 616). In embodiments of the present invention, the RNA molecule may further comprise a portion having a tracr mate sequence.

A "gene," for the purposes of the present disclosure, includes a DNA region encoding a gene product, as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Eukaryotic" cells include, but are not limited to, fungal cells (such as yeast), plant cells, animal cells, mammalian cells and human cells.

The term "nuclease" as used herein refers to an enzyme capable of cleaving the phosphodiester bonds between the nucleotide subunits of nucleic acid. A nuclease may be isolated or derived from a natural source. The natural source may be any living organism. Alternatively, a nuclease may be a modified or a synthetic protein which retains the phosphodiester bond cleaving activity. Gene modification can be achieved using a nuclease, for example a CRISPR nuclease.

EMBODIMENTS

The present disclosure provides a method for utilizing at least one naturally occurring nucleotide difference or polymorphism (e.g., single nucleotide polymorphism (SNP)) for distinguishing/discriminating between two alleles of a gene, one allele bearing a mutation such that it encodes a mutated protein causing a disease phenotype ("mutated allele"), and the other allele encoding for a functional protein ("functional allele"). The method further comprises the step of knocking out expression of the mutated protein and allowing expression of the functional protein. In some embodiments, the method is for treating, ameliorating, or preventing a dominant negative genetic disorder.

According to embodiments of the present invention, there is provided a first RNA molecule comprising a guide sequence portion having 17-20 nucleotides in the sequence of 17-20 contiguous nucleotides set forth in any one of SEQ ID NOs: 1-1990.

According to embodiments of the present invention, there is provided a first RNA molecule comprising a guide sequence portion having 17-20 contiguous nucleotides set forth in any one of SEQ ID NOs: 1-1990.

According embodiments of the present invention, an RNA molecule may further comprise a portion having a sequence which binds to a CRISPR nuclease.

According to embodiments of the present invention, the sequence which binds to a CRISPR nuclease is a tracrRNA sequence.

According to embodiments of the present invention, an RNA molecule may further comprise a portion having a tracr mate sequence.

According to embodiments of the present invention, an RNA molecule may further comprise one or more linker portions.

According to embodiments of the present invention, an RNA molecule may be up to 300, 290, 280, 270, 260, 250, 240, 230, 220, 210, 200, 190, 180, 170, 160, 150, 140, 130, 120, 110, or 100 nucleotides in length. Each possibility represents a separate embodiment. In embodiments of the present invention, the RNA molecule may be 17 up to 300 nucleotides in length, 100 up to 300 nucleotides in length, 150 up to 300 nucleotides in length, 200 up to 300 nucleotides in length, 100 to 200 nucleotides in length, or 150 up to 250 nucleotides in length. Each possibility represents a separate embodiment.

According to some embodiments of the present invention, there is provided a composition comprising an RNA molecule comprising a guide sequence portion having 17-20 nucleotides in the sequence of 17-20 contiguous nucleotides set forth in any one of SEQ ID NOs: 1-1990 and a CRISPR nuclease.

According to embodiments of the present invention, the composition may comprise a second RNA molecule comprising a guide sequence portion.

According to embodiments of the present invention, the guide sequence portion of the second RNA molecule comprises 17-20 nucleotides in the sequence of 17-20 contiguous nucleotides set forth in any one of SEQ ID NOs: 1-1990.

According to embodiments of the present invention, the 17-20 nucleotides of the guide sequence portion of the second RNA molecule are in a different sequence from the sequence of the guide sequence portion of the first RNA molecule Embodiments of the present invention may comprise a tracrRNA molecule.

According to some embodiments of the present invention, there is provided a method for inactivating a mutant FGA allele in a cell, the method comprising delivering to the cell a composition comprising an RNA molecule comprising a guide sequence portion having 17-20 nucleotides in the sequence of 17-20 contiguous nucleotides set forth in any one of SEQ ID NOs: 1-1990 and a CRISPR nuclease.

According to some embodiments of the present invention, there is provided a method for treating AFib amyloidosis, the method comprising delivering to a subject having AFib amyloidosis a composition comprising an RNA molecule comprising a guide sequence portion having 17-20 nucleotides in the sequence of 17-20 contiguous nucleotides set forth in any one of SEQ ID NOs: 1-1990 and a CRISPR nuclease.

According to embodiments of the present invention, the composition comprises a second RNA molecule comprising a guide sequence portion having 17-20 nucleotides in the sequence of 17-20 contiguous nucleotides set forth in any one of SEQ ID NOs: 1-1990.

According to embodiments of the present invention, the 17-20 nucleotides of the guide sequence portion of the second RNA molecule are in a different sequence from the sequence of the guide sequence portion of the first RNA molecule According to embodiments of the present invention, the CRISPR nuclease and the RNA molecule or RNA molecules are delivered to the subject and/or cells substantially at the same time or at different times.

According to embodiments of the present invention, the tracrRNA is delivered to the subject and/or cells substantially at the same time or at different times as the CRISPR nuclease and RNA molecule or RNA molecules.

According to embodiments of the present invention, the first RNA molecule targets a SNP or disease-causing mutation in an exon or promoter of a mutated allele, and wherein the second RNA molecule targets a SNP in the same or a different exon of the mutated allele, a SNP in an intron, or a sequence in an intron present in both the mutated or functional allele.

According to embodiments of the present invention, the first RNA molecule or the first and the second RNA molecules target a SNP in the promoter region, the start codon, or the untranslated region (UTR) of a mutated allele.

According to embodiments of the present invention, the first RNA molecule or the first and the second RNA molecules targets at least a portion of the promoter and/or the start codon and/or a portion of the UTR of a mutated allele.

According to embodiments of the present invention, the first RNA molecule targets a portion of the promoter, a first SNP in the promoter, or a SNP upstream to the promoter of a mutated allele and the second RNA molecule is targets a second SNP, which is downstream of the first SNP, and is in the promoter, in the UTR, or in an intron or in an exon of a mutated allele.

According to embodiments of the present invention, the first RNA molecule targets a SNP in the promoter, upstream of the promoter, or the UTR of a mutated allele and the second RNA molecule is designed to target a sequence which is present in an intron of both the mutated allele and the functional allele.

According to embodiments of the present invention, the first RNA molecule targets a sequence upstream of the promotor which is present in both a mutated and functional allele and the second RNA molecule targets a SNP or disease-causing mutation in any location of the gene.

According to embodiments of the present invention, there is provided a method comprising removing an exon containing a disease-causing mutation from a mutated allele, wherein the first RNA molecule or the first and the second RNA molecules target regions flanking an entire exon or a portion of the exon.

According to embodiments of the present invention, there is provided a method comprising removing multiple exons, the entire open reading frame of a gene, or removing the entire gene.

According to embodiments of the present invention, the first RNA molecule targets a SNP or disease-causing mutation in an exon or promoter of a mutated allele, and wherein the second RNA molecule targets a SNP in the same or a different exon of the mutated allele, a SNP in an intron, or a sequence in an intron present in both the mutated or functional allele.

According to embodiments of the present invention, the first RNA molecule or the first and the second RNA molecules target an alternative splicing signal sequence between an exon and an intron of a mutant allele.

According to embodiments of the present invention, the second RNA molecule targets a sequence present in both a mutated allele and a functional allele.

According to embodiments of the present invention, the second RNA molecule targets an intron.

According to embodiments of the present invention, there is provided a method comprising subjecting the mutant allele to insertion or deletion by an error prone non-homologous end joining (NHEJ) mechanism, generating a frameshift in the mutated allele's sequence.

According to embodiments of the present invention, the frameshift results in inactivation or knockout of the mutated allele.

According to embodiments of the present invention, the frameshift creates an early stop codon in the mutated allele.

According to embodiments of the present invention, the frameshift results in nonsense-mediated mRNA decay of the transcript of the mutant allele.

According to embodiments of the present invention, the inactivating or treating results in a truncated protein encoded by the mutated allele and a functional protein encoded by the functional allele.

According to some embodiments of the present invention, there is provided use of a composition comprising an RNA molecule comprising a guide sequence portion having 17-20 nucleotides in the sequence of 17-20 contiguous nucleotides set forth in any one of SEQ ID NOs: 1-1990 and a CRISPR nuclease inactivating a mutant FGA allele in a cell, comprising delivering to the cell the RNA molecule comprising a guide sequence portion having 17-20 nucleotides in the sequence of 17-20 contiguous nucleotides set forth in any one of SEQ ID NOs: 1-1990 and the CRISPR nuclease.

According to embodiments of the present invention, there is provided a medicament comprising an RNA molecule comprising a guide sequence portion having 17-20 nucleotides in the sequence of 17-20 contiguous nucleotides set forth in any one of SEQ ID NOs: 1-1990 and a CRISPR nuclease for use in inactivating a mutant FGA allele in a cell, wherein the medicament is administered by delivering to the cell the composition comprising an RNA molecule comprising a guide sequence portion having 17-20 nucleotides in the sequence of 17-20 contiguous nucleotides set forth in any one of SEQ ID NOs: 1-1990 and a CRISPR nuclease.

According to some embodiments of the present invention, there is provided use of a composition comprising an RNA molecule comprising a guide sequence portion having 17-20 nucleotides in the sequence of 17-20 contiguous nucleotides set forth in any one of SEQ ID NOs: 1-1990 and a CRISPR nuclease for treating ameliorating or preventing AFib amyloidosis, comprising delivering to a subject having or at risk of having AFib amyloidosis the composition of comprising an RNA molecule comprising a guide sequence portion having 17-20 nucleotides in the sequence of 17-20 contiguous nucleotides set forth in any one of SEQ ID NOs: 1-1990 and a CRISPR nuclease.

According to some embodiments of the present invention, there is provided a medicament comprising the composition comprising an RNA molecule comprising a guide sequence portion having 17-20 nucleotides in the sequence of 17-20 contiguous nucleotides set forth in any one of SEQ ID NOs: 1-1990 and a CRISPR nuclease for use in treating ameliorating or preventing AFib amyloidosis, wherein the medicament is administered by delivering to a subject having or at risk of having AFib amyloidosis: the composition comprising an RNA molecule comprising a guide sequence portion having 17-20 nucleotides in the sequence of 17-20 contiguous nucleotides set forth in any one of SEQ ID NOs: 1-1990 and a CRISPR nuclease.

According to some embodiments of the present invention, there is provided a kit for inactivating a mutant FGA allele in a cell, comprising an RNA molecule comprising a guide sequence portion having 17-20 nucleotides in the sequence of 17-20 contiguous nucleotides set forth in any one of SEQ ID NOs: 1-1990, a CRISPR nuclease, and/or a tracrRNA molecule; and instructions for delivering the RNA molecule; CRISPR nuclease, and/or the tracrRNA to the cell.

According to some embodiments of the present invention, there is provided a kit for treating AFib amyloidosis in a subject, comprising an RNA molecule comprising a guide sequence portion having 17-20 nucleotides in the sequence of 17-20 contiguous nucleotides set forth in any one of SEQ ID NOs: 1-1990, a CRISPR nuclease, and/or a tracrRNA molecule; and instructions for delivering the RNA molecule; CRISPR nuclease, and/or the tracrRNA to a subject having or at risk of having AFib amyloidosis.

In embodiments of the present invention, the RNA molecule comprises a guide sequence portion having 17-20 nucleotides in the sequence of 17-20 contiguous nucleotides set forth in any one of SEQ ID NOs: 1-409, SEQ ID NOs: 410-1990, or SEQ ID NOs 1-1990.

The compositions and methods of the present disclosure may be utilized for treating, preventing, ameliorating, or slowing progression of amyloidosis, such as AFib amyloidosis.

In some embodiments, a mutated allele is deactivated by delivering to a cell an RNA molecule which targets a SNP in the promoter region, the start codon, or the untranslated region (UTR) of the mutated allele.

In some embodiments, a mutated allele is inactivated by removing at least a portion of the promoter and/or removing the start codon and/or a portion of the UTR. In some embodiments, the method of deactivating a mutated allele comprises removing at least a portion of the promoter. In such embodiments one RNA molecule may be designed for targeting a first SNP in the promoter or upstream to the promoter and another RNA molecule is designed to target a second SNP, which is downstream of the first SNP, and is in the promoter, in the UTR, or in an intron or in an exon. Alternatively, one RNA molecule may be designed for targeting a SNP in the promoter, or upstream of the promoter, or the UTR and another RNA molecule is designed to target a sequence which is present in an intron of both the mutated allele and the functional allele. Alternatively, one RNA molecule may be designed for targeting a sequence upstream of the promotor which is present in both the mutated and functional allele and the other guide is designed to target a SNP or disease-causing mutation in any location of the gene e.g., in an exon, intron, UTR, or downstream of the promoter.

In some embodiments, the method of deactivating a mutated allele comprises an exon skipping step comprising removing an exon containing a disease-causing mutation from the mutated allele. Removing an exon containing a disease-causing mutation in the mutated allele requires two RNA molecules which target regions flanking the entire exon or a portion of the exon. Removal of an exon containing the disease-causing mutation may be designed to eliminate the disease-causing action of the protein while allowing for expression of the remaining protein product which retains some or all of the wild-type activity. As an alternative to single exon skipping, multiple exons, the entire open reading frame or the entire gene can be excised using two RNA molecules flanking the region desired to be excised.

In some embodiments, the method of deactivating a mutated allele comprises delivering two RNA molecules to a cell, wherein one RNA molecule targets a SNP or disease-causing mutation in an exon or promoter of the mutated allele, and wherein the other RNA molecule targets a SNP in the same or a different exon of the mutated allele, a SNP in an intron, or a sequence in an intron present in both the mutated or functional allele.

In some embodiments, an RNA molecule is used to target a CRISPR nuclease to an alternative splicing signal sequence between an exon and an intron of a mutant allele, thereby destroying the alternative splicing signal sequence in the mutant allele.

Any one of, or combination of, the above-mentioned strategies for deactivating a mutant allele may be used in the context of the invention.

Additional strategies may be used to deactivate a mutated allele. For example, in embodiments of the present invention, an RNA molecule is used to direct a CRISPR nuclease to an exon or a splice site of a mutated allele in order to create a double-stranded break (DSB), leading to insertion or deletion of nucleotides by an error-prone non-homologous end-joining (NHEJ) mechanism and formation of a frameshift mutation in the mutated allele. The frameshift mutation may result in: (1) inactivation or knockout of the mutated allele by generation of an early stop codon in the mutated allele, resulting in generation of a truncated protein; or (2) nonsense mediated mRNA decay of the transcript of the mutant allele. In further embodiments, one RNA molecule is used to direct a CRISPR nuclease to a promotor of a mutated allele.

In some embodiments, the method of deactivating a mutated allele further comprises enhancing activity of the functional protein such as by providing a protein/peptide, a nucleic acid encoding a protein/peptide, or a small molecule such as a chemical compound, capable of activating/enhancing activity of the functional protein.

According to some embodiments, the present disclosure provides an RNA sequence ('RNA molecule') which binds to/associates with and/or directs the RNA guided DNA nuclease e.g., CRISPR nuclease to a sequence comprising at least one nucleotide which differs between a mutated allele and a functional allele (e.g., SNP) of a gene of interest (i.e., a sequence of the mutated allele which is not present in the functional allele).

In some embodiments, the method comprises the steps of: contacting a mutated allele of a gene of interest with an allele-specific RNA molecule and a CRISPR nuclease e.g., a Cas9 protein, wherein the allele-specific RNA molecule and the CRISPR nuclease e.g., Cas9 associate with a nucleotide sequence of the mutated allele of the gene of interest which differs by at least one nucleotide from a nucleotide sequence of a functional allele of the gene of interest, thereby modifying or knocking-out the mutated allele.

In some embodiments, the allele-specific RNA molecule and a CRISPR nuclease is introduced to a cell encoding the gene of interest. In some embodiments, the cell encoding the gene of interest is in a mammalian subject. In some embodiments, the cell encoding the gene of interest is in a plant.

In some embodiments, the cleaved mutated allele is further subjected to insertion or deletion (indel) by an error prone non-homologous end joining (NHEJ) mechanism, generating a frameshift in the mutated allele's sequence. In some embodiments, the generated frameshift results in inactivation or knockout of the mutated allele. In some embodiments, the generated frameshift creates an early stop codon in the mutated allele and results in generation of a truncated protein. In such embodiments, the method results in the generation of a truncated protein encoded by the mutated allele and a functional protein encoded by the functional allele. In some embodiments, a frameshift generated in a mutated allele using the methods of the invention results in nonsense-mediated mRNA decay of the transcript of the mutant allele.

In some embodiments, the mutated allele is an allele of fibrinogen alpha chain (FGA) gene. In some embodiments, the RNA molecule targets a SNP which co-exists with/is genetically linked to the mutated sequence associated with AFib amyloidosis genetic disorder. In some embodiments, the RNA molecule targets a SNP which is highly prevalent in the population and exists in the mutated allele having the mutated sequence associated with AFib amyloidosis genetic disorder and not in the functional allele of an individual subject to be treated. In some embodiments, a disease-causing mutation within a mutated FGA allele is targeted.

In some embodiments, the SNP is within an exon of the gene of interest. In such embodiments, a guide sequence portion of an RNA molecule may be designed to associate with a sequence of the exon of the gene of interest.

In some embodiments, SNP is within an intron or an exon of the gene of interest. In some embodiments, SNP is in close proximity to a splice site between the intron and the exon. In some embodiments, the close proximity to a splice site is 1, 2, 3, 4, 5, 6, 7, 8, 9, 10, 11, 12, 13, 14, 15, 16, 17, 18, 19, or 20 nucleotides upstream or downstream to the splice site. Each possibility represents a separate embodiment of the present invention. In such embodiments, a guide sequence portion of an RNA molecule may be designed to associate with a sequence of the gene of interest which comprises the splice site.

In some embodiments, the method is utilized for treating a subject having a disease phenotype resulting from the heterozygote FGA gene. In such embodiments, the method results in improvement, amelioration or prevention of the disease phenotype.

Embodiments referred to above refer to a CRISPR nuclease, RNA molecule(s), and tracrRNA being effective in a subject or cells at the same time. The CRISPR, RNA molecule(s), and tracrRNA can be delivered substantially at the same time or can be delivered at different times but have effect at the same time. For example, this includes delivering the CRISPR nuclease to the subject or cells before the RNA molecule and/or tracr RNA is substantially extant in the subject or cells.

In some embodiments, the cell is a liver cell. In some embodiments, the cell is a hepatocyte cell.

Dominant Genetic Disorders

One of skill in the art will appreciate that all subjects with any type of heterozygote genetic disorder (e.g., dominant genetic disorder) may be subjected to the methods described herein. In one embodiment, the present invention may be used to target a gene involved in, associated with, or causative of dominant genetic disorders such as, for example, AFib amyloidosis. In some embodiments, the dominant genetic disorder is AFib amyloidosis. In some embodiments, the target gene is the FGA gene (Entrez Gene, gene ID No: 2243).

CRISPR Nucleases and PAM Recognition

In some embodiments, the sequence specific nuclease is selected from CRISPR nucleases, or a functional variant thereof. In some embodiments, the sequence specific nuclease is an RNA guided DNA nuclease. In such embodiments, the RNA sequence which guides the RNA guided DNA nuclease (e.g., Cpf1) binds to and/or directs the RNA guided DNA nuclease to the sequence comprising at least one nucleotide which differs between a mutated allele and its counterpart functional allele (e.g., SNP). In some embodiments, the CRISPR complex does not further comprise a tracrRNA. In a non-limiting example, in which the RNA guided DNA nuclease is a CRISPR protein, the at least one nucleotide which differs between the dominant mutated allele and the functional allele may be within the PAM site and/or proximal to the PAM site within the region that the RNA molecule is designed to hybridize to. A skilled artisan will appreciate that RNA molecules can be engineered to bind to a target of choice in a genome by commonly known methods in the art.

In embodiments of the present invention, a type II CRISPR system utilizes a mature crRNA:tracrRNA complex directs a CRISPR nuclease, e.g. Cas9, to the target DNA via Watson-Crick base-pairing between the crRNA and the protospacer on the target DNA next to the protospacer adjacent motif (PAM), an additional requirement for target recognition. The CRISPR nuclease then mediates cleavage of target DNA to create a double-stranded break within the protospacer. A skilled artisan will appreciate that each of the engineered RNA molecule of the present invention is further designed such as to associate with a target genomic DNA sequence of interest next to a protospacer adjacent motif (PAM), e.g., a PAM matching the sequence relevant for the type of CRISPR nuclease utilized, such as for a non-limiting example, NGG or NAG, wherein "N" is any nucleobase, for *Streptococcus pyogenes* Cas9 WT (Sp-CAS9); NNGRRT for *Staphylococcus aureus* (SaCas9); NNNVRYM for *Jejuni* Cas9 WT; NGAN or NGNG for SpCas9-VQR variant; NGCG for SpCas9-VRER variant; NGAG for SpCas9-EQR variant; NNNNGATT for *Neisseria meningitidis* (NmCas9); or TTTV for Cpf1. RNA molecules of the present invention are each designed to form complexes in conjunction with one or more different CRISPR nucleases and designed to target polynucleotide sequences of interest utilizing one or more different PAM sequences respective to the CRISPR nuclease utilized.

In some embodiments, an RNA-guided DNA nuclease e.g., a CRISPR nuclease, may be used to cause a DNA break at a desired location in the genome of a cell. The most commonly used RNA-guided DNA nucleases are derived from CRISPR systems, however, other RNA-guided DNA nucleases are also contemplated for use in the genome editing compositions and methods described herein. For instance, see U.S. Patent Publication No. 2015-0211023, incorporated herein by reference.

CRISPR systems that may be used in the practice of the invention vary greatly. CRISPR systems can be a type I, a type II, or a type III system. Non-limiting examples of suitable CRISPR proteins include Cas3, Cas4, Cas5, Cas5e (or CasD), Cas6, Cas6e, Cas6f, Cas7, Cas8a1, Cas8a2, Cas8b, Cas8c, Cas9, Cas10, Cas10d, CasF, CasG, CasH, Csy1, Csy2, Csy3, Cse1 (or CasA), Cse2 (or CasB), Cse3 (or CasE), Cse4 (or CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csxl7, Csx14, Csx10, Csxl6, CsaX, Csx3, Csz1, Csx15, Csf1, Csf2, Csf3, Csf4, and Cu966.

In some embodiments, the RNA-guided DNA nuclease is a CRISPR nuclease derived from a type II CRISPR system (e.g., Cas9). The CRISPR nuclease may be derived from *Streptococcus pyogenes, Streptococcus thermophilus, Streptococcus* sp., *Staphylococcus aureus, Neisseria meningitidis, Treponema denticola, Nocardiopsis dassonvillei, Streptomyces pristinaespiralis, Streptomyces viridochromogenes, Streptomyces viridochromogenes, Streptosporangium roseum, Streptosporangium roseum, Alicyclobacillus acidocaldarius, Bacillus pseudomycoides, Bacillus selenitireducens, Exiguobacterium sibiricum, Lactobacillus delbrueckii, Lactobacillus salivarius, Microscilla marina, Burkholderiales bacterium, Polaromonas naphthalenivorans, Polaromonas* sp., *Crocosphaera watsonii, Cyanothece* sp., *Microcystis aeruginosa, Synechococcus* sp., *Acetohalobium arabaticum, Ammonfex degensii, Caldicelulosiruptor becscii, Candidatus Desulforudis, Clostridium botulinum, Clostridium difficile, Finegoldia magna, Natranaerobius thermophilus, Pelotomaculumthermopropionicum, Acidithiobacillus caldus, Acidithiobacillus ferrooxidans, Allochromatium vinosum, Marinobacter* sp., *Nitrosococcus halophilus, Nitrosococcus watsoni, Pseudoalteromonas haloplanktis, Ktedonobacter racemfer, Methanohalobium evestigatum, Anabaena variabilis, Nodularia spumigena, Nostoc* sp., *Arthrospira maxima, Arthrospira platensis, Arthrospira* sp., *Lyngbya* sp., *Microcoleus chthonoplastes, Oscillatoria* sp., *Petrotoga mobilis, Thermosipho africanus, Acaryochloris marina*, or any species which encodes a CRISPR nuclease with a known PAM sequence. CRISPR nucleases encoded by uncultured bacteria may also be used in the context of the invention. (See Burstein et al. Nature, 2017). Variants of CRIPSR proteins having known PAM sequences e.g., spCas9 D1135E variant, spCas9 VQR variant, spCas9 EQR variant, or spCas9 VRER variant may also be used in the context of the invention.

Thus, an RNA guided DNA nuclease of a CRISPR system, such as a Cas9 protein or modified Cas9 or homolog or ortholog of Cas9, or other RNA guided DNA nucleases belonging to other types of CRISPR systems, such as Cpf1 and its homologs and orthologs, may be used in the compositions of the present invention.

In certain embodiments, the CRIPSR nuclease may be a "functional derivative" of a naturally occurring Cas protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. A biological activity contemplated herein is the ability of the functional derivative to hydrolyze a DNA substrate into fragments. The term "derivative" encompasses both amino acid sequence variants of polypeptide, covalent modifications, and fusions thereof. Suitable derivatives of a Cas polypeptide or a fragment thereof include but are not limited to, mutants, fusions, covalent modifications of Cas protein or a fragment thereof. Cas protein, which includes Cas protein or a fragment thereof, as well as derivatives of Cas protein or a fragment thereof, may be obtainable from a cell or synthesized chemically or by a combination of these two procedures. The cell may be a cell that naturally produces Cas protein, or a cell that naturally produces Cas protein and is genetically engineered to produce the endogenous Cas protein at a higher expression level or to produce a Cas protein from an exogenously introduced nucleic acid, which nucleic acid encodes a Cas that is same or different from the endogenous Cas. In some cases, the cell does not naturally produce Cas protein and is genetically engineered to produce a Cas protein.

In some embodiments, the CRISPR nuclease is Cpf1. Cpf1 is a single RNA-guided endonuclease which utilizes a T-rich protospacer-adjacent motif. Cpf1 cleaves DNA via a staggered DNA double-stranded break. Two Cpf1 enzymes from Acidaminococcus and Lachnospiraceae have been shown to carry out efficient genome-editing activity in human cells. (See Zetsche et al. (2015) Cell.).

Thus, an RNA guided DNA nuclease of a Type II CRISPR System, such as a Cas9 protein or modified Cas9 or homologs, orthologues, or variants of Cas9, or other RNA guided DNA nucleases belonging to other types of CRISPR systems, such as Cpf1 and its homologs, orthologues, or variants, may be used in the present invention.

In some embodiments, the guide molecule comprises one or more chemical modifications which imparts a new or improved property (e.g., improved stability from degradation, improved hybridization energetics, or improved binding properties with an RNA guided DNA nuclease). Suitable chemical modifications include, but are not limited to: modified bases, modified sugar moieties, or modified internucleoside linkages. Non-limiting examples of suitable chemical modifications include: 4-acetylcytidine, 5-(carboxyhydroxymethyl)uridine, 2'-O-methylcytidine, 5-carboxymethylaminomethyl-2-thiouridine, 5-carboxymethylaminomethyluridine, dihydrouridine, 2'-O-methylpseudouridine, "beta, D-galactosylqueuosine", 2'-O-methylguanosine, inosine, N6-isopentenyladenosine, 1-methyladenosine, 1-methylpseudouridine, 1-methylguanosine, I-methylinosine, "2,2-dimethylguanosine", 2-methyladenosine, 2-methylguanosine, 3-methylcytidine, 5-methylcytidine, N6-methyladenosine, 7-methylguanosine, 5-methylaminomethyluridine, 5-methoxyaminomethyl-2-thiouridine, "beta, D-mannosylqueuosine", 5-methoxycarbonylmethyl-2-thiouridine, 5-methoxycarbonylmethyluridine, 5-methoxyuridine, 2-methylthio-N6-isopentenyladenosine, N-((9-beta-D-ribofuranosyl-2-methylthiopurine-6-yl)carbamoyl)threonine, N-((9-beta-D-ribofuranosylpurine-6-yl)N-methylcarbamoyl)threonine, uridine-5-oxyacetic acid-methylester, uridine-5-oxyacetic acid, wybutoxosine, queuosine, 2-thiocytidine, 5-methyl-2-thiouridine, 2-thiouridine, 4-thiouridine, 5-methyluridine, N-((9-beta-D-ribofuranosylpurine-6-yl)-carbamoyl)threonine, 2'-O-methyl-5-methyluridine, 2'-O-methyluridine, wybutosine, "3-(3-amino-3-carboxy-propyl)uridine, (acp3) u", 2'-O-methyl (M), 3'-phosphorothioate (MS), 3'-thioPACE (MSP), pseudouridine, or 1-methyl pseudo-uridine. Each possibility represents a separate embodiment of the present invention.

Guide Sequences which Specifically Target a Mutant Allele

A given gene may contain thousands of SNPs. Utilizing a 24 base pair target window for targeting each SNP in a gene would require hundreds of thousands of guide sequences. Any given guide sequence when utilized to target a SNP may result in degradation of the guide sequence, limited activity, no activity, or off-target effects. Accordingly, suitable guide sequences are necessary for targeting a given gene. By the present invention, a novel set of guide sequences have been identified for knocking out expression of a mutated FGA protein, inactivating a mutant FGA gene allele, and treating Fibrinogen A alpha chain amyloidosis.

The present disclosure provides guide sequences capable of specifically targeting a mutated allele for inactivation while leaving the functional allele unmodified. The guide sequences of the present invention are designed to, and are most likely to, specifically differentiate between a mutated allele and a functional allele. Of all possible guide sequences which target a mutated allele desired to be inactivated, the specific guide sequences disclosed herein are specifically effective to function with the disclosed embodiments.

Briefly, the guide sequences may have properties as follows: (1) target SNP/insertion/deletion/indel with a high prevalence in the general population, in a specific ethnic population or in a patient population is above 1% and the SNP/insertion/deletion/indel heterozygosity rate in the same population is above 1%; (2) target a location of a SNP/insertion/deletion/indel proximal to a portion of the gene e.g., within 5k bases of any portion of the gene, for example, a promoter, a UTR, an exon or an intron; and (3) target a mutant allele using an RNA molecule which targets a founder or common pathogenic mutations for the disease/gene. In some embodiments, the prevalence of the SNP/insertion/deletion/indel in the general population, in a specific ethnic population or in a patient population is above 1%, 2%, 3%, 4%, 5%, 6%, 7%, 8%, 9%, 10%, 11%, 12%, 13%, 14%, or 15% and the SNP/insertion/deletion/indel heterozygosity rate in the same population is above 1%, 2%, 3%, 4%, 5%, 6%, 7%, 8%, 9%, 10%, 11%, 12%, 13%, 14%, or 15%. Each possibility represents a separate embodiment and may be combined at will.

For each gene, according to SNP/insertion/deletion/indel any one of the following strategies may be used to deactivate the mutated allele: (1) Knockout strategy using one RNA molecule—one RNA molecule is utilized to direct a CRISPR nuclease to a mutated allele and create a double-strand break (DSB) leading to formation of a frameshift mutation in an exon or in a splice site region of the mutated allele; (2) Knockout strategy using two RNA molecules—two RNA molecules are utilized. A first RNA molecule targets a region in the promoter or an upstream region of a mutated allele and another RNA molecule targets downstream of the first RNA molecule in a promoter, exon, or intron of the mutated allele; (3) Exon(s) skipping strategy—one RNA molecule may be used to target a CRISPR nuclease to a splice site region, either at the 5'end of an intron (donor sequence) or the 3' end of an intron (acceptor sequence), in order to destroy the splice site. Alternatively, two RNA molecules may be utilized such that a first RNA molecule targets an upstream region of an exon and a second RNA molecule targets a region downstream of the first RNA molecule, thereby excising the exon(s). Based on the locations of identified SNPs/insertions/deletions/indels for each mutant allele, any one of, or a combination of, the above-mentioned methods to deactivate the mutant allele may be utilized.

When only one RNA molecule is used is that the location of the SNP is in an exon or in close proximity (e.g., within 20 basepairs) to a splice site between the intron and the exon. When two RNA molecules are used, guide sequences may target two SNPs such that the first SNP is upstream of exon 1 e.g., within the 5' untranslated region, or within the promoter or within the first 2 kilobases 5' of the transcription start site, and the second SNP is downstream of the first SNP e.g., within the first 2 kilobases 5' of the transcription start site, or within intron 1, 2 or 3, or within exon 1, exon 2, or exon 3.

Guide sequences of the present invention may target a SNP in the upstream portion of the targeted gene, preferably upstream of the last exon of the targeted gene. Guide sequences may target a SNP upstream to exon 1, for example within the 5' untranslated region, or within the promoter or within the first 4-5 kilobases 5' of the transcription start site.

Guide sequences of the present invention may also target a SNP within close proximity (e.g., within 50 basepairs, more preferably with 20 basepairs) to a known protospacer adjacent motif (PAM) site.

Guide sequences of the present invention also may target: (1) a heterozygous SNP for the targeted gene; (2) a heterozygous SNPs upstream and downstream of the gene; (3) a SNPs with a prevalence of the SNP/insertion/deletion/indel in the general population, in a specific ethnic population, or in a patient population above 1%; (4) have a guanine-cytosine content of greater than 30% and less than 85%; (5) have no repeat of 4 or more thymine/uracil or 8 or more guanine, cytosine, or adenine; (6) having no off-target identified by off-target analysis; and (7) preferably target Exons over Introns or be upstream of a SNP rather than downstream of a SNP.

In embodiments of the present invention, the SNP may be upstream or downstream of the gene. In embodiments of the present invention, the SNP is within 4,000 base pairs upstream or downstream of the gene.

The at least one nucleotide which differs between the mutated allele and the functional allele, may be upstream, downstream or within the sequence of the disease-causing mutation of the gene of interest. The at least one nucleotide which differs between the mutated allele and the functional allele, may be within an exon or within an intron of the gene of interest. In some embodiments, the at least one nucleotide which differs between the mutated allele and the functional allele is within an exon of the gene of interest. In some embodiments, the at least one nucleotide which differs between the mutated allele and the functional allele is within an intron or an exon of the gene of interest, in close proximity to a splice site between the intron and the exon e.g., 1, 2, 3, 4, 5, 6, 7, 8, 9, 10, 11, 12, 13, 14, 15, 16, 17, 18, 19, or 20 nucleotides upstream or downstream to the splice site.

In some embodiments, the at least one nucleotide is a single nucleotide polymorphisms (SNPs). In some embodiments, each of the nucleotide variants of the SNP may be expressed in the mutated allele. In some embodiments, the SNP may be a founder or common pathogenic mutation.

Guide sequences may target a SNP which has both (1) a high prevalence in the general population e.g., above 1% in the population; and (2) a high heterozygosity rate in the population, e.g., above 1%. Guide sequences may target a SNP that is globally distributed. A SNP may be a founder or common pathogenic mutation. In some embodiments, the prevalence in the general population is above 1%, 2%, 3%, 4%, 5%, 6%, 7%, 8%, 9%, 10%, 11%, 12%, 13%, 14%, or 15%. Each possibility represents a separate embodiment. In some embodiments, the heterozygosity rate in the population is above 1%, 2%, 3%, 4%, 5%, 6%, 7%, 8%, 9%, 10%, 11%, 12%, 13%, 14%, or 15%. Each possibility represents a separate embodiment.

In some embodiments, the at least one nucleotide which differs between the mutated allele and the functional allele is linked to/co-exists with the disease-causing mutation in high prevalence in a population. In such embodiments, "high prevalence" refers to at least 92%, 93%, 94%, 95%, 96%, 97%, 98%, 99%, or 100%. Each possibility represents a separate embodiment of the present invention. In one embodiment, the at least one nucleotide which differs between the mutated allele and the functional allele, is a disease-associated mutation. In some embodiments, the SNP is highly prevalent in the population. In such embodiments, "highly prevalent" refers to at least 10%, 11%, 12%, 13%, 14%, 15%, 20%, 30%, 40%, 50%, 60%, or 70% of a population. Each possibility represents a separate embodiment of the present invention.

Guide sequences of the present invention may satisfy anyone of the above criteria and are most likely to differentiate between a mutated allele from its corresponding functional allele.

In some embodiments the RNA molecule targets a SNP/WT sequence linked to SNPs as shown in Table 1 below. The SNP details are indicated in the 1$^{st}$ column and include: SNP ID No. (based on NCBI's 2018 database of Single Nucleotide Polymorphisms (dbSNP)). For variants with no available rs number variants characteristic are indicated based on gnomAD 2018 browser database. The 2$^{nd}$ column indicates an assigned identifier for each SNP. The 3$^{rd}$ column indicates the location of each SNP on the FGA gene.

TABLE 1

| FGA gene SNPs | | |
|---|---|---|
| RSID | SNP No. | SNP location in the gene |
| rs28401745 | s1 | upstream −2871 bp |
| rs2070033 | s2 | Exon_6 of 6 |
| rs7659613 | s3 | upstream −3498 bp |
| rs4696596 | s4 | upstream −3944 bp |
| rs2070009 | s5 | upstream −1023 bp |
| rs2070006 | s6 | upstream −1948 bp |
| rs2070011 | s7 | Exon_1 of 6 |
| rs199768069 | s8 | Exon_6 of 6 |
| rs2070017 | s9 | Intron_2 of 5 |
| rs72955372 | s10 | upstream −2209 bp |
| rs77473178 | s11 | downstream +54 bp |
| rs2070027 | s12 | Intron_2 of 5 |
| rs6050 | s13 | Exon_5 of 6 |
| rs13109457 | s14 | upstream −2961 bp |
| rs2070014 | s15 | Intron_2 of 5 |
| rs2070022 | s16 | Exon_6 of 6 |
| rs1984906 | s17 | upstream −3568 bp |
| rs2070016 | s18 | Intron_2 of 5 |
| rs121909612 | s19 | Exon_5 of 6 |
| rs2070018 | s20 | Intron_4 of 5 |
| rs2070026 | s21 | Intron_2 of 5 |
| rs2070023 | s22 | upstream −1981 bp |
| rs7656433 | s23 | Intron_2 of 5 |
| rs6050 | S24 | Exon_5 of 6 |

In some embodiments, the RNA molecule targets SNP ID rs6050 located at exon 5 upstream to an FGA mutation.

In some embodiments, a first RNA molecule targets a SNP/WT sequence of SNP ID rs2070018 located at intron 4 upstream to an FGA mutation and another RNA molecule targets intron 5. (FIG. 1).

In some embodiments the suitable RNA molecules target the genomic region chr4:155,505,986-155,506,689 (hg19) of the FGA gene, which related to intron 5 of the long transcript NM_000508 of the FGA gene.

Figures 2A, 2B:
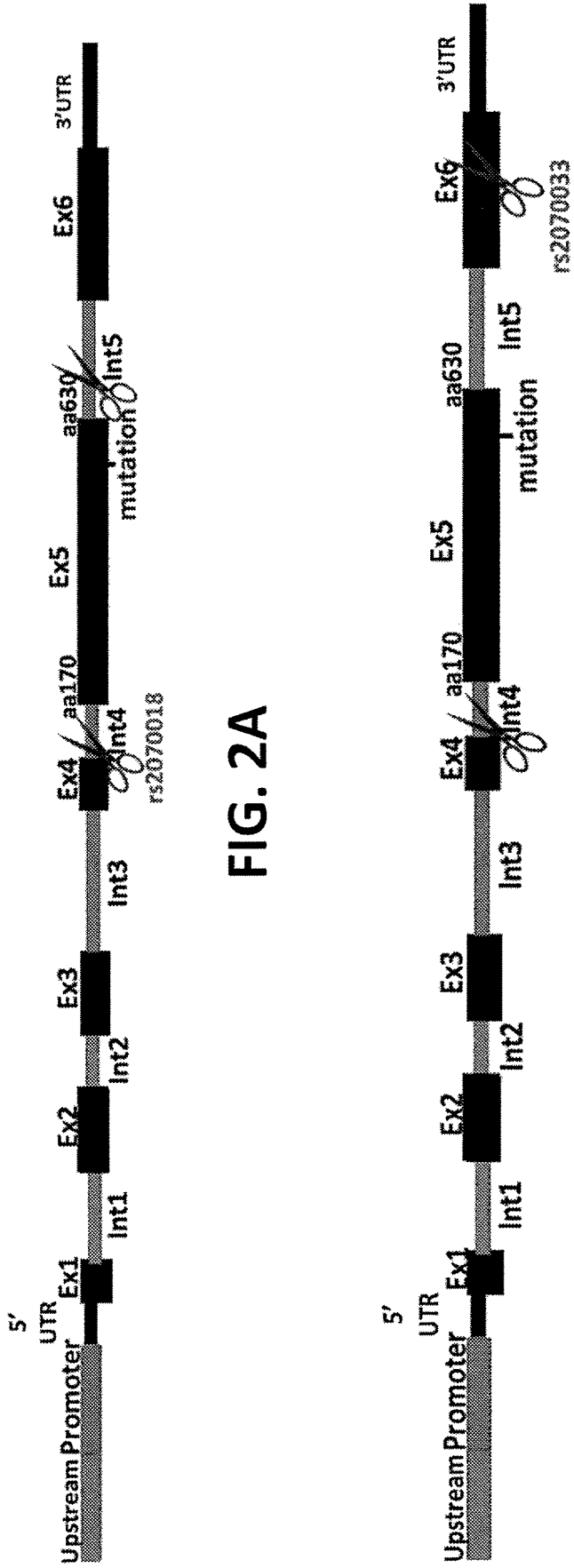
FIG. 2A: Utilization of two RNA molecules to remove exon 5 of the FGA gene.
FIG. 2B: Utilization of two RNA molecules to remove exon 5 and intron 1 of the FGA gene.
Figures 2C, 2D:
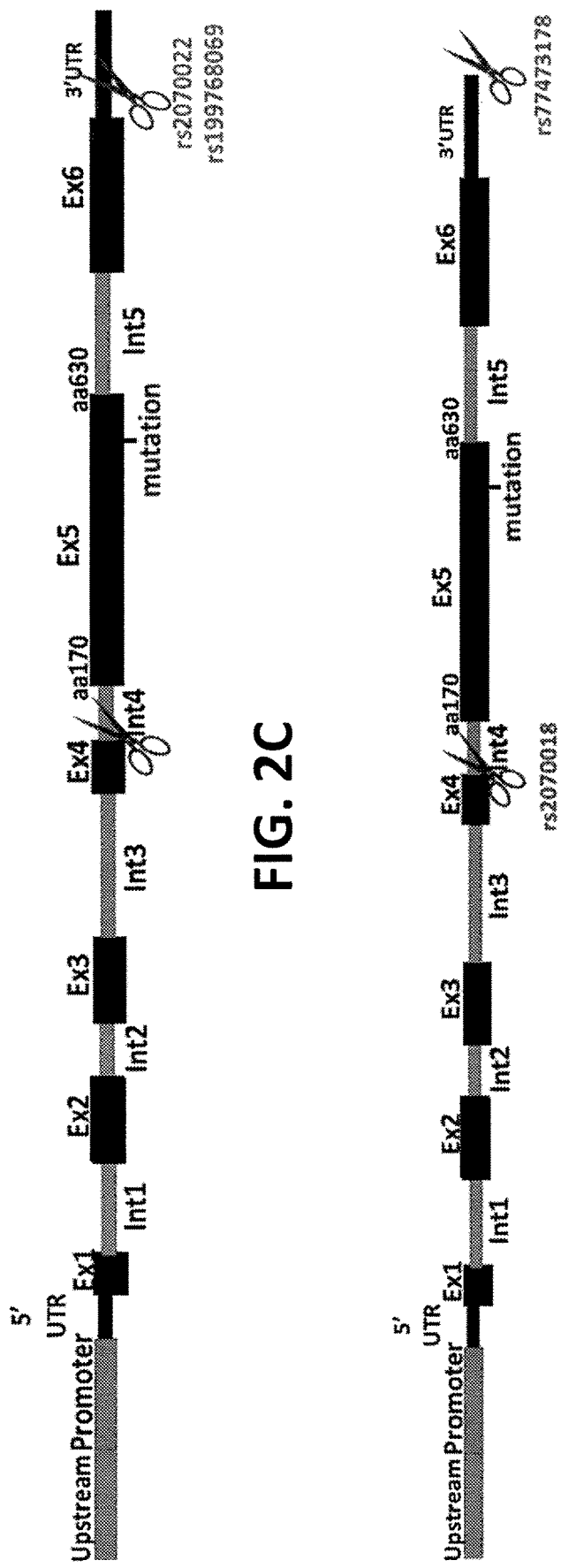
FIG. 2C: Utilization of two RNA molecules to remove exon 5, intron 5, and exon 6.
FIG. 2D Utilization of two RNA molecules to remove exon 5, intron 5, exon 6, and at least part of the 3' untranslated region (UTR).

In some embodiments a first RNA molecule comprises a nucleotide sequence located at intron 4, or a SNP/WT sequence of SNP ID rs2070018, and another RNA molecule targets a SNP/WT sequence located at exon 6 downstream of an FGA mutation, and optionally at least a portion of exon 6 may be removed. In some embodiments other RNA molecule targeting a SNP/WT sequence located at exon 6 downstream of the FGA mutation, targets one of SNP IDs rs2070033, rs19976806, or rs2070022. (FIG. 2A-FIG. 2C).

In some embodiments, a first RNA molecule targets a SNP/WT sequence of SNP ID rs2070018 located at intron 4 upstream to an FGA mutation, and another RNA molecule targets a SNP/WT sequence downstream to the gene such as SNP ID rs77473178. (FIG. 2D).

Figure 3:
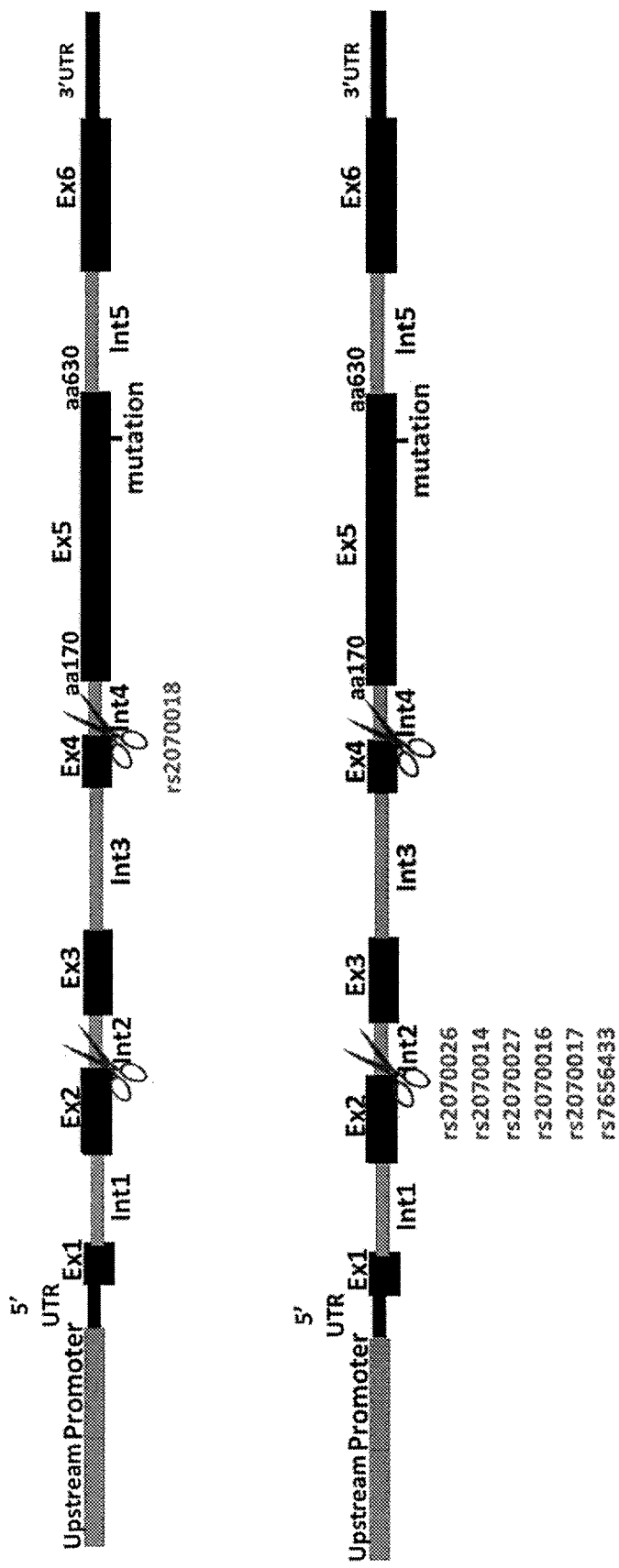
FIG. 3: Utilization of two RNA molecules to remove exon 3 and 4 of the FGA gene, which encode a portion of the coiled coil region essential for the assembly of fibrinogen, in order to produce a fibrinogen alpha subunit that does not assemble into a Fibrinogen hexamer secreted from the cell.

In some embodiments, a first RNA molecule targets a sequence in intron 4 and another RNA molecule targets a sequence in an upstream intron, such as intron 2. In further embodiments, to discriminate between the functional and mutated alleles, at least one sequence in intron 4 and the sequence in intron 2 is a SNP/WT sequence linked to an FGA mutation. In some embodiments the SNP in intron 4 is SNP ID rs2070018. In further embodiments, other sequences of intron 4 may be targeted. In some embodiments the target sequence in intron 2 is one of rs7656433, rs2070017, rs2070027, rs2070026, rs2070014, and rs2070016. In further embodiments, other sequences of intron 2 may be targeted. (FIG. 3).

Figure 4A:
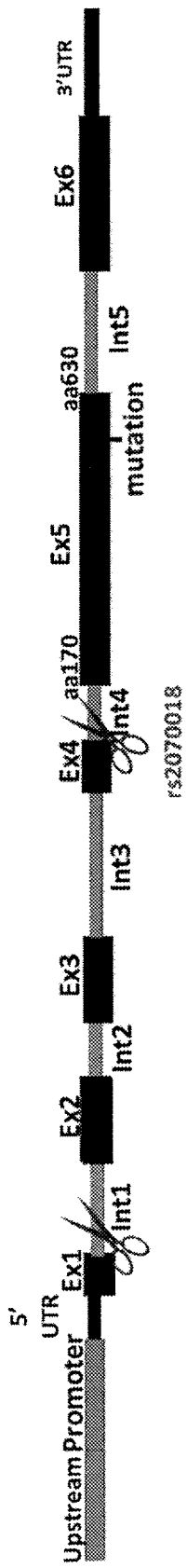
FIG. 4A: Utilization of two RNA molecules to remove exon 2, intron 2, exons 3, intron 3, and exon 4 of the FGA gene.

In some embodiments, a first RNA molecule targets a sequence in intron 1 and another RNA molecule targets a SNP/WT sequence of SNP ID rs2070018 located at intron 4 upstream to an FGA mutation. (FIG. 4A).

Figure 4B:
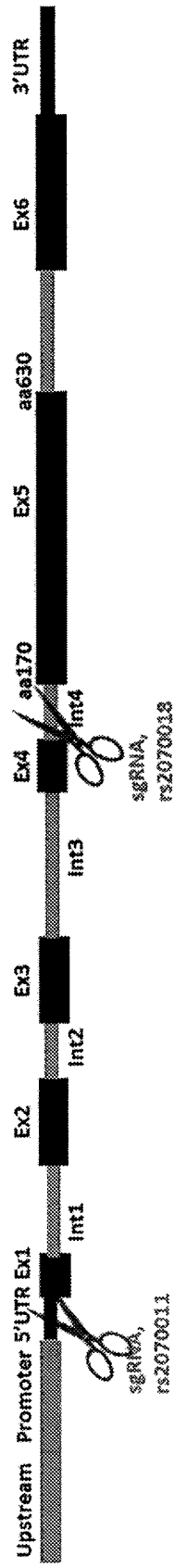
FIG. 4B: Utilization of two RNA molecules to remove exon 1, intron 1, exon 2, intron 2, exon 3, intron 3, and exon 4 of the FGA gene.

In some embodiments, a first RNA molecule targets a sequence in intron 4 of the FGA gene or a SNP in intron 4, such as SNP ID rs2070018, and another RNA molecule targets a SNP in exon 1, such as SNP ID rs2070011, optionally at least a portion of exon 1, which encodes a signal peptide, is also removed. In further embodiments, the sequence of intron 4 is targeted. (FIG. 4B).

Figure 5A:
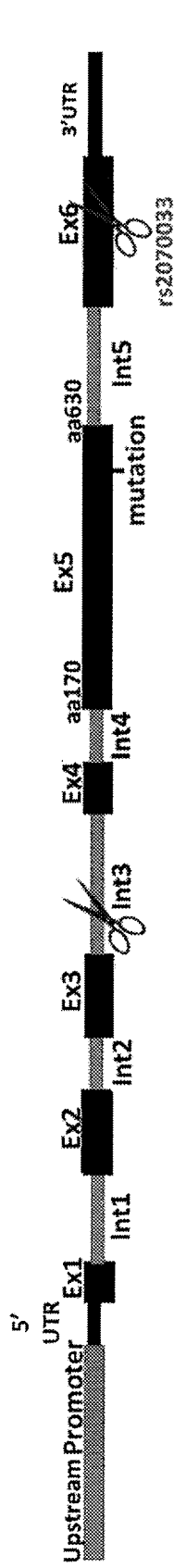
FIG. 5A: Utilization of two RNA molecules to remove exon 4, intron 4, exon, 5, and intron 5 of the FGA gene.
Figure 5B:
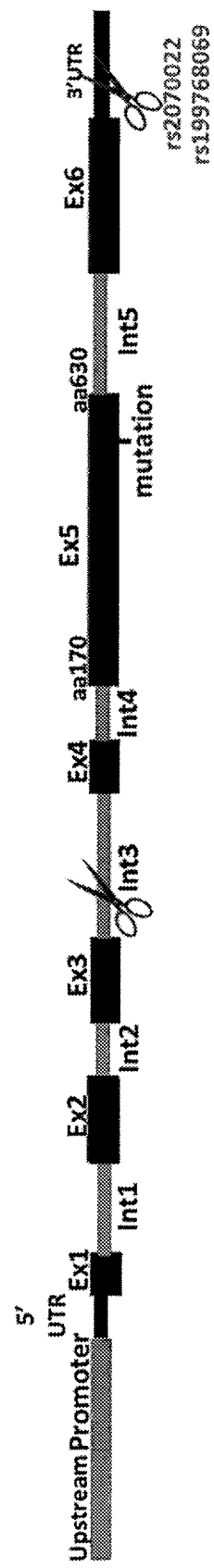
FIG. 5B: Utilization of two RNA molecules to remove exon 4, intron 4, exon 5, intron 5, and exon 6 of the FGA gene.

In some embodiments, a first RNA molecule targets a sequence located at intron 3 of the FGA gene and another RNA molecule targets a SNP sequence downstream of the gene. In further embodiments the other RNA molecule may target a SNP/WT sequence located at exon 6 downstream of an FGA mutation. In some embodiments the target SNP/WT sequence located at exon 6 downstream to the FGA mutation is one of SNP IDs rs2070033, rs19976806, or rs2070022. (FIG. 5A-FIG. 5B).

Figure 5C:
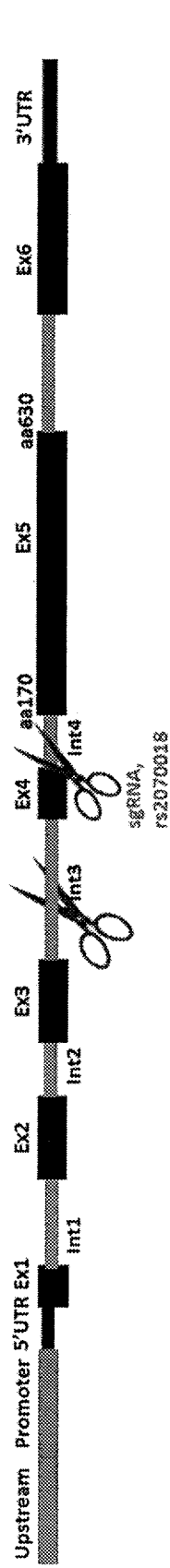
FIG. 5C: Utilization of two RNA molecules to remove exon 4 of the FGA gene.

In some embodiments, a first RNA molecule targets a SNP/WT sequence of SNP ID rs2070018 located at intron 4 upstream to an FGA mutation, including RNA sequences that target a SNP/WT sequence linked to the mutation, and another RNA molecule targets a sequence in intron 3 . . . (FIG. 5C).

Figure 6A:
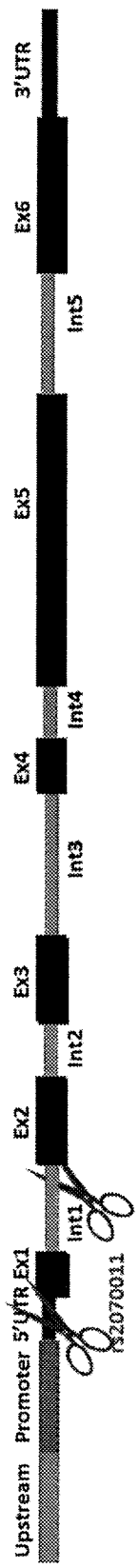
FIG. 6A: Utilization of two RNA molecules to remove exon 1 of the FGA gene.
Figure 6B:
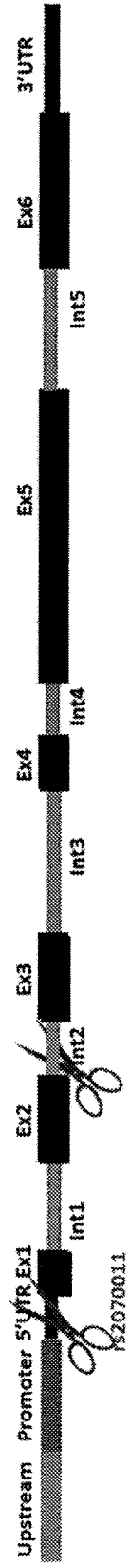
FIG. 6B: Utilization of two RNA molecules to remove exon 1 intron 1 and exon 2 of the FGA gene.

In some embodiments, a first RNA molecule targets a SNP/WT sequence linked to an FGA mutation in the 5'UTR region of the gene, and another RNA molecule targets a sequence in intron 1, a sequence in intron 2, or a SNP/WT sequence linked to the mutation in intron 2. (FIG. 6A-FIG. 6B).

In further embodiments the sequence linked to an FGA mutation in the 5'URT region of the gene is a sequence in intron 1, a sequence in intron 2, or a SNP/WT sequence linked to the mutation in intron2.

Figure 7:
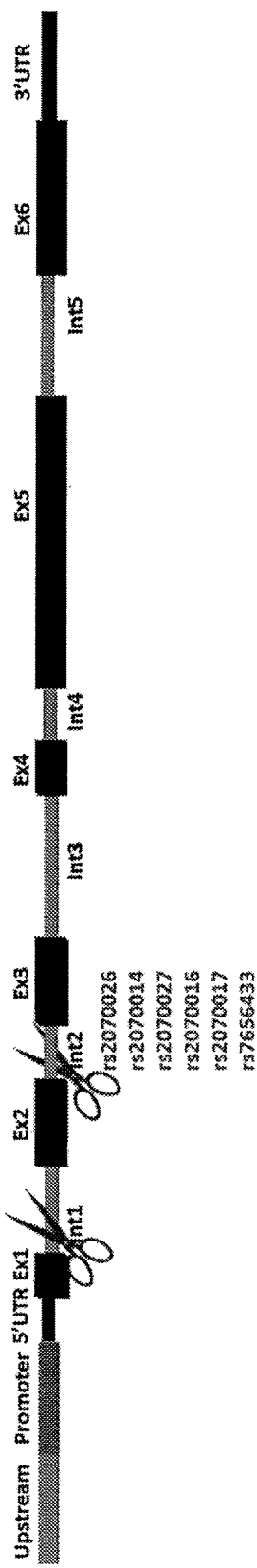
FIG. 7: Removing exon 2 of the FGA gene, which includes residues for binding distal domain of another fibrin gamma chain (this region is known as 'Knob A') and two residues (positions 47, 55) that have role in disulfide inter-chain bonding.

In some embodiments, a first RNA molecule targets a sequence in intron 1 of the FGA gene and another RNA molecule targets a SNP/WT sequence, linked to an FGA gene mutation, in intron 2 . . . (FIG. 7).

Figure 8:
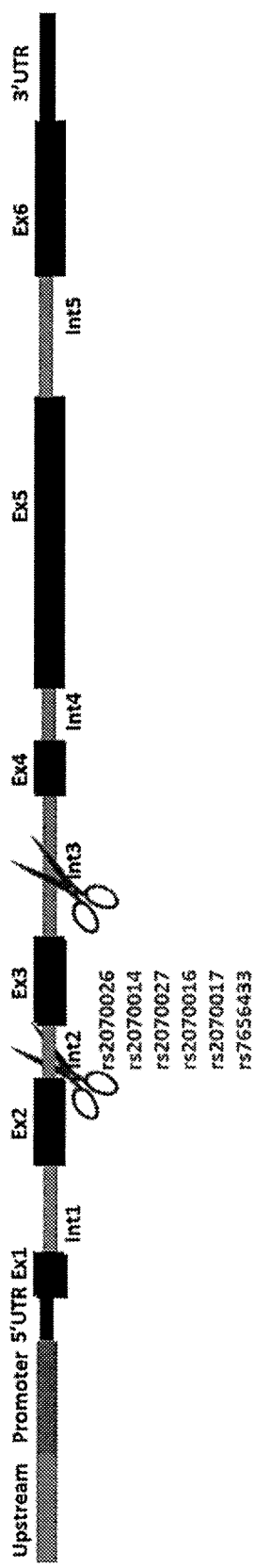
FIG. 8: Removing exon 3 of the FGA gene, which contains two residues with a role in disulfide inter-chain bonding (residues 64, 68).

In some embodiments, a first RNA molecule targets a SNP/WT sequence linked to an FGA gene mutation and another RNA molecule targets a sequence in intron 3. In some embodiments the first RNA molecule targets a SNP/WT sequence linked to an FGA gene mutation in intron 2. (FIG. 8).

Figure 9:
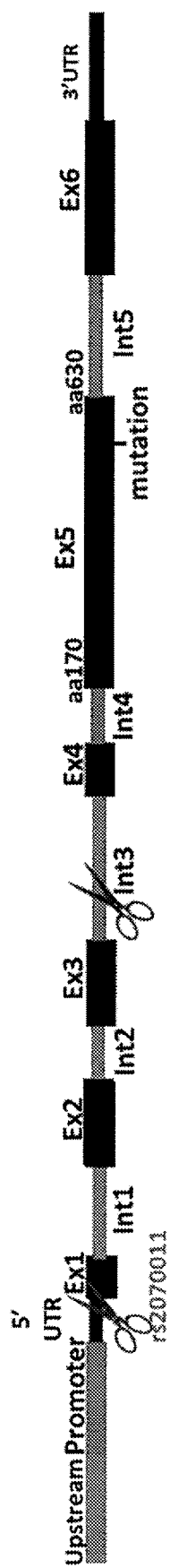
FIG. 9: Utilization of two RNA molecules to remove a portion of exon 1, which encodes the signal peptide, exon 2, which encodes residues that produce disulfide inter-chain bonds within the Fibrinogen hexamer, and exon 3, which encodes a portion of the coiled coil region essential for the assembly of fibrinogen in order to produce a fibrinogen alpha subunit which assembles to the Fibrinogen hexamer secreted from the cell.

In some embodiments, a first RNA molecule targets a sequence in intron 3 and another RNA molecule targets a SNP in exon 1. In some embodiments, the other RNA molecule targeting a SNP in exon 1 is rs2070011. (FIG. 9).

Delivery to Cells

The RNA molecule compositions described herein may be delivered to a target cell by any suitable means. RNA molecule compositions of the present invention may be targeted to any cell which contains and/or expresses a dominant negative allele, including any mammalian or plant cell. For example, in one embodiment the RNA molecule specifically targets a mutated FGA allele and the target cell is a hepatocyte cell.

In some embodiments, the RNA molecule comprises a chemical modification. Non-limiting examples of suitable chemical modifications include 2'-0-methyl (M), 2'-0-methyl, 3'phosphorothioate (MS) or 2'-0-methyl, 3'thio-PACE (MSP), pseudouridine, and 1-methyl pseudo-uridine. Each possibility represents a separate embodiment of the present invention.

Any suitable viral vector system may be used to deliver nucleic acid compositions e.g., the RNA molecule compositions of the subject invention. Conventional viral and non-viral based gene transfer methods can be used to introduce nucleic acids and target tissues. In certain embodiments, nucleic acids are administered for in vivo or ex vivo gene therapy uses. Non-viral vector delivery systems include naked nucleic acid, and nucleic acid complexed with a delivery vehicle such as a liposome or poloxamer. For a review of gene therapy procedures, see Anderson (1992) Science 256:808-813; Nabel & Felgner (1993) TIBTECH 11:211-217; Mitani & Caskey (1993) TIBTECH 11:162-166; Dillon (1993) TIBTECH 11:167-175; Miller (1992) Nature 357:455-460; Van Brunt (1988) Biotechnology 6(10):1149-1154; Vigne (1995) Restorative Neurology and Neuroscience 8:35-36; Kremer & Perricaudet (1995) British Medical Bulletin 51(1):31-44; Haddada et al. (1995) in Current Topics in Microbiology and Immunology Doerfler and Bohm (eds.); and Yu et al. (1994) Gene Therapy 1:13-26.

Methods of non-viral delivery of nucleic acids and/or proteins include electroporation, lipofection, microinjection, biolistics, particle gun acceleration, virosomes, liposomes, immunoliposomes, lipid nanoparticles (LNPs), polycation or lipid:nucleic acid conjugates, artificial virions, and agent-enhanced uptake of nucleic acids or can be delivered to plant cells by bacteria or viruses (e.g., *Agrobacterium, Rhizobium* sp. NGR234, Sinorhizoboiummeliloti, *Mesorhizobium loti*, tobacco mosaic virus, potato virus X, cauliflower mosaic virus and cassava vein mosaic virus). (See, e.g., Chung et al. (2006) Trends Plant Sci. 11(1):1-4). Sonoporation using, e.g., the Sonitron 2000 system (Rich-Mar), can also be used for delivery of nucleic acids. Cationic-lipid mediated delivery of proteins and/or nucleic acids is also contemplated as an in vivo or in vitro delivery method. (See Zuris et al. (2015) Nat. Biotechnol. 33(1):73-80; see also Coelho et al. (2013) N. Engl. J. Med. 369, 819-829; Judge et al. (2006) Mol. Ther. 13, 494-505; and Basha et al. (2011) Mol. Ther. 19, 2186-2200).

Additional exemplary nucleic acid delivery systems include those provided by Amaxa® Biosystems (Cologne, Germany), Maxcyte, Inc. (Rockville, Md.), BTX Molecular Delivery Systems (Holliston, Mass.) and Copernicus Therapeutics Inc., (see, e.g., U.S. Pat. No. 6,008,336). Lipofection is described in e.g., U.S. Pat. Nos. 5,049,386, 4,946,787; and 4,897,355, and lipofection reagents are sold commercially (e.g., Transfectam™, Lipofectin™ and Lipofectamine™ RNAiMAX). Cationic and neutral lipids that are suitable for efficient receptor-recognition lipofection of polynucleotides include those of Feigner, WO 91/17424, WO 91/16024. Delivery can be to cells (ex vivo administration) or target tissues (in vivo administration).

The preparation of lipid:nucleic acid complexes, including targeted liposomes such as immunolipid complexes, is well known to one of skill in the art (See, e.g., Crystal (1995) Science 270:404-410; Blaese et al. (1995) Cancer Gene Ther. 2:291-297; Behr et al. (1994) Bioconjugate Chem. 5:382-389; Remy et al. (1994) Bioconjugate Chem. 5:647-654; Gao et al. (1995) Gene Therapy 2:710-722; Ahmad et al. (1992) Cancer Res. 52:4817-4820; U.S. Pat. Nos. 4,186,183, 4,217,344, 4,235,871, 4,261,975, 4,485,054, 4,501,728, 4,774,085, 4,837,028, and 4,946,787).

Additional methods of delivery include the use of packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (See MacDiarmid et al (2009) Nature Biotechnology 27(7):643).

The use of RNA or DNA viral based systems for viral mediated delivery of nucleic acids take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of nucleic acids include, but are not limited to, retroviral, lentivirus, adenoviral, adeno-associated, vaccinia and herpes simplex virus vectors for gene transfer.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof (See, e.g., Buchschacher et al. (1992) J. Virol. 66:2731-2739; Johann et al. (1992) J. Virol. 66:1635-1640; Sommerfelt et al. (1990) Virol. 176:58-59; Wilson et al. (1989) J. Virol. 63:2374-2378; Miller et al. (1991) J. Virol. 65:2220-2224; PCT/US94/05700).

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al. (1995) Blood 85:3048-305; Kohn et al. (1995) Nat. Med. 1:1017-102; Malech et al. (1997) PNAS 94:22 12133-12138). PA317/pLASN was the first therapeutic vector used in a gene therapy trial. (Blaese et al. (1995). Transduction efficiencies of 50% or greater have been observed for MFG-S packaged vectors. (Ellem et al. (1997) Immunol Immunother. 44(1):10-20; Dranoff et al. (1997) Hum. Gene Ther. 1:111-2).

Packaging cells are used to form virus particles that are capable of infecting a host cell. Such cells include 293 cells, which package adenovirus, AAV, and Psi-2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV. Additionally, AAV can be produced at clinical scale using baculovirus systems (see U.S. Pat. No. 7,479,554).

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al. (1995) Proc. Natl. Acad. Sci. USA 92:9747-9751, reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Gene therapy vectors can be delivered in vivo by administration to an individual patient, typically by systemic administration (e.g., intravitreal, intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Ex vivo cell transfection for diagnostics, research, or for gene therapy (e.g., via re-infusion of the transfected cells into the host organism) is well known to those of skill in the art. In a preferred embodiment, cells are isolated from the subject organism, transfected with a nucleic acid composition, and re-infused back into the subject organism (e.g., patient). Various cell types suitable for ex vivo transfection are well known to those of skill in the art (See, e.g., Freshney et al. (1994) Culture of Animal Cells, A Manual of Basic Technique, 3rd ed, and the references cited therein for a discussion of how to isolate and culture cells from patients).

Suitable cells include, but are not limited to, eukaryotic cells and/or cell lines. Non-limiting examples of such cells or cell lines generated from such cells include COS, CHO (e.g., CHO-S, CHO-KI, CHO-DG44, CHO-DUXB11, CHO-DUKX, CHOK1SV), VERO, MDCK, W138, V79, B14AF28-G3, BHK, HaK, NSO, SP2/0-Ag14, HeLa, HEK293 (e.g., HEK293-F, HEK293-H, HEK293-T), perC6 cells, any plant cell (differentiated or undifferentiated), as well as insect cells such as Spodopterafugiperda (Sf), or fungal cells such as *Saccharomyces, Pichia* and *Schizosaccharomyces*. In certain embodiments, the cell line is a CHO-K, MDCK or HEK293 cell line. Additionally, primary cells may be isolated and used ex vivo for reintroduction into the subject to be treated following treatment with a guided nuclease system (e.g. CRISPR/Cas). Suitable primary cells include peripheral blood mononuclear cells (PBMC), and other blood cell subsets such as, but not limited to, CD4+ T cells or CD8+ T cells. Suitable cells also include stem cells such as, by way of example, embryonic stem cells, induced pluripotent stem cells, hematopoietic stem cells (CD34+), neuronal stem cells and mesenchymal stem cells.

In one embodiment, stem cells are used in ex vivo procedures for cell transfection and gene therapy. The advantage to using stem cells is that they can be differentiated into other cell types in vitro, or can be introduced into a mammal (such as the donor of the cells) where they will engraft in the bone marrow. Methods for differentiating CD34+ cells in vitro into clinically important immune cell types using cytokines such a GM-CSF, IFN-gamma, and TNF-alpha are known (as a non-limiting example see, Inaba et al., J. Exp. Med. 176:1693-1702 (1992)).

Stem cells are isolated for transduction and differentiation using known methods. For example, stem cells are isolated from bone marrow cells by panning the bone marrow cells with antibodies which bind unwanted cells, such as CD4+ and CD8+(T cells), CD45+(panB cells), GR-1 (granulocytes), and Iad (differentiated antigen presenting cells) (as a non-limiting example see Inaba et al. (1992) J. Exp. Med. 176:1693-1702). Stem cells that have been modified may also be used in some embodiments.

Any one of the RNA molecule compositions described herein is suitable for genome editing in post-mitotic cells or any cell which is not actively dividing, e.g., arrested cells. Examples of post-mitotic cells which may be edited using an RNA molecule composition of the present invention include, but are not limited to, a hepatocyte cell.

Vectors (e.g., retroviruses, liposomes, etc.) containing therapeutic nucleic acid compositions can also be administered directly to an organism for transduction of cells in vivo. Administration is by any of the routes normally used for introducing a molecule into ultimate contact with blood or tissue cells including, but not limited to, injection, infusion, topical application (e.g., eye drops and cream) and electroporation. Suitable methods of administering such nucleic acids are available and well known to those of skill in the art, and, although more than one route can be used to administer a particular composition, a particular route can often provide a more immediate and more effective reaction than another route. According to some embodiments, the composition is delivered via IV injection.

Vectors suitable for introduction of transgenes into immune cells (e.g., T-cells) include non-integrating lentivirus vectors. See, e.g., U.S. Patent Publication No. 2009-0117617.

Pharmaceutically acceptable carriers are determined in part by the particular composition being administered, as well as by the particular method used to administer the composition. Accordingly, there is a wide variety of suitable formulations of pharmaceutical compositions available, as described below (See, e.g., Remington's Pharmaceutical Sciences, 17th ed., 1989).

In accordance with some embodiments, there is provided an RNA molecule which binds to/associates with and/or directs the RNA guided DNA nuclease to a sequence comprising at least one nucleotide which differs between a mutated allele and a functional allele (e.g., SNP) of a gene of interest (i.e., a sequence of the mutated allele which is not present in the functional allele). The sequence may be within the disease associated mutation. The sequence may be upstream or downstream to the disease associated mutation. Any sequence difference between the mutated allele and the functional allele may be targeted by an RNA molecule of the present invention to inactivate the mutant allele, or otherwise disable its dominant disease-causing effects, while preserving the activity of the functional allele.

The disclosed compositions and methods may also be used in the manufacture of a medicament for treating dominant genetic disorders in a patient.

Mechanisms of Action for Several Embodiments Disclosed Herein

The FGA gene encodes the fibrinogen alpha subunit of the coagulation factor fibrinogen, which is a component of blood clots produced by the liver. Fibrinogen is produced from three homologous polypeptide chains, α, β and γ, which assemble to form a 340 kDa hexameric structure (αβγ)2 held together by 29 disulfide bonds. In the endoplasmic reticulum (ER), the signal peptide from each of the three chains (19 amino acids for α, 30 for β and 26 for γ) is co-translationally removed and later in the secretory pathway the last 15 residues of α are removed by a furin-like protease. Assembly of two copies of each of the three chains results in the formation of a symmetrical hexamer, with a central E domain connected by three-stranded coiled-coils to two peripheral D domains. The D domains consist of the globular C-termini of the β and γ chains and of a portion of the coiled-coils. Once the soluble hexamer has reached the circulation, fibrin is produced by proteolytic cleavage of the fibrinogen alpha and beta chains by thrombin, thus releasing fibrinopeptides A and B and allowing polymerization to occur.

FGA encodes for two alternative isoforms a short isoform which contains 5 exons—NM_021871 645aa and a long isoform which contains 6 exons—NM_000508 868aa. A missense mutation in exon 5 of the FGA gene (Gu545Val) leads to misfolding of fibrinogen and the deposition of mutant FGA amyloid, primarily in kidneys which is associated with Fibrinogen amyloidosis (AFib).

Without being bound by any theory or mechanism, the instant invention may be utilized to apply a CRISPR nuclease to process the mutated pathogenic FGA allele and not the functional FGA allele, such as to prevent expression of the mutated pathogenic allele or to produce a truncated non-pathogenic peptide from the mutated pathogenic allele, in order to prevent Fibrinogen amyloidosis (AFib).

In some embodiments, particularly those targeting exon 1 of the FGA gene, the resultant peptide will lack a portion of the coiled coil domain essential for assembly and the signal peptide essential for secretion.

Outcomes of the embodiments disclosed herein may be examined to identify whether the mutated allele is expressed. In case the mutated allele is expressed, its effect on cells, such as induced stress/toxicity, may be examined by the creation of amyloid fibrils. Further its ability to assemble peptides into fibrinogen hexamers, and thereby secrete fibrils from cells, may be assessed, inter alia, by the presence of fibrinogen aggregates and amyloid fibrils outside the cells. In addition, residual activity of a resultant truncated alpha subunit and/or fibrinogen, including the truncated alpha subunit, may be assessed.

Examples of RNA Guide Sequences which Specifically Target Mutated Alleles of FGA Gene Although a large number of guide sequences can be designed to target a mutated allele, the nucleotide sequences described in Tables 2 identified by SEQ ID NOs: 1-1984 below were specifically selected to effectively implement the methods set forth herein and to effectively discriminate between alleles.

Referring to columns 1-4, each of SEQ ID NOs. 1-1984 indicated in column 1 corresponds to an engineered guide sequence. The corresponding SNP details are indicated in column 2. The SNP details indicated in the 2nd column include the assigned identifier for each SNP corresponding to a SNP ID indicated in Table 1. Column 3 indicates whether the target of each guide sequence is the FGA gene polymorph or wild type sequence. Column 4 indicates the guanine-cytosine content of each guide sequence.

Table 2 shows guide sequences designed for use as described in the embodiments above to associate with different SNPs within a sequence of a mutated FGA allele. Each engineered guide molecule is further designed such as to associate with a target genomic DNA sequence of interest that lies next to a protospacer adjacent motif (PAM), e.g., a PAM matching the sequence NGG or NAG, where "N" is any nucleobase. The guide sequences were designed to work in conjunction with one or more different CRISPR nucleases, including, but not limited to, e.g. SpCas9WT (PAM SEQ: NGG), SpCas9.VQR.1 (PAM SEQ: NGAN), SpCas9.VQR.2 (PAM SEQ: NGNG), SpCas9.EQR (PAM SEQ: NGAG), SpCas9.VRER (PAM SEQ: NGCG), SaCas9WT (PAM SEQ: NNGRRT), NmCas9WT (PAM SEQ: NNNNGATT), Cpf1 (PAM SEQ: TTTV), or JeCas9WT (PAM SEQ: NNNVRYM). RNA molecules of the present invention are each designed to form complexes in conjunction with one or more different CRISPR nucleases and designed to target polynucleotide sequences of interest utilizing one or more different PAM sequences respective to the CRISPR nuclease utilized.

TABLE 2

Guide sequences designed to associate with specific SNPs of the FGA gene

| SEQ ID NO: | SNP ID (Table 1) | Target (SNP/WT) | % GC |
|---|---|---|---|
| 1 | s1 | BOTH | 0.35 |
| 2 | s1 | BOTH | 0.45 |
| 3 | s1 | BOTH | 0.45 |
| 4 | s1 | BOTH | 0.45 |
| 5 | s2 | BOTH | 0.5 |

TABLE 2-continued

Guide sequences designed to associate with specific SNPs of the FGA gene

| SEQ ID NO: | SNP ID (Table 1) | Target (SNP/WT) | % GC |
|---|---|---|---|
| 6 | s2 | BOTH | 0.5 |
| 7 | s2 | BOTH | 0.45 |
| 8 | s5 | BOTH | 0.35 |
| 9 | s3 | BOTH | 0.25 |
| 10 | s5 | BOTH | 0.3 |
| 11 | s3 | BOTH | 0.25 |
| 12 | s3 | BOTH | 0.25 |
| 13 | s6 | BOTH | 0.3 |
| 14 | s7 | BOTH | 0.55 |
| 15 | s7 | BOTH | 0.45 |
| 16 | s7 | BOTH | 0.45 |
| 17 | s7 | BOTH | 0.6 |
| 18 | s8 | BOTH | 0.4 |
| 19 | s8 | BOTH | 0.45 |
| 20 | s8 | BOTH | 0.45 |
| 21 | s8 | BOTH | 0.45 |
| 22 | s8 | BOTH | 0.45 |
| 23 | s8 | BOTH | 0.45 |
| 24 | s8 | BOTH | 0.45 |
| 25 | s8 | BOTH | 0.4 |
| 26 | s8 | BOTH | 0.45 |
| 27 | s8 | BOTH | 0.4 |
| 28 | s8 | BOTH | 0.45 |
| 29 | s8 | BOTH | 0.4 |
| 30 | s8 | BOTH | 0.4 |
| 31 | s9 | BOTH | 0.4 |
| 32 | s9 | BOTH | 0.5 |
| 33 | s9 | BOTH | 0.45 |
| 34 | s10 | BOTH | 0.45 |
| 35 | s10 | BOTH | 0.5 |
| 36 | s10 | BOTH | 0.7 |
| 37 | s11 | BOTH | 0.5 |
| 38 | s11 | BOTH | 0.45 |
| 39 | s11 | BOTH | 0.45 |
| 40 | s12 | BOTH | 0.45 |
| 41 | s13 | BOTH | 0.65 |
| 42 | s14 | BOTH | 0.55 |
| 43 | s15 | BOTH | 0.25 |
| 44 | s16 | BOTH | 0.3 |
| 45 | s16 | BOTH | 0.35 |
| 46 | s16 | BOTH | 0.35 |
| 47 | s17 | BOTH | 0.3 |
| 48 | s17 | BOTH | 0.3 |
| 49 | s17 | BOTH | 0.25 |
| 50 | s18 | BOTH | 0.5 |
| 51 | s19 | BOTH | 0.45 |
| 52 | s19 | BOTH | 0.55 |
| 53 | s19 | BOTH | 0.5 |
| 54 | s20 | BOTH | 0.5 |
| 55 | s20 | BOTH | 0.5 |
| 56 | s21 | BOTH | 0.55 |
| 57 | s21 | BOTH | 0.5 |
| 58 | s21 | BOTH | 0.55 |
| 59 | s22 | BOTH | 0.4 |
| 60 | s22 | BOTH | 0.45 |
| 61 | s22 | BOTH | 0.4 |
| 62 | s23 | BOTH | 0.45 |
| 63 | s23 | BOTH | 0.4 |
| 64 | s19 | WT | 0.55 |
| 65 | s19 | SNP | 0.55 |
| 66 | s19 | WT | 0.6 |
| 67 | s19 | SNP | 0.6 |
| 68 | s19 | SNP | 0.6 |
| 69 | s19 | WT | 0.6 |
| 70 | s19 | WT | 0.55 |
| 71 | s19 | SNP | 0.6 |
| 72 | s19 | WT | 0.6 |
| 73 | s19 | WT | 0.5 |
| 74 | s19 | SNP | 0.5 |
| 75 | s19 | SNP | 0.55 |
| 76 | s19 | WT | 0.55 |
| 77 | s19 | SNP | 0.55 |
| 78 | s19 | WT | 0.45 |
| 79 | s19 | SNP | 0.45 |
| 80 | s19 | WT | 0.45 |
| 81 | s19 | SNP | 0.45 |
| 82 | s5 | SNP | 0.35 |
| 83 | s5 | SNP | 0.3 |
| 84 | s5 | WT | 0.35 |
| 85 | s3 | WT | 0.25 |
| 86 | s3 | SNP | 0.25 |
| 87 | s5 | WT | 0.4 |
| 88 | s3 | SNP | 0.25 |
| 89 | s3 | WT | 0.25 |
| 90 | s4 | SNP | 0.2 |
| 91 | s4 | WT | 0.25 |
| 92 | s5 | SNP | 0.3 |
| 93 | s5 | WT | 0.35 |
| 94 | s4 | WT | 0.25 |
| 95 | s4 | SNP | 0.2 |
| 96 | s4 | SNP | 0.2 |
| 97 | s4 | WT | 0.25 |
| 98 | s4 | WT | 0.25 |
| 99 | s4 | SNP | 0.2 |
| 100 | s4 | WT | 0.25 |
| 101 | s4 | SNP | 0.2 |
| 102 | s4 | SNP | 0.2 |
| 103 | s4 | WT | 0.25 |
| 104 | s5 | SNP | 0.3 |
| 105 | s5 | WT | 0.35 |
| 106 | s4 | SNP | 0.2 |
| 107 | s4 | WT | 0.25 |
| 108 | s6 | SNP | 0.3 |
| 109 | s6 | WT | 0.25 |
| 110 | s6 | SNP | 0.3 |
| 111 | s6 | SNP | 0.35 |
| 112 | s6 | WT | 0.3 |
| 113 | s6 | SNP | 0.25 |
| 114 | s6 | WT | 0.2 |
| 115 | s6 | WT | 0.25 |
| 116 | s7 | WT | 0.4 |
| 117 | s7 | WT | 0.45 |
| 118 | s7 | SNP | 0.5 |
| 119 | s7 | SNP | 0.6 |
| 120 | s7 | WT | 0.55 |
| 121 | s7 | SNP | 0.45 |
| 122 | s13 | WT | 0.5 |
| 123 | s13 | SNP | 0.55 |
| 124 | s13 | WT | 0.55 |
| 125 | s13 | SNP | 0.6 |
| 126 | s13 | WT | 0.5 |
| 127 | s13 | SNP | 0.55 |
| 128 | s13 | SNP | 0.5 |
| 129 | s13 | WT | 0.45 |
| 130 | s13 | SNP | 0.6 |
| 131 | s13 | WT | 0.55 |
| 132 | s13 | WT | 0.55 |
| 133 | s13 | SNP | 0.6 |
| 134 | s13 | WT | 0.55 |
| 135 | s13 | SNP | 0.6 |
| 136 | s13 | WT | 0.5 |
| 137 | s13 | SNP | 0.55 |
| 138 | s13 | WT | 0.5 |
| 139 | s13 | SNP | 0.55 |
| 140 | s13 | SNP | 0.55 |
| 141 | s13 | WT | 0.5 |
| 142 | s14 | WT | 0.6 |
| 143 | s14 | SNP | 0.55 |
| 144 | s14 | WT | 0.5 |
| 145 | s14 | SNP | 0.45 |
| 146 | s14 | SNP | 0.6 |
| 147 | s14 | WT | 0.65 |
| 148 | s14 | SNP | 0.55 |
| 149 | s14 | WT | 0.6 |
| 150 | s14 | WT | 0.6 |
| 151 | s14 | WT | 0.6 |

TABLE 2-continued

Guide sequences designed to associate with specific SNPs of the FGA gene

| SEQ ID NO: | SNP ID (Table 1) | Target (SNP/WT) | % GC |
|---|---|---|---|
| 152 | s14 | SNP | 0.55 |
| 153 | s14 | SNP | 0.55 |
| 154 | s14 | SNP | 0.55 |
| 155 | s14 | WT | 0.6 |
| 156 | s14 | SNP | 0.5 |
| 157 | s14 | WT | 0.55 |
| 158 | s14 | WT | 0.55 |
| 159 | s14 | SNP | 0.5 |
| 160 | s15 | SNP | 0.2 |
| 161 | s15 | WT | 0.25 |
| 162 | s15 | WT | 0.25 |
| 163 | s15 | SNP | 0.2 |
| 164 | s15 | SNP | 0.25 |
| 165 | s15 | WT | 0.3 |
| 166 | s15 | WT | 0.2 |
| 167 | s15 | WT | 0.25 |
| 168 | s15 | SNP | 0.2 |
| 169 | s16 | WT | 0.5 |
| 170 | s16 | SNP | 0.45 |
| 171 | s16 | SNP | 0.35 |
| 172 | s16 | WT | 0.4 |
| 173 | s16 | SNP | 0.4 |
| 174 | s16 | WT | 0.45 |
| 175 | s16 | WT | 0.5 |
| 176 | s16 | SNP | 0.45 |
| 177 | s16 | SNP | 0.4 |
| 178 | s16 | WT | 0.45 |
| 179 | s16 | SNP | 0.4 |
| 180 | s16 | WT | 0.45 |
| 181 | s16 | SNP | 0.3 |
| 182 | s16 | WT | 0.35 |
| 183 | s16 | WT | 0.4 |
| 184 | s16 | SNP | 0.35 |
| 185 | s17 | WT | 0.35 |
| 186 | s17 | SNP | 0.3 |
| 187 | s17 | WT | 0.35 |
| 188 | s17 | SNP | 0.3 |
| 189 | s17 | SNP | 0.3 |
| 190 | s17 | WT | 0.35 |
| 191 | s17 | WT | 0.5 |
| 192 | s17 | SNP | 0.45 |
| 193 | s17 | SNP | 0.3 |
| 194 | s17 | WT | 0.35 |
| 195 | s18 | WT | 0.4 |
| 196 | s18 | SNP | 0.4 |
| 197 | s18 | WT | 0.35 |
| 198 | s18 | SNP | 0.4 |
| 199 | s18 | WT | 0.35 |
| 200 | s18 | SNP | 0.45 |
| 201 | s18 | SNP | 0.45 |
| 202 | s18 | WT | 0.4 |
| 203 | s18 | SNP | 0.45 |
| 204 | s18 | WT | 0.4 |
| 205 | s18 | WT | 0.4 |
| 206 | s18 | SNP | 0.45 |
| 207 | s18 | WT | 0.35 |
| 208 | s18 | SNP | 0.4 |
| 209 | s18 | WT | 0.35 |
| 210 | s18 | SNP | 0.4 |
| 211 | s18 | WT | 0.4 |
| 212 | s18 | SNP | 0.45 |
| 213 | s18 | SNP | 0.45 |
| 214 | s18 | WT | 0.4 |
| 215 | s18 | WT | 0.4 |
| 216 | s18 | SNP | 0.45 |
| 217 | s20 | SNP | 0.45 |
| 218 | s20 | SNP | 0.35 |
| 219 | s20 | WT | 0.4 |
| 220 | s20 | WT | 0.4 |
| 221 | s20 | SNP | 0.35 |
| 222 | s20 | WT | 0.4 |
| 223 | s20 | SNP | 0.35 |
| 224 | s20 | SNP | 0.4 |
| 225 | s20 | WT | 0.45 |
| 226 | s20 | WT | 0.45 |
| 227 | s20 | WT | 0.5 |
| 228 | s20 | WT | 0.5 |
| 229 | s20 | SNP | 0.45 |
| 230 | s20 | WT | 0.45 |
| 231 | s20 | SNP | 0.4 |
| 232 | s20 | WT | 0.4 |
| 233 | s20 | SNP | 0.35 |
| 234 | s20 | SNP | 0.35 |
| 235 | s20 | WT | 0.4 |
| 236 | s20 | SNP | 0.4 |
| 237 | s20 | WT | 0.45 |
| 238 | s20 | WT | 0.45 |
| 239 | s20 | WT | 0.4 |
| 240 | s20 | SNP | 0.35 |
| 241 | s20 | WT | 0.4 |
| 242 | s20 | SNP | 0.35 |
| 243 | s20 | SNP | 0.35 |
| 244 | s20 | WT | 0.4 |
| 245 | s20 | SNP | 0.4 |
| 246 | s20 | SNP | 0.35 |
| 247 | s20 | WT | 0.4 |
| 248 | s20 | WT | 0.4 |
| 249 | s20 | SNP | 0.4 |
| 250 | s20 | SNP | 0.35 |
| 251 | s20 | WT | 0.4 |
| 252 | s1 | WT | 0.45 |
| 253 | s1 | SNP | 0.45 |
| 254 | s1 | WT | 0.5 |
| 255 | s1 | SNP | 0.4 |
| 256 | s1 | WT | 0.45 |
| 257 | s1 | SNP | 0.4 |
| 258 | s1 | WT | 0.45 |
| 259 | s1 | SNP | 0.4 |
| 260 | s1 | WT | 0.45 |
| 261 | s1 | SNP | 0.4 |
| 262 | s1 | WT | 0.45 |
| 263 | s1 | SNP | 0.4 |
| 264 | s1 | WT | 0.45 |
| 265 | s1 | SNP | 0.35 |
| 266 | s1 | WT | 0.4 |
| 267 | s1 | SNP | 0.4 |
| 268 | s1 | WT | 0.45 |
| 269 | s1 | SNP | 0.4 |
| 270 | s2 | SNP | 0.35 |
| 271 | s2 | WT | 0.4 |
| 272 | s2 | SNP | 0.45 |
| 273 | s2 | WT | 0.5 |
| 274 | s2 | SNP | 0.4 |
| 275 | s2 | WT | 0.45 |
| 276 | s2 | SNP | 0.4 |
| 277 | s2 | WT | 0.45 |
| 278 | s2 | WT | 0.45 |
| 279 | s2 | SNP | 0.4 |
| 280 | s2 | WT | 0.6 |
| 281 | s2 | SNP | 0.55 |
| 282 | s2 | WT | 0.5 |
| 283 | s2 | SNP | 0.45 |
| 284 | s2 | WT | 0.45 |
| 285 | s2 | SNP | 0.4 |
| 286 | s2 | WT | 0.55 |
| 287 | s2 | SNP | 0.5 |
| 288 | s2 | WT | 0.5 |
| 289 | s9 | SNP | 0.45 |
| 290 | s9 | WT | 0.5 |
| 291 | s9 | WT | 0.55 |
| 292 | s9 | SNP | 0.5 |
| 293 | s9 | SNP | 0.45 |
| 294 | s9 | WT | 0.5 |
| 295 | s9 | WT | 0.55 |
| 296 | s9 | SNP | 0.5 |
| 297 | s9 | WT | 0.5 |

TABLE 2-continued

Guide sequences designed to associate with specific SNPs of the FGA gene

| SEQ ID NO: | SNP ID (Table 1) | Target (SNP/WT) | % GC |
|---|---|---|---|
| 298 | s9 | SNP | 0.45 |
| 299 | s9 | WT | 0.5 |
| 300 | s9 | SNP | 0.45 |
| 301 | s9 | WT | 0.45 |
| 302 | s9 | SNP | 0.45 |
| 303 | s9 | SNP | 0.4 |
| 304 | s10 | SNP | 0.5 |
| 305 | s10 | WT | 0.55 |
| 306 | s10 | SNP | 0.55 |
| 307 | s10 | WT | 0.6 |
| 308 | s10 | WT | 0.55 |
| 309 | s10 | SNP | 0.5 |
| 310 | s11 | WT | 0.4 |
| 311 | s11 | SNP | 0.35 |
| 312 | s11 | SNP | 0.3 |
| 313 | s11 | WT | 0.35 |
| 314 | s11 | WT | 0.35 |
| 315 | s11 | SNP | 0.3 |
| 316 | s11 | WT | 0.35 |
| 317 | s11 | SNP | 0.3 |
| 318 | s11 | WT | 0.4 |
| 319 | s11 | SNP | 0.35 |
| 320 | s11 | WT | 0.5 |
| 321 | s11 | WT | 0.4 |
| 322 | s11 | SNP | 0.35 |
| 323 | s11 | SNP | 0.3 |
| 324 | s11 | WT | 0.35 |
| 325 | s11 | WT | 0.45 |
| 326 | s11 | SNP | 0.4 |
| 327 | s11 | WT | 0.5 |
| 328 | s11 | SNP | 0.45 |
| 329 | s11 | SNP | 0.45 |
| 330 | s12 | SNP | 0.5 |
| 331 | s12 | WT | 0.45 |
| 332 | s12 | SNP | 0.5 |
| 333 | s12 | SNP | 0.5 |
| 334 | s12 | WT | 0.45 |
| 335 | s12 | WT | 0.5 |
| 336 | s12 | WT | 0.4 |
| 337 | s12 | SNP | 0.45 |
| 338 | s12 | WT | 0.45 |
| 339 | s12 | SNP | 0.55 |
| 340 | s21 | WT | 0.7 |
| 341 | s21 | SNP | 0.65 |
| 342 | s21 | WT | 0.6 |
| 343 | s21 | SNP | 0.6 |
| 344 | s21 | WT | 0.65 |
| 345 | s21 | SNP | 0.55 |
| 346 | s21 | WT | 0.6 |
| 347 | s21 | WT | 0.6 |
| 348 | s21 | SNP | 0.55 |
| 349 | s21 | SNP | 0.55 |
| 350 | s21 | WT | 0.6 |
| 351 | s21 | SNP | 0.65 |
| 352 | s21 | WT | 0.7 |
| 353 | s21 | SNP | 0.55 |
| 354 | s21 | SNP | 0.55 |
| 355 | s21 | WT | 0.6 |
| 356 | s21 | WT | 0.6 |
| 357 | s21 | SNP | 0.65 |
| 358 | s21 | WT | 0.7 |
| 359 | s21 | WT | 0.7 |
| 360 | s21 | SNP | 0.65 |
| 361 | s21 | WT | 0.6 |
| 362 | s21 | SNP | 0.55 |
| 363 | s21 | SNP | 0.55 |
| 364 | s21 | SNP | 0.55 |
| 365 | s21 | SNP | 0.5 |
| 366 | s21 | SNP | 0.6 |
| 367 | s21 | WT | 0.65 |
| 368 | s22 | WT | 0.4 |
| 369 | s22 | SNP | 0.35 |
| 370 | s22 | WT | 0.45 |
| 371 | s22 | SNP | 0.4 |
| 372 | s22 | WT | 0.45 |
| 373 | s22 | SNP | 0.4 |
| 374 | s22 | WT | 0.45 |
| 375 | s22 | SNP | 0.3 |
| 376 | s22 | WT | 0.35 |
| 377 | s22 | SNP | 0.4 |
| 378 | s22 | SNP | 0.4 |
| 379 | s22 | WT | 0.45 |
| 380 | s22 | SNP | 0.3 |
| 381 | s22 | WT | 0.35 |
| 382 | s22 | SNP | 0.4 |
| 383 | s22 | WT | 0.45 |
| 384 | s22 | SNP | 0.3 |
| 385 | s22 | WT | 0.35 |
| 386 | s23 | SNP | 0.4 |
| 387 | s23 | SNP | 0.4 |
| 388 | s23 | WT | 0.4 |
| 389 | s23 | WT | 0.4 |
| 390 | s23 | SNP | 0.35 |
| 391 | s23 | WT | 0.35 |
| 392 | s23 | SNP | 0.4 |
| 393 | s23 | WT | 0.4 |
| 394 | s23 | WT | 0.4 |
| 395 | s23 | SNP | 0.4 |
| 396 | s23 | SNP | 0.5 |
| 397 | s23 | WT | 0.5 |
| 398 | s23 | WT | 0.5 |
| 399 | s23 | SNP | 0.5 |
| 400 | s23 | SNP | 0.45 |
| 401 | s23 | SNP | 0.4 |
| 402 | s23 | WT | 0.4 |
| 403 | s23 | WT | 0.45 |
| 404 | s23 | SNP | 0.4 |
| 405 | s23 | WT | 0.4 |
| 406 | s23 | SNP | 0.4 |
| 407 | s23 | WT | 0.4 |
| 408 | s23 | WT | 0.4 |
| 409 | s23 | SNP | 0.4 |
| 410 | s1 | BOTH | 0.45 |
| 411 | s1 | BOTH | 0.4 |
| 412 | s1 | BOTH | 0.45 |
| 413 | s1 | BOTH | 0.4 |
| 414 | s2 | BOTH | 0.4 |
| 415 | s2 | BOTH | 0.4 |
| 416 | s2 | BOTH | 0.45 |
| 417 | s2 | BOTH | 0.5 |
| 418 | s2 | BOTH | 0.4 |
| 419 | s3 | BOTH | 0.3 |
| 420 | s4 | BOTH | 0.25 |
| 421 | s5 | BOTH | 0.3 |
| 422 | s5 | BOTH | 0.4 |
| 423 | s4 | BOTH | 0.25 |
| 424 | s3 | BOTH | 0.25 |
| 425 | s4 | BOTH | 0.15 |
| 426 | s5 | BOTH | 0.4 |
| 427 | s3 | BOTH | 0.3 |
| 428 | s5 | BOTH | 0.45 |
| 429 | s4 | BOTH | 0.3 |
| 430 | s5 | BOTH | 0.45 |
| 431 | s4 | BOTH | 0.3 |
| 432 | s5 | BOTH | 0.35 |
| 433 | s3 | BOTH | 0.25 |
| 434 | s4 | BOTH | 0.15 |
| 435 | s4 | BOTH | 0.15 |
| 436 | s4 | BOTH | 0.15 |
| 437 | s3 | BOTH | 0.25 |
| 438 | s6 | BOTH | 0.25 |
| 439 | s6 | BOTH | 0.35 |
| 440 | s6 | BOTH | 0.3 |
| 441 | s6 | BOTH | 0.3 |
| 442 | s6 | BOTH | 0.35 |
| 443 | s6 | BOTH | 0.35 |

TABLE 2-continued

Guide sequences designed to associate with specific SNPs of the FGA gene

| SEQ ID NO: | SNP ID (Table 1) | Target (SNP/WT) | % GC |
|---|---|---|---|
| 444 | s6 | BOTH | 0.3 |
| 445 | s7 | BOTH | 0.45 |
| 446 | s7 | BOTH | 0.45 |
| 447 | s7 | BOTH | 0.5 |
| 448 | s7 | BOTH | 0.4 |
| 449 | s8 | BOTH | 0.5 |
| 450 | s8 | BOTH | 0.5 |
| 451 | s8 | BOTH | 0.5 |
| 452 | s8 | BOTH | 0.4 |
| 453 | s8 | BOTH | 0.5 |
| 454 | s8 | BOTH | 0.45 |
| 455 | s8 | BOTH | 0.5 |
| 456 | s8 | BOTH | 0.5 |
| 457 | s8 | BOTH | 0.4 |
| 458 | s8 | BOTH | 0.45 |
| 459 | s8 | BOTH | 0.45 |
| 460 | s8 | BOTH | 0.45 |
| 461 | s8 | BOTH | 0.45 |
| 462 | s8 | BOTH | 0.4 |
| 463 | s8 | BOTH | 0.4 |
| 464 | s8 | BOTH | 0.5 |
| 465 | s8 | BOTH | 0.5 |
| 466 | s8 | BOTH | 0.5 |
| 467 | s8 | BOTH | 0.45 |
| 468 | s8 | BOTH | 0.55 |
| 469 | s8 | BOTH | 0.5 |
| 470 | s8 | BOTH | 0.6 |
| 471 | s8 | BOTH | 0.5 |
| 472 | s8 | BOTH | 0.45 |
| 473 | s8 | BOTH | 0.4 |
| 474 | s8 | BOTH | 0.4 |
| 475 | s8 | BOTH | 0.45 |
| 476 | s8 | BOTH | 0.4 |
| 477 | s8 | BOTH | 0.4 |
| 478 | s8 | BOTH | 0.5 |
| 479 | s8 | BOTH | 0.45 |
| 480 | s8 | BOTH | 0.4 |
| 481 | s8 | BOTH | 0.45 |
| 482 | s8 | BOTH | 0.45 |
| 483 | s8 | BOTH | 0.4 |
| 484 | s9 | BOTH | 0.45 |
| 485 | s9 | BOTH | 0.45 |
| 486 | s9 | BOTH | 0.45 |
| 487 | s9 | BOTH | 0.4 |
| 488 | s9 | BOTH | 0.45 |
| 489 | s10 | BOTH | 0.5 |
| 490 | s10 | BOTH | 0.45 |
| 491 | s10 | BOTH | 0.65 |
| 492 | s10 | BOTH | 0.65 |
| 493 | s10 | BOTH | 0.75 |
| 494 | s11 | BOTH | 0.25 |
| 495 | s11 | BOTH | 0.5 |
| 496 | s11 | BOTH | 0.25 |
| 497 | s11 | BOTH | 0.3 |
| 498 | s11 | BOTH | 0.25 |
| 499 | s12 | BOTH | 0.45 |
| 500 | s12 | BOTH | 0.5 |
| 501 | s12 | BOTH | 0.5 |
| 502 | s12 | BOTH | 0.5 |
| 503 | s12 | BOTH | 0.5 |
| 504 | s12 | BOTH | 0.5 |
| 505 | s12 | BOTH | 0.45 |
| 506 | s13 | BOTH | 0.6 |
| 507 | s13 | BOTH | 0.6 |
| 508 | s13 | BOTH | 0.6 |
| 509 | s13 | BOTH | 0.6 |
| 510 | s13 | BOTH | 0.65 |
| 511 | s13 | BOTH | 0.55 |
| 512 | s13 | BOTH | 0.6 |
| 513 | s14 | BOTH | 0.5 |
| 514 | s14 | BOTH | 0.55 |
| 515 | s14 | BOTH | 0.45 |
| 516 | s14 | BOTH | 0.55 |
| 517 | s14 | BOTH | 0.5 |
| 518 | s14 | BOTH | 0.5 |
| 519 | s14 | BOTH | 0.45 |
| 520 | s15 | BOTH | 0.25 |
| 521 | s15 | BOTH | 0.3 |
| 522 | s15 | BOTH | 0.3 |
| 523 | s15 | BOTH | 0.25 |
| 524 | s15 | BOTH | 0.3 |
| 525 | s15 | BOTH | 0.25 |
| 526 | s15 | BOTH | 0.25 |
| 527 | s16 | BOTH | 0.4 |
| 528 | s16 | BOTH | 0.45 |
| 529 | s16 | BOTH | 0.45 |
| 530 | s16 | BOTH | 0.4 |
| 531 | s16 | BOTH | 0.35 |
| 532 | s17 | BOTH | 0.2 |
| 533 | s17 | BOTH | 0.35 |
| 534 | s17 | BOTH | 0.3 |
| 535 | s17 | BOTH | 0.25 |
| 536 | s17 | BOTH | 0.3 |
| 537 | s18 | BOTH | 0.5 |
| 538 | s18 | BOTH | 0.5 |
| 539 | s18 | BOTH | 0.45 |
| 540 | s18 | BOTH | 0.55 |
| 541 | s18 | BOTH | 0.55 |
| 542 | s18 | BOTH | 0.4 |
| 543 | s18 | BOTH | 0.5 |
| 544 | s19 | BOTH | 0.45 |
| 545 | s19 | BOTH | 0.55 |
| 546 | s19 | BOTH | 0.45 |
| 547 | s19 | BOTH | 0.6 |
| 548 | s19 | BOTH | 0.55 |
| 549 | s20 | BOTH | 0.55 |
| 550 | s20 | BOTH | 0.45 |
| 551 | s20 | BOTH | 0.5 |
| 552 | s20 | BOTH | 0.55 |
| 553 | s20 | BOTH | 0.5 |
| 554 | s20 | BOTH | 0.55 |
| 555 | s21 | BOTH | 0.55 |
| 556 | s21 | BOTH | 0.55 |
| 557 | s21 | BOTH | 0.55 |
| 558 | s21 | BOTH | 0.55 |
| 559 | s21 | BOTH | 0.55 |
| 560 | s22 | BOTH | 0.4 |
| 561 | s22 | BOTH | 0.4 |
| 562 | s22 | BOTH | 0.45 |
| 563 | s22 | BOTH | 0.45 |
| 564 | s22 | BOTH | 0.45 |
| 565 | s23 | BOTH | 0.4 |
| 566 | s23 | BOTH | 0.45 |
| 567 | s23 | BOTH | 0.55 |
| 568 | s23 | BOTH | 0.55 |
| 569 | s23 | BOTH | 0.55 |
| 570 | s23 | BOTH | 0.6 |
| 571 | s19 | SNP | 0.45 |
| 572 | s19 | SNP | 0.45 |
| 573 | s19 | WT | 0.45 |
| 574 | s19 | WT | 0.55 |
| 575 | s19 | SNP | 0.55 |
| 576 | s19 | SNP | 0.45 |
| 577 | s19 | WT | 0.45 |
| 578 | s19 | WT | 0.55 |
| 579 | s19 | SNP | 0.55 |
| 580 | s19 | SNP | 0.5 |
| 581 | s19 | WT | 0.5 |
| 582 | s19 | SNP | 0.55 |
| 583 | s19 | WT | 0.55 |
| 584 | s19 | WT | 0.5 |
| 585 | s19 | WT | 0.55 |
| 586 | s19 | SNP | 0.55 |
| 587 | s19 | WT | 0.45 |
| 588 | s19 | SNP | 0.45 |
| 589 | s19 | SNP | 0.5 |

TABLE 2-continued

Guide sequences designed to associate with specific SNPs of the FGA gene

| SEQ ID NO: | SNP ID (Table 1) | Target (SNP/WT) | % GC |
|---|---|---|---|
| 590 | s19 | WT | 0.5 |
| 591 | s19 | SNP | 0.45 |
| 592 | s19 | WT | 0.55 |
| 593 | s19 | SNP | 0.55 |
| 594 | s19 | SNP | 0.55 |
| 595 | s19 | WT | 0.55 |
| 596 | s19 | SNP | 0.55 |
| 597 | s19 | WT | 0.55 |
| 598 | s19 | SNP | 0.5 |
| 599 | s19 | WT | 0.5 |
| 600 | s19 | SNP | 0.5 |
| 601 | s19 | WT | 0.5 |
| 602 | s19 | WT | 0.45 |
| 603 | s19 | SNP | 0.6 |
| 604 | s19 | WT | 0.6 |
| 605 | s19 | SNP | 0.45 |
| 606 | s19 | WT | 0.45 |
| 607 | s19 | WT | 0.6 |
| 608 | s19 | SNP | 0.6 |
| 609 | s19 | WT | 0.45 |
| 610 | s19 | SNP | 0.45 |
| 611 | s19 | SNP | 0.55 |
| 612 | s19 | WT | 0.55 |
| 613 | s19 | WT | 0.6 |
| 614 | s19 | SNP | 0.6 |
| 615 | s19 | WT | 0.45 |
| 616 | s19 | SNP | 0.45 |
| 617 | s19 | SNP | 0.45 |
| 618 | s19 | WT | 0.45 |
| 619 | s19 | WT | 0.45 |
| 620 | s19 | WT | 0.5 |
| 621 | s19 | SNP | 0.5 |
| 622 | s19 | SNP | 0.55 |
| 623 | s19 | WT | 0.55 |
| 624 | s19 | SNP | 0.55 |
| 625 | s19 | WT | 0.55 |
| 626 | s19 | WT | 0.5 |
| 627 | s19 | SNP | 0.5 |
| 628 | s19 | SNP | 0.5 |
| 629 | s19 | SNP | 0.55 |
| 630 | s19 | WT | 0.55 |
| 631 | s19 | WT | 0.45 |
| 632 | s19 | SNP | 0.45 |
| 633 | s4 | SNP | 0.15 |
| 634 | s4 | SNP | 0.2 |
| 635 | s3 | WT | 0.35 |
| 636 | s3 | SNP | 0.35 |
| 637 | s4 | WT | 0.2 |
| 638 | s3 | SNP | 0.35 |
| 639 | s3 | WT | 0.35 |
| 640 | s4 | SNP | 0.2 |
| 641 | s3 | WT | 0.4 |
| 642 | s3 | SNP | 0.4 |
| 643 | s4 | WT | 0.25 |
| 644 | s4 | SNP | 0.2 |
| 645 | s4 | WT | 0.25 |
| 646 | s5 | SNP | 0.35 |
| 647 | s3 | SNP | 0.35 |
| 648 | s3 | WT | 0.35 |
| 649 | s4 | SNP | 0.2 |
| 650 | s5 | WT | 0.35 |
| 651 | s5 | SNP | 0.3 |
| 652 | s3 | WT | 0.4 |
| 653 | s3 | SNP | 0.4 |
| 654 | s3 | WT | 0.35 |
| 655 | s4 | WT | 0.25 |
| 656 | s3 | SNP | 0.35 |
| 657 | s3 | WT | 0.25 |
| 658 | s3 | SNP | 0.25 |
| 659 | s5 | SNP | 0.3 |
| 660 | s5 | WT | 0.35 |
| 661 | s4 | SNP | 0.2 |
| 662 | s4 | WT | 0.25 |
| 663 | s3 | SNP | 0.4 |
| 664 | s3 | WT | 0.4 |
| 665 | s3 | SNP | 0.35 |
| 666 | s3 | WT | 0.35 |
| 667 | s4 | SNP | 0.25 |
| 668 | s5 | SNP | 0.25 |
| 669 | s5 | WT | 0.3 |
| 670 | s5 | SNP | 0.3 |
| 671 | s5 | WT | 0.35 |
| 672 | s5 | WT | 0.35 |
| 673 | s5 | SNP | 0.3 |
| 674 | s3 | WT | 0.4 |
| 675 | s3 | SNP | 0.4 |
| 676 | s3 | WT | 0.35 |
| 677 | s5 | WT | 0.4 |
| 678 | s5 | SNP | 0.35 |
| 679 | s4 | WT | 0.25 |
| 680 | s3 | SNP | 0.35 |
| 681 | s5 | WT | 0.3 |
| 682 | s5 | SNP | 0.25 |
| 683 | s3 | WT | 0.25 |
| 684 | s3 | SNP | 0.25 |
| 685 | s3 | SNP | 0.4 |
| 686 | s3 | WT | 0.4 |
| 687 | s5 | SNP | 0.3 |
| 688 | s5 | WT | 0.35 |
| 689 | s5 | SNP | 0.25 |
| 690 | s5 | WT | 0.3 |
| 691 | s4 | WT | 0.25 |
| 692 | s4 | SNP | 0.2 |
| 693 | s4 | WT | 0.25 |
| 694 | s4 | SNP | 0.2 |
| 695 | s4 | WT | 0.25 |
| 696 | s4 | SNP | 0.2 |
| 697 | s5 | SNP | 0.35 |
| 698 | s5 | WT | 0.4 |
| 699 | s3 | WT | 0.35 |
| 700 | s3 | SNP | 0.35 |
| 701 | s4 | WT | 0.25 |
| 702 | s4 | SNP | 0.2 |
| 703 | s4 | SNP | 0.2 |
| 704 | s4 | WT | 0.25 |
| 705 | s3 | SNP | 0.25 |
| 706 | s3 | WT | 0.25 |
| 707 | s5 | WT | 0.35 |
| 708 | s5 | SNP | 0.3 |
| 709 | s4 | SNP | 0.2 |
| 710 | s4 | WT | 0.25 |
| 711 | s3 | WT | 0.25 |
| 712 | s3 | SNP | 0.25 |
| 713 | s3 | SNP | 0.3 |
| 714 | s3 | WT | 0.3 |
| 715 | s5 | WT | 0.4 |
| 716 | s5 | SNP | 0.25 |
| 717 | s5 | WT | 0.3 |
| 718 | s5 | WT | 0.3 |
| 719 | s5 | SNP | 0.25 |
| 720 | s3 | WT | 0.4 |
| 721 | s3 | SNP | 0.4 |
| 722 | s4 | SNP | 0.25 |
| 723 | s4 | WT | 0.3 |
| 724 | s3 | SNP | 0.25 |
| 725 | s3 | WT | 0.25 |
| 726 | s3 | SNP | 0.4 |
| 727 | s3 | SNP | 0.35 |
| 728 | s3 | WT | 0.4 |
| 729 | s3 | WT | 0.3 |
| 730 | s5 | WT | 0.4 |
| 731 | s5 | SNP | 0.35 |
| 732 | s4 | WT | 0.3 |
| 733 | s4 | SNP | 0.25 |
| 734 | s5 | WT | 0.35 |
| 735 | s4 | SNP | 0.2 |

TABLE 2-continued

Guide sequences designed to associate with specific SNPs of the FGA gene

| SEQ ID NO: | SNP ID (Table 1) | Target (SNP/WT) | % GC |
|---|---|---|---|
| 736 | s4 | WT | 0.25 |
| 737 | s5 | SNP | 0.3 |
| 738 | s4 | WT | 0.2 |
| 739 | s5 | SNP | 0.35 |
| 740 | s5 | SNP | 0.3 |
| 741 | s5 | WT | 0.35 |
| 742 | s3 | WT | 0.3 |
| 743 | s3 | SNP | 0.3 |
| 744 | s5 | WT | 0.4 |
| 745 | s5 | SNP | 0.35 |
| 746 | s5 | WT | 0.4 |
| 747 | s3 | SNP | 0.4 |
| 748 | s3 | WT | 0.4 |
| 749 | s5 | SNP | 0.25 |
| 750 | s5 | WT | 0.3 |
| 751 | s4 | WT | 0.25 |
| 752 | s4 | SNP | 0.2 |
| 753 | s4 | WT | 0.3 |
| 754 | s4 | SNP | 0.25 |
| 755 | s3 | SNP | 0.35 |
| 756 | s3 | WT | 0.35 |
| 757 | s5 | SNP | 0.3 |
| 758 | s5 | WT | 0.35 |
| 759 | s5 | WT | 0.35 |
| 760 | s5 | SNP | 0.3 |
| 761 | s3 | WT | 0.4 |
| 762 | s3 | SNP | 0.4 |
| 763 | s3 | WT | 0.35 |
| 764 | s5 | WT | 0.4 |
| 765 | s5 | SNP | 0.35 |
| 766 | s3 | WT | 0.35 |
| 767 | s4 | WT | 0.3 |
| 768 | s3 | SNP | 0.35 |
| 769 | s3 | SNP | 0.3 |
| 770 | s5 | WT | 0.3 |
| 771 | s5 | SNP | 0.25 |
| 772 | s5 | WT | 0.35 |
| 773 | s5 | WT | 0.4 |
| 774 | s5 | SNP | 0.35 |
| 775 | s3 | WT | 0.35 |
| 776 | s3 | SNP | 0.35 |
| 777 | s3 | SNP | 0.3 |
| 778 | s3 | WT | 0.3 |
| 779 | s4 | SNP | 0.2 |
| 780 | s4 | WT | 0.25 |
| 781 | s5 | WT | 0.35 |
| 782 | s5 | SNP | 0.3 |
| 783 | s3 | WT | 0.3 |
| 784 | s3 | SNP | 0.3 |
| 785 | s3 | SNP | 0.4 |
| 786 | s3 | WT | 0.4 |
| 787 | s5 | SNP | 0.3 |
| 788 | s5 | WT | 0.35 |
| 789 | s5 | SNP | 0.3 |
| 790 | s5 | WT | 0.35 |
| 791 | s4 | WT | 0.25 |
| 792 | s4 | SNP | 0.2 |
| 793 | s4 | WT | 0.25 |
| 794 | s4 | WT | 0.25 |
| 795 | s4 | SNP | 0.2 |
| 796 | s4 | SNP | 0.2 |
| 797 | s4 | SNP | 0.15 |
| 798 | s4 | WT | 0.2 |
| 799 | s5 | WT | 0.3 |
| 800 | s5 | SNP | 0.25 |
| 801 | s4 | SNP | 0.2 |
| 802 | s4 | WT | 0.25 |
| 803 | s4 | WT | 0.25 |
| 804 | s4 | WT | 0.25 |
| 805 | s4 | SNP | 0.2 |
| 806 | s5 | WT | 0.35 |
| 807 | s5 | SNP | 0.3 |
| 808 | s4 | SNP | 0.2 |
| 809 | s3 | WT | 0.3 |
| 810 | s3 | SNP | 0.3 |
| 811 | s5 | SNP | 0.35 |
| 812 | s5 | WT | 0.4 |
| 813 | s4 | WT | 0.25 |
| 814 | s4 | SNP | 0.2 |
| 815 | s3 | SNP | 0.35 |
| 816 | s3 | WT | 0.35 |
| 817 | s5 | WT | 0.35 |
| 818 | s5 | WT | 0.4 |
| 819 | s5 | SNP | 0.35 |
| 820 | s3 | WT | 0.35 |
| 821 | s3 | SNP | 0.35 |
| 822 | s4 | WT | 0.25 |
| 823 | s4 | SNP | 0.2 |
| 824 | s3 | SNP | 0.3 |
| 825 | s3 | WT | 0.3 |
| 826 | s4 | SNP | 0.2 |
| 827 | s4 | WT | 0.25 |
| 828 | s4 | SNP | 0.2 |
| 829 | s4 | WT | 0.25 |
| 830 | s5 | SNP | 0.3 |
| 831 | s4 | WT | 0.25 |
| 832 | s4 | SNP | 0.2 |
| 833 | s3 | SNP | 0.35 |
| 834 | s3 | WT | 0.35 |
| 835 | s5 | WT | 0.4 |
| 836 | s5 | SNP | 0.35 |
| 837 | s3 | SNP | 0.25 |
| 838 | s3 | WT | 0.25 |
| 839 | s5 | SNP | 0.3 |
| 840 | s4 | WT | 0.2 |
| 841 | s4 | SNP | 0.15 |
| 842 | s3 | SNP | 0.3 |
| 843 | s3 | WT | 0.3 |
| 844 | s5 | WT | 0.35 |
| 845 | s5 | SNP | 0.3 |
| 846 | s4 | SNP | 0.15 |
| 847 | s6 | WT | 0.25 |
| 848 | s6 | SNP | 0.3 |
| 849 | s6 | WT | 0.3 |
| 850 | s6 | SNP | 0.35 |
| 851 | s6 | WT | 0.25 |
| 852 | s6 | SNP | 0.3 |
| 853 | s6 | WT | 0.25 |
| 854 | s6 | SNP | 0.3 |
| 855 | s6 | WT | 0.25 |
| 856 | s6 | SNP | 0.3 |
| 857 | s6 | WT | 0.25 |
| 858 | s6 | WT | 0.3 |
| 859 | s6 | SNP | 0.35 |
| 860 | s6 | WT | 0.25 |
| 861 | s6 | SNP | 0.3 |
| 862 | s6 | WT | 0.25 |
| 863 | s6 | SNP | 0.3 |
| 864 | s6 | SNP | 0.35 |
| 865 | s6 | WT | 0.3 |
| 866 | s6 | WT | 0.25 |
| 867 | s6 | SNP | 0.3 |
| 868 | s6 | SNP | 0.3 |
| 869 | s6 | WT | 0.25 |
| 870 | s6 | SNP | 0.3 |
| 871 | s6 | WT | 0.3 |
| 872 | s6 | SNP | 0.3 |
| 873 | s6 | WT | 0.25 |
| 874 | s6 | SNP | 0.3 |
| 875 | s6 | WT | 0.25 |
| 876 | s6 | WT | 0.25 |
| 877 | s6 | SNP | 0.3 |
| 878 | s6 | WT | 0.3 |
| 879 | s6 | SNP | 0.35 |
| 880 | s6 | WT | 0.3 |
| 881 | s6 | SNP | 0.35 |

TABLE 2-continued

Guide sequences designed to associate with specific SNPs of the FGA gene

| SEQ ID NO: | SNP ID (Table 1) | Target (SNP/WT) | % GC |
|---|---|---|---|
| 882 | s6 | SNP | 0.3 |
| 883 | s6 | WT | 0.25 |
| 884 | s6 | WT | 0.25 |
| 885 | s6 | SNP | 0.3 |
| 886 | s6 | WT | 0.25 |
| 887 | s6 | SNP | 0.3 |
| 888 | s6 | SNP | 0.35 |
| 889 | s6 | WT | 0.3 |
| 890 | s6 | WT | 0.25 |
| 891 | s6 | SNP | 0.3 |
| 892 | s6 | SNP | 0.35 |
| 893 | s6 | WT | 0.3 |
| 894 | s6 | SNP | 0.35 |
| 895 | s6 | SNP | 0.3 |
| 896 | s6 | WT | 0.25 |
| 897 | s6 | SNP | 0.3 |
| 898 | s6 | WT | 0.25 |
| 899 | s6 | WT | 0.2 |
| 900 | s6 | SNP | 0.25 |
| 901 | s6 | SNP | 0.3 |
| 902 | s6 | WT | 0.25 |
| 903 | s6 | SNP | 0.3 |
| 904 | s6 | SNP | 0.35 |
| 905 | s6 | WT | 0.3 |
| 906 | s6 | WT | 0.25 |
| 907 | s6 | SNP | 0.3 |
| 908 | s6 | WT | 0.25 |
| 909 | s6 | WT | 0.25 |
| 910 | s6 | SNP | 0.3 |
| 911 | s6 | SNP | 0.3 |
| 912 | s6 | WT | 0.25 |
| 913 | s6 | SNP | 0.3 |
| 914 | s6 | WT | 0.25 |
| 915 | s6 | WT | 0.25 |
| 916 | s6 | SNP | 0.3 |
| 917 | s6 | WT | 0.25 |
| 918 | s6 | SNP | 0.3 |
| 919 | s7 | SNP | 0.5 |
| 920 | s7 | WT | 0.45 |
| 921 | s7 | SNP | 0.55 |
| 922 | s7 | WT | 0.5 |
| 923 | s7 | WT | 0.5 |
| 924 | s7 | SNP | 0.55 |
| 925 | s7 | SNP | 0.5 |
| 926 | s7 | WT | 0.45 |
| 927 | s7 | SNP | 0.55 |
| 928 | s7 | WT | 0.5 |
| 929 | s7 | WT | 0.55 |
| 930 | s7 | SNP | 0.6 |
| 931 | s7 | SNP | 0.55 |
| 932 | s7 | WT | 0.5 |
| 933 | s7 | SNP | 0.45 |
| 934 | s7 | WT | 0.4 |
| 935 | s7 | WT | 0.5 |
| 936 | s7 | SNP | 0.55 |
| 937 | s7 | SNP | 0.6 |
| 938 | s7 | WT | 0.55 |
| 939 | s7 | WT | 0.45 |
| 940 | s7 | SNP | 0.5 |
| 941 | s7 | WT | 0.55 |
| 942 | s7 | SNP | 0.6 |
| 943 | s7 | SNP | 0.55 |
| 944 | s7 | WT | 0.5 |
| 945 | s7 | SNP | 0.6 |
| 946 | s7 | SNP | 0.6 |
| 947 | s7 | WT | 0.55 |
| 948 | s7 | SNP | 0.6 |
| 949 | s7 | SNP | 0.5 |
| 950 | s7 | WT | 0.45 |
| 951 | s7 | WT | 0.55 |
| 952 | s7 | SNP | 0.5 |
| 953 | s7 | WT | 0.45 |
| 954 | s7 | SNP | 0.6 |
| 955 | s7 | WT | 0.55 |
| 956 | s7 | WT | 0.5 |
| 957 | s7 | SNP | 0.55 |
| 958 | s7 | WT | 0.5 |
| 959 | s7 | SNP | 0.55 |
| 960 | s7 | WT | 0.55 |
| 961 | s7 | SNP | 0.6 |
| 962 | s7 | SNP | 0.55 |
| 963 | s7 | WT | 0.5 |
| 964 | s7 | WT | 0.45 |
| 965 | s7 | SNP | 0.65 |
| 966 | s7 | SNP | 0.5 |
| 967 | s7 | SNP | 0.5 |
| 968 | s7 | WT | 0.45 |
| 969 | s7 | WT | 0.6 |
| 970 | s7 | WT | 0.55 |
| 971 | s7 | SNP | 0.6 |
| 972 | s7 | WT | 0.55 |
| 973 | s7 | SNP | 0.6 |
| 974 | s7 | WT | 0.45 |
| 975 | s7 | SNP | 0.5 |
| 976 | s7 | WT | 0.6 |
| 977 | s7 | SNP | 0.65 |
| 978 | s7 | WT | 0.45 |
| 979 | s7 | SNP | 0.5 |
| 980 | s7 | WT | 0.5 |
| 981 | s7 | SNP | 0.55 |
| 982 | s7 | SNP | 0.5 |
| 983 | s7 | WT | 0.45 |
| 984 | s7 | WT | 0.55 |
| 985 | s7 | SNP | 0.65 |
| 986 | s7 | WT | 0.6 |
| 987 | s7 | WT | 0.45 |
| 988 | s7 | SNP | 0.5 |
| 989 | s7 | WT | 0.6 |
| 990 | s7 | SNP | 0.65 |
| 991 | s7 | SNP | 0.6 |
| 992 | s7 | WT | 0.55 |
| 993 | s13 | WT | 0.45 |
| 994 | s13 | SNP | 0.5 |
| 995 | s13 | WT | 0.55 |
| 996 | s13 | SNP | 0.55 |
| 997 | s13 | WT | 0.5 |
| 998 | s13 | SNP | 0.6 |
| 999 | s13 | SNP | 0.55 |
| 1000 | s13 | WT | 0.5 |
| 1001 | s13 | WT | 0.55 |
| 1002 | s13 | SNP | 0.6 |
| 1003 | s13 | SNP | 0.55 |
| 1004 | s13 | WT | 0.5 |
| 1005 | s13 | SNP | 0.6 |
| 1006 | s13 | SNP | 0.6 |
| 1007 | s13 | WT | 0.55 |
| 1008 | s13 | WT | 0.55 |
| 1009 | s13 | SNP | 0.6 |
| 1010 | s13 | WT | 0.55 |
| 1011 | s13 | SNP | 0.6 |
| 1012 | s13 | SNP | 0.6 |
| 1013 | s13 | WT | 0.55 |
| 1014 | s13 | WT | 0.55 |
| 1015 | s13 | WT | 0.55 |
| 1016 | s13 | SNP | 0.6 |
| 1017 | s13 | WT | 0.55 |
| 1018 | s13 | SNP | 0.6 |
| 1019 | s13 | WT | 0.55 |
| 1020 | s13 | SNP | 0.6 |
| 1021 | s13 | WT | 0.55 |
| 1022 | s13 | SNP | 0.6 |
| 1023 | s13 | WT | 0.5 |
| 1024 | s13 | SNP | 0.55 |
| 1025 | s13 | WT | 0.55 |
| 1026 | s13 | SNP | 0.6 |
| 1027 | s13 | SNP | 0.55 |

TABLE 2-continued

Guide sequences designed to associate with specific SNPs of the FGA gene

| SEQ ID NO: | SNP ID (Table 1) | Target (SNP/WT) | % GC |
|---|---|---|---|
| 1028 | s13 | WT | 0.5 |
| 1029 | s13 | SNP | 0.6 |
| 1030 | s13 | SNP | 0.6 |
| 1031 | s13 | SNP | 0.6 |
| 1032 | s13 | WT | 0.55 |
| 1033 | s13 | WT | 0.5 |
| 1034 | s13 | SNP | 0.55 |
| 1035 | s13 | WT | 0.55 |
| 1036 | s13 | SNP | 0.6 |
| 1037 | s13 | WT | 0.55 |
| 1038 | s13 | SNP | 0.55 |
| 1039 | s13 | WT | 0.5 |
| 1040 | s13 | WT | 0.55 |
| 1041 | s13 | SNP | 0.6 |
| 1042 | s13 | SNP | 0.55 |
| 1043 | s13 | WT | 0.5 |
| 1044 | s13 | WT | 0.55 |
| 1045 | s13 | WT | 0.55 |
| 1046 | s13 | SNP | 0.6 |
| 1047 | s13 | WT | 0.5 |
| 1048 | s13 | SNP | 0.55 |
| 1049 | s13 | WT | 0.5 |
| 1050 | s13 | SNP | 0.55 |
| 1051 | s13 | SNP | 0.55 |
| 1052 | s13 | WT | 0.5 |
| 1053 | s14 | SNP | 0.5 |
| 1054 | s14 | WT | 0.55 |
| 1055 | s14 | SNP | 0.5 |
| 1056 | s14 | SNP | 0.55 |
| 1057 | s14 | WT | 0.6 |
| 1058 | s14 | WT | 0.55 |
| 1059 | s14 | SNP | 0.45 |
| 1060 | s14 | SNP | 0.5 |
| 1061 | s14 | SNP | 0.55 |
| 1062 | s14 | WT | 0.6 |
| 1063 | s14 | WT | 0.55 |
| 1064 | s14 | SNP | 0.55 |
| 1065 | s14 | WT | 0.6 |
| 1066 | s14 | SNP | 0.55 |
| 1067 | s14 | WT | 0.6 |
| 1068 | s14 | WT | 0.6 |
| 1069 | s14 | SNP | 0.55 |
| 1070 | s14 | SNP | 0.55 |
| 1071 | s14 | WT | 0.6 |
| 1072 | s14 | WT | 0.65 |
| 1073 | s14 | SNP | 0.6 |
| 1074 | s14 | WT | 0.55 |
| 1075 | s14 | WT | 0.65 |
| 1076 | s14 | SNP | 0.6 |
| 1077 | s14 | SNP | 0.55 |
| 1078 | s14 | WT | 0.6 |
| 1079 | s14 | WT | 0.6 |
| 1080 | s14 | SNP | 0.55 |
| 1081 | s14 | SNP | 0.5 |
| 1082 | s14 | SNP | 0.55 |
| 1083 | s14 | WT | 0.6 |
| 1084 | s14 | WT | 0.5 |
| 1085 | s14 | SNP | 0.6 |
| 1086 | s14 | WT | 0.65 |
| 1087 | s14 | WT | 0.65 |
| 1088 | s14 | SNP | 0.6 |
| 1089 | s14 | SNP | 0.6 |
| 1090 | s14 | WT | 0.65 |
| 1091 | s14 | WT | 0.55 |
| 1092 | s14 | SNP | 0.6 |
| 1093 | s14 | WT | 0.65 |
| 1094 | s14 | WT | 0.6 |
| 1095 | s14 | SNP | 0.55 |
| 1096 | s14 | WT | 0.65 |
| 1097 | s14 | SNP | 0.6 |
| 1098 | s14 | SNP | 0.55 |
| 1099 | s14 | WT | 0.6 |
| 1100 | s14 | WT | 0.6 |
| 1101 | s14 | SNP | 0.55 |
| 1102 | s14 | SNP | 0.5 |
| 1103 | s14 | WT | 0.6 |
| 1104 | s14 | SNP | 0.55 |
| 1105 | s14 | WT | 0.6 |
| 1106 | s14 | SNP | 0.55 |
| 1107 | s14 | WT | 0.55 |
| 1108 | s14 | SNP | 0.5 |
| 1109 | s14 | WT | 0.6 |
| 1110 | s14 | SNP | 0.55 |
| 1111 | s14 | WT | 0.55 |
| 1112 | s14 | SNP | 0.5 |
| 1113 | s14 | WT | 0.55 |
| 1114 | s14 | SNP | 0.5 |
| 1115 | s15 | SNP | 0.25 |
| 1116 | s15 | SNP | 0.25 |
| 1117 | s15 | WT | 0.3 |
| 1118 | s15 | SNP | 0.3 |
| 1119 | s15 | SNP | 0.2 |
| 1120 | s15 | WT | 0.25 |
| 1121 | s15 | SNP | 0.25 |
| 1122 | s15 | WT | 0.3 |
| 1123 | s15 | WT | 0.3 |
| 1124 | s15 | SNP | 0.25 |
| 1125 | s15 | WT | 0.3 |
| 1126 | s15 | SNP | 0.2 |
| 1127 | s15 | WT | 0.25 |
| 1128 | s15 | SNP | 0.25 |
| 1129 | s15 | WT | 0.3 |
| 1130 | s15 | WT | 0.3 |
| 1131 | s15 | SNP | 0.25 |
| 1132 | s15 | SNP | 0.25 |
| 1133 | s15 | WT | 0.3 |
| 1134 | s15 | SNP | 0.25 |
| 1135 | s15 | WT | 0.3 |
| 1136 | s15 | WT | 0.3 |
| 1137 | s15 | SNP | 0.25 |
| 1138 | s15 | WT | 0.3 |
| 1139 | s15 | WT | 0.3 |
| 1140 | s15 | SNP | 0.25 |
| 1141 | s15 | SNP | 0.3 |
| 1142 | s15 | WT | 0.35 |
| 1143 | s15 | WT | 0.35 |
| 1144 | s15 | WT | 0.35 |
| 1145 | s15 | WT | 0.35 |
| 1146 | s15 | SNP | 0.3 |
| 1147 | s15 | SNP | 0.3 |
| 1148 | s15 | WT | 0.3 |
| 1149 | s15 | SNP | 0.25 |
| 1150 | s15 | SNP | 0.2 |
| 1151 | s15 | SNP | 0.15 |
| 1152 | s15 | SNP | 0.25 |
| 1153 | s15 | WT | 0.3 |
| 1154 | s15 | WT | 0.25 |
| 1155 | s15 | SNP | 0.25 |
| 1156 | s15 | WT | 0.3 |
| 1157 | s15 | WT | 0.3 |
| 1158 | s15 | SNP | 0.25 |
| 1159 | s15 | WT | 0.3 |
| 1160 | s15 | SNP | 0.25 |
| 1161 | s15 | SNP | 0.3 |
| 1162 | s15 | WT | 0.35 |
| 1163 | s15 | WT | 0.35 |
| 1164 | s15 | SNP | 0.3 |
| 1165 | s15 | SNP | 0.2 |
| 1166 | s15 | WT | 0.25 |
| 1167 | s15 | SNP | 0.25 |
| 1168 | s15 | WT | 0.3 |
| 1169 | s15 | SNP | 0.25 |
| 1170 | s15 | WT | 0.25 |
| 1171 | s15 | SNP | 0.2 |
| 1172 | s15 | WT | 0.3 |
| 1173 | s15 | SNP | 0.25 |

TABLE 2-continued

Guide sequences designed to associate with specific SNPs of the FGA gene

| SEQ ID NO: | SNP ID (Table 1) | Target (SNP/WT) | % GC |
|---|---|---|---|
| 1174 | s15 | SNP | 0.25 |
| 1175 | s15 | WT | 0.3 |
| 1176 | s15 | WT | 0.3 |
| 1177 | s15 | SNP | 0.25 |
| 1178 | s15 | WT | 0.25 |
| 1179 | s15 | SNP | 0.2 |
| 1180 | s15 | WT | 0.25 |
| 1181 | s15 | SNP | 0.2 |
| 1182 | s15 | WT | 0.3 |
| 1183 | s15 | SNP | 0.25 |
| 1184 | s15 | WT | 0.2 |
| 1185 | s15 | SNP | 0.15 |
| 1186 | s16 | WT | 0.45 |
| 1187 | s16 | SNP | 0.4 |
| 1188 | s16 | WT | 0.45 |
| 1189 | s16 | SNP | 0.4 |
| 1190 | s16 | SNP | 0.4 |
| 1191 | s16 | SNP | 0.4 |
| 1192 | s16 | WI | 0.45 |
| 1193 | s16 | WT | 0.35 |
| 1194 | s16 | WT | 0.4 |
| 1195 | s16 | WT | 0.45 |
| 1196 | s16 | SNP | 0.4 |
| 1197 | s16 | SNP | 0.35 |
| 1198 | s16 | WT | 0.5 |
| 1199 | s16 | SNP | 0.45 |
| 1200 | s16 | WT | 0.45 |
| 1201 | s16 | SNP | 0.4 |
| 1202 | s16 | WT | 0.55 |
| 1203 | s16 | SNP | 0.5 |
| 1204 | s16 | WT | 0.45 |
| 1205 | s16 | SNP | 0.4 |
| 1206 | s16 | WT | 0.45 |
| 1207 | s16 | SNP | 0.4 |
| 1208 | s16 | SNP | 0.4 |
| 1209 | s16 | WT | 0.45 |
| 1210 | s16 | WT | 0.45 |
| 1211 | s16 | SNP | 0.5 |
| 1212 | s16 | WT | 0.55 |
| 1213 | s16 | SNP | 0.4 |
| 1214 | s16 | WT | 0.45 |
| 1215 | s16 | SNP | 0.45 |
| 1216 | s16 | WT | 0.5 |
| 1217 | s16 | SNP | 0.4 |
| 1218 | s16 | WT | 0.45 |
| 1219 | s16 | SNP | 0.4 |
| 1220 | s16 | WT | 0.45 |
| 1221 | s16 | WT | 0.45 |
| 1222 | s16 | SNP | 0.4 |
| 1723 | s16 | SNP | 0.35 |
| 1224 | s16 | SNP | 0.3 |
| 1225 | s16 | SNP | 0.35 |
| 1226 | s16 | SNP | 0.35 |
| 1227 | s16 | WT | 0.4 |
| 1228 | s16 | WT | 0.4 |
| 1229 | s16 | WT | 0.45 |
| 1230 | s16 | SNP | 0.4 |
| 1231 | s16 | WT | 0.45 |
| 1232 | s16 | SNP | 0.4 |
| 1233 | s16 | WT | 0.4 |
| 1234 | s16 | SNP | 0.35 |
| 1235 | s16 | WT | 0.4 |
| 1236 | s16 | SNP | 0.45 |
| 1237 | s16 | WT | 0.5 |
| 1238 | s16 | WT | 0.45 |
| 1239 | s16 | SNP | 0.4 |
| 1240 | s16 | WT | 0.5 |
| 1241 | s16 | SNP | 0.45 |
| 1242 | s16 | WT | 0.4 |
| 1243 | s16 | SNP | 0.35 |
| 1244 | s16 | SNP | 0.45 |
| 1245 | s16 | WT | 0.5 |
| 1246 | s16 | SNP | 0.45 |
| 1247 | s16 | WT | 0.5 |
| 1248 | s16 | SNP | 0.4 |
| 1249 | s16 | WT | 0.45 |
| 1250 | s17 | WT | 0.5 |
| 1251 | s17 | SNP | 0.45 |
| 1252 | s17 | WT | 0.5 |
| 1253 | s17 | SNP | 0.45 |
| 1254 | s17 | WT | 0.4 |
| 1255 | s17 | SNP | 0.35 |
| 1256 | s17 | WT | 0.5 |
| 1257 | s17 | SNP | 0.45 |
| 1258 | s17 | SNP | 0.3 |
| 1259 | s17 | WT | 0.35 |
| 1260 | s17 | WT | 0.45 |
| 1261 | s17 | SNP | 0.4 |
| 1262 | s17 | WT | 0.5 |
| 1263 | s17 | SNP | 0.45 |
| 1264 | s17 | SNP | 0.45 |
| 1265 | s17 | WT | 0.5 |
| 1266 | s17 | WT | 0.3 |
| 1267 | s17 | WT | 0.5 |
| 1268 | s17 | SNP | 0.45 |
| 1269 | s17 | SNP | 0.45 |
| 1270 | s17 | WT | 0.5 |
| 1271 | s17 | SNP | 0.45 |
| 1272 | s17 | WT | 0.5 |
| 1273 | s17 | WT | 0.35 |
| 1274 | s17 | SNP | 0.3 |
| 1275 | s17 | SNP | 0.25 |
| 1276 | s17 | SNP | 0.3 |
| 1277 | s17 | WT | 0.35 |
| 1278 | s17 | WT | 0.4 |
| 1279 | s17 | SNP | 0.35 |
| 1280 | s17 | WT | 0.3 |
| 1281 | s17 | SNP | 0.35 |
| 1282 | s17 | SNP | 0.25 |
| 1283 | s17 | WT | 0.45 |
| 1284 | s17 | SNP | 0.4 |
| 1285 | s17 | SNP | 0.4 |
| 1286 | s17 | WT | 0.45 |
| 1287 | s17 | WT | 0.35 |
| 1288 | s17 | WT | 0.4 |
| 1289 | s17 | SNP | 0.45 |
| 1290 | s17 | WT | 0.5 |
| 1291 | s17 | SNP | 0.25 |
| 1292 | s17 | WT | 0.3 |
| 1293 | s17 | WT | 0.5 |
| 1294 | s17 | SNP | 0.45 |
| 1295 | s17 | WT | 0.35 |
| 1296 | s17 | SNP | 0.3 |
| 1297 | s17 | WT | 0.5 |
| 1298 | s17 | SNP | 0.45 |
| 1299 | s17 | SNP | 0.45 |
| 1300 | s17 | WT | 0.5 |
| 1301 | s17 | SNP | 0.3 |
| 1302 | s17 | WT | 0.35 |
| 1303 | s17 | SNP | 0.3 |
| 1304 | s17 | WT | 0.35 |
| 1305 | s17 | SNP | 0.45 |
| 1306 | s17 | WT | 0.5 |
| 1307 | s17 | SNP | 0.4 |
| 1308 | s17 | WT | 0.45 |
| 1309 | s17 | SNP | 0.45 |
| 1310 | s17 | WT | 0.5 |
| 1311 | s17 | WT | 0.35 |
| 1312 | s17 | SNP | 0.3 |
| 1313 | s17 | SNP | 0.45 |
| 1314 | s17 | WT | 0.5 |
| 1315 | s17 | SNP | 0.3 |
| 1316 | s17 | SNP | 0.25 |
| 1317 | s17 | WT | 0.3 |
| 1318 | s17 | SNP | 0.35 |
| 1319 | s17 | WT | 0.4 |

TABLE 2-continued

Guide sequences designed to associate with specific SNPs of the FGA gene

| SEQ ID NO: | SNP ID (Table 1) | Target (SNP/WT) | % GC |
|---|---|---|---|
| 1320 | s18 | WT | 0.35 |
| 1321 | s18 | SNP | 0.45 |
| 1322 | s18 | WT | 0.4 |
| 1323 | s18 | SNP | 0.4 |
| 1324 | s18 | WT | 0.35 |
| 1325 | s18 | SNP | 0.4 |
| 1326 | s18 | WT | 0.35 |
| 1327 | s18 | WT | 0.35 |
| 1328 | s18 | SNP | 0.4 |
| 1329 | s18 | SNP | 0.4 |
| 1330 | s18 | WT | 0.45 |
| 1331 | s18 | SNP | 0.5 |
| 1332 | s18 | WT | 0.45 |
| 1333 | s18 | SNP | 0.5 |
| 1334 | s18 | WT | 0.35 |
| 1335 | s18 | SNP | 0.4 |
| 1336 | s18 | SNP | 0.5 |
| 1337 | s18 | WT | 0.45 |
| 1338 | s18 | SNP | 0.45 |
| 1339 | s18 | WT | 0.4 |
| 1340 | s18 | WT | 0.35 |
| 1341 | s18 | SNP | 0.4 |
| 1342 | s18 | WT | 0.4 |
| 1343 | s18 | SNP | 0.45 |
| 1344 | s18 | WT | 0.4 |
| 1345 | s18 | SNP | 0.45 |
| 1346 | s18 | WT | 0.45 |
| 1347 | s18 | SNP | 0.5 |
| 1348 | s18 | SNP | 0.45 |
| 1349 | s18 | WT | 0.4 |
| 1350 | s18 | SNP | 0.55 |
| 1351 | s18 | WT | 0.5 |
| 1352 | s18 | SNP | 0.4 |
| 1353 | s18 | WT | 0.35 |
| 1354 | s18 | SNP | 0.55 |
| 1355 | s18 | SNP | 0.5 |
| 1356 | s18 | WT | 0.45 |
| 1357 | s18 | WT | 0.4 |
| 1358 | s18 | SNP | 0.45 |
| 1359 | s18 | WT | 0.5 |
| 1360 | s18 | SNP | 0.55 |
| 1361 | s18 | WT | 0.5 |
| 1362 | s18 | SNP | 0.55 |
| 1363 | s18 | WT | 0.45 |
| 1364 | s18 | SNP | 0.5 |
| 1365 | s18 | SNP | 0.4 |
| 1366 | s18 | WT | 0.35 |
| 1367 | s18 | WT | 0.35 |
| 1368 | s18 | SNP | 0.4 |
| 1369 | s18 | SNP | 0.5 |
| 1370 | s18 | WT | 0.45 |
| 1371 | s18 | SNP | 0.5 |
| 1372 | s18 | WT | 0.5 |
| 1373 | s18 | SNP | 0.45 |
| 1374 | s18 | WT | 0.4 |
| 1375 | s18 | WT | 0.45 |
| 1376 | s18 | SNP | 0.4 |
| 1377 | s18 | WT | 0.35 |
| 1378 | s20 | SNP | 0.4 |
| 1379 | s20 | WT | 0.45 |
| 1380 | s20 | SNP | 0.45 |
| 1381 | s20 | WT | 0.5 |
| 1382 | s20 | WT | 0.45 |
| 1383 | s20 | SNP | 0.4 |
| 1384 | s20 | WT | 0.45 |
| 1385 | s20 | SNP | 0.4 |
| 1386 | s20 | WT | 0.5 |
| 1387 | s20 | SNP | 0.45 |
| 1388 | s20 | SNP | 0.45 |
| 1389 | s20 | WT | 0.5 |
| 1390 | s20 | SNP | 0.4 |
| 1391 | s20 | WT | 0.45 |
| 1392 | s20 | WT | 0.5 |
| 1393 | s20 | SNP | 0.45 |
| 1394 | s20 | SNP | 0.4 |
| 1395 | s20 | WT | 0.45 |
| 1396 | s20 | SNP | 0.35 |
| 1397 | s20 | WT | 0.4 |
| 1398 | s20 | SNP | 0.4 |
| 1399 | s20 | WT | 0.45 |
| 1400 | s20 | WT | 0.45 |
| 1401 | s20 | SNP | 0.4 |
| 1402 | s20 | SNP | 0.35 |
| 1403 | s20 | WT | 0.4 |
| 1404 | s20 | WT | 0.4 |
| 1405 | s20 | SNP | 0.35 |
| 1406 | s20 | WT | 0.45 |
| 1407 | s20 | SNP | 0.4 |
| 1408 | s20 | SNP | 0.4 |
| 1409 | s20 | WT | 0.45 |
| 1410 | s20 | WT | 0.45 |
| 1411 | s20 | SNP | 0.4 |
| 1412 | s20 | SNP | 0.4 |
| 1413 | s20 | WT | 0.45 |
| 1414 | s20 | SNP | 0.35 |
| 1415 | s20 | WT | 0.4 |
| 1416 | s20 | SNP | 0.4 |
| 1417 | s20 | WT | 0.45 |
| 1418 | s20 | WT | 0.45 |
| 1419 | s20 | WT | 0.4 |
| 1420 | s20 | SNP | 0.35 |
| 1421 | s20 | SNP | 0.4 |
| 1422 | s20 | SNP | 0.35 |
| 1423 | s1 | SNP | 0.4 |
| 1424 | s1 | WT | 0.45 |
| 1425 | s1 | WT | 0.45 |
| 1426 | s1 | SNP | 0.4 |
| 1427 | s1 | SNP | 0.45 |
| 1428 | s1 | WT | 0.5 |
| 1429 | s1 | SNP | 0.35 |
| 1430 | s1 | WT | 0.4 |
| 1431 | s1 | SNP | 0.4 |
| 1432 | s1 | SNP | 0.45 |
| 1433 | s1 | WT | 0.45 |
| 1434 | s1 | SNP | 0.4 |
| 1435 | s1 | WT | 0.5 |
| 1436 | s1 | WT | 0.5 |
| 1437 | s1 | SNP | 0.45 |
| 1438 | s1 | SNP | 0.45 |
| 1439 | s1 | WT | 0.5 |
| 1440 | s1 | WT | 0.5 |
| 1441 | s1 | SNP | 0.45 |
| 1442 | s1 | WT | 0.45 |
| 1443 | s1 | SNP | 0.4 |
| 1444 | s1 | SNP | 0.4 |
| 1445 | s1 | WT | 0.45 |
| 1446 | s1 | SNP | 0.45 |
| 1447 | s1 | WT | 0.5 |
| 1448 | s1 | WT | 0.5 |
| 1449 | s1 | SNP | 0.45 |
| 1450 | s1 | SNP | 0.45 |
| 1451 | s1 | WT | 0.5 |
| 1452 | s1 | WT | 0.5 |
| 1453 | s1 | SNP | 0.45 |
| 1454 | s1 | SNP | 0.4 |
| 1455 | s1 | WT | 0.45 |
| 1456 | s1 | WT | 0.45 |
| 1457 | s1 | SNP | 0.4 |
| 1458 | s1 | WT | 0.45 |
| 1459 | s1 | WT | 0.45 |
| 1460 | s1 | SNP | 0.4 |
| 1461 | s1 | SNP | 0.35 |
| 1462 | s1 | WT | 0.4 |
| 1463 | s1 | WT | 0.45 |
| 1464 | s1 | SNP | 0.4 |
| 1465 | s1 | WT | 0.5 |

TABLE 2-continued

Guide sequences designed to associate with specific SNPs of the FGA gene

| SEQ ID NO: | SNP ID (Table 1) | Target (SNP/WT) | % GC |
|---|---|---|---|
| 1466 | s1 | SNP | 0.45 |
| 1467 | s1 | SNP | 0.45 |
| 1468 | s1 | WT | 0.5 |
| 1469 | s1 | WT | 0.5 |
| 1470 | s1 | SNP | 0.45 |
| 1471 | s1 | WT | 0.5 |
| 1472 | s1 | SNP | 0.45 |
| 1473 | s1 | SNP | 0.35 |
| 1474 | s1 | WT | 0.4 |
| 1475 | s1 | WT | 0.4 |
| 1476 | s1 | SNP | 0.35 |
| 1477 | s1 | WT | 0.45 |
| 1478 | s1 | SNP | 0.4 |
| 1479 | s1 | WT | 0.4 |
| 1480 | s1 | SNP | 0.35 |
| 1481 | s1 | WT | 0.4 |
| 1482 | s1 | SNP | 0.35 |
| 1483 | s1 | WT | 0.4 |
| 1484 | s1 | SNP | 0.35 |
| 1485 | s2 | WT | 0.45 |
| 1486 | s2 | SNP | 0.4 |
| 1487 | s2 | WT | 0.5 |
| 1488 | s2 | SNP | 0.45 |
| 1489 | s2 | SNP | 0.4 |
| 1490 | s2 | WT | 0.45 |
| 1491 | s2 | WT | 0.55 |
| 1492 | s2 | SNP | 0.5 |
| 1493 | s2 | SNP | 0.5 |
| 1494 | s2 | WT | 0.55 |
| 1495 | s2 | WT | 0.55 |
| 1496 | s2 | SNP | 0.4 |
| 1497 | s2 | SNP | 0.5 |
| 1498 | s2 | WT | 0.4 |
| 1499 | s2 | SNP | 0.35 |
| 1500 | s2 | WT | 0.55 |
| 1501 | s2 | SNP | 0.5 |
| 1502 | s2 | SNP | 0.5 |
| 1503 | s2 | WT | 0.55 |
| 1504 | s2 | SNP | 0.5 |
| 1505 | s2 | WT | 0.55 |
| 1506 | s2 | WT | 0.55 |
| 1507 | s2 | SNP | 0.55 |
| 1508 | s2 | WT | 0.6 |
| 1509 | s2 | WT | 0.55 |
| 1510 | s2 | SNP | 0.55 |
| 1511 | s2 | WT | 0.6 |
| 1512 | s2 | SNP | 0.5 |
| 1513 | s2 | SNP | 0.45 |
| 1514 | s2 | WT | 0.45 |
| 1515 | s2 | SNP | 0.4 |
| 1516 | s2 | WT | 0.6 |
| 1517 | s2 | SNP | 0.55 |
| 1518 | s2 | WT | 0.6 |
| 1519 | s2 | SNP | 0.55 |
| 1520 | s2 | WT | 0.6 |
| 1521 | s2 | SNP | 0.55 |
| 1522 | s2 | WT | 0.45 |
| 1523 | s2 | WT | 0.5 |
| 1524 | s2 | SNP | 0.5 |
| 1525 | s2 | WT | 0.55 |
| 1526 | s2 | SNP | 0.45 |
| 1527 | s2 | WT | 0.5 |
| 1528 | s2 | SNP | 0.4 |
| 1529 | s2 | WT | 0.45 |
| 1530 | s2 | SNP | 0.5 |
| 1531 | s2 | WT | 0.55 |
| 1532 | s2 | SNP | 0.4 |
| 1533 | s2 | WT | 0.45 |
| 1534 | s2 | WT | 0.5 |
| 1535 | s2 | SNP | 0.45 |
| 1536 | s2 | SNP | 0.5 |
| 1537 | s2 | WT | 0.45 |
| 1538 | s2 | SNP | 0.4 |
| 1539 | s2 | SNP | 0.5 |
| 1540 | s2 | WT | 0.55 |
| 1541 | s2 | WT | 0.55 |
| 1542 | s2 | SNP | 0.5 |
| 1543 | s2 | WT | 0.45 |
| 1544 | s2 | SNP | 0.4 |
| 1545 | s2 | SNP | 0.5 |
| 1546 | s2 | WT | 0.55 |
| 1547 | s9 | SNP | 0.4 |
| 1548 | s9 | WT | 0.45 |
| 1549 | s9 | SNP | 0.4 |
| 1550 | s9 | WT | 0.5 |
| 1551 | s9 | SNP | 0.45 |
| 1552 | s9 | WT | 0.5 |
| 1553 | s9 | SNP | 0.45 |
| 1554 | s9 | SNP | 0.45 |
| 1555 | s9 | WT | 0.5 |
| 1556 | s9 | WT | 0.5 |
| 1557 | s9 | SNP | 0.45 |
| 1558 | s9 | WT | 0.55 |
| 1559 | s9 | SNP | 0.5 |
| 1560 | s9 | WT | 0.45 |
| 1561 | s9 | SNP | 0.4 |
| 1562 | s9 | SNP | 0.4 |
| 1563 | s9 | WT | 0.45 |
| 1564 | s9 | SNP | 0.4 |
| 1565 | s9 | WT | 0.45 |
| 1566 | s9 | SNP | 0.45 |
| 1567 | s9 | SNP | 0.5 |
| 1568 | s9 | WT | 0.55 |
| 1569 | s9 | SNP | 0.45 |
| 1570 | s9 | WT | 0.5 |
| 1571 | s9 | SNP | 0.5 |
| 1572 | s9 | WT | 0.55 |
| 1573 | s9 | WT | 0.5 |
| 1574 | s9 | WT | 0.5 |
| 1575 | s9 | SNP | 0.45 |
| 1576 | s9 | SNP | 0.45 |
| 1577 | s9 | WT | 0.5 |
| 1578 | s9 | SNP | 0.5 |
| 1579 | s9 | WT | 0.55 |
| 1580 | s9 | WT | 0.45 |
| 1581 | s9 | WT | 0.5 |
| 1582 | s9 | SNP | 0.45 |
| 1583 | s9 | WT | 0.55 |
| 1584 | s9 | SNP | 0.5 |
| 1585 | s9 | SNP | 0.5 |
| 1586 | s9 | WT | 0.55 |
| 1587 | s9 | WT | 0.55 |
| 1588 | s9 | SNP | 0.5 |
| 1589 | s9 | WT | 0.5 |
| 1590 | s9 | SNP | 0.45 |
| 1591 | s9 | SNP | 0.45 |
| 1592 | s9 | WT | 0.5 |
| 1593 | s9 | WT | 0.45 |
| 1594 | s9 | SNP | 0.4 |
| 1595 | s9 | SNP | 0.5 |
| 1596 | s9 | WT | 0.55 |
| 1597 | s9 | SNP | 0.45 |
| 1598 | s9 | WT | 0.5 |
| 1599 | s9 | SNP | 0.45 |
| 1600 | s9 | WT | 0.5 |
| 1601 | s9 | SNP | 0.45 |
| 1602 | s9 | WT | 0.5 |
| 1603 | s9 | WT | 0.45 |
| 1604 | s9 | SNP | 0.4 |
| 1605 | s9 | SNP | 0.45 |
| 1606 | s9 | WT | 0.5 |
| 1607 | s9 | SNP | 0.4 |
| 1608 | s9 | WT | 0.45 |
| 1609 | s9 | SNP | 0.4 |
| 1610 | s9 | WT | 0.45 |
| 1611 | s10 | SNP | 0.45 |

TABLE 2-continued

Guide sequences designed to associate with specific SNPs of the FGA gene

| SEQ ID NO: | SNP ID (Table 1) | Target (SNP/WT) | % GC |
|---|---|---|---|
| 1612 | s10 | WT | 0.5 |
| 1613 | s10 | WT | 0.55 |
| 1614 | s10 | SNP | 0.5 |
| 1615 | s10 | SNP | 0.45 |
| 1616 | s10 | SNP | 0.5 |
| 1617 | s10 | WT | 0.55 |
| 1618 | s10 | WT | 0.55 |
| 1619 | s10 | SNP | 0.5 |
| 1620 | s10 | WT | 0.55 |
| 1621 | s10 | SNP | 0.5 |
| 1622 | s10 | SNP | 0.5 |
| 1623 | sl 0 | WT | 0.55 |
| 1624 | s10 | SNP | 0.5 |
| 1625 | s10 | WT | 0.55 |
| 1626 | s10 | SNP | 0.6 |
| 1627 | s10 | WT | 0.65 |
| 1628 | s10 | WT | 0.55 |
| 1629 | s10 | SNP | 0.5 |
| 1630 | s10 | WT | 0.6 |
| 1631 | s10 | SNP | 0.55 |
| 1632 | s10 | SNP | 0.45 |
| 1633 | s10 | WT | 0.5 |
| 1634 | s10 | SNP | 0.5 |
| 1635 | s10 | WT | 0.55 |
| 1636 | s10 | SNP | 0.5 |
| 1637 | s10 | SNP | 0.55 |
| 1638 | s10 | WT | 0.6 |
| 1639 | s10 | SNP | 0.5 |
| 1640 | s10 | WT | 0.55 |
| 1641 | s10 | WT | 0.55 |
| 1642 | s10 | SNP | 0.5 |
| 1643 | s10 | WT | 0.65 |
| 1644 | s10 | WT | 0.55 |
| 1645 | s10 | SNP | 0.5 |
| 1646 | s10 | WT | 0.55 |
| 1647 | s10 | WT | 0.6 |
| 1648 | s10 | SNP | 0.55 |
| 1649 | s10 | SNP | 0.6 |
| 1650 | s10 | WT | 0.65 |
| 1651 | s10 | WT | 0.6 |
| 1652 | s10 | SNP | 0.55 |
| 1653 | s10 | SNP | 0.45 |
| 1654 | s10 | WT | 0.5 |
| 1655 | s10 | SNP | 0.55 |
| 1656 | s10 | WT | 0.6 |
| 1657 | s10 | WT | 0.5 |
| 1658 | s10 | WT | 0.65 |
| 1659 | s10 | SNP | 0.5 |
| 1660 | s10 | WT | 0.55 |
| 1661 | s10 | SNP | 0.6 |
| 1662 | s10 | WT | 0.65 |
| 1663 | s10 | WT | 0.55 |
| 1664 | s10 | SNP | 0.5 |
| 1665 | s10 | WT | 0.5 |
| 1666 | s10 | SNP | 0.45 |
| 1667 | s10 | SNP | 0.6 |
| 1668 | s10 | WT | 0.55 |
| 1669 | s10 | SNP | 0.5 |
| 1670 | s10 | WT | 0.5 |
| 1671 | s10 | SNP | 0.45 |
| 1672 | s10 | WT | 0.5 |
| 1673 | s10 | SNP | 0.45 |
| 1674 | s10 | SNP | 0.5 |
| 1675 | s10 | WT | 0.55 |
| 1676 | s10 | SNP | 0.6 |
| 1677 | s10 | WT | 0.65 |
| 1678 | s10 | WT | 0.55 |
| 1679 | s10 | SNP | 0.5 |
| 1680 | s10 | SNP | 0.6 |
| 1681 | s10 | SNP | 0.5 |
| 1682 | s10 | WT | 0.5 |
| 1683 | s10 | SNP | 0.45 |
| 1684 | s10 | WT | 0.55 |
| 1685 | s11 | WT | 0.4 |
| 1686 | s11 | SNP | 0.35 |
| 1687 | s11 | SNP | 0.3 |
| 1688 | s11 | WT | 0.35 |
| 1689 | s11 | SNP | 0.3 |
| 1690 | s11 | WT | 0.45 |
| 1691 | s11 | SNP | 0.4 |
| 1692 | s11 | WT | 0.5 |
| 1693 | s11 | SNP | 0.4 |
| 1694 | s11 | WT | 0.45 |
| 1695 | s11 | SNP | 0.4 |
| 1696 | s11 | WT | 0.45 |
| 1697 | s11 | SNP | 0.45 |
| 1698 | s11 | WT | 0.5 |
| 1699 | s11 | SNP | 0.45 |
| 1700 | s11 | SNP | 0.45 |
| 1701 | s11 | WT | 0.5 |
| 1702 | s11 | WT | 0.35 |
| 1703 | s11 | SNP | 0.3 |
| 1704 | s11 | SNP | 0.35 |
| 1705 | s11 | WT | 0.4 |
| 1706 | s11 | SNP | 0.35 |
| 1707 | s11 | WT | 0.4 |
| 1708 | s11 | SNP | 0.35 |
| 1709 | s11 | WT | 0.4 |
| 1710 | s11 | SNP | 0.3 |
| 1711 | s11 | WT | 0.35 |
| 1712 | s11 | SNP | 0.3 |
| 1713 | s11 | WT | 0.45 |
| 1714 | s11 | SNP | 0.4 |
| 1715 | s11 | WT | 0.35 |
| 1716 | s11 | WT | 0.35 |
| 1717 | s11 | WT | 0.35 |
| 1718 | s11 | SNP | 0.3 |
| 1719 | s11 | WT | 0.35 |
| 1720 | s11 | SNP | 0.3 |
| 1721 | s11 | SNP | 0.4 |
| 1722 | s11 | WT | 0.45 |
| 1723 | s11 | SNP | 0.35 |
| 1724 | s11 | WT | 0.4 |
| 1725 | s11 | SNP | 0.45 |
| 1726 | s11 | WT | 0.5 |
| 1727 | s11 | SNP | 0.35 |
| 1728 | s11 | WT | 0.4 |
| 1729 | s11 | SNP | 0.3 |
| 1730 | s11 | WT | 0.35 |
| 1731 | s11 | WT | 0.35 |
| 1732 | s11 | SNP | 0.3 |
| 1733 | s11 | WT | 0.4 |
| 1734 | s11 | SNP | 0.35 |
| 1735 | s11 | WT | 0.4 |
| 1736 | s11 | SNP | 0.35 |
| 1737 | s11 | SNP | 0.3 |
| 1738 | s11 | WT | 0.35 |
| 1739 | s11 | SNP | 0.35 |
| 1740 | s11 | WT | 0.4 |
| 1741 | s11 | SNP | 0.3 |
| 1742 | s11 | WT | 0.35 |
| 1743 | s11 | SNP | 0.3 |
| 1744 | s11 | WT | 0.35 |
| 1745 | s12 | WT | 0.45 |
| 1746 | s12 | SNP | 0.45 |
| 1747 | s12 | WT | 0.4 |
| 1748 | s12 | WT | 0.4 |
| 1749 | s12 | SNP | 0.45 |
| 1750 | s12 | SNP | 0.5 |
| 1751 | s12 | WT | 0.5 |
| 1752 | s12 | SNP | 0.5 |
| 1753 | s12 | WT | 0.45 |
| 1754 | s12 | WT | 0.4 |
| 1755 | s12 | SNP | 0.45 |
| 1756 | s12 | SNP | 0.45 |
| 1757 | s12 | WT | 0.4 |

TABLE 2-continued

Guide sequences designed to associate with specific SNPs of the FGA gene

| SEQ ID NO: | SNP ID (Table 1) | Target (SNP/WT) | % GC |
|---|---|---|---|
| 1758 | s12 | WT | 0.45 |
| 1759 | s12 | SNP | 0.5 |
| 1760 | s12 | SNP | 0.55 |
| 1761 | s12 | SNP | 0.55 |
| 1762 | s12 | WT | 0.5 |
| 1763 | s12 | WT | 0.4 |
| 1764 | s12 | SNP | 0.45 |
| 1765 | s12 | SNP | 0.5 |
| 1766 | s12 | WT | 0.45 |
| 1767 | s12 | SNP | 0.5 |
| 1768 | s12 | WT | 0.45 |
| 1769 | s12 | WT | 0.45 |
| 1770 | s12 | SNP | 0.5 |
| 1771 | s12 | WT | 0.45 |
| 1772 | s12 | SNP | 0.5 |
| 1773 | s12 | WT | 0.45 |
| 1774 | s12 | SNP | 0.5 |
| 1775 | s12 | WT | 0.45 |
| 1776 | s12 | SNP | 0.5 |
| 1777 | s12 | SNP | 0.55 |
| 1778 | s12 | WT | 0.5 |
| 1779 | s12 | SNP | 0.45 |
| 1780 | s12 | WT | 0.4 |
| 1781 | s12 | SNP | 0.55 |
| 1782 | s12 | SNP | 0.5 |
| 1783 | s12 | WT | 0.45 |
| 1784 | s12 | SNP | 0.5 |
| 1785 | s12 | WT | 0.45 |
| 1786 | s12 | SNP | 0.5 |
| 1787 | s12 | WT | 0.45 |
| 1788 | s12 | WT | 0.45 |
| 1789 | s12 | SNP | 0.5 |
| 1790 | s12 | WT | 0.45 |
| 1791 | s12 | SNP | 0.5 |
| 1792 | s12 | WT | 0.5 |
| 1793 | s12 | SNP | 0.55 |
| 1794 | s12 | SNP | 0.5 |
| 1795 | s12 | WT | 0.45 |
| 1796 | s12 | SNP | 0.55 |
| 1797 | s12 | WT | 0.5 |
| 1798 | s12 | SNP | 0.5 |
| 1799 | s12 | WT | 0.45 |
| 1800 | s12 | SNP | 0.5 |
| 1801 | s12 | WT | 0.45 |
| 1802 | s12 | SNP | 0.55 |
| 1803 | s12 | WT | 0.5 |
| 1804 | s12 | WT | 0.45 |
| 1805 | s12 | SNP | 0.45 |
| 1806 | s12 | WT | 0.4 |
| 1807 | s12 | SNP | 0.5 |
| 1808 | s12 | WT | 0.45 |
| 1809 | s12 | SNP | 0.5 |
| 1810 | s12 | WT | 0.45 |
| 1811 | s12 | SNP | 0.5 |
| 1812 | s12 | SNP | 0.5 |
| 1813 | s12 | WT | 0.45 |
| 1814 | s12 | WT | 0.5 |
| 1815 | s21 | WT | 0.55 |
| 1816 | s21 | SNP | 0.5 |
| 1817 | s21 | SNP | 0.5 |
| 1818 | s21 | SNP | 0.6 |
| 1819 | s21 | WT | 0.65 |
| 1820 | s21 | WT | 0.6 |
| 1821 | s21 | WT | 0.65 |
| 1822 | s21 | SNP | 0.6 |
| 1823 | s21 | SNP | 0.6 |
| 1824 | s21 | WT | 0.65 |
| 1825 | s21 | WT | 0.65 |
| 1826 | s21 | SNP | 0.6 |
| 1827 | s21 | SNP | 0.55 |
| 1828 | s21 | WT | 0.6 |
| 1829 | s21 | SNP | 0.55 |
| 1830 | s21 | SNP | 0.55 |
| 1831 | s21 | WT | 0.6 |
| 1832 | s21 | WT | 0.65 |
| 1833 | s21 | SNP | 0.6 |
| 1834 | s21 | SNP | 0.6 |
| 1835 | s21 | WT | 0.65 |
| 1836 | s21 | SNP | 0.55 |
| 1837 | s21 | WT | 0.6 |
| 1838 | s21 | WT | 0.6 |
| 1839 | s21 | SNP | 0.55 |
| 1840 | s21 | SNP | 0.55 |
| 1841 | s21 | WT | 0.6 |
| 1842 | s21 | WT | 0.65 |
| 1843 | s21 | WT | 0.65 |
| 1844 | s21 | SNP | 0.6 |
| 1845 | s21 | SNP | 0.6 |
| 1846 | s21 | WT | 0.65 |
| 1847 | s21 | WT | 0.55 |
| 1848 | s21 | SNP | 0.6 |
| 1849 | s21 | WT | 0.65 |
| 1850 | s21 | WT | 0.65 |
| 1851 | s21 | SNP | 0.6 |
| 1852 | s21 | SNP | 0.6 |
| 1853 | s21 | SNP | 0.55 |
| 1854 | s21 | WT | 0.6 |
| 1855 | s21 | WT | 0.6 |
| 1856 | s21 | SNP | 0.55 |
| 1857 | s21 | WT | 0.65 |
| 1858 | s21 | SNP | 0.6 |
| 1859 | s21 | SNP | 0.55 |
| 1860 | s21 | WT | 0.6 |
| 1861 | s21 | SNP | 0.5 |
| 1862 | s21 | WT | 0.55 |
| 1863 | s21 | SNP | 0.5 |
| 1864 | s21 | WT | 0.55 |
| 1865 | s21 | WT | 0.55 |
| 1866 | s21 | SNP | 0.5 |
| 1867 | s22 | WT | 0.35 |
| 1868 | s22 | SNP | 0.3 |
| 1869 | s22 | SNP | 0.4 |
| 1870 | s22 | WT | 0.4 |
| 1871 | s22 | SNP | 0.35 |
| 1872 | s22 | SNP | 0.45 |
| 1873 | s22 | WT | 0.45 |
| 1874 | s22 | WT | 0.45 |
| 1875 | s22 | SNP | 0.4 |
| 1876 | s22 | SNP | 0.4 |
| 1877 | s22 | WT | 0.45 |
| 1878 | s22 | WT | 0.4 |
| 1879 | s22 | SNP | 0.35 |
| 1880 | s22 | WT | 0.35 |
| 1881 | s22 | SNP | 0.3 |
| 1882 | s22 | WT | 0.5 |
| 1883 | s22 | SNP | 0.45 |
| 1884 | s22 | WT | 0.4 |
| 1885 | s22 | SNP | 0.35 |
| 1886 | s22 | SNP | 0.4 |
| 1887 | s22 | WT | 0.45 |
| 1888 | s22 | WT | 0.45 |
| 1889 | s22 | WT | 0.4 |
| 1890 | s22 | SNP | 0.35 |
| 1891 | s22 | SNP | 0.4 |
| 1892 | s22 | WT | 0.45 |
| 1893 | s22 | SNP | 0.35 |
| 1894 | s22 | WT | 0.4 |
| 1895 | s22 | WT | 0.5 |
| 1896 | s22 | WT | 0.35 |
| 1897 | s22 | SNP | 0.3 |
| 1898 | s22 | SNP | 0.4 |
| 1899 | s22 | WT | 0.45 |
| 1900 | s22 | SNP | 0.35 |
| 1901 | s22 | WT | 0.4 |
| 1902 | s22 | WT | 0.45 |
| 1903 | s22 | SNP | 0.4 |

TABLE 2-continued

Guide sequences designed to associate with specific SNPs of the FGA gene

| SEQ ID NO: | SNP ID (Table 1) | Target (SNP/WT) | % GC |
|---|---|---|---|
| 1904 | s22 | SNP | 0.3 |
| 1905 | s22 | WT | 0.35 |
| 1906 | s22 | WT | 0.45 |
| 1907 | s22 | SNP | 0.4 |
| 1908 | s22 | SNP | 0.4 |
| 1909 | s22 | WT | 0.45 |
| 1910 | s22 | WT | 0.45 |
| 1911 | s22 | SNP | 0.4 |
| 1912 | s22 | WT | 0.45 |
| 1913 | s22 | SNP | 0.4 |
| 1914 | s22 | WT | 0.45 |
| 1915 | s22 | WT | 0.35 |
| 1916 | s22 | SNP | 0.3 |
| 1917 | s22 | SNP | 0.35 |
| 1918 | s22 | WT | 0.4 |
| 1919 | s22 | WT | 0.45 |
| 1920 | s22 | SNP | 0.4 |
| 1921 | s22 | SNP | 0.4 |
| 1922 | s22 | SNP | 0.4 |
| 1923 | s22 | WT | 0.45 |
| 1924 | s22 | SNP | 0.35 |
| 1925 | s22 | WT | 0.4 |
| 1926 | s22 | SNP | 0.4 |
| 1927 | s22 | SNP | 0.35 |
| 1928 | s22 | WT | 0.4 |
| 1929 | s23 | SNP | 0.45 |
| 1930 | s23 | SNP | 0.35 |
| 1931 | s23 | WT | 0.35 |
| 1932 | s23 | SNP | 0.4 |
| 1933 | s23 | WT | 0.4 |
| 1934 | s23 | SNP | 0.5 |
| 1935 | s23 | WT | 0.4 |
| 1936 | s23 | SNP | 0.4 |
| 1937 | s23 | SNP | 0.4 |
| 1938 | s23 | WT | 0.4 |
| 1939 | s23 | WT | 0.45 |
| 1940 | s23 | WT | 0.4 |
| 1941 | s23 | SNP | 0.45 |
| 1942 | s23 | WT | 0.45 |
| 1943 | s23 | WT | 0.4 |
| 1944 | s23 | SNP | 0.4 |
| 1945 | s23 | WT | 0.4 |
| 1946 | s23 | SNP | 0.4 |
| 1947 | s23 | WT | 0.45 |
| 1948 | s23 | SNP | 0.45 |
| 1949 | s23 | WT | 0.45 |
| 1950 | s23 | SNP | 0.45 |
| 1951 | s23 | WT | 0.5 |
| 1952 | s23 | SNP | 0.5 |
| 1953 | s23 | WT | 0.45 |
| 1954 | s23 | SNP | 0.45 |
| 1955 | s23 | WT | 0.5 |
| 1956 | s23 | SNP | 0.5 |
| 1957 | s23 | WT | 0.45 |
| 1958 | s23 | SNP | 0.45 |
| 1959 | s23 | WT | 0.35 |
| 1960 | s23 | SNP | 0.45 |
| 1961 | s23 | WT | 0.45 |
| 1962 | s23 | SNP | 0.35 |
| 1963 | s23 | SNP | 0.45 |
| 1964 | s23 | WT | 0.45 |
| 1965 | s23 | SNP | 0.5 |
| 1966 | s23 | WT | 0.5 |
| 1967 | s23 | WT | 0.4 |
| 1968 | s23 | SNP | 0.4 |
| 1969 | s23 | WT | 0.5 |
| 1970 | s23 | WT | 0.35 |
| 1971 | s23 | WT | 0.5 |
| 1972 | s23 | SNP | 0.5 |
| 1973 | s23 | SNP | 0.5 |
| 1974 | s23 | WT | 0.5 |
| 1975 | s23 | WT | 0.45 |
| 1976 | s23 | SNP | 0.45 |
| 1977 | s23 | SNP | 0.45 |
| 1978 | s23 | WT | 0.45 |
| 1979 | s23 | WT | 0.45 |
| 1980 | s23 | SNP | 0.45 |
| 1981 | s23 | SNP | 0.4 |
| 1982 | s23 | SNP | 0.35 |
| 1983 | s23 | WT | 0.4 |
| 1984 | s23 | SNP | 0.4 |

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only.

EXPERIMENTAL DETAILS

Example 1: FGA Correction Strategies

Figure 10A:
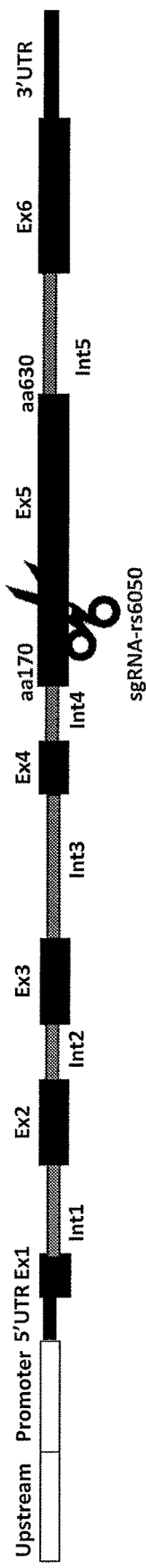
FIG. 10A and FIG. 10B: Two exemplary strategies are proposed to tackle the Fibrinogen amyloidosis with SpCas9 at a genomic DNA level.
Figure 10B:
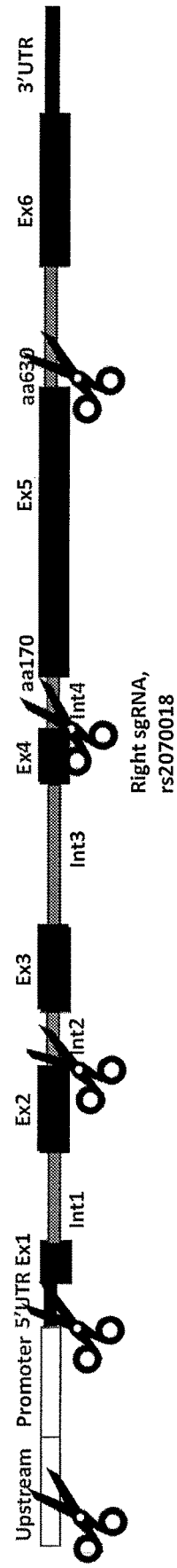

Two strategies are proposed to tackle the Fibrinogen amyloidosis at a genomic DNA level. In the first indels are introduced on rs6050 SNP resulting with truncated protein without the putative amyloid forming region. (FIG. 10A). In the second exclusion of the coiled-coil domain or FGA Exon 5 by knock-out is effected with two RNA molecules. (FIG. 10B). One guide targets a SNP and the second guide a sequence common to both alleles. The first guide targets a SNP/SEQ in either Intron 4, Intron2, 5'UTR, or promoter region while a second guide targets a sequence in Intron 5, a common region to both transcripts.

Figure 11A:
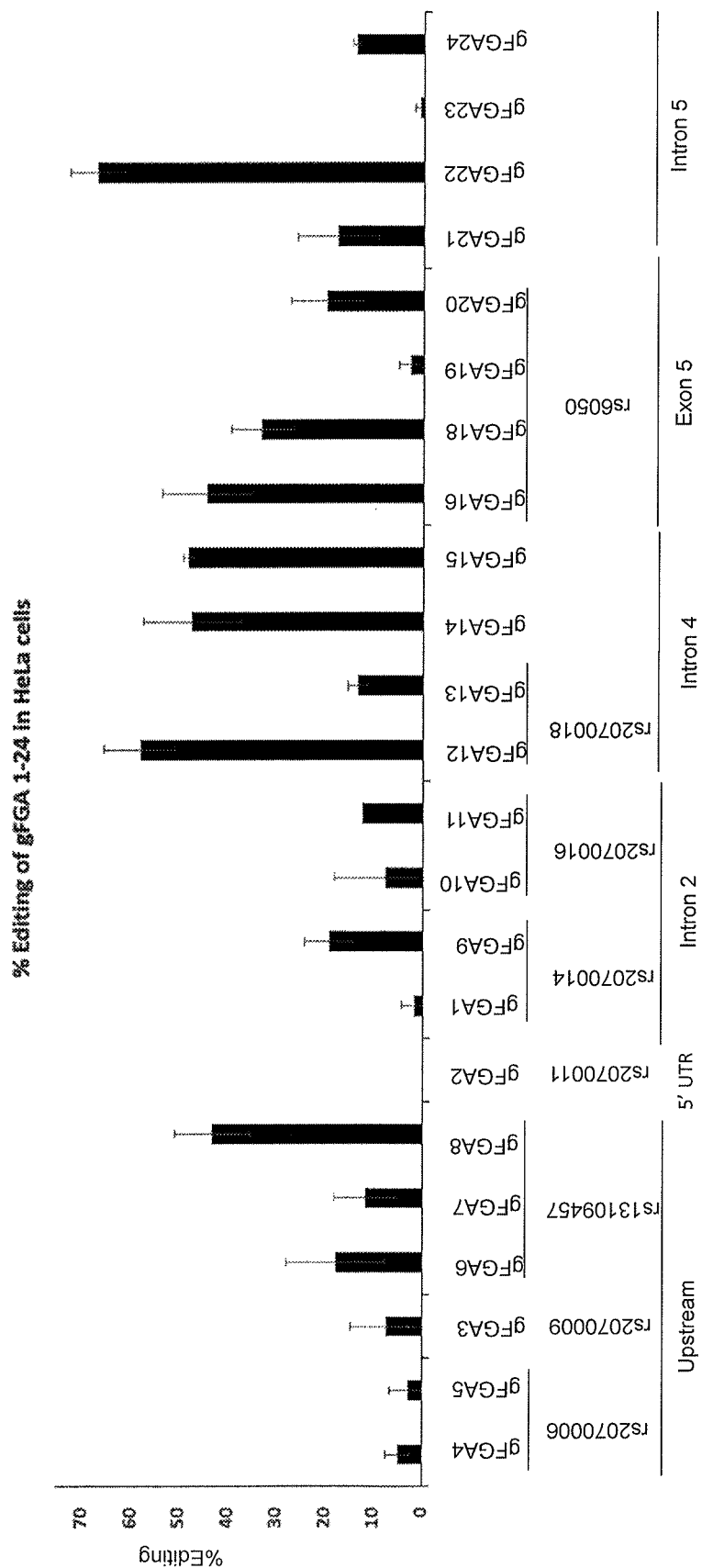
FIG. 11A-FIG. 11D: 24 different guide sequences, identified as gFGA 1 through gFGA 24 were screened for high on target activity.
Figure 11B:
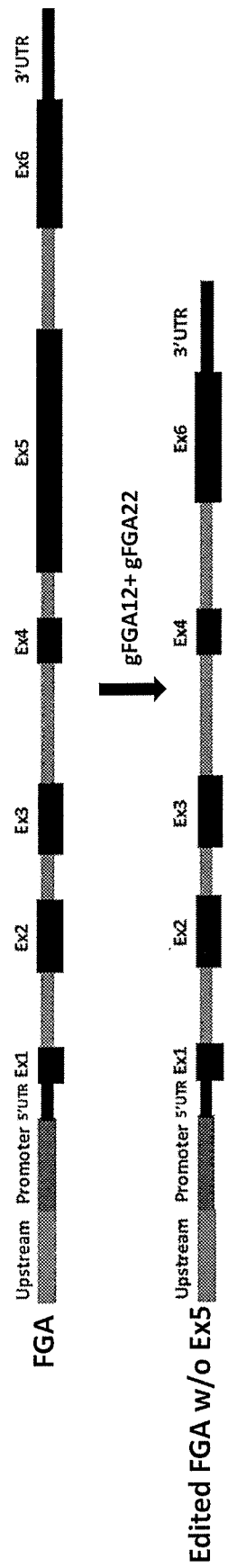

When using SpCas9, 24 different guide sequences, identified as gFGA 1 through gFGA 24, identified by SEQ ID NO. in Table 3, are screened for high on target activity using spCas9 in HeLa cells. In brief, spCas9 coding plasmid (390 ng) is co-transfected with each of the guide sequence expression plasmids (120 ng) in 24 well plate format using Turbofect reagent (Thermo fisher scientific). Cells are harvested 72 h post DNA transfection. On target activity is determined by DNA capillary electrophoresis. According to DNA capillary electrophoresis analysis, either gFGA16 or gFGA18 which target rs6050 SNP and show activity of ~30-40%, can be used for correction utilizing the first strategy. (FIG. 11A). gFGA 12 and gFGA22 that target rs2070018 and Intron 5, respectively, show activity of ~50-60%, and can be used for Exon 5 excision in the second strategy. (FIG. 11A).

Figure 11D:
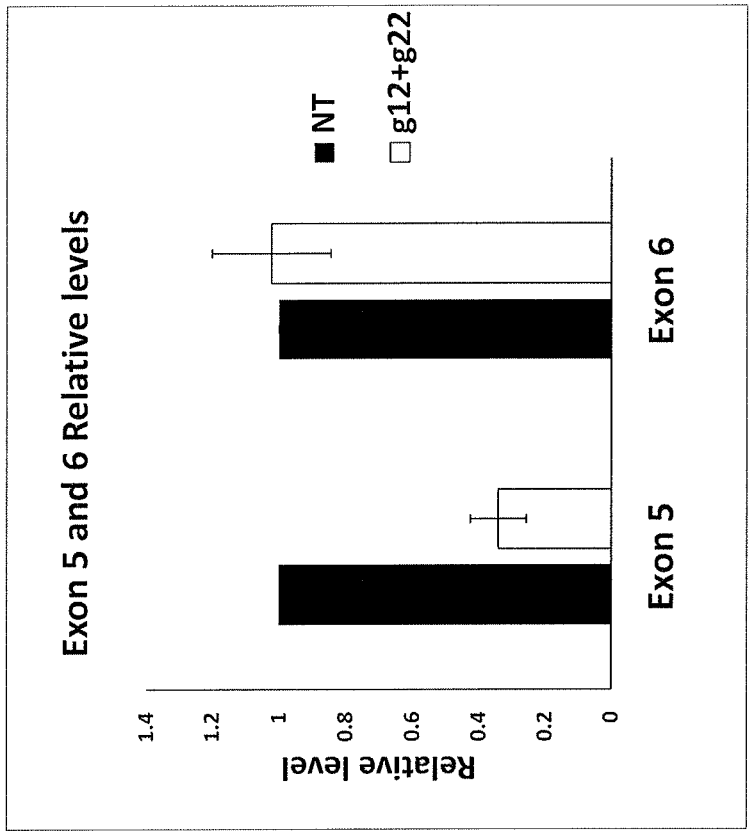
Figure 11C:
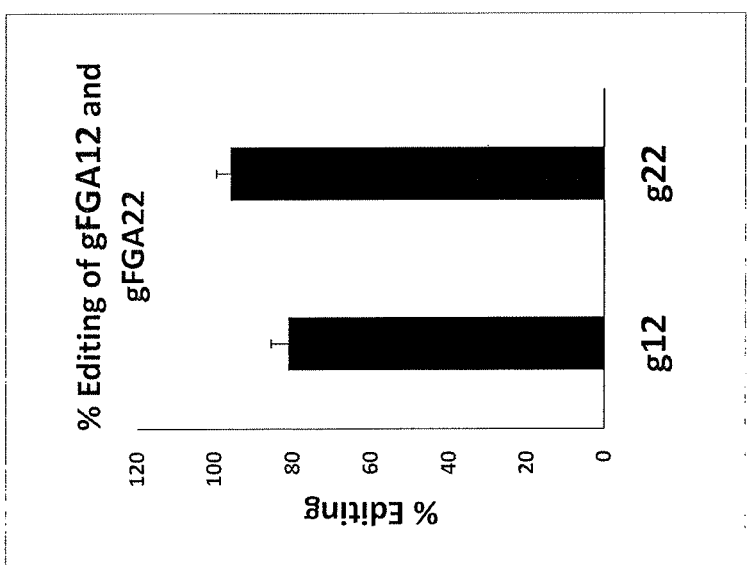

To test Exon 5 excision rate using gFGA12 and gFGA22, spCas9 coding plasmid (390 ng) is co-transfected with gFGA12 and gFGA22 plasmids (60 ng of each) in 24 well plate format using Turbofect reagent (Thermo fisher scientific). Cells are harvested 72 h post DNA transfection. Genomic DNA is extracted using EZNA tissue DNA kit (Omega). On target activity is determined by DNA capillary electrophoresis. (FIG. 11C). To determine the excision rate, genomic DNAs of treated and non-treated cells are subjected to RT-PCR using FAST SYBR mix (Applied bio-systems) and primers for FGA Exon 5, FGA Exon 6 and GAPDH, as shown in Table 4, which serves as an endogenous control. The data shows a decrease of approximately 60% in Exon 5 levels of treated cells, while no significant change is detected in Exon 6 levels. (FIG. 11D).

TABLE 3 gFGA1 through gFGA24 of Example 1 as identified by SEQ ID NO.

| Guide sequence | Example 1 gFGA ID | SEQ ID NO: |
|---|---|---|
| CUUUUCUUUAUUUGCUAUGU | gFGA1 | 162 |
| CAGCAAUCCUUUCUUUCAGC | gFGA2 | 117 |
| ACAGACAAAUACUGCUUAGC | gFGA3 | 87 |
| UUGAAUGUUUACUAAGUCUU | gFGA4 | 115 |
| AUUGAAUGUUUACUAAGUCU | gFGA5 | 109 |
| AGUCCUUGUGCCUUGGCCUC | gFGA6 | 142 |
| UUGUGCCAGUCCUUGUGCCU | gFGA7 | 158 |
| UGAGGCCAAGGCACAAGGAC | gFGA8 | 155 |
| CUACAUAGCAAAUAAAGAAA | gFGA9 | 161 |
| UUAGCCAUAAAUUAGGUGCC | gFGA10 | 215 |
| GCACCUAAUUUAUGGCUAAG | gFGA11 | 202 |
| ACUCAGAAACAAGGACAUCU | gFGA12 | 219 |
| AUGUCCUUGUUUCUGAGUAG | gFGA13 | 222 |
| UUCCACUGAGGGUGCUCGAU | gFGA14 | 1985 |
| UGCCUAUCGAGCACCCUCAG | gFGA15 | 1986 |
| UUCCAGCUUCCAGUACUUCC | gFGA16 | 141 |
| AGCUCUGGACCUGGAAGUAC | gFGA17 | 124 |
| GACCUGGAAGUACUGGAAGC | gFGA18 | 132 |
| AGUACUGGAAGCUGGAACUC | gFGA19 | 126 |
| GUACUGGAAGCUGGAACUCU | gFGA20 | 136 |
| AAGGAAAUGCAAGGGGCCAU | gFGA21 | 1987 |
| AGUCAUGGCUCUGUACUGUU | gFGA22 | 1988 |
| UUAACUUAGUCUAGGGGGAC | gFGA23 | 1989 |
| CGUGUAACAGAGAGUUAAGA | gFGA24 | 1990 |

TABLE 4

Primers used for RT-PCR analysis of Example 1

FGA Exon6-F-TGATGCTCTGATTGAGGGTTCC
(SEQ ID NO: 1991)

FGA Exon6-R-AGGTGCTGAACTGCATGTTG
(SEQ ID NO: 1992)

FGA Exon5-F-ACATGCCGCAGATGAGAATG
(SEQ ID NO: 1993)

FGA Exon5-R-TTTCCGTCTCTGATCCGGTTC
(SEQ ID NO: 1994)

GAPDH-F-CACACACATGCACTTACCTGTG
(SEQ ID NO: 1995)

TABLE 4-continued

Primers used for RT-PCR analysis of Example 1

GAPDH-R-ATTTGCCAAGTTGCCTGTCC
(SEQ ID NO: 1996)

Example 2: FGA Correction Analysis

Guide sequences comprising 17-20 nucleotides in the sequences of 17-20 contiguous nucleotides set forth in SEQ ID NOs: 1-1990 are screened for high on target activity. On target activity is determined by DNA capillary electrophoresis analysis.

According to DNA capillary electrophoresis analysis, guide sequences comprising 17-20 nucleotides in the sequences of 17-20 contiguous nucleotides set forth in SEQ ID NOs: 1-1990 are found to be suitable for correction of the FGA gene.

Discussion

The guide sequences of the present invention are determined to be suitable for targeting the FGA gene.

REFERENCES

1. Ahmad and Allen (1992) "Antibody-mediated Specific Binging and Cytotoxicity of Lipsome-entrapped Doxorubicin to Lung Cancer Cells in Vitro", Cancer Research 52:4817-20
2. Anders (1992) "Human gene therapy", Science 256:808-13
3. Basha et al. (2011) "Influence of Cationic Lipid Composition on Gene Silencing Properties of Lipid Nanoparticle Formulations of siRNA in Antigen-Presenting Cells", Mol. Ther. 19(12):2186-200
4. Behr (1994) Gene transfer with synthetic cationic amphiphiles: Prospects for gene therapy", Bioconjuage Chem 5:382-89
5. Blaese (1995) "Vectors in cancer therapy: how will they deliver", Cancer Gene Ther. 2:291-97
6. Blaese et al. (1995) "T lympocyte-directed gene therapy for ADA-SCID: initial trial results after 4 years", Science 270(5235):475-80
7. Buchschacher and Panganiban (1992) "Human immunodeficiency virus vectors for inducible expression of foreign genes", J. Virol. 66:2731-39
8. Burstein et al. (2017) "New CRISPR-Cas systems from uncultivated microbes", Nature 542:237-41
9. Chung et al. (2006) "*Agrobacterium* is not alone: gene transfer to plants by viruses and other bacteria", Trends Plant Sci. 11(1):1-4
10. Coelho et al. (2013) "Safety and Efficacy of RNAi Therapy for Transthyretin Amyloidosis", N Engl J. Med 369:819-29
11. Crystal (1995) "Transfer of genes to humans: early lessons and obstacles to success", Science 270(5235): 404-10
12. Dillon (1993) "Regulation gene expression in gene therapy" Trends in Biotechnology 11(5):167-173
13. Dranoff et al. (1997) "A phase I study of vaccination with autologous, irradiated melanoma cells engineered to secrete human granulocyte macrophage colony stimulating factor", Hum. Gene Ther. 8(1):111-23
14. Dunbar et al. (1995) "Retrovirally marked CD34-enriched peripheral blood and bone marrow cells contribute to long-term engraftment after autologous transplantation", Blood 85:3048-57

15. Ellem et al. (1997) "A case report: immune responses and clinical course of the first human use of ganulocyte/macrophage-colony-stimulating-factor-tranduced autologous melanoma cells for immunotherapy", Cancer Immunol Immunother 44:10-20
16. Gao and Huang (1995) "Cationic liposome-mediated gene transfer" Gene Ther. 2(10):710-22
17. Haddada et al. (1995) "Gene Therapy Using Adenovirus Vectors", in: The Molecular Repertoire of Adenoviruses III: Biology and Pathogenesis, ed. Doerfler and Böhm, pp. 297-306
18. Han et al. (1995) "Ligand-directed retro-viral targeting of human breast cancer cells", Proc Natl Acad Sci U.S.A. 92(21):9747-51
19. Inaba et al. (1992) "Generation of large numbers of dendritic cells from mouse bone marrow cultures supplemented with granulocyte/macrophage colony-stimulating factor", J Exp Med. 176(6):1693-702
20. Jinek et al. (2012) "A programmable dual-RNA-guided DNA endonuclease in adaptive bacterial immunity," Science 337(6096):816-21
21. Johan et al. (1992) "GLVR1, a receptor for gibbon ape leukemia virus, is homologous to a phosphate permease of *Neurospora crassa* and is expressed at high levels in the brain and thymus", J Virol 66(3):1635-40
22. Judge et al. (2006) "Design of noninflammatory synthetic siRNA mediating potent gene silencing in vivo", Mol Ther. 13(3):494-505
23. Kohn et al. (1995) "Engraftment of gene-modified umbilical cord blood cells in neonates with adnosine deaminase deficiency", Nature Medicine 1:1017-23
24. Kremer and Perricaudet (1995) "Adenovirus and adeno-associated virus mediated gene transfer", Br. Med. Bull. 51(1):31-44
25. Macdiarmid et al. (2009) "Sequential treatment of drug-resistant tumors with targeted minicells containing siRNA or a cytotoxic drug", Nat Biotechnol. 27(7):643-51
26. Malech et al. (1997) "Prolonged production of NADPH oxidase-corrected granulocyes after gene therapy of chronic granulomatous disease", PNAS 94(22):12133-38
27. Miller et al. (1991) "Construction and properties of retrovirus packaging cells based on gibbon ape leukemia virus", J Virol. 65(5):2220-24
28. Miller (1992) "Human gene therapy comes of age", Nature 357:455-60
29. Mitani and Caskey (1993) "Delivering therapeutic genes—matching approach and application", Trends in Biotechnology 11(5):162-66
30. Nabel and Felgner (1993) "Direct gene transfer for immunotherapy and immunization", Trends in Biotechnology 11(5):211-15
31. Remy et al. (1994) "Gene Transfer with a Series of Lipophilic DNA-Binding Molecules", Bioconjugate Chem. 5(6):647-54
32. Sentmanat et al. (2018) "A Survey of Validation Strategies for CRISPR-Cas9 Editing", Scientific Reports 8:888, doi:10.1038/s41598-018-19441-8
33. Sommerfelt et al. (1990) "Localization of the receptor gene for type D simian retroviruses on human chromosome 19", J. Virol. 64(12):6214-20
34. Van Brunt (1988) "Molecular framing: transgenic animals as bioactors" Biotechnology 6:1149-54
35. Vigne et al. (1995) "Third-generation adenovectors for gene therapy", Restorative Neurology and Neuroscience 8(1,2): 35-36
36. Wilson et al. (1989) "Formation of infectious hybrid virion with gibbon ape leukemia virus and human T-cell leukemia virus retroviral envelope glycoproteins and the gag and pol proteins of Moloney murine leukemia virus", J. Virol. 63:2374-78
37. Yu et al. (1994) "Progress towards gene therapy for HIV infection", Gene Ther. 1(1):13-26
38. Zetsche et al. (2015) "Cpf1 is a single RNA-guided endonuclease of a class 2 CRIPSR-Cas system" Cell 163(3):759-71
39. Zuris et al. (2015) "Cationic lipid-mediated delivery of proteins enables efficient protein based genome editing in vitro and in vivo" Nat Biotechnol. 33(1):73-80

What is claimed:

1. An isolated guide RNA molecule comprising a guide sequence portion, wherein the guide sequence portion consists of any one of the following SEQ ID NOs: 141, 124, 126, or 136, and
   wherein the guide RNA molecule further comprises:
   a) a portion having a sequence which binds to a CRISPR nuclease; or
   b) a portion having a tracr mate sequence.

2. A composition comprising the guide RNA molecule of claim 1, the composition further comprising a CRISPR nuclease, wherein if the guide RNA further comprises a portion having a tracr mate sequence, then the composition further comprises a tracrRNA molecule.

3. A method for inactivating a mutant FGA allele in a cell, the method comprising delivering to the cell the composition of claim 2.

* * * * *

SEQUENCE LISTING

```
<160> NUMBER OF SEQ ID NOS: 1996

<210> SEQ ID NO 1
<211> LENGTH: 20
<212> TYPE: RNA
<213> ORGANISM: Artificial Sequence
<220> FEATURE:
<223> OTHER INFORMATION: synthesized

<400> SEQUENCE: 1
auugacucug cuugguuuuu                                                  20

<210> SEQ ID NO 2
<211> LENGTH: 20
<212> TYPE: RNA
<213> ORGANISM: Artificial Sequence
<220> FEATURE:
<223> OTHER INFORMATION: synthesized

<400> SEQUENCE: 2
ccaggaguua uaagguacug                                                  20

<210> SEQ ID NO 3
<211> LENGTH: 20
```

```
<212> TYPE: RNA
<213> ORGANISM: Artificial Sequence
<220> FEATURE:
<223> OTHER INFORMATION: synthesized

<400> SEQUENCE: 3
gacucugcuu gguuuuucca                                          20

<210> SEQ ID NO 4
<211> LENGTH: 20
<212> TYPE: RNA
<213> ORGANISM: Artificial Sequence
<220> FEATURE:
<223> OTHER INFORMATION: synthesized

<400> SEQUENCE: 4
guccaggagu uauaagguac                                          20

<210> SEQ ID NO 5
<211> LENGTH: 20
<212> TYPE: RNA
<213> ORGANISM: Artificial Sequence
<220> FEATURE:
<223> OTHER INFORMATION: synthesized

<400> SEQUENCE: 5
cuucagccua uugggucaca                                          20

<210> SEQ ID NO 6
<211> LENGTH: 20
<212> TYPE: RNA
<213> ORGANISM: Artificial Sequence
<220> FEATURE:
<223> OTHER INFORMATION: synthesized

<400> SEQUENCE: 6
ucagccuauu gggucacaag                                          20

<210> SEQ ID NO 7
<211> LENGTH: 20
<212> TYPE: RNA
<213> ORGANISM: Artificial Sequence
<220> FEATURE:
<223> OTHER INFORMATION: synthesized

<400> SEQUENCE: 7
uucagccuau ugggucacaa                                          20

<210> SEQ ID NO 8
<211> LENGTH: 20
<212> TYPE: RNA
<213> ORGANISM: Artificial Sequence
<220> FEATURE:
<223> OTHER INFORMATION: synthesized

<400> SEQUENCE: 8
agugaaauga gcagauauag                                          20

<210> SEQ ID NO 9
<211> LENGTH: 20
<212> TYPE: RNA
<213> ORGANISM: Artificial Sequence
<220> FEATURE:
<223> OTHER INFORMATION: synthesized

<400> SEQUENCE: 9
```
uaaaaagcau gugacaauaa                                           20

<210> SEQ ID NO 10
<211> LENGTH: 20
<212> TYPE: RNA
<213> ORGANISM: Artificial Sequence
<220> FEATURE:
<223> OTHER INFORMATION: synthesized

<400> SEQUENCE: 10
uaagugaaau gagcagauau                                           20

<210> SEQ ID NO 11
<211> LENGTH: 20
<212> TYPE: RNA
<213> ORGANISM: Artificial Sequence
<220> FEATURE:
<223> OTHER INFORMATION: synthesized

<400> SEQUENCE: 11
uuaaaaagca ugugacaaua                                           20

<210> SEQ ID NO 12
<211> LENGTH: 20
<212> TYPE: RNA
<213> ORGANISM: Artificial Sequence
<220> FEATURE:
<223> OTHER INFORMATION: synthesized

<400> SEQUENCE: 12
uuuaaaaagc augugacaau                                           20

<210> SEQ ID NO 13
<211> LENGTH: 20
<212> TYPE: RNA
<213> ORGANISM: Artificial Sequence
<220> FEATURE:
<223> OTHER INFORMATION: synthesized

<400> SEQUENCE: 13
caagacuuag uaaacauuca                                           20

<210> SEQ ID NO 14
<211> LENGTH: 20
<212> TYPE: RNA
<213> ORGANISM: Artificial Sequence
<220> FEATURE:
<223> OTHER INFORMATION: synthesized

<400> SEQUENCE: 14
aggaugggaa cuaggagugg                                           20

<210> SEQ ID NO 15
<211> LENGTH: 20
<212> TYPE: RNA
<213> ORGANISM: Artificial Sequence
<220> FEATURE:
<223> OTHER INFORMATION: synthesized

<400> SEQUENCE: 15
auaggauggg aacuaggagu                                           20

<210> SEQ ID NO 16
<211> LENGTH: 20
<212> TYPE: RNA
<213> ORGANISM: Artificial Sequence
<220> FEATURE:
<223> OTHER INFORMATION: synthesized

<400> SEQUENCE: 16
cuccagcuga aagaaaggau                                                 20

<210> SEQ ID NO 17
<211> LENGTH: 20
<212> TYPE: RNA
<213> ORGANISM: Artificial Sequence
<220> FEATURE:
<223> OTHER INFORMATION: synthesized

<400> SEQUENCE: 17
ggaugggaac uaggaguggc                                                 20

<210> SEQ ID NO 18
<211> LENGTH: 20
<212> TYPE: RNA
<213> ORGANISM: Artificial Sequence
<220> FEATURE:
<223> OTHER INFORMATION: synthesized

<400> SEQUENCE: 18
acuucucuag caaagaagac                                                 20

<210> SEQ ID NO 19
<211> LENGTH: 20
<212> TYPE: RNA
<213> ORGANISM: Artificial Sequence
<220> FEATURE:
<223> OTHER INFORMATION: synthesized

<400> SEQUENCE: 19
agcacucugu cuucuuugcu                                                 20

<210> SEQ ID NO 20
<211> LENGTH: 20
<212> TYPE: RNA
<213> ORGANISM: Artificial Sequence
<220> FEATURE:
<223> OTHER INFORMATION: synthesized

<400> SEQUENCE: 20
cacucugucu ucuuugcuag                                                 20

<210> SEQ ID NO 21
<211> LENGTH: 20
<212> TYPE: RNA
<213> ORGANISM: Artificial Sequence
<220> FEATURE:
<223> OTHER INFORMATION: synthesized

<400> SEQUENCE: 21
cuccacuucu cuagcaaaga                                                 20

<210> SEQ ID NO 22
<211> LENGTH: 20
<212> TYPE: RNA
<213> ORGANISM: Artificial Sequence
<220> FEATURE:
<223> OTHER INFORMATION: synthesized

<400> SEQUENCE: 22
cucuccacuu cucuagcaaa                                                 20

<210> SEQ ID NO 23
<211> LENGTH: 20
<212> TYPE: RNA
<213> ORGANISM: Artificial Sequence
<220> FEATURE:
<223> OTHER INFORMATION: synthesized

<400> SEQUENCE: 23
cuucuuugcu agagaagugg                                               20

<210> SEQ ID NO 24
<211> LENGTH: 20
<212> TYPE: RNA
<213> ORGANISM: Artificial Sequence
<220> FEATURE:
<223> OTHER INFORMATION: synthesized

<400> SEQUENCE: 24
cuuugcuaga gaaguggaga                                               20

<210> SEQ ID NO 25
<211> LENGTH: 20
<212> TYPE: RNA
<213> ORGANISM: Artificial Sequence
<220> FEATURE:
<223> OTHER INFORMATION: synthesized

<400> SEQUENCE: 25
gucuucuuug cuagagaagu                                               20

<210> SEQ ID NO 26
<211> LENGTH: 20
<212> TYPE: RNA
<213> ORGANISM: Artificial Sequence
<220> FEATURE:
<223> OTHER INFORMATION: synthesized

<400> SEQUENCE: 26
ucucuccacu ucucuagcaa                                               20

<210> SEQ ID NO 27
<211> LENGTH: 20
<212> TYPE: RNA
<213> ORGANISM: Artificial Sequence
<220> FEATURE:
<223> OTHER INFORMATION: synthesized

<400> SEQUENCE: 27
ucugucuucu uugcuagaga                                               20

<210> SEQ ID NO 28
<211> LENGTH: 20
<212> TYPE: RNA
<213> ORGANISM: Artificial Sequence
<220> FEATURE:
<223> OTHER INFORMATION: synthesized

<400> SEQUENCE: 28
ucuuugcuag agaaguggag                                               20

<210> SEQ ID NO 29
<211> LENGTH: 20
<212> TYPE: RNA
<213> ORGANISM: Artificial Sequence
<220> FEATURE:
<223> OTHER INFORMATION: synthesized

```
<400> SEQUENCE: 29
ugucuucuuu gcuagagaag                                          20

<210> SEQ ID NO 30
<211> LENGTH: 20
<212> TYPE: RNA
<213> ORGANISM: Artificial Sequence
<220> FEATURE:
<223> OTHER INFORMATION: synthesized

<400> SEQUENCE: 30
uucucuagca aagaagacag                                          20

<210> SEQ ID NO 31
<211> LENGTH: 20
<212> TYPE: RNA
<213> ORGANISM: Artificial Sequence
<220> FEATURE:
<223> OTHER INFORMATION: synthesized

<400> SEQUENCE: 31
agguaagagg acuaguuaga                                          20

<210> SEQ ID NO 32
<211> LENGTH: 20
<212> TYPE: RNA
<213> ORGANISM: Artificial Sequence
<220> FEATURE:
<223> OTHER INFORMATION: synthesized

<400> SEQUENCE: 32
cccucauucc agaguuucuc                                          20

<210> SEQ ID NO 33
<211> LENGTH: 20
<212> TYPE: RNA
<213> ORGANISM: Artificial Sequence
<220> FEATURE:
<223> OTHER INFORMATION: synthesized

<400> SEQUENCE: 33
cucauuccag aguuucucug                                          20

<210> SEQ ID NO 34
<211> LENGTH: 20
<212> TYPE: RNA
<213> ORGANISM: Artificial Sequence
<220> FEATURE:
<223> OTHER INFORMATION: synthesized

<400> SEQUENCE: 34
auaagugggu uccagagaug                                          20

<210> SEQ ID NO 35
<211> LENGTH: 20
<212> TYPE: RNA
<213> ORGANISM: Artificial Sequence
<220> FEATURE:
<223> OTHER INFORMATION: synthesized

<400> SEQUENCE: 35
gcauaagugg guuccagaga                                          20

<210> SEQ ID NO 36
```

```
<211> LENGTH: 20
<212> TYPE: RNA
<213> ORGANISM: Artificial Sequence
<220> FEATURE:
<223> OTHER INFORMATION: synthesized

<400> SEQUENCE: 36
gggagggcag ccaggcaacu                                          20

<210> SEQ ID NO 37
<211> LENGTH: 20
<212> TYPE: RNA
<213> ORGANISM: Artificial Sequence
<220> FEATURE:
<223> OTHER INFORMATION: synthesized

<400> SEQUENCE: 37
ccucucuccu uccuucuuug                                          20

<210> SEQ ID NO 38
<211> LENGTH: 20
<212> TYPE: RNA
<213> ORGANISM: Artificial Sequence
<220> FEATURE:
<223> OTHER INFORMATION: synthesized

<400> SEQUENCE: 38
cucucuccuu ccuucuuuga                                          20

<210> SEQ ID NO 39
<211> LENGTH: 20
<212> TYPE: RNA
<213> ORGANISM: Artificial Sequence
<220> FEATURE:
<223> OTHER INFORMATION: synthesized

<400> SEQUENCE: 39
ucucuccuuc cuucuuugag                                          20

<210> SEQ ID NO 40
<211> LENGTH: 20
<212> TYPE: RNA
<213> ORGANISM: Artificial Sequence
<220> FEATURE:
<223> OTHER INFORMATION: synthesized

<400> SEQUENCE: 40
cauuaguggg ugaacagaca                                          20

<210> SEQ ID NO 41
<211> LENGTH: 20
<212> TYPE: RNA
<213> ORGANISM: Artificial Sequence
<220> FEATURE:
<223> OTHER INFORMATION: synthesized

<400> SEQUENCE: 41
cugggagcuc uggaccugga                                          20

<210> SEQ ID NO 42
<211> LENGTH: 20
<212> TYPE: RNA
<213> ORGANISM: Artificial Sequence
<220> FEATURE:
<223> OTHER INFORMATION: synthesized

<400> SEQUENCE: 42
```
cacaaagcuu ccugaggcca                                              20

<210> SEQ ID NO 43
<211> LENGTH: 20
<212> TYPE: RNA
<213> ORGANISM: Artificial Sequence
<220> FEATURE:
<223> OTHER INFORMATION: synthesized

<400> SEQUENCE: 43
auugaauagu uaccuacaua                                              20

<210> SEQ ID NO 44
<211> LENGTH: 20
<212> TYPE: RNA
<213> ORGANISM: Artificial Sequence
<220> FEATURE:
<223> OTHER INFORMATION: synthesized

<400> SEQUENCE: 44
auuaugauuu ugggugguau                                              20

<210> SEQ ID NO 45
<211> LENGTH: 20
<212> TYPE: RNA
<213> ORGANISM: Artificial Sequence
<220> FEATURE:
<223> OTHER INFORMATION: synthesized

<400> SEQUENCE: 45
auugguuuga gaacuucucu                                              20

<210> SEQ ID NO 46
<211> LENGTH: 20
<212> TYPE: RNA
<213> ORGANISM: Artificial Sequence
<220> FEATURE:
<223> OTHER INFORMATION: synthesized

<400> SEQUENCE: 46
cauuaugauu uuggguggua                                              20

<210> SEQ ID NO 47
<211> LENGTH: 20
<212> TYPE: RNA
<213> ORGANISM: Artificial Sequence
<220> FEATURE:
<223> OTHER INFORMATION: synthesized

<400> SEQUENCE: 47
aaaaagaaaa agccaaugca                                              20

<210> SEQ ID NO 48
<211> LENGTH: 20
<212> TYPE: RNA
<213> ORGANISM: Artificial Sequence
<220> FEATURE:
<223> OTHER INFORMATION: synthesized

<400> SEQUENCE: 48
ucaaaaagaa aaagccaaug                                              20

<210> SEQ ID NO 49
<211> LENGTH: 20
<212> TYPE: RNA

```
<213> ORGANISM: Artificial Sequence
<220> FEATURE:
<223> OTHER INFORMATION: synthesized

<400> SEQUENCE: 49
uugcuuaaau uauaaucugc                                              20

<210> SEQ ID NO 50
<211> LENGTH: 20
<212> TYPE: RNA
<213> ORGANISM: Artificial Sequence
<220> FEATURE:
<223> OTHER INFORMATION: synthesized

<400> SEQUENCE: 50
augagggucc acuuagccau                                              20

<210> SEQ ID NO 51
<211> LENGTH: 20
<212> TYPE: RNA
<213> ORGANISM: Artificial Sequence
<220> FEATURE:
<223> OTHER INFORMATION: synthesized

<400> SEQUENCE: 51
aggagaguuu gucagugaga                                              20

<210> SEQ ID NO 52
<211> LENGTH: 20
<212> TYPE: RNA
<213> ORGANISM: Artificial Sequence
<220> FEATURE:
<223> OTHER INFORMATION: synthesized

<400> SEQUENCE: 52
ccagauucug agccccuaga                                              20

<210> SEQ ID NO 53
<211> LENGTH: 20
<212> TYPE: RNA
<213> ORGANISM: Artificial Sequence
<220> FEATURE:
<223> OTHER INFORMATION: synthesized

<400> SEQUENCE: 53
ggagaguuug ucagugagac                                              20

<210> SEQ ID NO 54
<211> LENGTH: 20
<212> TYPE: RNA
<213> ORGANISM: Artificial Sequence
<220> FEATURE:
<223> OTHER INFORMATION: synthesized

<400> SEQUENCE: 54
ccuuccuuuu cccucuacuc                                              20

<210> SEQ ID NO 55
<211> LENGTH: 20
<212> TYPE: RNA
<213> ORGANISM: Artificial Sequence
<220> FEATURE:
<223> OTHER INFORMATION: synthesized

<400> SEQUENCE: 55
ggucccagau guccuuguuu                                              20
```

<210> SEQ ID NO 56
<211> LENGTH: 20
<212> TYPE: RNA
<213> ORGANISM: Artificial Sequence
<220> FEATURE:
<223> OTHER INFORMATION: synthesized

<400> SEQUENCE: 56
ccuucccucu gaugcuagag                                               20

<210> SEQ ID NO 57
<211> LENGTH: 20
<212> TYPE: RNA
<213> ORGANISM: Artificial Sequence
<220> FEATURE:
<223> OTHER INFORMATION: synthesized

<400> SEQUENCE: 57
uccuucccuc ugaugcuaga                                               20

<210> SEQ ID NO 58
<211> LENGTH: 20
<212> TYPE: RNA
<213> ORGANISM: Artificial Sequence
<220> FEATURE:
<223> OTHER INFORMATION: synthesized

<400> SEQUENCE: 58
uucccucuga ugcuagaggg                                               20

<210> SEQ ID NO 59
<211> LENGTH: 20
<212> TYPE: RNA
<213> ORGANISM: Artificial Sequence
<220> FEATURE:
<223> OTHER INFORMATION: synthesized

<400> SEQUENCE: 59
acuaagucuu ggguucuuug                                               20

<210> SEQ ID NO 60
<211> LENGTH: 20
<212> TYPE: RNA
<213> ORGANISM: Artificial Sequence
<220> FEATURE:
<223> OTHER INFORMATION: synthesized

<400> SEQUENCE: 60
aucagguacc cugcaaaaug                                               20

<210> SEQ ID NO 61
<211> LENGTH: 20
<212> TYPE: RNA
<213> ORGANISM: Artificial Sequence
<220> FEATURE:
<223> OTHER INFORMATION: synthesized

<400> SEQUENCE: 61
uaagucuugg guucuuugcu                                               20

<210> SEQ ID NO 62
<211> LENGTH: 20
<212> TYPE: RNA
<213> ORGANISM: Artificial Sequence
<220> FEATURE:

<223> OTHER INFORMATION: synthesized

<400> SEQUENCE: 62
gccaacuuau cuggaagaga                                          20

<210> SEQ ID NO 63
<211> LENGTH: 20
<212> TYPE: RNA
<213> ORGANISM: Artificial Sequence
<220> FEATURE:
<223> OTHER INFORMATION: synthesized

<400> SEQUENCE: 63
uaagccaacu uaucuggaag                                          20

<210> SEQ ID NO 64
<211> LENGTH: 20
<212> TYPE: RNA
<213> ORGANISM: Artificial Sequence
<220> FEATURE:
<223> OTHER INFORMATION: synthesized

<400> SEQUENCE: 64
cugagucuag gggcucagaa                                          20

<210> SEQ ID NO 65
<211> LENGTH: 20
<212> TYPE: RNA
<213> ORGANISM: Artificial Sequence
<220> FEATURE:
<223> OTHER INFORMATION: synthesized

<400> SEQUENCE: 65
cugugucuag gggcucagaa                                          20

<210> SEQ ID NO 66
<211> LENGTH: 20
<212> TYPE: RNA
<213> ORGANISM: Artificial Sequence
<220> FEATURE:
<223> OTHER INFORMATION: synthesized

<400> SEQUENCE: 66
gagacugagu cuaggggcuc                                          20

<210> SEQ ID NO 67
<211> LENGTH: 20
<212> TYPE: RNA
<213> ORGANISM: Artificial Sequence
<220> FEATURE:
<223> OTHER INFORMATION: synthesized

<400> SEQUENCE: 67
gagacugugu cuaggggcuc                                          20

<210> SEQ ID NO 68
<211> LENGTH: 20
<212> TYPE: RNA
<213> ORGANISM: Artificial Sequence
<220> FEATURE:
<223> OTHER INFORMATION: synthesized

<400> SEQUENCE: 68
gagccccuag acacagucuc                                          20

```
<210> SEQ ID NO 69
<211> LENGTH: 20
<212> TYPE: RNA
<213> ORGANISM: Artificial Sequence
<220> FEATURE:
<223> OTHER INFORMATION: synthesized

<400> SEQUENCE: 69
gagccccuag acucagucuc                                               20

<210> SEQ ID NO 70
<211> LENGTH: 20
<212> TYPE: RNA
<213> ORGANISM: Artificial Sequence
<220> FEATURE:
<223> OTHER INFORMATION: synthesized

<400> SEQUENCE: 70
gagucuaggg gcucagaauc                                               20

<210> SEQ ID NO 71
<211> LENGTH: 20
<212> TYPE: RNA
<213> ORGANISM: Artificial Sequence
<220> FEATURE:
<223> OTHER INFORMATION: synthesized

<400> SEQUENCE: 71
gccccuagac acagucucac                                               20

<210> SEQ ID NO 72
<211> LENGTH: 20
<212> TYPE: RNA
<213> ORGANISM: Artificial Sequence
<220> FEATURE:
<223> OTHER INFORMATION: synthesized

<400> SEQUENCE: 72
gccccuagac ucagucucac                                               20

<210> SEQ ID NO 73
<211> LENGTH: 20
<212> TYPE: RNA
<213> ORGANISM: Artificial Sequence
<220> FEATURE:
<223> OTHER INFORMATION: synthesized

<400> SEQUENCE: 73
gucagugaga cugagucuag                                               20

<210> SEQ ID NO 74
<211> LENGTH: 20
<212> TYPE: RNA
<213> ORGANISM: Artificial Sequence
<220> FEATURE:
<223> OTHER INFORMATION: synthesized

<400> SEQUENCE: 74
gucagugaga cugugucuag                                               20

<210> SEQ ID NO 75
<211> LENGTH: 20
<212> TYPE: RNA
<213> ORGANISM: Artificial Sequence
<220> FEATURE:
<223> OTHER INFORMATION: synthesized
```

```
<400> SEQUENCE: 75
gugucuaggg gcucagaauc                                          20

<210> SEQ ID NO 76
<211> LENGTH: 20
<212> TYPE: RNA
<213> ORGANISM: Artificial Sequence
<220> FEATURE:
<223> OTHER INFORMATION: synthesized

<400> SEQUENCE: 76
ugagacugag ucuaggggcu                                          20

<210> SEQ ID NO 77
<211> LENGTH: 20
<212> TYPE: RNA
<213> ORGANISM: Artificial Sequence
<220> FEATURE:
<223> OTHER INFORMATION: synthesized

<400> SEQUENCE: 77
ugagacugug ucuaggggcu                                          20

<210> SEQ ID NO 78
<211> LENGTH: 20
<212> TYPE: RNA
<213> ORGANISM: Artificial Sequence
<220> FEATURE:
<223> OTHER INFORMATION: synthesized

<400> SEQUENCE: 78
ugucagugag acugagucua                                          20

<210> SEQ ID NO 79
<211> LENGTH: 20
<212> TYPE: RNA
<213> ORGANISM: Artificial Sequence
<220> FEATURE:
<223> OTHER INFORMATION: synthesized

<400> SEQUENCE: 79
ugucagugag acugugucua                                          20

<210> SEQ ID NO 80
<211> LENGTH: 20
<212> TYPE: RNA
<213> ORGANISM: Artificial Sequence
<220> FEATURE:
<223> OTHER INFORMATION: synthesized

<400> SEQUENCE: 80
uugucaguga gacugagucu                                          20

<210> SEQ ID NO 81
<211> LENGTH: 20
<212> TYPE: RNA
<213> ORGANISM: Artificial Sequence
<220> FEATURE:
<223> OTHER INFORMATION: synthesized

<400> SEQUENCE: 81
uugucaguga gacugugucu                                          20

<210> SEQ ID NO 82
<211> LENGTH: 20
```

```
<212> TYPE: RNA
<213> ORGANISM: Artificial Sequence
<220> FEATURE:
<223> OTHER INFORMATION: synthesized

<400> SEQUENCE: 82
aaagacaaau acugcuuagc                                               20

<210> SEQ ID NO 83
<211> LENGTH: 20
<212> TYPE: RNA
<213> ORGANISM: Artificial Sequence
<220> FEATURE:
<223> OTHER INFORMATION: synthesized

<400> SEQUENCE: 83
aaaugagcag auauagaaag                                               20

<210> SEQ ID NO 84
<211> LENGTH: 20
<212> TYPE: RNA
<213> ORGANISM: Artificial Sequence
<220> FEATURE:
<223> OTHER INFORMATION: synthesized

<400> SEQUENCE: 84
aaaugagcag auauagacag                                               20

<210> SEQ ID NO 85
<211> LENGTH: 20
<212> TYPE: RNA
<213> ORGANISM: Artificial Sequence
<220> FEATURE:
<223> OTHER INFORMATION: synthesized

<400> SEQUENCE: 85
acaauaagcg uaucuuuaaa                                               20

<210> SEQ ID NO 86
<211> LENGTH: 20
<212> TYPE: RNA
<213> ORGANISM: Artificial Sequence
<220> FEATURE:
<223> OTHER INFORMATION: synthesized

<400> SEQUENCE: 86
acaauaaggg uaucuuuaaa                                               20

<210> SEQ ID NO 87
<211> LENGTH: 20
<212> TYPE: RNA
<213> ORGANISM: Artificial Sequence
<220> FEATURE:
<223> OTHER INFORMATION: synthesized

<400> SEQUENCE: 87
acagacaaau acugcuuagc                                               20

<210> SEQ ID NO 88
<211> LENGTH: 20
<212> TYPE: RNA
<213> ORGANISM: Artificial Sequence
<220> FEATURE:
<223> OTHER INFORMATION: synthesized

<400> SEQUENCE: 88
```
acauuuaaag auacccuuau                                                          20

<210> SEQ ID NO 89
<211> LENGTH: 20
<212> TYPE: RNA
<213> ORGANISM: Artificial Sequence
<220> FEATURE:
<223> OTHER INFORMATION: synthesized

<400> SEQUENCE: 89
acauuuaaag auacgcuuau                                                          20

<210> SEQ ID NO 90
<211> LENGTH: 20
<212> TYPE: RNA
<213> ORGANISM: Artificial Sequence
<220> FEATURE:
<223> OTHER INFORMATION: synthesized

<400> SEQUENCE: 90
acuucaaaaa gauagauaua                                                          20

<210> SEQ ID NO 91
<211> LENGTH: 20
<212> TYPE: RNA
<213> ORGANISM: Artificial Sequence
<220> FEATURE:
<223> OTHER INFORMATION: synthesized

<400> SEQUENCE: 91
acuucaaaag gauagauaua                                                          20

<210> SEQ ID NO 92
<211> LENGTH: 20
<212> TYPE: RNA
<213> ORGANISM: Artificial Sequence
<220> FEATURE:
<223> OTHER INFORMATION: synthesized

<400> SEQUENCE: 92
agaaagacaa auacugcuua                                                          20

<210> SEQ ID NO 93
<211> LENGTH: 20
<212> TYPE: RNA
<213> ORGANISM: Artificial Sequence
<220> FEATURE:
<223> OTHER INFORMATION: synthesized

<400> SEQUENCE: 93
agacagacaa auacugcuua                                                          20

<210> SEQ ID NO 94
<211> LENGTH: 20
<212> TYPE: RNA
<213> ORGANISM: Artificial Sequence
<220> FEATURE:
<223> OTHER INFORMATION: synthesized

<400> SEQUENCE: 94
aucuauccuu uugaaguuaa                                                          20

<210> SEQ ID NO 95
<211> LENGTH: 20
<212> TYPE: RNA
<213> ORGANISM: Artificial Sequence

```
<220> FEATURE:
<223> OTHER INFORMATION: synthesized

<400> SEQUENCE: 95
aucuaucuuu uugaaguuaa                                          20

<210> SEQ ID NO 96
<211> LENGTH: 20
<212> TYPE: RNA
<213> ORGANISM: Artificial Sequence
<220> FEATURE:
<223> OTHER INFORMATION: synthesized

<400> SEQUENCE: 96
auuacauuaa cuucaaaaag                                          20

<210> SEQ ID NO 97
<211> LENGTH: 20
<212> TYPE: RNA
<213> ORGANISM: Artificial Sequence
<220> FEATURE:
<223> OTHER INFORMATION: synthesized

<400> SEQUENCE: 97
auuacauuaa cuucaaaagg                                          20

<210> SEQ ID NO 98
<211> LENGTH: 20
<212> TYPE: RNA
<213> ORGANISM: Artificial Sequence
<220> FEATURE:
<223> OTHER INFORMATION: synthesized

<400> SEQUENCE: 98
ccuuuugaag uuaauguaau                                          20

<210> SEQ ID NO 99
<211> LENGTH: 20
<212> TYPE: RNA
<213> ORGANISM: Artificial Sequence
<220> FEATURE:
<223> OTHER INFORMATION: synthesized

<400> SEQUENCE: 99
cuuuuugaag uuaauguaau                                          20

<210> SEQ ID NO 100
<211> LENGTH: 20
<212> TYPE: RNA
<213> ORGANISM: Artificial Sequence
<220> FEATURE:
<223> OTHER INFORMATION: synthesized

<400> SEQUENCE: 100
guuugauaua ucuauccuuu                                          20

<210> SEQ ID NO 101
<211> LENGTH: 20
<212> TYPE: RNA
<213> ORGANISM: Artificial Sequence
<220> FEATURE:
<223> OTHER INFORMATION: synthesized

<400> SEQUENCE: 101
guuugauaua ucuaucuuuu                                          20
```

<210> SEQ ID NO 102
<211> LENGTH: 20
<212> TYPE: RNA
<213> ORGANISM: Artificial Sequence
<220> FEATURE:
<223> OTHER INFORMATION: synthesized

<400> SEQUENCE: 102
uacauuaacu ucaaaaagau                                           20

<210> SEQ ID NO 103
<211> LENGTH: 20
<212> TYPE: RNA
<213> ORGANISM: Artificial Sequence
<220> FEATURE:
<223> OTHER INFORMATION: synthesized

<400> SEQUENCE: 103
uacauuaacu ucaaaaggau                                           20

<210> SEQ ID NO 104
<211> LENGTH: 20
<212> TYPE: RNA
<213> ORGANISM: Artificial Sequence
<220> FEATURE:
<223> OTHER INFORMATION: synthesized

<400> SEQUENCE: 104
ugaaaugagc agauauagaa                                           20

<210> SEQ ID NO 105
<211> LENGTH: 20
<212> TYPE: RNA
<213> ORGANISM: Artificial Sequence
<220> FEATURE:
<223> OTHER INFORMATION: synthesized

<400> SEQUENCE: 105
ugaaaugagc agauauagac                                           20

<210> SEQ ID NO 106
<211> LENGTH: 20
<212> TYPE: RNA
<213> ORGANISM: Artificial Sequence
<220> FEATURE:
<223> OTHER INFORMATION: synthesized

<400> SEQUENCE: 106
uucaaaaaga uagauauauc                                           20

<210> SEQ ID NO 107
<211> LENGTH: 20
<212> TYPE: RNA
<213> ORGANISM: Artificial Sequence
<220> FEATURE:
<223> OTHER INFORMATION: synthesized

<400> SEQUENCE: 107
uucaaaagga uagauauauc                                           20

<210> SEQ ID NO 108
<211> LENGTH: 20
<212> TYPE: RNA
<213> ORGANISM: Artificial Sequence
<220> FEATURE:
<223> OTHER INFORMATION: synthesized

<400> SEQUENCE: 108
acugaauguu uacuaagucu                                           20

<210> SEQ ID NO 109
<211> LENGTH: 20
<212> TYPE: RNA
<213> ORGANISM: Artificial Sequence
<220> FEATURE:
<223> OTHER INFORMATION: synthesized

<400> SEQUENCE: 109
auugaauguu uacuaagucu                                           20

<210> SEQ ID NO 110
<211> LENGTH: 20
<212> TYPE: RNA
<213> ORGANISM: Artificial Sequence
<220> FEATURE:
<223> OTHER INFORMATION: synthesized

<400> SEQUENCE: 110
cugaauguuu acuaagucuu                                           20

<210> SEQ ID NO 111
<211> LENGTH: 20
<212> TYPE: RNA
<213> ORGANISM: Artificial Sequence
<220> FEATURE:
<223> OTHER INFORMATION: synthesized

<400> SEQUENCE: 111
gaguaauagc uaauguguac                                           20

<210> SEQ ID NO 112
<211> LENGTH: 20
<212> TYPE: RNA
<213> ORGANISM: Artificial Sequence
<220> FEATURE:
<223> OTHER INFORMATION: synthesized

<400> SEQUENCE: 112
gaguaauagc uaauguguau                                           20

<210> SEQ ID NO 113
<211> LENGTH: 20
<212> TYPE: RNA
<213> ORGANISM: Artificial Sequence
<220> FEATURE:
<223> OTHER INFORMATION: synthesized

<400> SEQUENCE: 113
uaauguguac ugaauguuua                                           20

<210> SEQ ID NO 114
<211> LENGTH: 20
<212> TYPE: RNA
<213> ORGANISM: Artificial Sequence
<220> FEATURE:
<223> OTHER INFORMATION: synthesized

<400> SEQUENCE: 114
uaauguguau ugaauguuua                                           20

<210> SEQ ID NO 115

```
<211> LENGTH: 20
<212> TYPE: RNA
<213> ORGANISM: Artificial Sequence
<220> FEATURE:
<223> OTHER INFORMATION: synthesized

<400> SEQUENCE: 115
uugaauguuu acuaagucuu                                               20

<210> SEQ ID NO 116
<211> LENGTH: 20
<212> TYPE: RNA
<213> ORGANISM: Artificial Sequence
<220> FEATURE:
<223> OTHER INFORMATION: synthesized

<400> SEQUENCE: 116
agcaauccuu ucuuucagcu                                               20

<210> SEQ ID NO 117
<211> LENGTH: 20
<212> TYPE: RNA
<213> ORGANISM: Artificial Sequence
<220> FEATURE:
<223> OTHER INFORMATION: synthesized

<400> SEQUENCE: 117
cagcaauccu uucuuucagc                                               20

<210> SEQ ID NO 118
<211> LENGTH: 20
<212> TYPE: RNA
<213> ORGANISM: Artificial Sequence
<220> FEATURE:
<223> OTHER INFORMATION: synthesized

<400> SEQUENCE: 118
cggcaauccu uucuuucagc                                               20

<210> SEQ ID NO 119
<211> LENGTH: 20
<212> TYPE: RNA
<213> ORGANISM: Artificial Sequence
<220> FEATURE:
<223> OTHER INFORMATION: synthesized

<400> SEQUENCE: 119
ggauugccgc cacuccuagu                                               20

<210> SEQ ID NO 120
<211> LENGTH: 20
<212> TYPE: RNA
<213> ORGANISM: Artificial Sequence
<220> FEATURE:
<223> OTHER INFORMATION: synthesized

<400> SEQUENCE: 120
ggauugcugc cacuccuagu                                               20

<210> SEQ ID NO 121
<211> LENGTH: 20
<212> TYPE: RNA
<213> ORGANISM: Artificial Sequence
<220> FEATURE:
<223> OTHER INFORMATION: synthesized

<400> SEQUENCE: 121
```

```
ggcaauccuu ucuuucagcu                                          20

<210> SEQ ID NO 122
<211> LENGTH: 20
<212> TYPE: RNA
<213> ORGANISM: Artificial Sequence
<220> FEATURE:
<223> OTHER INFORMATION: synthesized

<400> SEQUENCE: 122
accuggaagu acuggaagcu                                          20

<210> SEQ ID NO 123
<211> LENGTH: 20
<212> TYPE: RNA
<213> ORGANISM: Artificial Sequence
<220> FEATURE:
<223> OTHER INFORMATION: synthesized

<400> SEQUENCE: 123
accuggaagu gcuggaagcu                                          20

<210> SEQ ID NO 124
<211> LENGTH: 20
<212> TYPE: RNA
<213> ORGANISM: Artificial Sequence
<220> FEATURE:
<223> OTHER INFORMATION: synthesized

<400> SEQUENCE: 124
agcucuggac cuggaaguac                                          20

<210> SEQ ID NO 125
<211> LENGTH: 20
<212> TYPE: RNA
<213> ORGANISM: Artificial Sequence
<220> FEATURE:
<223> OTHER INFORMATION: synthesized

<400> SEQUENCE: 125
agcucuggac cuggaagugc                                          20

<210> SEQ ID NO 126
<211> LENGTH: 20
<212> TYPE: RNA
<213> ORGANISM: Artificial Sequence
<220> FEATURE:
<223> OTHER INFORMATION: synthesized

<400> SEQUENCE: 126
aguacuggaa gcuggaacuc                                          20

<210> SEQ ID NO 127
<211> LENGTH: 20
<212> TYPE: RNA
<213> ORGANISM: Artificial Sequence
<220> FEATURE:
<223> OTHER INFORMATION: synthesized

<400> SEQUENCE: 127
agugcuggaa gcuggaacuc                                          20

<210> SEQ ID NO 128
<211> LENGTH: 20
<212> TYPE: RNA
```

```
<213> ORGANISM: Artificial Sequence
<220> FEATURE:
<223> OTHER INFORMATION: synthesized

<400> SEQUENCE: 128
aguuccagcu uccagcacuu                                              20

<210> SEQ ID NO 129
<211> LENGTH: 20
<212> TYPE: RNA
<213> ORGANISM: Artificial Sequence
<220> FEATURE:
<223> OTHER INFORMATION: synthesized

<400> SEQUENCE: 129
aguuccagcu uccaguacuu                                              20

<210> SEQ ID NO 130
<211> LENGTH: 20
<212> TYPE: RNA
<213> ORGANISM: Artificial Sequence
<220> FEATURE:
<223> OTHER INFORMATION: synthesized

<400> SEQUENCE: 130
cuuccagcac uuccaggucc                                              20

<210> SEQ ID NO 131
<211> LENGTH: 20
<212> TYPE: RNA
<213> ORGANISM: Artificial Sequence
<220> FEATURE:
<223> OTHER INFORMATION: synthesized

<400> SEQUENCE: 131
cuuccaguac uuccaggucc                                              20

<210> SEQ ID NO 132
<211> LENGTH: 20
<212> TYPE: RNA
<213> ORGANISM: Artificial Sequence
<220> FEATURE:
<223> OTHER INFORMATION: synthesized

<400> SEQUENCE: 132
gaccuggaag uacuggaagc                                              20

<210> SEQ ID NO 133
<211> LENGTH: 20
<212> TYPE: RNA
<213> ORGANISM: Artificial Sequence
<220> FEATURE:
<223> OTHER INFORMATION: synthesized

<400> SEQUENCE: 133
gaccuggaag ugcuggaagc                                              20

<210> SEQ ID NO 134
<211> LENGTH: 20
<212> TYPE: RNA
<213> ORGANISM: Artificial Sequence
<220> FEATURE:
<223> OTHER INFORMATION: synthesized

<400> SEQUENCE: 134
gcucuggacc uggaaguacu                                              20
```

```
<210> SEQ ID NO 135
<211> LENGTH: 20
<212> TYPE: RNA
<213> ORGANISM: Artificial Sequence
<220> FEATURE:
<223> OTHER INFORMATION: synthesized

<400> SEQUENCE: 135
gcucuggacc uggaagugcu                                                   20

<210> SEQ ID NO 136
<211> LENGTH: 20
<212> TYPE: RNA
<213> ORGANISM: Artificial Sequence
<220> FEATURE:
<223> OTHER INFORMATION: synthesized

<400> SEQUENCE: 136
guacuggaag cuggaacucu                                                   20

<210> SEQ ID NO 137
<211> LENGTH: 20
<212> TYPE: RNA
<213> ORGANISM: Artificial Sequence
<220> FEATURE:
<223> OTHER INFORMATION: synthesized

<400> SEQUENCE: 137
gugcuggaag cuggaacucu                                                   20

<210> SEQ ID NO 138
<211> LENGTH: 20
<212> TYPE: RNA
<213> ORGANISM: Artificial Sequence
<220> FEATURE:
<223> OTHER INFORMATION: synthesized

<400> SEQUENCE: 138
uacuggaagc uggaacucug                                                   20

<210> SEQ ID NO 139
<211> LENGTH: 20
<212> TYPE: RNA
<213> ORGANISM: Artificial Sequence
<220> FEATURE:
<223> OTHER INFORMATION: synthesized

<400> SEQUENCE: 139
ugcuggaagc uggaacucug                                                   20

<210> SEQ ID NO 140
<211> LENGTH: 20
<212> TYPE: RNA
<213> ORGANISM: Artificial Sequence
<220> FEATURE:
<223> OTHER INFORMATION: synthesized

<400> SEQUENCE: 140
uuccagcuuc cagcacuucc                                                   20

<210> SEQ ID NO 141
<211> LENGTH: 20
<212> TYPE: RNA
<213> ORGANISM: Artificial Sequence
<220> FEATURE:
```

<223> OTHER INFORMATION: synthesized

<400> SEQUENCE: 141
uuccagcuuc caguacuucc                                               20

<210> SEQ ID NO 142
<211> LENGTH: 20
<212> TYPE: RNA
<213> ORGANISM: Artificial Sequence
<220> FEATURE:
<223> OTHER INFORMATION: synthesized

<400> SEQUENCE: 142
aguccuugug ccuuggccuc                                               20

<210> SEQ ID NO 143
<211> LENGTH: 20
<212> TYPE: RNA
<213> ORGANISM: Artificial Sequence
<220> FEATURE:
<223> OTHER INFORMATION: synthesized

<400> SEQUENCE: 143
aguccuugug ucuuggccuc                                               20

<210> SEQ ID NO 144
<211> LENGTH: 20
<212> TYPE: RNA
<213> ORGANISM: Artificial Sequence
<220> FEATURE:
<223> OTHER INFORMATION: synthesized

<400> SEQUENCE: 144
auuugugcca guccuugugc                                               20

<210> SEQ ID NO 145
<211> LENGTH: 20
<212> TYPE: RNA
<213> ORGANISM: Artificial Sequence
<220> FEATURE:
<223> OTHER INFORMATION: synthesized

<400> SEQUENCE: 145
auuugugcca guccuugugu                                               20

<210> SEQ ID NO 146
<211> LENGTH: 20
<212> TYPE: RNA
<213> ORGANISM: Artificial Sequence
<220> FEATURE:
<223> OTHER INFORMATION: synthesized

<400> SEQUENCE: 146
ccugaggcca agacacaagg                                               20

<210> SEQ ID NO 147
<211> LENGTH: 20
<212> TYPE: RNA
<213> ORGANISM: Artificial Sequence
<220> FEATURE:
<223> OTHER INFORMATION: synthesized

<400> SEQUENCE: 147
ccugaggcca aggcacaagg                                               20

```
<210> SEQ ID NO 148
<211> LENGTH: 20
<212> TYPE: RNA
<213> ORGANISM: Artificial Sequence
<220> FEATURE:
<223> OTHER INFORMATION: synthesized

<400> SEQUENCE: 148
cuuccugagg ccaagacaca                                               20

<210> SEQ ID NO 149
<211> LENGTH: 20
<212> TYPE: RNA
<213> ORGANISM: Artificial Sequence
<220> FEATURE:
<223> OTHER INFORMATION: synthesized

<400> SEQUENCE: 149
cuuccugagg ccaaggcaca                                               20

<210> SEQ ID NO 150
<211> LENGTH: 20
<212> TYPE: RNA
<213> ORGANISM: Artificial Sequence
<220> FEATURE:
<223> OTHER INFORMATION: synthesized

<400> SEQUENCE: 150
gccuuggccu caggaagcuu                                               20

<210> SEQ ID NO 151
<211> LENGTH: 20
<212> TYPE: RNA
<213> ORGANISM: Artificial Sequence
<220> FEATURE:
<223> OTHER INFORMATION: synthesized

<400> SEQUENCE: 151
guccuugugc cuuggccuca                                               20

<210> SEQ ID NO 152
<211> LENGTH: 20
<212> TYPE: RNA
<213> ORGANISM: Artificial Sequence
<220> FEATURE:
<223> OTHER INFORMATION: synthesized

<400> SEQUENCE: 152
guccuugugu cuuggccuca                                               20

<210> SEQ ID NO 153
<211> LENGTH: 20
<212> TYPE: RNA
<213> ORGANISM: Artificial Sequence
<220> FEATURE:
<223> OTHER INFORMATION: synthesized

<400> SEQUENCE: 153
gucuuggccu caggaagcuu                                               20

<210> SEQ ID NO 154
<211> LENGTH: 20
<212> TYPE: RNA
<213> ORGANISM: Artificial Sequence
<220> FEATURE:
<223> OTHER INFORMATION: synthesized
```

```
<400> SEQUENCE: 154
ugaggccaag acacaaggac                                               20

<210> SEQ ID NO 155
<211> LENGTH: 20
<212> TYPE: RNA
<213> ORGANISM: Artificial Sequence
<220> FEATURE:
<223> OTHER INFORMATION: synthesized

<400> SEQUENCE: 155
ugaggccaag gcacaaggac                                               20

<210> SEQ ID NO 156
<211> LENGTH: 20
<212> TYPE: RNA
<213> ORGANISM: Artificial Sequence
<220> FEATURE:
<223> OTHER INFORMATION: synthesized

<400> SEQUENCE: 156
uuccugaggc caagacacaa                                               20

<210> SEQ ID NO 157
<211> LENGTH: 20
<212> TYPE: RNA
<213> ORGANISM: Artificial Sequence
<220> FEATURE:
<223> OTHER INFORMATION: synthesized

<400> SEQUENCE: 157
uuccugaggc caaggcacaa                                               20

<210> SEQ ID NO 158
<211> LENGTH: 20
<212> TYPE: RNA
<213> ORGANISM: Artificial Sequence
<220> FEATURE:
<223> OTHER INFORMATION: synthesized

<400> SEQUENCE: 158
uugugccagu ccuugugccu                                               20

<210> SEQ ID NO 159
<211> LENGTH: 20
<212> TYPE: RNA
<213> ORGANISM: Artificial Sequence
<220> FEATURE:
<223> OTHER INFORMATION: synthesized

<400> SEQUENCE: 159
uugugccagu ccuugugucu                                               20

<210> SEQ ID NO 160
<211> LENGTH: 20
<212> TYPE: RNA
<213> ORGANISM: Artificial Sequence
<220> FEATURE:
<223> OTHER INFORMATION: synthesized

<400> SEQUENCE: 160
cuacauaaca aauaaagaaa                                               20

<210> SEQ ID NO 161
<211> LENGTH: 20
```

```
<212> TYPE: RNA
<213> ORGANISM: Artificial Sequence
<220> FEATURE:
<223> OTHER INFORMATION: synthesized

<400> SEQUENCE: 161
cuacauagca aauaaagaaa                                               20

<210> SEQ ID NO 162
<211> LENGTH: 20
<212> TYPE: RNA
<213> ORGANISM: Artificial Sequence
<220> FEATURE:
<223> OTHER INFORMATION: synthesized

<400> SEQUENCE: 162 cuuucuuua uuugcuaugu                                                20

<210> SEQ ID NO 163
<211> LENGTH: 20
<212> TYPE: RNA
<213> ORGANISM: Artificial Sequence
<220> FEATURE:
<223> OTHER INFORMATION: synthesized

<400> SEQUENCE: 163 cuuucuuua uuuguuaugu                                                20

<210> SEQ ID NO 164
<211> LENGTH: 20
<212> TYPE: RNA
<213> ORGANISM: Artificial Sequence
<220> FEATURE:
<223> OTHER INFORMATION: synthesized

<400> SEQUENCE: 164
guuaccuaca uaacaaauaa                                               20

<210> SEQ ID NO 165
<211> LENGTH: 20
<212> TYPE: RNA
<213> ORGANISM: Artificial Sequence
<220> FEATURE:
<223> OTHER INFORMATION: synthesized

<400> SEQUENCE: 165
guuaccuaca uagcaaauaa                                               20

<210> SEQ ID NO 166
<211> LENGTH: 20
<212> TYPE: RNA
<213> ORGANISM: Artificial Sequence
<220> FEATURE:
<223> OTHER INFORMATION: synthesized

<400> SEQUENCE: 166
uacauagcaa auaaagaaaa                                               20

<210> SEQ ID NO 167
<211> LENGTH: 20
<212> TYPE: RNA
<213> ORGANISM: Artificial Sequence
<220> FEATURE:
<223> OTHER INFORMATION: synthesized

<400> SEQUENCE: 167
```
uccuuuucuu uauuugcuau                                                    20

<210> SEQ ID NO 168
<211> LENGTH: 20
<212> TYPE: RNA
<213> ORGANISM: Artificial Sequence
<220> FEATURE:
<223> OTHER INFORMATION: synthesized

<400> SEQUENCE: 168
uccuuuucuu uauuuguuau                                                    20

<210> SEQ ID NO 169
<211> LENGTH: 20
<212> TYPE: RNA
<213> ORGANISM: Artificial Sequence
<220> FEATURE:
<223> OTHER INFORMATION: synthesized

<400> SEQUENCE: 169
acuucucuuc ccauaccacc                                                    20

<210> SEQ ID NO 170
<211> LENGTH: 20
<212> TYPE: RNA
<213> ORGANISM: Artificial Sequence
<220> FEATURE:
<223> OTHER INFORMATION: synthesized

<400> SEQUENCE: 170
acuucucuuc cuauaccacc                                                    20

<210> SEQ ID NO 171
<211> LENGTH: 20
<212> TYPE: RNA
<213> ORGANISM: Artificial Sequence
<220> FEATURE:
<223> OTHER INFORMATION: synthesized

<400> SEQUENCE: 171
auaggaagag aaguucucaa                                                    20

<210> SEQ ID NO 172
<211> LENGTH: 20
<212> TYPE: RNA
<213> ORGANISM: Artificial Sequence
<220> FEATURE:
<223> OTHER INFORMATION: synthesized

<400> SEQUENCE: 172
augggaagag aaguucucaa                                                    20

<210> SEQ ID NO 173
<211> LENGTH: 20
<212> TYPE: RNA
<213> ORGANISM: Artificial Sequence
<220> FEATURE:
<223> OTHER INFORMATION: synthesized

<400> SEQUENCE: 173
auuuugggug guauaggaag                                                    20

<210> SEQ ID NO 174
<211> LENGTH: 20
<212> TYPE: RNA
<213> ORGANISM: Artificial Sequence

```
<220> FEATURE:
<223> OTHER INFORMATION: synthesized

<400> SEQUENCE: 174
auuuugggug guaugggaag                                               20

<210> SEQ ID NO 175
<211> LENGTH: 20
<212> TYPE: RNA
<213> ORGANISM: Artificial Sequence
<220> FEATURE:
<223> OTHER INFORMATION: synthesized

<400> SEQUENCE: 175
ucucuuccca uaccacccaa                                               20

<210> SEQ ID NO 176
<211> LENGTH: 20
<212> TYPE: RNA
<213> ORGANISM: Artificial Sequence
<220> FEATURE:
<223> OTHER INFORMATION: synthesized

<400> SEQUENCE: 176
ucucuuccua uaccacccaa                                               20

<210> SEQ ID NO 177
<211> LENGTH: 20
<212> TYPE: RNA
<213> ORGANISM: Artificial Sequence
<220> FEATURE:
<223> OTHER INFORMATION: synthesized

<400> SEQUENCE: 177 ugauuuggg ugguauagga                                                20

<210> SEQ ID NO 178
<211> LENGTH: 20
<212> TYPE: RNA
<213> ORGANISM: Artificial Sequence
<220> FEATURE:
<223> OTHER INFORMATION: synthesized

<400> SEQUENCE: 178 ugauuuggg ugguauggga                                                20

<210> SEQ ID NO 179
<211> LENGTH: 20
<212> TYPE: RNA
<213> ORGANISM: Artificial Sequence
<220> FEATURE:
<223> OTHER INFORMATION: synthesized

<400> SEQUENCE: 179
ugguauagga agagaaguuc                                               20

<210> SEQ ID NO 180
<211> LENGTH: 20
<212> TYPE: RNA
<213> ORGANISM: Artificial Sequence
<220> FEATURE:
<223> OTHER INFORMATION: synthesized

<400> SEQUENCE: 180
ugguauggga agagaaguuc                                               20
```

<210> SEQ ID NO 181
<211> LENGTH: 20
<212> TYPE: RNA
<213> ORGANISM: Artificial Sequence
<220> FEATURE:
<223> OTHER INFORMATION: synthesized

<400> SEQUENCE: 181
uuaugauuuu ggguggauaua                                              20

<210> SEQ ID NO 182
<211> LENGTH: 20
<212> TYPE: RNA
<213> ORGANISM: Artificial Sequence
<220> FEATURE:
<223> OTHER INFORMATION: synthesized

<400> SEQUENCE: 182
uuaugauuuu ggguggauaug                                              20

<210> SEQ ID NO 183
<211> LENGTH: 20
<212> TYPE: RNA
<213> ORGANISM: Artificial Sequence
<220> FEATURE:
<223> OTHER INFORMATION: synthesized

<400> SEQUENCE: 183
uuugagaacu ucucuuccca                                               20

<210> SEQ ID NO 184
<211> LENGTH: 20
<212> TYPE: RNA
<213> ORGANISM: Artificial Sequence
<220> FEATURE:
<223> OTHER INFORMATION: synthesized

<400> SEQUENCE: 184
uuugagaacu ucucuuccua                                               20

<210> SEQ ID NO 185
<211> LENGTH: 20
<212> TYPE: RNA
<213> ORGANISM: Artificial Sequence
<220> FEATURE:
<223> OTHER INFORMATION: synthesized

<400> SEQUENCE: 185
aaaagaaaaa gccaaugcac                                               20

<210> SEQ ID NO 186
<211> LENGTH: 20
<212> TYPE: RNA
<213> ORGANISM: Artificial Sequence
<220> FEATURE:
<223> OTHER INFORMATION: synthesized

<400> SEQUENCE: 186
aaaagaaaaa gccaaugcau                                               20

<210> SEQ ID NO 187
<211> LENGTH: 20
<212> TYPE: RNA
<213> ORGANISM: Artificial Sequence
<220> FEATURE:
<223> OTHER INFORMATION: synthesized

```
<400> SEQUENCE: 187
aaugcacggc agauuauaau                                              20

<210> SEQ ID NO 188
<211> LENGTH: 20
<212> TYPE: RNA
<213> ORGANISM: Artificial Sequence
<220> FEATURE:
<223> OTHER INFORMATION: synthesized

<400> SEQUENCE: 188
aaugcauggc agauuauaau                                              20

<210> SEQ ID NO 189
<211> LENGTH: 20
<212> TYPE: RNA
<213> ORGANISM: Artificial Sequence
<220> FEATURE:
<223> OTHER INFORMATION: synthesized

<400> SEQUENCE: 189
aauuauaauc ugccaugcau                                              20

<210> SEQ ID NO 190
<211> LENGTH: 20
<212> TYPE: RNA
<213> ORGANISM: Artificial Sequence
<220> FEATURE:
<223> OTHER INFORMATION: synthesized

<400> SEQUENCE: 190
aauuauaauc ugccgugcau                                              20

<210> SEQ ID NO 191
<211> LENGTH: 20
<212> TYPE: RNA
<213> ORGANISM: Artificial Sequence
<220> FEATURE:
<223> OTHER INFORMATION: synthesized

<400> SEQUENCE: 191
agaaaaagcc aaugcacggc                                              20

<210> SEQ ID NO 192
<211> LENGTH: 20
<212> TYPE: RNA
<213> ORGANISM: Artificial Sequence
<220> FEATURE:
<223> OTHER INFORMATION: synthesized

<400> SEQUENCE: 192
agaaaaagcc aaugcauggc                                              20

<210> SEQ ID NO 193
<211> LENGTH: 20
<212> TYPE: RNA
<213> ORGANISM: Artificial Sequence
<220> FEATURE:
<223> OTHER INFORMATION: synthesized

<400> SEQUENCE: 193 augcauggc uuuuucuuuu                                               20

<210> SEQ ID NO 194
```

```
<211> LENGTH: 20
<212> TYPE: RNA
<213> ORGANISM: Artificial Sequence
<220> FEATURE:
<223> OTHER INFORMATION: synthesized

<400> SEQUENCE: 194
gugcauuggc uuuuucuuuu                                            20

<210> SEQ ID NO 195
<211> LENGTH: 20
<212> TYPE: RNA
<213> ORGANISM: Artificial Sequence
<220> FEATURE:
<223> OTHER INFORMATION: synthesized

<400> SEQUENCE: 195
aauuaggugc caggaaauug                                            20

<210> SEQ ID NO 196
<211> LENGTH: 20
<212> TYPE: RNA
<213> ORGANISM: Artificial Sequence
<220> FEATURE:
<223> OTHER INFORMATION: synthesized

<400> SEQUENCE: 196
auuuccuggc accuaaucua                                            20

<210> SEQ ID NO 197
<211> LENGTH: 20
<212> TYPE: RNA
<213> ORGANISM: Artificial Sequence
<220> FEATURE:
<223> OTHER INFORMATION: synthesized

<400> SEQUENCE: 197
auuuccuggc accuaauuua                                            20

<210> SEQ ID NO 198
<211> LENGTH: 20
<212> TYPE: RNA
<213> ORGANISM: Artificial Sequence
<220> FEATURE:
<223> OTHER INFORMATION: synthesized

<400> SEQUENCE: 198
caccuaaucu auggcuaagu                                            20

<210> SEQ ID NO 199
<211> LENGTH: 20
<212> TYPE: RNA
<213> ORGANISM: Artificial Sequence
<220> FEATURE:
<223> OTHER INFORMATION: synthesized

<400> SEQUENCE: 199
caccuaauuu auggcuaagu                                            20

<210> SEQ ID NO 200
<211> LENGTH: 20
<212> TYPE: RNA
<213> ORGANISM: Artificial Sequence
<220> FEATURE:
<223> OTHER INFORMATION: synthesized

<400> SEQUENCE: 200
```

```
gauuaggugc caggaaauug                                              20

<210> SEQ ID NO 201
<211> LENGTH: 20
<212> TYPE: RNA
<213> ORGANISM: Artificial Sequence
<220> FEATURE:
<223> OTHER INFORMATION: synthesized

<400> SEQUENCE: 201
gcaccuaauc uauggcuaag                                              20

<210> SEQ ID NO 202
<211> LENGTH: 20
<212> TYPE: RNA
<213> ORGANISM: Artificial Sequence
<220> FEATURE:
<223> OTHER INFORMATION: synthesized

<400> SEQUENCE: 202
gcaccuaauu uauggcuaag                                              20

<210> SEQ ID NO 203
<211> LENGTH: 20
<212> TYPE: RNA
<213> ORGANISM: Artificial Sequence
<220> FEATURE:
<223> OTHER INFORMATION: synthesized

<400> SEQUENCE: 203
ggcaccuaau cuauggcuaa                                              20

<210> SEQ ID NO 204
<211> LENGTH: 20
<212> TYPE: RNA
<213> ORGANISM: Artificial Sequence
<220> FEATURE:
<223> OTHER INFORMATION: synthesized

<400> SEQUENCE: 204
ggcaccuaau uuauggcuaa                                              20

<210> SEQ ID NO 205
<211> LENGTH: 20
<212> TYPE: RNA
<213> ORGANISM: Artificial Sequence
<220> FEATURE:
<223> OTHER INFORMATION: synthesized

<400> SEQUENCE: 205
gguccacuua gccauaaauu                                              20

<210> SEQ ID NO 206
<211> LENGTH: 20
<212> TYPE: RNA
<213> ORGANISM: Artificial Sequence
<220> FEATURE:
<223> OTHER INFORMATION: synthesized

<400> SEQUENCE: 206
gguccacuua gccauagauu                                              20

<210> SEQ ID NO 207
<211> LENGTH: 20
<212> TYPE: RNA
```

```
<213> ORGANISM: Artificial Sequence
<220> FEATURE:
<223> OTHER INFORMATION: synthesized

<400> SEQUENCE: 207
guccacuuag ccauaaauua                                               20

<210> SEQ ID NO 208
<211> LENGTH: 20
<212> TYPE: RNA
<213> ORGANISM: Artificial Sequence
<220> FEATURE:
<223> OTHER INFORMATION: synthesized

<400> SEQUENCE: 208
guccacuuag ccauagauua                                               20

<210> SEQ ID NO 209
<211> LENGTH: 20
<212> TYPE: RNA
<213> ORGANISM: Artificial Sequence
<220> FEATURE:
<223> OTHER INFORMATION: synthesized

<400> SEQUENCE: 209
uaaauuaggu gccaggaaau                                               20

<210> SEQ ID NO 210
<211> LENGTH: 20
<212> TYPE: RNA
<213> ORGANISM: Artificial Sequence
<220> FEATURE:
<223> OTHER INFORMATION: synthesized

<400> SEQUENCE: 210
uagauuaggu gccaggaaau                                               20

<210> SEQ ID NO 211
<211> LENGTH: 20
<212> TYPE: RNA
<213> ORGANISM: Artificial Sequence
<220> FEATURE:
<223> OTHER INFORMATION: synthesized

<400> SEQUENCE: 211
uagccauaaa uuaggugcca                                               20

<210> SEQ ID NO 212
<211> LENGTH: 20
<212> TYPE: RNA
<213> ORGANISM: Artificial Sequence
<220> FEATURE:
<223> OTHER INFORMATION: synthesized

<400> SEQUENCE: 212
uagccauaga uuaggugcca                                               20

<210> SEQ ID NO 213
<211> LENGTH: 20
<212> TYPE: RNA
<213> ORGANISM: Artificial Sequence
<220> FEATURE:
<223> OTHER INFORMATION: synthesized

<400> SEQUENCE: 213
uggcaccuaa ucuauggcua                                               20
```

-continued

```
<210> SEQ ID NO 214
<211> LENGTH: 20
<212> TYPE: RNA
<213> ORGANISM: Artificial Sequence
<220> FEATURE:
<223> OTHER INFORMATION: synthesized

<400> SEQUENCE: 214
uggcaccuaa uuuauggcua                                              20

<210> SEQ ID NO 215
<211> LENGTH: 20
<212> TYPE: RNA
<213> ORGANISM: Artificial Sequence
<220> FEATURE:
<223> OTHER INFORMATION: synthesized

<400> SEQUENCE: 215
uuagccauaa auuaggugcc                                              20

<210> SEQ ID NO 216
<211> LENGTH: 20
<212> TYPE: RNA
<213> ORGANISM: Artificial Sequence
<220> FEATURE:
<223> OTHER INFORMATION: synthesized

<400> SEQUENCE: 216
uuagccauag auuaggugcc                                              20

<210> SEQ ID NO 217
<211> LENGTH: 20
<212> TYPE: RNA
<213> ORGANISM: Artificial Sequence
<220> FEATURE:
<223> OTHER INFORMATION: synthesized

<400> SEQUENCE: 217
aaaacaagga caucugggac                                              20

<210> SEQ ID NO 218
<211> LENGTH: 20
<212> TYPE: RNA
<213> ORGANISM: Artificial Sequence
<220> FEATURE:
<223> OTHER INFORMATION: synthesized

<400> SEQUENCE: 218
acucaaaaac aaggacaucu                                              20

<210> SEQ ID NO 219
<211> LENGTH: 20
<212> TYPE: RNA
<213> ORGANISM: Artificial Sequence
<220> FEATURE:
<223> OTHER INFORMATION: synthesized

<400> SEQUENCE: 219
acucagaaac aaggacaucu                                              20

<210> SEQ ID NO 220
<211> LENGTH: 20
<212> TYPE: RNA
<213> ORGANISM: Artificial Sequence
<220> FEATURE:
```

<223> OTHER INFORMATION: synthesized

<400> SEQUENCE: 220
agauguccuu guuucugagu                                          20

<210> SEQ ID NO 221
<211> LENGTH: 20
<212> TYPE: RNA
<213> ORGANISM: Artificial Sequence
<220> FEATURE:
<223> OTHER INFORMATION: synthesized

<400> SEQUENCE: 221
agauguccuu guuuuugagu                                          20

<210> SEQ ID NO 222
<211> LENGTH: 20
<212> TYPE: RNA
<213> ORGANISM: Artificial Sequence
<220> FEATURE:
<223> OTHER INFORMATION: synthesized

<400> SEQUENCE: 222
auguccuugu uucugaguag                                          20

<210> SEQ ID NO 223
<211> LENGTH: 20
<212> TYPE: RNA
<213> ORGANISM: Artificial Sequence
<220> FEATURE:
<223> OTHER INFORMATION: synthesized

<400> SEQUENCE: 223
auguccuugu uuuugaguag                                          20

<210> SEQ ID NO 224
<211> LENGTH: 20
<212> TYPE: RNA
<213> ORGANISM: Artificial Sequence
<220> FEATURE:
<223> OTHER INFORMATION: synthesized

<400> SEQUENCE: 224
cucaaaaaca aggacaucug                                          20

<210> SEQ ID NO 225
<211> LENGTH: 20
<212> TYPE: RNA
<213> ORGANISM: Artificial Sequence
<220> FEATURE:
<223> OTHER INFORMATION: synthesized

<400> SEQUENCE: 225
cucagaaaca aggacaucug                                          20

<210> SEQ ID NO 226
<211> LENGTH: 20
<212> TYPE: RNA
<213> ORGANISM: Artificial Sequence
<220> FEATURE:
<223> OTHER INFORMATION: synthesized

<400> SEQUENCE: 226
cugaguagag ggaaaaggaa                                          20

```
<210> SEQ ID NO 227
<211> LENGTH: 20
<212> TYPE: RNA
<213> ORGANISM: Artificial Sequence
<220> FEATURE:
<223> OTHER INFORMATION: synthesized

<400> SEQUENCE: 227
gaaacaagga caucugggac                                                    20

<210> SEQ ID NO 228
<211> LENGTH: 20
<212> TYPE: RNA
<213> ORGANISM: Artificial Sequence
<220> FEATURE:
<223> OTHER INFORMATION: synthesized

<400> SEQUENCE: 228
gucccagaug uccuuguuuc                                                    20

<210> SEQ ID NO 229
<211> LENGTH: 20
<212> TYPE: RNA
<213> ORGANISM: Artificial Sequence
<220> FEATURE:
<223> OTHER INFORMATION: synthesized

<400> SEQUENCE: 229
gucccagaug uccuuguuuu                                                    20

<210> SEQ ID NO 230
<211> LENGTH: 20
<212> TYPE: RNA
<213> ORGANISM: Artificial Sequence
<220> FEATURE:
<223> OTHER INFORMATION: synthesized

<400> SEQUENCE: 230
guccuuguuu cugaguagag                                                    20

<210> SEQ ID NO 231
<211> LENGTH: 20
<212> TYPE: RNA
<213> ORGANISM: Artificial Sequence
<220> FEATURE:
<223> OTHER INFORMATION: synthesized

<400> SEQUENCE: 231
guccuuguuu uugaguagag                                                    20

<210> SEQ ID NO 232
<211> LENGTH: 20
<212> TYPE: RNA
<213> ORGANISM: Artificial Sequence
<220> FEATURE:
<223> OTHER INFORMATION: synthesized

<400> SEQUENCE: 232
guuucugagu agagggaaaa                                                    20

<210> SEQ ID NO 233
<211> LENGTH: 20
<212> TYPE: RNA
<213> ORGANISM: Artificial Sequence
<220> FEATURE:
<223> OTHER INFORMATION: synthesized
```

```
<400> SEQUENCE: 233
guuuuugagu agagggaaaa                                              20

<210> SEQ ID NO 234
<211> LENGTH: 20
<212> TYPE: RNA
<213> ORGANISM: Artificial Sequence
<220> FEATURE:
<223> OTHER INFORMATION: synthesized

<400> SEQUENCE: 234
uacucaaaaa caaggacauc                                              20

<210> SEQ ID NO 235
<211> LENGTH: 20
<212> TYPE: RNA
<213> ORGANISM: Artificial Sequence
<220> FEATURE:
<223> OTHER INFORMATION: synthesized

<400> SEQUENCE: 235
uacucagaaa caaggacauc                                              20

<210> SEQ ID NO 236
<211> LENGTH: 20
<212> TYPE: RNA
<213> ORGANISM: Artificial Sequence
<220> FEATURE:
<223> OTHER INFORMATION: synthesized

<400> SEQUENCE: 236
ucaaaaacaa ggacaucugg                                              20

<210> SEQ ID NO 237
<211> LENGTH: 20
<212> TYPE: RNA
<213> ORGANISM: Artificial Sequence
<220> FEATURE:
<223> OTHER INFORMATION: synthesized

<400> SEQUENCE: 237
ucagaaacaa ggacaucugg                                              20

<210> SEQ ID NO 238
<211> LENGTH: 20
<212> TYPE: RNA
<213> ORGANISM: Artificial Sequence
<220> FEATURE:
<223> OTHER INFORMATION: synthesized

<400> SEQUENCE: 238
ucugaguaga gggaaaagga                                              20

<210> SEQ ID NO 239
<211> LENGTH: 20
<212> TYPE: RNA
<213> ORGANISM: Artificial Sequence
<220> FEATURE:
<223> OTHER INFORMATION: synthesized

<400> SEQUENCE: 239
uguccuuguu ucugaguaga                                              20

<210> SEQ ID NO 240
<211> LENGTH: 20
```

```
<212> TYPE: RNA
<213> ORGANISM: Artificial Sequence
<220> FEATURE:
<223> OTHER INFORMATION: synthesized

<400> SEQUENCE: 240
uguccuuguu uuugaguaga                                              20

<210> SEQ ID NO 241
<211> LENGTH: 20
<212> TYPE: RNA
<213> ORGANISM: Artificial Sequence
<220> FEATURE:
<223> OTHER INFORMATION: synthesized

<400> SEQUENCE: 241
uguuucugag uagagggaaa                                              20

<210> SEQ ID NO 242
<211> LENGTH: 20
<212> TYPE: RNA
<213> ORGANISM: Artificial Sequence
<220> FEATURE:
<223> OTHER INFORMATION: synthesized

<400> SEQUENCE: 242 uguuuugag uagagggaaa                                               20

<210> SEQ ID NO 243
<211> LENGTH: 20
<212> TYPE: RNA
<213> ORGANISM: Artificial Sequence
<220> FEATURE:
<223> OTHER INFORMATION: synthesized

<400> SEQUENCE: 243
uucccucuac ucaaaaacaa                                              20

<210> SEQ ID NO 244
<211> LENGTH: 20
<212> TYPE: RNA
<213> ORGANISM: Artificial Sequence
<220> FEATURE:
<223> OTHER INFORMATION: synthesized

<400> SEQUENCE: 244
uucccucuac ucagaaacaa                                              20

<210> SEQ ID NO 245
<211> LENGTH: 20
<212> TYPE: RNA
<213> ORGANISM: Artificial Sequence
<220> FEATURE:
<223> OTHER INFORMATION: synthesized

<400> SEQUENCE: 245
uugaguagag ggaaaaggaa                                              20

<210> SEQ ID NO 246
<211> LENGTH: 20
<212> TYPE: RNA
<213> ORGANISM: Artificial Sequence
<220> FEATURE:
<223> OTHER INFORMATION: synthesized

<400> SEQUENCE: 246
```
uuucccucua cucaaaaaca                                                    20

<210> SEQ ID NO 247
<211> LENGTH: 20
<212> TYPE: RNA
<213> ORGANISM: Artificial Sequence
<220> FEATURE:
<223> OTHER INFORMATION: synthesized

<400> SEQUENCE: 247
uuucccucua cucagaaaca                                                    20

<210> SEQ ID NO 248
<211> LENGTH: 20
<212> TYPE: RNA
<213> ORGANISM: Artificial Sequence
<220> FEATURE:
<223> OTHER INFORMATION: synthesized

<400> SEQUENCE: 248
uuucugagua gagggaaaag                                                    20

<210> SEQ ID NO 249
<211> LENGTH: 20
<212> TYPE: RNA
<213> ORGANISM: Artificial Sequence
<220> FEATURE:
<223> OTHER INFORMATION: synthesized

<400> SEQUENCE: 249
uuugaguaga gggaaaagga                                                    20

<210> SEQ ID NO 250
<211> LENGTH: 20
<212> TYPE: RNA
<213> ORGANISM: Artificial Sequence
<220> FEATURE:
<223> OTHER INFORMATION: synthesized

<400> SEQUENCE: 250
uuuucccucu acucaaaaac                                                    20

<210> SEQ ID NO 251
<211> LENGTH: 20
<212> TYPE: RNA
<213> ORGANISM: Artificial Sequence
<220> FEATURE:
<223> OTHER INFORMATION: synthesized

<400> SEQUENCE: 251
uuuucccucu acucagaaac                                                    20

<210> SEQ ID NO 252
<211> LENGTH: 20
<212> TYPE: RNA
<213> ORGANISM: Artificial Sequence
<220> FEATURE:
<223> OTHER INFORMATION: synthesized

<400> SEQUENCE: 252
acgcaguacc uuauaacucc                                                    20

<210> SEQ ID NO 253
<211> LENGTH: 20
<212> TYPE: RNA
<213> ORGANISM: Artificial Sequence

```
<220> FEATURE:
<223> OTHER INFORMATION: synthesized

<400> SEQUENCE: 253
acugcaugga aaaaccaagc                                                     20

<210> SEQ ID NO 254
<211> LENGTH: 20
<212> TYPE: RNA
<213> ORGANISM: Artificial Sequence
<220> FEATURE:
<223> OTHER INFORMATION: synthesized

<400> SEQUENCE: 254
acugcgugga aaaccaagc                                                      20

<210> SEQ ID NO 255
<211> LENGTH: 20
<212> TYPE: RNA
<213> ORGANISM: Artificial Sequence
<220> FEATURE:
<223> OTHER INFORMATION: synthesized

<400> SEQUENCE: 255
aggaguuaua agguacugca                                                     20

<210> SEQ ID NO 256
<211> LENGTH: 20
<212> TYPE: RNA
<213> ORGANISM: Artificial Sequence
<220> FEATURE:
<223> OTHER INFORMATION: synthesized

<400> SEQUENCE: 256
aggaguuaua agguacugcg                                                     20

<210> SEQ ID NO 257
<211> LENGTH: 20
<212> TYPE: RNA
<213> ORGANISM: Artificial Sequence
<220> FEATURE:
<223> OTHER INFORMATION: synthesized

<400> SEQUENCE: 257
aguuauaagg uacugcaugg                                                     20

<210> SEQ ID NO 258
<211> LENGTH: 20
<212> TYPE: RNA
<213> ORGANISM: Artificial Sequence
<220> FEATURE:
<223> OTHER INFORMATION: synthesized

<400> SEQUENCE: 258
aguuauaagg uacugcgugg                                                     20

<210> SEQ ID NO 259
<211> LENGTH: 20
<212> TYPE: RNA
<213> ORGANISM: Artificial Sequence
<220> FEATURE:
<223> OTHER INFORMATION: synthesized

<400> SEQUENCE: 259
augcaguacc uuauaacucc                                                     20
```

```
<210> SEQ ID NO 260
<211> LENGTH: 20
<212> TYPE: RNA
<213> ORGANISM: Artificial Sequence
<220> FEATURE:
<223> OTHER INFORMATION: synthesized

<400> SEQUENCE: 260
cacgcaguac cuuauaacuc                                              20

<210> SEQ ID NO 261
<211> LENGTH: 20
<212> TYPE: RNA
<213> ORGANISM: Artificial Sequence
<220> FEATURE:
<223> OTHER INFORMATION: synthesized

<400> SEQUENCE: 261
caugcaguac cuuauaacuc                                              20

<210> SEQ ID NO 262
<211> LENGTH: 20
<212> TYPE: RNA
<213> ORGANISM: Artificial Sequence
<220> FEATURE:
<223> OTHER INFORMATION: synthesized

<400> SEQUENCE: 262
cgcaguaccu uauaacuccu                                              20

<210> SEQ ID NO 263
<211> LENGTH: 20
<212> TYPE: RNA
<213> ORGANISM: Artificial Sequence
<220> FEATURE:
<223> OTHER INFORMATION: synthesized

<400> SEQUENCE: 263
ggaguuauaa gguacugcau                                              20

<210> SEQ ID NO 264
<211> LENGTH: 20
<212> TYPE: RNA
<213> ORGANISM: Artificial Sequence
<220> FEATURE:
<223> OTHER INFORMATION: synthesized

<400> SEQUENCE: 264
ggaguuauaa gguacugcgu                                              20

<210> SEQ ID NO 265
<211> LENGTH: 20
<212> TYPE: RNA
<213> ORGANISM: Artificial Sequence
<220> FEATURE:
<223> OTHER INFORMATION: synthesized

<400> SEQUENCE: 265
uaagguacug cauggaaaaa                                              20

<210> SEQ ID NO 266
<211> LENGTH: 20
<212> TYPE: RNA
<213> ORGANISM: Artificial Sequence
<220> FEATURE:
<223> OTHER INFORMATION: synthesized
```

```
<400> SEQUENCE: 266
uaagguacug cguggaaaaa                                                    20

<210> SEQ ID NO 267
<211> LENGTH: 20
<212> TYPE: RNA
<213> ORGANISM: Artificial Sequence
<220> FEATURE:
<223> OTHER INFORMATION: synthesized

<400> SEQUENCE: 267
uacugcaugg aaaaaccaag                                                    20

<210> SEQ ID NO 268
<211> LENGTH: 20
<212> TYPE: RNA
<213> ORGANISM: Artificial Sequence
<220> FEATURE:
<223> OTHER INFORMATION: synthesized

<400> SEQUENCE: 268
uacugcgugg aaaaaccaag                                                    20

<210> SEQ ID NO 269
<211> LENGTH: 20
<212> TYPE: RNA
<213> ORGANISM: Artificial Sequence
<220> FEATURE:
<223> OTHER INFORMATION: synthesized

<400> SEQUENCE: 269
ugcaguaccu uauaacuccu                                                    20

<210> SEQ ID NO 270
<211> LENGTH: 20
<212> TYPE: RNA
<213> ORGANISM: Artificial Sequence
<220> FEATURE:
<223> OTHER INFORMATION: synthesized

<400> SEQUENCE: 270
acaagaggcc uaauuuucau                                                    20

<210> SEQ ID NO 271
<211> LENGTH: 20
<212> TYPE: RNA
<213> ORGANISM: Artificial Sequence
<220> FEATURE:
<223> OTHER INFORMATION: synthesized

<400> SEQUENCE: 271
acaaggggcc uaauuuucau                                                    20

<210> SEQ ID NO 272
<211> LENGTH: 20
<212> TYPE: RNA
<213> ORGANISM: Artificial Sequence
<220> FEATURE:
<223> OTHER INFORMATION: synthesized

<400> SEQUENCE: 272
agaggccuaa uuucaugcg                                                     20

<210> SEQ ID NO 273
```

```
<211> LENGTH: 20
<212> TYPE: RNA
<213> ORGANISM: Artificial Sequence
<220> FEATURE:
<223> OTHER INFORMATION: synthesized

<400> SEQUENCE: 273
aggggccuaa uuuucaugcg                                           20

<210> SEQ ID NO 274
<211> LENGTH: 20
<212> TYPE: RNA
<213> ORGANISM: Artificial Sequence
<220> FEATURE:
<223> OTHER INFORMATION: synthesized

<400> SEQUENCE: 274
caagaggccu aauuuucaug                                           20

<210> SEQ ID NO 275
<211> LENGTH: 20
<212> TYPE: RNA
<213> ORGANISM: Artificial Sequence
<220> FEATURE:
<223> OTHER INFORMATION: synthesized

<400> SEQUENCE: 275
caaggggccu aauuuucaug                                           20

<210> SEQ ID NO 276
<211> LENGTH: 20
<212> TYPE: RNA
<213> ORGANISM: Artificial Sequence
<220> FEATURE:
<223> OTHER INFORMATION: synthesized

<400> SEQUENCE: 276
cacaagaggc cuaauuuuca                                           20

<210> SEQ ID NO 277
<211> LENGTH: 20
<212> TYPE: RNA
<213> ORGANISM: Artificial Sequence
<220> FEATURE:
<223> OTHER INFORMATION: synthesized

<400> SEQUENCE: 277
cacaaggggc cuaauuuuca                                           20

<210> SEQ ID NO 278
<211> LENGTH: 20
<212> TYPE: RNA
<213> ORGANISM: Artificial Sequence
<220> FEATURE:
<223> OTHER INFORMATION: synthesized

<400> SEQUENCE: 278
caugaaaauu aggcccccuug                                          20

<210> SEQ ID NO 279
<211> LENGTH: 20
<212> TYPE: RNA
<213> ORGANISM: Artificial Sequence
<220> FEATURE:
<223> OTHER INFORMATION: synthesized

<400> SEQUENCE: 279
```

```
caugaaaauu aggccucuug                                                    20

<210> SEQ ID NO 280
<211> LENGTH: 20
<212> TYPE: RNA
<213> ORGANISM: Artificial Sequence
<220> FEATURE:
<223> OTHER INFORMATION: synthesized

<400> SEQUENCE: 280
ccccuuguga cccaauaggc                                                    20

<210> SEQ ID NO 281
<211> LENGTH: 20
<212> TYPE: RNA
<213> ORGANISM: Artificial Sequence
<220> FEATURE:
<223> OTHER INFORMATION: synthesized

<400> SEQUENCE: 281
ccucuuguga cccaauaggc                                                    20

<210> SEQ ID NO 282
<211> LENGTH: 20
<212> TYPE: RNA
<213> ORGANISM: Artificial Sequence
<220> FEATURE:
<223> OTHER INFORMATION: synthesized

<400> SEQUENCE: 282
cgcaugaaaa uuaggccccu                                                    20

<210> SEQ ID NO 283
<211> LENGTH: 20
<212> TYPE: RNA
<213> ORGANISM: Artificial Sequence
<220> FEATURE:
<223> OTHER INFORMATION: synthesized

<400> SEQUENCE: 283
cgcaugaaaa uuaggccucu                                                    20

<210> SEQ ID NO 284
<211> LENGTH: 20
<212> TYPE: RNA
<213> ORGANISM: Artificial Sequence
<220> FEATURE:
<223> OTHER INFORMATION: synthesized

<400> SEQUENCE: 284
gaaaauuagg ccccuuguga                                                    20

<210> SEQ ID NO 285
<211> LENGTH: 20
<212> TYPE: RNA
<213> ORGANISM: Artificial Sequence
<220> FEATURE:
<223> OTHER INFORMATION: synthesized

<400> SEQUENCE: 285
gaaaauuagg ccucuuguga                                                    20

<210> SEQ ID NO 286
<211> LENGTH: 20
<212> TYPE: RNA
```

```
<213> ORGANISM: Artificial Sequence
<220> FEATURE:
<223> OTHER INFORMATION: synthesized

<400> SEQUENCE: 286
uaggcccuuu gugacccaau                                               20

<210> SEQ ID NO 287
<211> LENGTH: 20
<212> TYPE: RNA
<213> ORGANISM: Artificial Sequence
<220> FEATURE:
<223> OTHER INFORMATION: synthesized

<400> SEQUENCE: 287
uaggccucuu gugacccaau                                               20

<210> SEQ ID NO 288
<211> LENGTH: 20
<212> TYPE: RNA
<213> ORGANISM: Artificial Sequence
<220> FEATURE:
<223> OTHER INFORMATION: synthesized

<400> SEQUENCE: 288
agaggucgca gagaaacucu                                               20

<210> SEQ ID NO 289
<211> LENGTH: 20
<212> TYPE: RNA
<213> ORGANISM: Artificial Sequence
<220> FEATURE:
<223> OTHER INFORMATION: synthesized

<400> SEQUENCE: 289
agagguugca gagaaacucu                                               20

<210> SEQ ID NO 290
<211> LENGTH: 20
<212> TYPE: RNA
<213> ORGANISM: Artificial Sequence
<220> FEATURE:
<223> OTHER INFORMATION: synthesized

<400> SEQUENCE: 290
cgcagagaaa cucuggaaug                                               20

<210> SEQ ID NO 291
<211> LENGTH: 20
<212> TYPE: RNA
<213> ORGANISM: Artificial Sequence
<220> FEATURE:
<223> OTHER INFORMATION: synthesized

<400> SEQUENCE: 291
gaggacuagu uagaggucgc                                               20

<210> SEQ ID NO 292
<211> LENGTH: 20
<212> TYPE: RNA
<213> ORGANISM: Artificial Sequence
<220> FEATURE:
<223> OTHER INFORMATION: synthesized

<400> SEQUENCE: 292
gaggacuagu uagagguugc                                               20
```

<210> SEQ ID NO 293
<211> LENGTH: 20
<212> TYPE: RNA
<213> ORGANISM: Artificial Sequence
<220> FEATURE:
<223> OTHER INFORMATION: synthesized

<400> SEQUENCE: 293
gaguuucucu gcaaccucua                                              20

<210> SEQ ID NO 294
<211> LENGTH: 20
<212> TYPE: RNA
<213> ORGANISM: Artificial Sequence
<220> FEATURE:
<223> OTHER INFORMATION: synthesized

<400> SEQUENCE: 294
gaguuucucu gcgaccucua                                              20

<210> SEQ ID NO 295
<211> LENGTH: 20
<212> TYPE: RNA
<213> ORGANISM: Artificial Sequence
<220> FEATURE:
<223> OTHER INFORMATION: synthesized

<400> SEQUENCE: 295
ggacuaguua gaggucgcag                                              20

<210> SEQ ID NO 296
<211> LENGTH: 20
<212> TYPE: RNA
<213> ORGANISM: Artificial Sequence
<220> FEATURE:
<223> OTHER INFORMATION: synthesized

<400> SEQUENCE: 296
ggacuaguua gagguugcag                                              20

<210> SEQ ID NO 297
<211> LENGTH: 20
<212> TYPE: RNA
<213> ORGANISM: Artificial Sequence
<220> FEATURE:
<223> OTHER INFORMATION: synthesized

<400> SEQUENCE: 297
gucgcagaga aacucuggaa                                              20

<210> SEQ ID NO 298
<211> LENGTH: 20
<212> TYPE: RNA
<213> ORGANISM: Artificial Sequence
<220> FEATURE:
<223> OTHER INFORMATION: synthesized

<400> SEQUENCE: 298
guugcagaga aacucuggaa                                              20

<210> SEQ ID NO 299
<211> LENGTH: 20
<212> TYPE: RNA
<213> ORGANISM: Artificial Sequence
<220> FEATURE:

<223> OTHER INFORMATION: synthesized

<400> SEQUENCE: 299
uagaggucgc agagaaacuc                                            20

<210> SEQ ID NO 300
<211> LENGTH: 20
<212> TYPE: RNA
<213> ORGANISM: Artificial Sequence
<220> FEATURE:
<223> OTHER INFORMATION: synthesized

<400> SEQUENCE: 300
uagagguugc agagaaacuc                                            20

<210> SEQ ID NO 301
<211> LENGTH: 20
<212> TYPE: RNA
<213> ORGANISM: Artificial Sequence
<220> FEATURE:
<223> OTHER INFORMATION: synthesized

<400> SEQUENCE: 301
ucgcagagaa acucuggaau                                            20

<210> SEQ ID NO 302
<211> LENGTH: 20
<212> TYPE: RNA
<213> ORGANISM: Artificial Sequence
<220> FEATURE:
<223> OTHER INFORMATION: synthesized

<400> SEQUENCE: 302
ugcagagaaa cucuggaaug                                            20

<210> SEQ ID NO 303
<211> LENGTH: 20
<212> TYPE: RNA
<213> ORGANISM: Artificial Sequence
<220> FEATURE:
<223> OTHER INFORMATION: synthesized

<400> SEQUENCE: 303
uugcagagaa acucuggaau                                            20

<210> SEQ ID NO 304
<211> LENGTH: 20
<212> TYPE: RNA
<213> ORGANISM: Artificial Sequence
<220> FEATURE:
<223> OTHER INFORMATION: synthesized

<400> SEQUENCE: 304
ccaggcaacu ucacaucucu                                            20

<210> SEQ ID NO 305
<211> LENGTH: 20
<212> TYPE: RNA
<213> ORGANISM: Artificial Sequence
<220> FEATURE:
<223> OTHER INFORMATION: synthesized

<400> SEQUENCE: 305
ccaggcaacu ucgcaucucu                                            20

```
<210> SEQ ID NO 306
<211> LENGTH: 20
<212> TYPE: RNA
<213> ORGANISM: Artificial Sequence
<220> FEATURE:
<223> OTHER INFORMATION: synthesized

<400> SEQUENCE: 306
gccaggcaac uucacaucuc                                              20

<210> SEQ ID NO 307
<211> LENGTH: 20
<212> TYPE: RNA
<213> ORGANISM: Artificial Sequence
<220> FEATURE:
<223> OTHER INFORMATION: synthesized

<400> SEQUENCE: 307
gccaggcaac uucgcaucuc                                              20

<210> SEQ ID NO 308
<211> LENGTH: 20
<212> TYPE: RNA
<213> ORGANISM: Artificial Sequence
<220> FEATURE:
<223> OTHER INFORMATION: synthesized

<400> SEQUENCE: 308
uccagagaug cgaaguugcc                                              20

<210> SEQ ID NO 309
<211> LENGTH: 20
<212> TYPE: RNA
<213> ORGANISM: Artificial Sequence
<220> FEATURE:
<223> OTHER INFORMATION: synthesized

<400> SEQUENCE: 309
uccagagaug ugaaguugcc                                              20

<210> SEQ ID NO 310
<211> LENGTH: 20
<212> TYPE: RNA
<213> ORGANISM: Artificial Sequence
<220> FEATURE:
<223> OTHER INFORMATION: synthesized

<400> SEQUENCE: 310
acugcauuau cccucaaaga                                              20

<210> SEQ ID NO 311
<211> LENGTH: 20
<212> TYPE: RNA
<213> ORGANISM: Artificial Sequence
<220> FEATURE:
<223> OTHER INFORMATION: synthesized

<400> SEQUENCE: 311
acugcauuau cucucaaaga                                              20

<210> SEQ ID NO 312
<211> LENGTH: 20
<212> TYPE: RNA
<213> ORGANISM: Artificial Sequence
<220> FEATURE:
<223> OTHER INFORMATION: synthesized
```

-continued

<400> SEQUENCE: 312
agagauaaug caguuauauc                                                    20

<210> SEQ ID NO 313
<211> LENGTH: 20
<212> TYPE: RNA
<213> ORGANISM: Artificial Sequence
<220> FEATURE:
<223> OTHER INFORMATION: synthesized

<400> SEQUENCE: 313
agggauaaug caguuauauc                                                    20

<210> SEQ ID NO 314
<211> LENGTH: 20
<212> TYPE: RNA
<213> ORGANISM: Artificial Sequence
<220> FEATURE:
<223> OTHER INFORMATION: synthesized

<400> SEQUENCE: 314
auaacugcau uaucccucaa                                                    20

<210> SEQ ID NO 315
<211> LENGTH: 20
<212> TYPE: RNA
<213> ORGANISM: Artificial Sequence
<220> FEATURE:
<223> OTHER INFORMATION: synthesized

<400> SEQUENCE: 315
auaacugcau uaucucucaa                                                    20

<210> SEQ ID NO 316
<211> LENGTH: 20
<212> TYPE: RNA
<213> ORGANISM: Artificial Sequence
<220> FEATURE:
<223> OTHER INFORMATION: synthesized

<400> SEQUENCE: 316
auuaucccuc aaagaaggaa                                                    20

<210> SEQ ID NO 317
<211> LENGTH: 20
<212> TYPE: RNA
<213> ORGANISM: Artificial Sequence
<220> FEATURE:
<223> OTHER INFORMATION: synthesized

<400> SEQUENCE: 317
auuaucucuc aaagaaggaa                                                    20

<210> SEQ ID NO 318
<211> LENGTH: 20
<212> TYPE: RNA
<213> ORGANISM: Artificial Sequence
<220> FEATURE:
<223> OTHER INFORMATION: synthesized

<400> SEQUENCE: 318
cauuaucccu caaagaagga                                                    20

<210> SEQ ID NO 319
<211> LENGTH: 20

```
<212> TYPE: RNA
<213> ORGANISM: Artificial Sequence
<220> FEATURE:
<223> OTHER INFORMATION: synthesized

<400> SEQUENCE: 319
cauuaucucu caaagaagga                                                       20

<210> SEQ ID NO 320
<211> LENGTH: 20
<212> TYPE: RNA
<213> ORGANISM: Artificial Sequence
<220> FEATURE:
<223> OTHER INFORMATION: synthesized

<400> SEQUENCE: 320
ccucaaagaa ggaaggagag                                                       20

<210> SEQ ID NO 321
<211> LENGTH: 20
<212> TYPE: RNA
<213> ORGANISM: Artificial Sequence
<220> FEATURE:
<223> OTHER INFORMATION: synthesized

<400> SEQUENCE: 321
cugcauuauc ccucaaagaa                                                       20

<210> SEQ ID NO 322
<211> LENGTH: 20
<212> TYPE: RNA
<213> ORGANISM: Artificial Sequence
<220> FEATURE:
<223> OTHER INFORMATION: synthesized

<400> SEQUENCE: 322
cugcauuauc ucucaaagaa                                                       20

<210> SEQ ID NO 323
<211> LENGTH: 20
<212> TYPE: RNA
<213> ORGANISM: Artificial Sequence
<220> FEATURE:
<223> OTHER INFORMATION: synthesized

<400> SEQUENCE: 323
gagagauaau gcaguuauau                                                       20

<210> SEQ ID NO 324
<211> LENGTH: 20
<212> TYPE: RNA
<213> ORGANISM: Artificial Sequence
<220> FEATURE:
<223> OTHER INFORMATION: synthesized

<400> SEQUENCE: 324
gagggauaau gcaguuauau                                                       20

<210> SEQ ID NO 325
<211> LENGTH: 20
<212> TYPE: RNA
<213> ORGANISM: Artificial Sequence
<220> FEATURE:
<223> OTHER INFORMATION: synthesized

<400> SEQUENCE: 325
```
uaucccucaa agaaggaagg                                                    20

<210> SEQ ID NO 326
<211> LENGTH: 20
<212> TYPE: RNA
<213> ORGANISM: Artificial Sequence
<220> FEATURE:
<223> OTHER INFORMATION: synthesized

<400> SEQUENCE: 326
uaucucucaa agaaggaagg                                                    20

<210> SEQ ID NO 327
<211> LENGTH: 20
<212> TYPE: RNA
<213> ORGANISM: Artificial Sequence
<220> FEATURE:
<223> OTHER INFORMATION: synthesized

<400> SEQUENCE: 327
ucccucaaag aaggaaggag                                                    20

<210> SEQ ID NO 328
<211> LENGTH: 20
<212> TYPE: RNA
<213> ORGANISM: Artificial Sequence
<220> FEATURE:
<223> OTHER INFORMATION: synthesized

<400> SEQUENCE: 328
ucucaaagaa ggaaggagag                                                    20

<210> SEQ ID NO 329
<211> LENGTH: 20
<212> TYPE: RNA
<213> ORGANISM: Artificial Sequence
<220> FEATURE:
<223> OTHER INFORMATION: synthesized

<400> SEQUENCE: 329
ucucucaaag aaggaaggag                                                    20

<210> SEQ ID NO 330
<211> LENGTH: 20
<212> TYPE: RNA
<213> ORGANISM: Artificial Sequence
<220> FEATURE:
<223> OTHER INFORMATION: synthesized

<400> SEQUENCE: 330
acaggacuuc aguugcaugc                                                    20

<210> SEQ ID NO 331
<211> LENGTH: 20
<212> TYPE: RNA
<213> ORGANISM: Artificial Sequence
<220> FEATURE:
<223> OTHER INFORMATION: synthesized

<400> SEQUENCE: 331
acaggauuuc aguugcaugc                                                    20

<210> SEQ ID NO 332
<211> LENGTH: 20
<212> TYPE: RNA
<213> ORGANISM: Artificial Sequence

```
<220> FEATURE:
<223> OTHER INFORMATION: synthesized

<400> SEQUENCE: 332
acuucaguug caugcucagg                                          20

<210> SEQ ID NO 333
<211> LENGTH: 20
<212> TYPE: RNA
<213> ORGANISM: Artificial Sequence
<220> FEATURE:
<223> OTHER INFORMATION: synthesized

<400> SEQUENCE: 333
aggacuucag uugcaugcuc                                          20

<210> SEQ ID NO 334
<211> LENGTH: 20
<212> TYPE: RNA
<213> ORGANISM: Artificial Sequence
<220> FEATURE:
<223> OTHER INFORMATION: synthesized

<400> SEQUENCE: 334
aggauuucag uugcaugcuc                                          20

<210> SEQ ID NO 335
<211> LENGTH: 20
<212> TYPE: RNA
<213> ORGANISM: Artificial Sequence
<220> FEATURE:
<223> OTHER INFORMATION: synthesized

<400> SEQUENCE: 335
auccugucug uucacccacu                                          20

<210> SEQ ID NO 336
<211> LENGTH: 20
<212> TYPE: RNA
<213> ORGANISM: Artificial Sequence
<220> FEATURE:
<223> OTHER INFORMATION: synthesized

<400> SEQUENCE: 336
augcaacuga aauccugucu                                          20

<210> SEQ ID NO 337
<211> LENGTH: 20
<212> TYPE: RNA
<213> ORGANISM: Artificial Sequence
<220> FEATURE:
<223> OTHER INFORMATION: synthesized

<400> SEQUENCE: 337
augcaacuga aguccugucu                                          20

<210> SEQ ID NO 338
<211> LENGTH: 20
<212> TYPE: RNA
<213> ORGANISM: Artificial Sequence
<220> FEATURE:
<223> OTHER INFORMATION: synthesized

<400> SEQUENCE: 338
auuucaguug caugcucagg                                          20
```

```
<210> SEQ ID NO 339
<211> LENGTH: 20
<212> TYPE: RNA
<213> ORGANISM: Artificial Sequence
<220> FEATURE:
<223> OTHER INFORMATION: synthesized

<400> SEQUENCE: 339
guccugucug uucacccacu                                               20

<210> SEQ ID NO 340
<211> LENGTH: 20
<212> TYPE: RNA
<213> ORGANISM: Artificial Sequence
<220> FEATURE:
<223> OTHER INFORMATION: synthesized

<400> SEQUENCE: 340
caggucagcc ugugagcccc                                               20

<210> SEQ ID NO 341
<211> LENGTH: 20
<212> TYPE: RNA
<213> ORGANISM: Artificial Sequence
<220> FEATURE:
<223> OTHER INFORMATION: synthesized

<400> SEQUENCE: 341
caggucagcc ugugaguccc                                               20

<210> SEQ ID NO 342
<211> LENGTH: 20
<212> TYPE: RNA
<213> ORGANISM: Artificial Sequence
<220> FEATURE:
<223> OTHER INFORMATION: synthesized

<400> SEQUENCE: 342
ccccucuagc aucagaggga                                               20

<210> SEQ ID NO 343
<211> LENGTH: 20
<212> TYPE: RNA
<213> ORGANISM: Artificial Sequence
<220> FEATURE:
<223> OTHER INFORMATION: synthesized

<400> SEQUENCE: 343
cuagagggac ucacaggcug                                               20

<210> SEQ ID NO 344
<211> LENGTH: 20
<212> TYPE: RNA
<213> ORGANISM: Artificial Sequence
<220> FEATURE:
<223> OTHER INFORMATION: synthesized

<400> SEQUENCE: 344
cuagaggggc ucacaggcug                                               20

<210> SEQ ID NO 345
<211> LENGTH: 20
<212> TYPE: RNA
<213> ORGANISM: Artificial Sequence
<220> FEATURE:
<223> OTHER INFORMATION: synthesized
```

```
<400> SEQUENCE: 345
cugaugcuag agggacucac                                          20

<210> SEQ ID NO 346
<211> LENGTH: 20
<212> TYPE: RNA
<213> ORGANISM: Artificial Sequence
<220> FEATURE:
<223> OTHER INFORMATION: synthesized

<400> SEQUENCE: 346
cugaugcuag aggggcucac                                          20

<210> SEQ ID NO 347
<211> LENGTH: 20
<212> TYPE: RNA
<213> ORGANISM: Artificial Sequence
<220> FEATURE:
<223> OTHER INFORMATION: synthesized

<400> SEQUENCE: 347
cugugagccc cucuagcauc                                          20

<210> SEQ ID NO 348
<211> LENGTH: 20
<212> TYPE: RNA
<213> ORGANISM: Artificial Sequence
<220> FEATURE:
<223> OTHER INFORMATION: synthesized

<400> SEQUENCE: 348
cugugagucc cucuagcauc                                          20

<210> SEQ ID NO 349
<211> LENGTH: 20
<212> TYPE: RNA
<213> ORGANISM: Artificial Sequence
<220> FEATURE:
<223> OTHER INFORMATION: synthesized

<400> SEQUENCE: 349
gacucacagg cugaccugau                                          20

<210> SEQ ID NO 350
<211> LENGTH: 20
<212> TYPE: RNA
<213> ORGANISM: Artificial Sequence
<220> FEATURE:
<223> OTHER INFORMATION: synthesized

<400> SEQUENCE: 350
gagccccucu agcaucagag                                          20

<210> SEQ ID NO 351
<211> LENGTH: 20
<212> TYPE: RNA
<213> ORGANISM: Artificial Sequence
<220> FEATURE:
<223> OTHER INFORMATION: synthesized

<400> SEQUENCE: 351
gagggacuca caggcugacc                                          20

<210> SEQ ID NO 352
```

```
<211> LENGTH: 20
<212> TYPE: RNA
<213> ORGANISM: Artificial Sequence
<220> FEATURE:
<223> OTHER INFORMATION: synthesized

<400> SEQUENCE: 352
gaggggcuca caggcugacc                                                       20

<210> SEQ ID NO 353
<211> LENGTH: 20
<212> TYPE: RNA
<213> ORGANISM: Artificial Sequence
<220> FEATURE:
<223> OTHER INFORMATION: synthesized

<400> SEQUENCE: 353
gagucccucu agcaucagag                                                       20

<210> SEQ ID NO 354
<211> LENGTH: 20
<212> TYPE: RNA
<213> ORGANISM: Artificial Sequence
<220> FEATURE:
<223> OTHER INFORMATION: synthesized

<400> SEQUENCE: 354
gaugcuagag ggacucacag                                                       20

<210> SEQ ID NO 355
<211> LENGTH: 20
<212> TYPE: RNA
<213> ORGANISM: Artificial Sequence
<220> FEATURE:
<223> OTHER INFORMATION: synthesized

<400> SEQUENCE: 355
gaugcuagag gggcucacag                                                       20

<210> SEQ ID NO 356
<211> LENGTH: 20
<212> TYPE: RNA
<213> ORGANISM: Artificial Sequence
<220> FEATURE:
<223> OTHER INFORMATION: synthesized

<400> SEQUENCE: 356
ggcucacagg cugaccugau                                                       20

<210> SEQ ID NO 357
<211> LENGTH: 20
<212> TYPE: RNA
<213> ORGANISM: Artificial Sequence
<220> FEATURE:
<223> OTHER INFORMATION: synthesized

<400> SEQUENCE: 357
gggacucaca ggcugaccug                                                       20

<210> SEQ ID NO 358
<211> LENGTH: 20
<212> TYPE: RNA
<213> ORGANISM: Artificial Sequence
<220> FEATURE:
<223> OTHER INFORMATION: synthesized

<400> SEQUENCE: 358
```

-continued ggggcucaca ggcugaccug                          20

<210> SEQ ID NO 359
<211> LENGTH: 20
<212> TYPE: RNA
<213> ORGANISM: Artificial Sequence
<220> FEATURE:
<223> OTHER INFORMATION: synthesized

<400> SEQUENCE: 359
ggucagccug ugagccccuc                          20

<210> SEQ ID NO 360
<211> LENGTH: 20
<212> TYPE: RNA
<213> ORGANISM: Artificial Sequence
<220> FEATURE:
<223> OTHER INFORMATION: synthesized

<400> SEQUENCE: 360
ggucagccug ugagucccuc                          20

<210> SEQ ID NO 361
<211> LENGTH: 20
<212> TYPE: RNA
<213> ORGANISM: Artificial Sequence
<220> FEATURE:
<223> OTHER INFORMATION: synthesized

<400> SEQUENCE: 361
gugagccccu cuagcaucag                          20

<210> SEQ ID NO 362
<211> LENGTH: 20
<212> TYPE: RNA
<213> ORGANISM: Artificial Sequence
<220> FEATURE:
<223> OTHER INFORMATION: synthesized

<400> SEQUENCE: 362
gugagucccu cuagcaucag                          20

<210> SEQ ID NO 363
<211> LENGTH: 20
<212> TYPE: RNA
<213> ORGANISM: Artificial Sequence
<220> FEATURE:
<223> OTHER INFORMATION: synthesized

<400> SEQUENCE: 363
ucccucuagc aucagaggga                          20

<210> SEQ ID NO 364
<211> LENGTH: 20
<212> TYPE: RNA
<213> ORGANISM: Artificial Sequence
<220> FEATURE:
<223> OTHER INFORMATION: synthesized

<400> SEQUENCE: 364 ugagcccuc uagcaucaga                           20

<210> SEQ ID NO 365
<211> LENGTH: 20
<212> TYPE: RNA

```
<213> ORGANISM: Artificial Sequence
<220> FEATURE:
<223> OTHER INFORMATION: synthesized

<400> SEQUENCE: 365
ugagucccuc uagcaucaga                                               20

<210> SEQ ID NO 366
<211> LENGTH: 20
<212> TYPE: RNA
<213> ORGANISM: Artificial Sequence
<220> FEATURE:
<223> OTHER INFORMATION: synthesized

<400> SEQUENCE: 366
ugcuagaggg acucacaggc                                               20

<210> SEQ ID NO 367
<211> LENGTH: 20
<212> TYPE: RNA
<213> ORGANISM: Artificial Sequence
<220> FEATURE:
<223> OTHER INFORMATION: synthesized

<400> SEQUENCE: 367
ugcuagaggg gcucacaggc                                               20

<210> SEQ ID NO 368
<211> LENGTH: 20
<212> TYPE: RNA
<213> ORGANISM: Artificial Sequence
<220> FEATURE:
<223> OTHER INFORMATION: synthesized

<400> SEQUENCE: 368
aaugucuagc aaagaaccca                                               20

<210> SEQ ID NO 369
<211> LENGTH: 20
<212> TYPE: RNA
<213> ORGANISM: Artificial Sequence
<220> FEATURE:
<223> OTHER INFORMATION: synthesized

<400> SEQUENCE: 369
aauguuuagc aaagaaccca                                               20

<210> SEQ ID NO 370
<211> LENGTH: 20
<212> TYPE: RNA
<213> ORGANISM: Artificial Sequence
<220> FEATURE:
<223> OTHER INFORMATION: synthesized

<400> SEQUENCE: 370
acccugcaaa augucuagca                                               20

<210> SEQ ID NO 371
<211> LENGTH: 20
<212> TYPE: RNA
<213> ORGANISM: Artificial Sequence
<220> FEATURE:
<223> OTHER INFORMATION: synthesized

<400> SEQUENCE: 371
acccugcaaa auguuuagca                                               20
```

```
<210> SEQ ID NO 372
<211> LENGTH: 20
<212> TYPE: RNA
<213> ORGANISM: Artificial Sequence
<220> FEATURE:
<223> OTHER INFORMATION: synthesized

<400> SEQUENCE: 372
cccugcaaaa ugucuagcaa                                          20

<210> SEQ ID NO 373
<211> LENGTH: 20
<212> TYPE: RNA
<213> ORGANISM: Artificial Sequence
<220> FEATURE:
<223> OTHER INFORMATION: synthesized

<400> SEQUENCE: 373
cccugcaaaa uguuuagcaa                                          20

<210> SEQ ID NO 374
<211> LENGTH: 20
<212> TYPE: RNA
<213> ORGANISM: Artificial Sequence
<220> FEATURE:
<223> OTHER INFORMATION: synthesized

<400> SEQUENCE: 374
gucuagcaaa gaacccaaga                                          20

<210> SEQ ID NO 375
<211> LENGTH: 20
<212> TYPE: RNA
<213> ORGANISM: Artificial Sequence
<220> FEATURE:
<223> OTHER INFORMATION: synthesized

<400> SEQUENCE: 375
guucuuugcu aaacauuuug                                          20

<210> SEQ ID NO 376
<211> LENGTH: 20
<212> TYPE: RNA
<213> ORGANISM: Artificial Sequence
<220> FEATURE:
<223> OTHER INFORMATION: synthesized

<400> SEQUENCE: 376
guucuuugcu agacauuuug                                          20

<210> SEQ ID NO 377
<211> LENGTH: 20
<212> TYPE: RNA
<213> ORGANISM: Artificial Sequence
<220> FEATURE:
<223> OTHER INFORMATION: synthesized

<400> SEQUENCE: 377
guuuagcaaa gaacccaaga                                          20

<210> SEQ ID NO 378
<211> LENGTH: 20
<212> TYPE: RNA
<213> ORGANISM: Artificial Sequence
<220> FEATURE:
```

<223> OTHER INFORMATION: synthesized

<400> SEQUENCE: 378
uaaacauuuu gcaggguacc					20

<210> SEQ ID NO 379
<211> LENGTH: 20
<212> TYPE: RNA
<213> ORGANISM: Artificial Sequence
<220> FEATURE:
<223> OTHER INFORMATION: synthesized

<400> SEQUENCE: 379
uagacauuuu gcaggguacc					20

<210> SEQ ID NO 380
<211> LENGTH: 20
<212> TYPE: RNA
<213> ORGANISM: Artificial Sequence
<220> FEATURE:
<223> OTHER INFORMATION: synthesized

<400> SEQUENCE: 380
ucuuugcuaa acauuuugca					20

<210> SEQ ID NO 381
<211> LENGTH: 20
<212> TYPE: RNA
<213> ORGANISM: Artificial Sequence
<220> FEATURE:
<223> OTHER INFORMATION: synthesized

<400> SEQUENCE: 381
ucuuugcuag acauuuugca					20

<210> SEQ ID NO 382
<211> LENGTH: 20
<212> TYPE: RNA
<213> ORGANISM: Artificial Sequence
<220> FEATURE:
<223> OTHER INFORMATION: synthesized

<400> SEQUENCE: 382
ugcuaaacau uuugcagggu					20

<210> SEQ ID NO 383
<211> LENGTH: 20
<212> TYPE: RNA
<213> ORGANISM: Artificial Sequence
<220> FEATURE:
<223> OTHER INFORMATION: synthesized

<400> SEQUENCE: 383
ugcuagacau uuugcagggu					20

<210> SEQ ID NO 384
<211> LENGTH: 20
<212> TYPE: RNA
<213> ORGANISM: Artificial Sequence
<220> FEATURE:
<223> OTHER INFORMATION: synthesized

<400> SEQUENCE: 384
uucuuugcua aacauuuugc					20

```
<210> SEQ ID NO 385
<211> LENGTH: 20
<212> TYPE: RNA
<213> ORGANISM: Artificial Sequence
<220> FEATURE:
<223> OTHER INFORMATION: synthesized

<400> SEQUENCE: 385
uucuuugcua gacauuuugc                                                    20

<210> SEQ ID NO 386
<211> LENGTH: 20
<212> TYPE: RNA
<213> ORGANISM: Artificial Sequence
<220> FEATURE:
<223> OTHER INFORMATION: synthesized

<400> SEQUENCE: 386
agaaagggua ggaagaaaug                                                    20

<210> SEQ ID NO 387
<211> LENGTH: 20
<212> TYPE: RNA
<213> ORGANISM: Artificial Sequence
<220> FEATURE:
<223> OTHER INFORMATION: synthesized

<400> SEQUENCE: 387
agagaaaggg uaggaagaaa                                                    20

<210> SEQ ID NO 388
<211> LENGTH: 20
<212> TYPE: RNA
<213> ORGANISM: Artificial Sequence
<220> FEATURE:
<223> OTHER INFORMATION: synthesized

<400> SEQUENCE: 388
agagauaggg uaggaagaaa                                                    20

<210> SEQ ID NO 389
<211> LENGTH: 20
<212> TYPE: RNA
<213> ORGANISM: Artificial Sequence
<220> FEATURE:
<223> OTHER INFORMATION: synthesized

<400> SEQUENCE: 389
agauagggua ggaagaaaug                                                    20

<210> SEQ ID NO 390
<211> LENGTH: 20
<212> TYPE: RNA
<213> ORGANISM: Artificial Sequence
<220> FEATURE:
<223> OTHER INFORMATION: synthesized

<400> SEQUENCE: 390
caacuuaucu ggaagagaaa                                                    20

<210> SEQ ID NO 391
<211> LENGTH: 20
<212> TYPE: RNA
<213> ORGANISM: Artificial Sequence
<220> FEATURE:
<223> OTHER INFORMATION: synthesized
```

```
<400> SEQUENCE: 391
caacuuaucu ggaagagaua                                            20

<210> SEQ ID NO 392
<211> LENGTH: 20
<212> TYPE: RNA
<213> ORGANISM: Artificial Sequence
<220> FEATURE:
<223> OTHER INFORMATION: synthesized

<400> SEQUENCE: 392
ccaacuuauc uggaagagaa                                            20

<210> SEQ ID NO 393
<211> LENGTH: 20
<212> TYPE: RNA
<213> ORGANISM: Artificial Sequence
<220> FEATURE:
<223> OTHER INFORMATION: synthesized

<400> SEQUENCE: 393
ccaacuuauc uggaagagau                                            20

<210> SEQ ID NO 394
<211> LENGTH: 20
<212> TYPE: RNA
<213> ORGANISM: Artificial Sequence
<220> FEATURE:
<223> OTHER INFORMATION: synthesized

<400> SEQUENCE: 394
ccuaucucuu ccagauaagu                                            20

<210> SEQ ID NO 395
<211> LENGTH: 20
<212> TYPE: RNA
<213> ORGANISM: Artificial Sequence
<220> FEATURE:
<223> OTHER INFORMATION: synthesized

<400> SEQUENCE: 395
ccuuucucuu ccagauaagu                                            20

<210> SEQ ID NO 396
<211> LENGTH: 20
<212> TYPE: RNA
<213> ORGANISM: Artificial Sequence
<220> FEATURE:
<223> OTHER INFORMATION: synthesized

<400> SEQUENCE: 396
cuggaagaga aagguagga                                             20

<210> SEQ ID NO 397
<211> LENGTH: 20
<212> TYPE: RNA
<213> ORGANISM: Artificial Sequence
<220> FEATURE:
<223> OTHER INFORMATION: synthesized

<400> SEQUENCE: 397
cuggaagaga uagguagga                                             20

<210> SEQ ID NO 398
<211> LENGTH: 20
```

```
<212> TYPE: RNA
<213> ORGANISM: Artificial Sequence
<220> FEATURE:
<223> OTHER INFORMATION: synthesized

<400> SEQUENCE: 398
cuuccuaccc uaucucuucc                                               20

<210> SEQ ID NO 399
<211> LENGTH: 20
<212> TYPE: RNA
<213> ORGANISM: Artificial Sequence
<220> FEATURE:
<223> OTHER INFORMATION: synthesized

<400> SEQUENCE: 399
cuuccuaccc uuucucuucc                                               20

<210> SEQ ID NO 400
<211> LENGTH: 20
<212> TYPE: RNA
<213> ORGANISM: Artificial Sequence
<220> FEATURE:
<223> OTHER INFORMATION: synthesized

<400> SEQUENCE: 400
gaaaggguag gaagaaaugg                                               20

<210> SEQ ID NO 401
<211> LENGTH: 20
<212> TYPE: RNA
<213> ORGANISM: Artificial Sequence
<220> FEATURE:
<223> OTHER INFORMATION: synthesized

<400> SEQUENCE: 401
gagaaagggu aggaagaaau                                               20

<210> SEQ ID NO 402
<211> LENGTH: 20
<212> TYPE: RNA
<213> ORGANISM: Artificial Sequence
<220> FEATURE:
<223> OTHER INFORMATION: synthesized

<400> SEQUENCE: 402
gagauagggu aggaagaaau                                               20

<210> SEQ ID NO 403
<211> LENGTH: 20
<212> TYPE: RNA
<213> ORGANISM: Artificial Sequence
<220> FEATURE:
<223> OTHER INFORMATION: synthesized

<400> SEQUENCE: 403
gauaggguag gaagaaaugg                                               20

<210> SEQ ID NO 404
<211> LENGTH: 20
<212> TYPE: RNA
<213> ORGANISM: Artificial Sequence
<220> FEATURE:
<223> OTHER INFORMATION: synthesized

<400> SEQUENCE: 404
```
uaucuggaag agaaagggua                                            20

<210> SEQ ID NO 405
<211> LENGTH: 20
<212> TYPE: RNA
<213> ORGANISM: Artificial Sequence
<220> FEATURE:
<223> OTHER INFORMATION: synthesized

<400> SEQUENCE: 405
uaucuggaag agauagggua                                            20

<210> SEQ ID NO 406
<211> LENGTH: 20
<212> TYPE: RNA
<213> ORGANISM: Artificial Sequence
<220> FEATURE:
<223> OTHER INFORMATION: synthesized

<400> SEQUENCE: 406
uuaucuggaa gagaaagggu                                            20

<210> SEQ ID NO 407
<211> LENGTH: 20
<212> TYPE: RNA
<213> ORGANISM: Artificial Sequence
<220> FEATURE:
<223> OTHER INFORMATION: synthesized

<400> SEQUENCE: 407
uuaucuggaa gagauagggu                                            20

<210> SEQ ID NO 408
<211> LENGTH: 20
<212> TYPE: RNA
<213> ORGANISM: Artificial Sequence
<220> FEATURE:
<223> OTHER INFORMATION: synthesized

<400> SEQUENCE: 408
uucuuccuac ccuaucucuu                                            20

<210> SEQ ID NO 409
<211> LENGTH: 20
<212> TYPE: RNA
<213> ORGANISM: Artificial Sequence
<220> FEATURE:
<223> OTHER INFORMATION: synthesized

<400> SEQUENCE: 409
uucuuccuac ccuuucucuu                                            20

<210> SEQ ID NO 410
<211> LENGTH: 20
<212> TYPE: RNA
<213> ORGANISM: Artificial Sequence
<220> FEATURE:
<223> OTHER INFORMATION: synthesized

<400> SEQUENCE: 410
caggaguuau aagguacugc                                            20

<210> SEQ ID NO 411
<211> LENGTH: 20
<212> TYPE: RNA
<213> ORGANISM: Artificial Sequence
<220> FEATURE:
<223> OTHER INFORMATION: synthesized

<400> SEQUENCE: 411
uccaggaguu auaagguacu                                              20

<210> SEQ ID NO 412
<211> LENGTH: 20
<212> TYPE: RNA
<213> ORGANISM: Artificial Sequence
<220> FEATURE:
<223> OTHER INFORMATION: synthesized

<400> SEQUENCE: 412
ugacucugcu ugguuuuucc                                              20

<210> SEQ ID NO 413
<211> LENGTH: 20
<212> TYPE: RNA
<213> ORGANISM: Artificial Sequence
<220> FEATURE:
<223> OTHER INFORMATION: synthesized

<400> SEQUENCE: 413
uugacucugc uugguuuuuc                                              20

<210> SEQ ID NO 414
<211> LENGTH: 20
<212> TYPE: RNA
<213> ORGANISM: Artificial Sequence
<220> FEATURE:
<223> OTHER INFORMATION: synthesized

<400> SEQUENCE: 414
cuguucgcau gaaaauuagg                                              20

<210> SEQ ID NO 415
<211> LENGTH: 20
<212> TYPE: RNA
<213> ORGANISM: Artificial Sequence
<220> FEATURE:
<223> OTHER INFORMATION: synthesized

<400> SEQUENCE: 415
gcuguucgca ugaaaauuag                                              20

<210> SEQ ID NO 416
<211> LENGTH: 20
<212> TYPE: RNA
<213> ORGANISM: Artificial Sequence
<220> FEATURE:
<223> OTHER INFORMATION: synthesized

<400> SEQUENCE: 416
guucgcauga aaauuaggcc                                              20

<210> SEQ ID NO 417
<211> LENGTH: 20
<212> TYPE: RNA
<213> ORGANISM: Artificial Sequence
<220> FEATURE:
<223> OTHER INFORMATION: synthesized

<400> SEQUENCE: 417
ucuucagccu auugggucac                                              20

<210> SEQ ID NO 418
<211> LENGTH: 20
<212> TYPE: RNA
<213> ORGANISM: Artificial Sequence
<220> FEATURE:
<223> OTHER INFORMATION: synthesized

<400> SEQUENCE: 418
uguucgcaug aaaauuaggc                                                  20

<210> SEQ ID NO 419
<211> LENGTH: 20
<212> TYPE: RNA
<213> ORGANISM: Artificial Sequence
<220> FEATURE:
<223> OTHER INFORMATION: synthesized

<400> SEQUENCE: 419
aaaaagcaug ugacaauaag                                                  20

<210> SEQ ID NO 420
<211> LENGTH: 20
<212> TYPE: RNA
<213> ORGANISM: Artificial Sequence
<220> FEATURE:
<223> OTHER INFORMATION: synthesized

<400> SEQUENCE: 420
aaggauguuu gauauaucua                                                  20

<210> SEQ ID NO 421
<211> LENGTH: 20
<212> TYPE: RNA
<213> ORGANISM: Artificial Sequence
<220> FEATURE:
<223> OTHER INFORMATION: synthesized

<400> SEQUENCE: 421
aagugaaaug agcagauaua                                                  20

<210> SEQ ID NO 422
<211> LENGTH: 20
<212> TYPE: RNA
<213> ORGANISM: Artificial Sequence
<220> FEATURE:
<223> OTHER INFORMATION: synthesized

<400> SEQUENCE: 422
accagcuaag caguauuugu                                                  20

<210> SEQ ID NO 423
<211> LENGTH: 20
<212> TYPE: RNA
<213> ORGANISM: Artificial Sequence
<220> FEATURE:
<223> OTHER INFORMATION: synthesized

<400> SEQUENCE: 423
aggauguuug auauaucuau                                                  20

<210> SEQ ID NO 424
<211> LENGTH: 20
<212> TYPE: RNA
<213> ORGANISM: Artificial Sequence
<220> FEATURE:
<223> OTHER INFORMATION: synthesized

<400> SEQUENCE: 424
aguuuugcac auuuaaagau                                              20

<210> SEQ ID NO 425
<211> LENGTH: 20
<212> TYPE: RNA
<213> ORGANISM: Artificial Sequence
<220> FEATURE:
<223> OTHER INFORMATION: synthesized

<400> SEQUENCE: 425
auauuacauu aacuucaaaa                                              20

<210> SEQ ID NO 426
<211> LENGTH: 20
<212> TYPE: RNA
<213> ORGANISM: Artificial Sequence
<220> FEATURE:
<223> OTHER INFORMATION: synthesized

<400> SEQUENCE: 426
cagcuaagca guauuugucu                                              20

<210> SEQ ID NO 427
<211> LENGTH: 20
<212> TYPE: RNA
<213> ORGANISM: Artificial Sequence
<220> FEATURE:
<223> OTHER INFORMATION: synthesized

<400> SEQUENCE: 427
caguuuugca cauuuaaaga                                              20

<210> SEQ ID NO 428
<211> LENGTH: 20
<212> TYPE: RNA
<213> ORGANISM: Artificial Sequence
<220> FEATURE:
<223> OTHER INFORMATION: synthesized

<400> SEQUENCE: 428
ccagcuaagc aguauuuguc                                              20

<210> SEQ ID NO 429
<211> LENGTH: 20
<212> TYPE: RNA
<213> ORGANISM: Artificial Sequence
<220> FEATURE:
<223> OTHER INFORMATION: synthesized

<400> SEQUENCE: 429
gaaggauguu ugauauaucu                                              20

<210> SEQ ID NO 430
<211> LENGTH: 20
<212> TYPE: RNA
<213> ORGANISM: Artificial Sequence
<220> FEATURE:
<223> OTHER INFORMATION: synthesized

<400> SEQUENCE: 430
gaccagcuaa gcaguauuug                                              20

<210> SEQ ID NO 431

```
<211> LENGTH: 20
<212> TYPE: RNA
<213> ORGANISM: Artificial Sequence
<220> FEATURE:
<223> OTHER INFORMATION: synthesized

<400> SEQUENCE: 431
ggauguuuga uauaucuauc                                              20

<210> SEQ ID NO 432
<211> LENGTH: 20
<212> TYPE: RNA
<213> ORGANISM: Artificial Sequence
<220> FEATURE:
<223> OTHER INFORMATION: synthesized

<400> SEQUENCE: 432
gugaaaugag cagauauaga                                              20

<210> SEQ ID NO 433
<211> LENGTH: 20
<212> TYPE: RNA
<213> ORGANISM: Artificial Sequence
<220> FEATURE:
<223> OTHER INFORMATION: synthesized

<400> SEQUENCE: 433
guuuugcaca uuuaaagaua                                              20

<210> SEQ ID NO 434
<211> LENGTH: 20
<212> TYPE: RNA
<213> ORGANISM: Artificial Sequence
<220> FEATURE:
<223> OTHER INFORMATION: synthesized

<400> SEQUENCE: 434
uauauuacau uaacuucaaa                                              20

<210> SEQ ID NO 435
<211> LENGTH: 20
<212> TYPE: RNA
<213> ORGANISM: Artificial Sequence
<220> FEATURE:
<223> OTHER INFORMATION: synthesized

<400> SEQUENCE: 435
uuauauuaca uuaacuucaa                                              20

<210> SEQ ID NO 436
<211> LENGTH: 20
<212> TYPE: RNA
<213> ORGANISM: Artificial Sequence
<220> FEATURE:
<223> OTHER INFORMATION: synthesized

<400> SEQUENCE: 436
uuuauauuac auuaacuuca                                              20

<210> SEQ ID NO 437
<211> LENGTH: 20
<212> TYPE: RNA
<213> ORGANISM: Artificial Sequence
<220> FEATURE:
<223> OTHER INFORMATION: synthesized

<400> SEQUENCE: 437
```
uuuugcacau uuaaagauac 20

<210> SEQ ID NO 438
<211> LENGTH: 20
<212> TYPE: RNA
<213> ORGANISM: Artificial Sequence
<220> FEATURE:
<223> OTHER INFORMATION: synthesized

<400> SEQUENCE: 438
aauagaguaa uagcuaaugu 20

<210> SEQ ID NO 439
<211> LENGTH: 20
<212> TYPE: RNA
<213> ORGANISM: Artificial Sequence
<220> FEATURE:
<223> OTHER INFORMATION: synthesized

<400> SEQUENCE: 439
acccaagacu uaguaaacau 20

<210> SEQ ID NO 440
<211> LENGTH: 20
<212> TYPE: RNA
<213> ORGANISM: Artificial Sequence
<220> FEATURE:
<223> OTHER INFORMATION: synthesized

<400> SEQUENCE: 440
agaguaauag cuaugugua 20

<210> SEQ ID NO 441
<211> LENGTH: 20
<212> TYPE: RNA
<213> ORGANISM: Artificial Sequence
<220> FEATURE:
<223> OTHER INFORMATION: synthesized

<400> SEQUENCE: 441
auagaguaau agcuaaugug 20

<210> SEQ ID NO 442
<211> LENGTH: 20
<212> TYPE: RNA
<213> ORGANISM: Artificial Sequence
<220> FEATURE:
<223> OTHER INFORMATION: synthesized

<400> SEQUENCE: 442
ccaagacuua guaaacauuc 20

<210> SEQ ID NO 443
<211> LENGTH: 20
<212> TYPE: RNA
<213> ORGANISM: Artificial Sequence
<220> FEATURE:
<223> OTHER INFORMATION: synthesized

<400> SEQUENCE: 443
cccaagacuu aguaaacauu 20

<210> SEQ ID NO 444
<211> LENGTH: 20
<212> TYPE: RNA

```
<213> ORGANISM: Artificial Sequence
<220> FEATURE:
<223> OTHER INFORMATION: synthesized

<400> SEQUENCE: 444
uagaguaaua gcuaaugugu                                               20

<210> SEQ ID NO 445
<211> LENGTH: 20
<212> TYPE: RNA
<213> ORGANISM: Artificial Sequence
<220> FEATURE:
<223> OTHER INFORMATION: synthesized

<400> SEQUENCE: 445
cagcugaaag aaaggauugc                                               20

<210> SEQ ID NO 446
<211> LENGTH: 20
<212> TYPE: RNA
<213> ORGANISM: Artificial Sequence
<220> FEATURE:
<223> OTHER INFORMATION: synthesized

<400> SEQUENCE: 446
ccagcugaaa gaaaggauug                                               20

<210> SEQ ID NO 447
<211> LENGTH: 20
<212> TYPE: RNA
<213> ORGANISM: Artificial Sequence
<220> FEATURE:
<223> OTHER INFORMATION: synthesized

<400> SEQUENCE: 447
uaggauggga acuaggagug                                               20

<210> SEQ ID NO 448
<211> LENGTH: 20
<212> TYPE: RNA
<213> ORGANISM: Artificial Sequence
<220> FEATURE:
<223> OTHER INFORMATION: synthesized

<400> SEQUENCE: 448
uccagcugaa agaaaggauu                                               20

<210> SEQ ID NO 449
<211> LENGTH: 20
<212> TYPE: RNA
<213> ORGANISM: Artificial Sequence
<220> FEATURE:
<223> OTHER INFORMATION: synthesized

<400> SEQUENCE: 449
aaagaagaca gagugcuccc                                               20

<210> SEQ ID NO 450
<211> LENGTH: 20
<212> TYPE: RNA
<213> ORGANISM: Artificial Sequence
<220> FEATURE:
<223> OTHER INFORMATION: synthesized

<400> SEQUENCE: 450
aagaagacag agugcuccca                                               20
```

<210> SEQ ID NO 451
<211> LENGTH: 20
<212> TYPE: RNA
<213> ORGANISM: Artificial Sequence
<220> FEATURE:
<223> OTHER INFORMATION: synthesized

<400> SEQUENCE: 451
aaugggagca cucugucuuc                                               20

<210> SEQ ID NO 452
<211> LENGTH: 20
<212> TYPE: RNA
<213> ORGANISM: Artificial Sequence
<220> FEATURE:
<223> OTHER INFORMATION: synthesized

<400> SEQUENCE: 452
acucugucuu cuuugcuaga                                               20

<210> SEQ ID NO 453
<211> LENGTH: 20
<212> TYPE: RNA
<213> ORGANISM: Artificial Sequence
<220> FEATURE:
<223> OTHER INFORMATION: synthesized

<400> SEQUENCE: 453
agaagacaga gugcucccau                                               20

<210> SEQ ID NO 454
<211> LENGTH: 20
<212> TYPE: RNA
<213> ORGANISM: Artificial Sequence
<220> FEATURE:
<223> OTHER INFORMATION: synthesized

<400> SEQUENCE: 454
agcaaagaag acagagugcu                                               20

<210> SEQ ID NO 455
<211> LENGTH: 20
<212> TYPE: RNA
<213> ORGANISM: Artificial Sequence
<220> FEATURE:
<223> OTHER INFORMATION: synthesized

<400> SEQUENCE: 455
augggagcac ucugucuucu                                               20

<210> SEQ ID NO 456
<211> LENGTH: 20
<212> TYPE: RNA
<213> ORGANISM: Artificial Sequence
<220> FEATURE:
<223> OTHER INFORMATION: synthesized

<400> SEQUENCE: 456
caaagaagac agagugcucc                                               20

<210> SEQ ID NO 457
<211> LENGTH: 20
<212> TYPE: RNA
<213> ORGANISM: Artificial Sequence
<220> FEATURE:

<223> OTHER INFORMATION: synthesized

<400> SEQUENCE: 457
cacuucucua gcaaagaaga                                                     20

<210> SEQ ID NO 458
<211> LENGTH: 20
<212> TYPE: RNA
<213> ORGANISM: Artificial Sequence
<220> FEATURE:
<223> OTHER INFORMATION: synthesized

<400> SEQUENCE: 458
ccacuucucu agcaaagaag                                                     20

<210> SEQ ID NO 459
<211> LENGTH: 20
<212> TYPE: RNA
<213> ORGANISM: Artificial Sequence
<220> FEATURE:
<223> OTHER INFORMATION: synthesized

<400> SEQUENCE: 459
cuagcaaaga agacagagug                                                     20

<210> SEQ ID NO 460
<211> LENGTH: 20
<212> TYPE: RNA
<213> ORGANISM: Artificial Sequence
<220> FEATURE:
<223> OTHER INFORMATION: synthesized

<400> SEQUENCE: 460
cucuagcaaa gaagacagag                                                     20

<210> SEQ ID NO 461
<211> LENGTH: 20
<212> TYPE: RNA
<213> ORGANISM: Artificial Sequence
<220> FEATURE:
<223> OTHER INFORMATION: synthesized

<400> SEQUENCE: 461
cucugucuuc uuugcuagag                                                     20

<210> SEQ ID NO 462
<211> LENGTH: 20
<212> TYPE: RNA
<213> ORGANISM: Artificial Sequence
<220> FEATURE:
<223> OTHER INFORMATION: synthesized

<400> SEQUENCE: 462
cugucuucuu ugcuagagaa                                                     20

<210> SEQ ID NO 463
<211> LENGTH: 20
<212> TYPE: RNA
<213> ORGANISM: Artificial Sequence
<220> FEATURE:
<223> OTHER INFORMATION: synthesized

<400> SEQUENCE: 463
cuucucuagc aaagaagaca                                                     20

```
<210> SEQ ID NO 464
<211> LENGTH: 20
<212> TYPE: RNA
<213> ORGANISM: Artificial Sequence
<220> FEATURE:
<223> OTHER INFORMATION: synthesized

<400> SEQUENCE: 464
gaaugggagc acucugucuu                                              20

<210> SEQ ID NO 465
<211> LENGTH: 20
<212> TYPE: RNA
<213> ORGANISM: Artificial Sequence
<220> FEATURE:
<223> OTHER INFORMATION: synthesized

<400> SEQUENCE: 465
gagcacucug ucuucuuugc                                              20

<210> SEQ ID NO 466
<211> LENGTH: 20
<212> TYPE: RNA
<213> ORGANISM: Artificial Sequence
<220> FEATURE:
<223> OTHER INFORMATION: synthesized

<400> SEQUENCE: 466
gcaaagaaga cagagugcuc                                              20

<210> SEQ ID NO 467
<211> LENGTH: 20
<212> TYPE: RNA
<213> ORGANISM: Artificial Sequence
<220> FEATURE:
<223> OTHER INFORMATION: synthesized

<400> SEQUENCE: 467 gcacucguc uucuuugcua                                               20

<210> SEQ ID NO 468
<211> LENGTH: 20
<212> TYPE: RNA
<213> ORGANISM: Artificial Sequence
<220> FEATURE:
<223> OTHER INFORMATION: synthesized

<400> SEQUENCE: 468
ggaaugggag cacucugucu                                              20

<210> SEQ ID NO 469
<211> LENGTH: 20
<212> TYPE: RNA
<213> ORGANISM: Artificial Sequence
<220> FEATURE:
<223> OTHER INFORMATION: synthesized

<400> SEQUENCE: 469
ggagcacucu gucuucuuug                                              20

<210> SEQ ID NO 470
<211> LENGTH: 20
<212> TYPE: RNA
<213> ORGANISM: Artificial Sequence
<220> FEATURE:
<223> OTHER INFORMATION: synthesized
```

```
<400> SEQUENCE: 470
gggaauggga gcacucuguc                                              20

<210> SEQ ID NO 471
<211> LENGTH: 20
<212> TYPE: RNA
<213> ORGANISM: Artificial Sequence
<220> FEATURE:
<223> OTHER INFORMATION: synthesized

<400> SEQUENCE: 471
gggagcacuc ugucuucuuu                                              20

<210> SEQ ID NO 472
<211> LENGTH: 20
<212> TYPE: RNA
<213> ORGANISM: Artificial Sequence
<220> FEATURE:
<223> OTHER INFORMATION: synthesized

<400> SEQUENCE: 472
uagcaaagaa gacagagugc                                              20

<210> SEQ ID NO 473
<211> LENGTH: 20
<212> TYPE: RNA
<213> ORGANISM: Artificial Sequence
<220> FEATURE:
<223> OTHER INFORMATION: synthesized

<400> SEQUENCE: 473
uccacuucuc uagcaaagaa                                              20

<210> SEQ ID NO 474
<211> LENGTH: 20
<212> TYPE: RNA
<213> ORGANISM: Artificial Sequence
<220> FEATURE:
<223> OTHER INFORMATION: synthesized

<400> SEQUENCE: 474
ucuagcaaag aagacagagu                                              20

<210> SEQ ID NO 475
<211> LENGTH: 20
<212> TYPE: RNA
<213> ORGANISM: Artificial Sequence
<220> FEATURE:
<223> OTHER INFORMATION: synthesized

<400> SEQUENCE: 475
ucuccacuuc ucuagcaaag                                              20

<210> SEQ ID NO 476
<211> LENGTH: 20
<212> TYPE: RNA
<213> ORGANISM: Artificial Sequence
<220> FEATURE:
<223> OTHER INFORMATION: synthesized

<400> SEQUENCE: 476
ucucuagcaa agaagacaga                                              20

<210> SEQ ID NO 477
<211> LENGTH: 20
```

```
<212> TYPE: RNA
<213> ORGANISM: Artificial Sequence
<220> FEATURE:
<223> OTHER INFORMATION: synthesized

<400> SEQUENCE: 477
ucuucuuugc uagagaagug                                            20

<210> SEQ ID NO 478
<211> LENGTH: 20
<212> TYPE: RNA
<213> ORGANISM: Artificial Sequence
<220> FEATURE:
<223> OTHER INFORMATION: synthesized

<400> SEQUENCE: 478
ugggagcacu cugucuucuu                                            20

<210> SEQ ID NO 479
<211> LENGTH: 20
<212> TYPE: RNA
<213> ORGANISM: Artificial Sequence
<220> FEATURE:
<223> OTHER INFORMATION: synthesized

<400> SEQUENCE: 479
uucucuccac uucucuagca                                            20

<210> SEQ ID NO 480
<211> LENGTH: 20
<212> TYPE: RNA
<213> ORGANISM: Artificial Sequence
<220> FEATURE:
<223> OTHER INFORMATION: synthesized

<400> SEQUENCE: 480
uucuuugcua gagaagugga                                            20

<210> SEQ ID NO 481
<211> LENGTH: 20
<212> TYPE: RNA
<213> ORGANISM: Artificial Sequence
<220> FEATURE:
<223> OTHER INFORMATION: synthesized

<400> SEQUENCE: 481
uuucucucca cuucucuagc                                            20

<210> SEQ ID NO 482
<211> LENGTH: 20
<212> TYPE: RNA
<213> ORGANISM: Artificial Sequence
<220> FEATURE:
<223> OTHER INFORMATION: synthesized

<400> SEQUENCE: 482
uuugcuagag aaguggagag                                            20

<210> SEQ ID NO 483
<211> LENGTH: 20
<212> TYPE: RNA
<213> ORGANISM: Artificial Sequence
<220> FEATURE:
<223> OTHER INFORMATION: synthesized

<400> SEQUENCE: 483
```
uuuucucucc acuucucuag					20

<210> SEQ ID NO 484
<211> LENGTH: 20
<212> TYPE: RNA
<213> ORGANISM: Artificial Sequence
<220> FEATURE:
<223> OTHER INFORMATION: synthesized

<400> SEQUENCE: 484
ccucauucca gaguuucucu					20

<210> SEQ ID NO 485
<211> LENGTH: 20
<212> TYPE: RNA
<213> ORGANISM: Artificial Sequence
<220> FEATURE:
<223> OTHER INFORMATION: synthesized

<400> SEQUENCE: 485
gguaagagga cuaguuagag					20

<210> SEQ ID NO 486
<211> LENGTH: 20
<212> TYPE: RNA
<213> ORGANISM: Artificial Sequence
<220> FEATURE:
<223> OTHER INFORMATION: synthesized

<400> SEQUENCE: 486
guaagaggac uaguuagagg					20

<210> SEQ ID NO 487
<211> LENGTH: 20
<212> TYPE: RNA
<213> ORGANISM: Artificial Sequence
<220> FEATURE:
<223> OTHER INFORMATION: synthesized

<400> SEQUENCE: 487
uaagaggacu aguuagaggu					20

<210> SEQ ID NO 488
<211> LENGTH: 20
<212> TYPE: RNA
<213> ORGANISM: Artificial Sequence
<220> FEATURE:
<223> OTHER INFORMATION: synthesized

<400> SEQUENCE: 488
ucauuccaga guuucucugc					20

<210> SEQ ID NO 489
<211> LENGTH: 20
<212> TYPE: RNA
<213> ORGANISM: Artificial Sequence
<220> FEATURE:
<223> OTHER INFORMATION: synthesized

<400> SEQUENCE: 489
agcauaagug gguuccagag					20

<210> SEQ ID NO 490
<211> LENGTH: 20
<212> TYPE: RNA
<213> ORGANISM: Artificial Sequence

```
<220> FEATURE:
<223> OTHER INFORMATION: synthesized

<400> SEQUENCE: 490
cauaaguggg uuccagagau                                               20

<210> SEQ ID NO 491
<211> LENGTH: 20
<212> TYPE: RNA
<213> ORGANISM: Artificial Sequence
<220> FEATURE:
<223> OTHER INFORMATION: synthesized

<400> SEQUENCE: 491
ggaggcagcc aggcaacuuc                                               20

<210> SEQ ID NO 492
<211> LENGTH: 20
<212> TYPE: RNA
<213> ORGANISM: Artificial Sequence
<220> FEATURE:
<223> OTHER INFORMATION: synthesized

<400> SEQUENCE: 492
gggaggcagc caggcaacuu                                               20

<210> SEQ ID NO 493
<211> LENGTH: 20
<212> TYPE: RNA
<213> ORGANISM: Artificial Sequence
<220> FEATURE:
<223> OTHER INFORMATION: synthesized

<400> SEQUENCE: 493
gggggaggca gccaggcaac                                               20

<210> SEQ ID NO 494
<211> LENGTH: 20
<212> TYPE: RNA
<213> ORGANISM: Artificial Sequence
<220> FEATURE:
<223> OTHER INFORMATION: synthesized

<400> SEQUENCE: 494
auucugauau aacugcauua                                               20

<210> SEQ ID NO 495
<211> LENGTH: 20
<212> TYPE: RNA
<213> ORGANISM: Artificial Sequence
<220> FEATURE:
<223> OTHER INFORMATION: synthesized

<400> SEQUENCE: 495
cccucucucc uuccuucuuu                                               20

<210> SEQ ID NO 496
<211> LENGTH: 20
<212> TYPE: RNA
<213> ORGANISM: Artificial Sequence
<220> FEATURE:
<223> OTHER INFORMATION: synthesized

<400> SEQUENCE: 496
uauucugaua uaacugcauu                                               20
```

```
<210> SEQ ID NO 497
<211> LENGTH: 20
<212> TYPE: RNA
<213> ORGANISM: Artificial Sequence
<220> FEATURE:
<223> OTHER INFORMATION: synthesized

<400> SEQUENCE: 497
ucugauauaa cugcauuauc                                               20

<210> SEQ ID NO 498
<211> LENGTH: 20
<212> TYPE: RNA
<213> ORGANISM: Artificial Sequence
<220> FEATURE:
<223> OTHER INFORMATION: synthesized

<400> SEQUENCE: 498
uucugauaua acugcauuau                                               20

<210> SEQ ID NO 499
<211> LENGTH: 20
<212> TYPE: RNA
<213> ORGANISM: Artificial Sequence
<220> FEATURE:
<223> OTHER INFORMATION: synthesized

<400> SEQUENCE: 499
auuagugggu gaacagacag                                               20

<210> SEQ ID NO 500
<211> LENGTH: 20
<212> TYPE: RNA
<213> ORGANISM: Artificial Sequence
<220> FEATURE:
<223> OTHER INFORMATION: synthesized

<400> SEQUENCE: 500
uaguggguga acagacagga                                               20

<210> SEQ ID NO 501
<211> LENGTH: 20
<212> TYPE: RNA
<213> ORGANISM: Artificial Sequence
<220> FEATURE:
<223> OTHER INFORMATION: synthesized

<400> SEQUENCE: 501
ugccugagca ugcaacugaa                                               20

<210> SEQ ID NO 502
<211> LENGTH: 20
<212> TYPE: RNA
<213> ORGANISM: Artificial Sequence
<220> FEATURE:
<223> OTHER INFORMATION: synthesized

<400> SEQUENCE: 502
uuagugggug aacagacagg                                               20

<210> SEQ ID NO 503
<211> LENGTH: 20
<212> TYPE: RNA
<213> ORGANISM: Artificial Sequence
<220> FEATURE:
<223> OTHER INFORMATION: synthesized
```

<400> SEQUENCE: 503
uugccugagc augcaacuga                                               20

<210> SEQ ID NO 504
<211> LENGTH: 20
<212> TYPE: RNA
<213> ORGANISM: Artificial Sequence
<220> FEATURE:
<223> OTHER INFORMATION: synthesized

<400> SEQUENCE: 504
uuugccugag caugcaacug                                               20

<210> SEQ ID NO 505
<211> LENGTH: 20
<212> TYPE: RNA
<213> ORGANISM: Artificial Sequence
<220> FEATURE:
<223> OTHER INFORMATION: synthesized

<400> SEQUENCE: 505
uuuugccuga gcaugcaacu                                               20

<210> SEQ ID NO 506
<211> LENGTH: 20
<212> TYPE: RNA
<213> ORGANISM: Artificial Sequence
<220> FEATURE:
<223> OTHER INFORMATION: synthesized

<400> SEQUENCE: 506
cccagaguuc cagcuuccag                                               20

<210> SEQ ID NO 507
<211> LENGTH: 20
<212> TYPE: RNA
<213> ORGANISM: Artificial Sequence
<220> FEATURE:
<223> OTHER INFORMATION: synthesized

<400> SEQUENCE: 507
cucccagagu uccagcuucc                                               20

<210> SEQ ID NO 508
<211> LENGTH: 20
<212> TYPE: RNA
<213> ORGANISM: Artificial Sequence
<220> FEATURE:
<223> OTHER INFORMATION: synthesized

<400> SEQUENCE: 508
gcucccagag uuccagcuuc                                               20

<210> SEQ ID NO 509
<211> LENGTH: 20
<212> TYPE: RNA
<213> ORGANISM: Artificial Sequence
<220> FEATURE:
<223> OTHER INFORMATION: synthesized

<400> SEQUENCE: 509
ggagcucugg accuggaagu                                               20

<210> SEQ ID NO 510

```
<211> LENGTH: 20
<212> TYPE: RNA
<213> ORGANISM: Artificial Sequence
<220> FEATURE:
<223> OTHER INFORMATION: synthesized

<400> SEQUENCE: 510
gggagcucug gaccuggaag                                                     20

<210> SEQ ID NO 511
<211> LENGTH: 20
<212> TYPE: RNA
<213> ORGANISM: Artificial Sequence
<220> FEATURE:
<223> OTHER INFORMATION: synthesized

<400> SEQUENCE: 511
ucccagaguu ccagcuucca                                                     20

<210> SEQ ID NO 512
<211> LENGTH: 20
<212> TYPE: RNA
<213> ORGANISM: Artificial Sequence
<220> FEATURE:
<223> OTHER INFORMATION: synthesized

<400> SEQUENCE: 512
ugggagcucu ggaccuggaa                                                     20

<210> SEQ ID NO 513
<211> LENGTH: 20
<212> TYPE: RNA
<213> ORGANISM: Artificial Sequence
<220> FEATURE:
<223> OTHER INFORMATION: synthesized

<400> SEQUENCE: 513
acaaagcuuc cugaggccaa                                                     20

<210> SEQ ID NO 514
<211> LENGTH: 20
<212> TYPE: RNA
<213> ORGANISM: Artificial Sequence
<220> FEATURE:
<223> OTHER INFORMATION: synthesized

<400> SEQUENCE: 514
acacaaagcu uccugaggcc                                                     20

<210> SEQ ID NO 515
<211> LENGTH: 20
<212> TYPE: RNA
<213> ORGANISM: Artificial Sequence
<220> FEATURE:
<223> OTHER INFORMATION: synthesized

<400> SEQUENCE: 515
acauuugugc caguccuugu                                                     20

<210> SEQ ID NO 516
<211> LENGTH: 20
<212> TYPE: RNA
<213> ORGANISM: Artificial Sequence
<220> FEATURE:
<223> OTHER INFORMATION: synthesized

<400> SEQUENCE: 516
```

| | |
|---|---|
| caaagcuucc ugaggccaag | 20 |

<210> SEQ ID NO 517
<211> LENGTH: 20
<212> TYPE: RNA
<213> ORGANISM: Artificial Sequence
<220> FEATURE:
<223> OTHER INFORMATION: synthesized

<400> SEQUENCE: 517

| | |
|---|---|
| cauuugugcc aguccuugug | 20 |

<210> SEQ ID NO 518
<211> LENGTH: 20
<212> TYPE: RNA
<213> ORGANISM: Artificial Sequence
<220> FEATURE:
<223> OTHER INFORMATION: synthesized

<400> SEQUENCE: 518

| | |
|---|---|
| gacauuugug ccaguccuug | 20 |

<210> SEQ ID NO 519
<211> LENGTH: 20
<212> TYPE: RNA
<213> ORGANISM: Artificial Sequence
<220> FEATURE:
<223> OTHER INFORMATION: synthesized

<400> SEQUENCE: 519

| | |
|---|---|
| ugacauuugu gccaguccuu | 20 |

<210> SEQ ID NO 520
<211> LENGTH: 20
<212> TYPE: RNA
<213> ORGANISM: Artificial Sequence
<220> FEATURE:
<223> OTHER INFORMATION: synthesized

<400> SEQUENCE: 520

| | |
|---|---|
| aauugaauag uuaccuacau | 20 |

<210> SEQ ID NO 521
<211> LENGTH: 20
<212> TYPE: RNA
<213> ORGANISM: Artificial Sequence
<220> FEATURE:
<223> OTHER INFORMATION: synthesized

<400> SEQUENCE: 521

| | |
|---|---|
| agguuccuuu ucuuuauuug | 20 |

<210> SEQ ID NO 522
<211> LENGTH: 20
<212> TYPE: RNA
<213> ORGANISM: Artificial Sequence
<220> FEATURE:
<223> OTHER INFORMATION: synthesized

<400> SEQUENCE: 522

| | |
|---|---|
| aguagguucc uuuucuuuau | 20 |

<210> SEQ ID NO 523
<211> LENGTH: 20
<212> TYPE: RNA

```
<213> ORGANISM: Artificial Sequence
<220> FEATURE:
<223> OTHER INFORMATION: synthesized

<400> SEQUENCE: 523
auaauugaau aguuaccuac                                          20

<210> SEQ ID NO 524
<211> LENGTH: 20
<212> TYPE: RNA
<213> ORGANISM: Artificial Sequence
<220> FEATURE:
<223> OTHER INFORMATION: synthesized

<400> SEQUENCE: 524
guagguuccu uuucuuuauu                                          20

<210> SEQ ID NO 525
<211> LENGTH: 20
<212> TYPE: RNA
<213> ORGANISM: Artificial Sequence
<220> FEATURE:
<223> OTHER INFORMATION: synthesized

<400> SEQUENCE: 525
uaauugaaua guuaccuaca                                          20

<210> SEQ ID NO 526
<211> LENGTH: 20
<212> TYPE: RNA
<213> ORGANISM: Artificial Sequence
<220> FEATURE:
<223> OTHER INFORMATION: synthesized

<400> SEQUENCE: 526
uagguuccuu uucuuuauuu                                          20

<210> SEQ ID NO 527
<211> LENGTH: 20
<212> TYPE: RNA
<213> ORGANISM: Artificial Sequence
<220> FEATURE:
<223> OTHER INFORMATION: synthesized

<400> SEQUENCE: 527
gcauuaugau uuuggguggu                                          20

<210> SEQ ID NO 528
<211> LENGTH: 20
<212> TYPE: RNA
<213> ORGANISM: Artificial Sequence
<220> FEATURE:
<223> OTHER INFORMATION: synthesized

<400> SEQUENCE: 528
ggcauuauga uuuugggugg                                          20

<210> SEQ ID NO 529
<211> LENGTH: 20
<212> TYPE: RNA
<213> ORGANISM: Artificial Sequence
<220> FEATURE:
<223> OTHER INFORMATION: synthesized

<400> SEQUENCE: 529
gguuugagaa cuucucuucc                                          20
```

```
<210> SEQ ID NO 530
<211> LENGTH: 20
<212> TYPE: RNA
<213> ORGANISM: Artificial Sequence
<220> FEATURE:
<223> OTHER INFORMATION: synthesized

<400> SEQUENCE: 530
ugguuugaga acuucucuuc                                                    20

<210> SEQ ID NO 531
<211> LENGTH: 20
<212> TYPE: RNA
<213> ORGANISM: Artificial Sequence
<220> FEATURE:
<223> OTHER INFORMATION: synthesized

<400> SEQUENCE: 531
uugguuugag aacuucucuu                                                    20

<210> SEQ ID NO 532
<211> LENGTH: 20
<212> TYPE: RNA
<213> ORGANISM: Artificial Sequence
<220> FEATURE:
<223> OTHER INFORMATION: synthesized

<400> SEQUENCE: 532
aguugcuuaa auuauaaucu                                                    20

<210> SEQ ID NO 533
<211> LENGTH: 20
<212> TYPE: RNA
<213> ORGANISM: Artificial Sequence
<220> FEATURE:
<223> OTHER INFORMATION: synthesized

<400> SEQUENCE: 533
caaaaagaaa aagccaaugc                                                    20

<210> SEQ ID NO 534
<211> LENGTH: 20
<212> TYPE: RNA
<213> ORGANISM: Artificial Sequence
<220> FEATURE:
<223> OTHER INFORMATION: synthesized

<400> SEQUENCE: 534
cucaaaaaga aaagccaau                                                     20

<210> SEQ ID NO 535
<211> LENGTH: 20
<212> TYPE: RNA
<213> ORGANISM: Artificial Sequence
<220> FEATURE:
<223> OTHER INFORMATION: synthesized

<400> SEQUENCE: 535
guugcuuaaa uuauaaucug                                                    20

<210> SEQ ID NO 536
<211> LENGTH: 20
<212> TYPE: RNA
<213> ORGANISM: Artificial Sequence
<220> FEATURE:
```

```
<223> OTHER INFORMATION: synthesized

<400> SEQUENCE: 536
ugcuuaaauu auaaucugcc                                               20

<210> SEQ ID NO 537
<211> LENGTH: 20
<212> TYPE: RNA
<213> ORGANISM: Artificial Sequence
<220> FEATURE:
<223> OTHER INFORMATION: synthesized

<400> SEQUENCE: 537 aaugagggu cacuuagcca                                                20

<210> SEQ ID NO 538
<211> LENGTH: 20
<212> TYPE: RNA
<213> ORGANISM: Artificial Sequence
<220> FEATURE:
<223> OTHER INFORMATION: synthesized

<400> SEQUENCE: 538
ccucaauuuc cuggcaccua                                               20

<210> SEQ ID NO 539
<211> LENGTH: 20
<212> TYPE: RNA
<213> ORGANISM: Artificial Sequence
<220> FEATURE:
<223> OTHER INFORMATION: synthesized

<400> SEQUENCE: 539
cucaauuucc uggcaccuaa                                               20

<210> SEQ ID NO 540
<211> LENGTH: 20
<212> TYPE: RNA
<213> ORGANISM: Artificial Sequence
<220> FEATURE:
<223> OTHER INFORMATION: synthesized

<400> SEQUENCE: 540
gaaugagggu ccacuuagcc                                               20

<210> SEQ ID NO 541
<211> LENGTH: 20
<212> TYPE: RNA
<213> ORGANISM: Artificial Sequence
<220> FEATURE:
<223> OTHER INFORMATION: synthesized

<400> SEQUENCE: 541
gccucaauuu ccuggcaccu                                               20

<210> SEQ ID NO 542
<211> LENGTH: 20
<212> TYPE: RNA
<213> ORGANISM: Artificial Sequence
<220> FEATURE:
<223> OTHER INFORMATION: synthesized

<400> SEQUENCE: 542
ucaauuuccu ggcaccuaau                                               20
```

```
<210> SEQ ID NO 543
<211> LENGTH: 20
<212> TYPE: RNA
<213> ORGANISM: Artificial Sequence
<220> FEATURE:
<223> OTHER INFORMATION: synthesized

<400> SEQUENCE: 543
ugagggucca cuuagccaua                                               20

<210> SEQ ID NO 544
<211> LENGTH: 20
<212> TYPE: RNA
<213> ORGANISM: Artificial Sequence
<220> FEATURE:
<223> OTHER INFORMATION: synthesized

<400> SEQUENCE: 544
agaguuuguc agugagacug                                               20

<210> SEQ ID NO 545
<211> LENGTH: 20
<212> TYPE: RNA
<213> ORGANISM: Artificial Sequence
<220> FEATURE:
<223> OTHER INFORMATION: synthesized

<400> SEQUENCE: 545
cagauucuga gccccuagac                                               20

<210> SEQ ID NO 546
<211> LENGTH: 20
<212> TYPE: RNA
<213> ORGANISM: Artificial Sequence
<220> FEATURE:
<223> OTHER INFORMATION: synthesized

<400> SEQUENCE: 546
gagaguuugu cagugagacu                                               20

<210> SEQ ID NO 547
<211> LENGTH: 20
<212> TYPE: RNA
<213> ORGANISM: Artificial Sequence
<220> FEATURE:
<223> OTHER INFORMATION: synthesized

<400> SEQUENCE: 547
gccagauucu gagccccuag                                               20

<210> SEQ ID NO 548
<211> LENGTH: 20
<212> TYPE: RNA
<213> ORGANISM: Artificial Sequence
<220> FEATURE:
<223> OTHER INFORMATION: synthesized

<400> SEQUENCE: 548
ugccagauuc ugagccccua                                               20

<210> SEQ ID NO 549
<211> LENGTH: 20
<212> TYPE: RNA
<213> ORGANISM: Artificial Sequence
<220> FEATURE:
<223> OTHER INFORMATION: synthesized
```

```
<400> SEQUENCE: 549
cgccuuccuu uucccucuac                                              20

<210> SEQ ID NO 550
<211> LENGTH: 20
<212> TYPE: RNA
<213> ORGANISM: Artificial Sequence
<220> FEATURE:
<223> OTHER INFORMATION: synthesized

<400> SEQUENCE: 550
cuuccuuuuc ccucuacuca                                              20

<210> SEQ ID NO 551
<211> LENGTH: 20
<212> TYPE: RNA
<213> ORGANISM: Artificial Sequence
<220> FEATURE:
<223> OTHER INFORMATION: synthesized

<400> SEQUENCE: 551
gccuuccuuu ucccucuacu                                              20

<210> SEQ ID NO 552
<211> LENGTH: 20
<212> TYPE: RNA
<213> ORGANISM: Artificial Sequence
<220> FEATURE:
<223> OTHER INFORMATION: synthesized

<400> SEQUENCE: 552
guggucccag auguccuugu                                              20

<210> SEQ ID NO 553
<211> LENGTH: 20
<212> TYPE: RNA
<213> ORGANISM: Artificial Sequence
<220> FEATURE:
<223> OTHER INFORMATION: synthesized

<400> SEQUENCE: 553
uggucccaga uguccuuguu                                              20

<210> SEQ ID NO 554
<211> LENGTH: 20
<212> TYPE: RNA
<213> ORGANISM: Artificial Sequence
<220> FEATURE:
<223> OTHER INFORMATION: synthesized

<400> SEQUENCE: 554
uguggcccca gauguccuug                                              20

<210> SEQ ID NO 555
<211> LENGTH: 20
<212> TYPE: RNA
<213> ORGANISM: Artificial Sequence
<220> FEATURE:
<223> OTHER INFORMATION: synthesized

<400> SEQUENCE: 555
accaaucagg ucagccugug                                              20

<210> SEQ ID NO 556
<211> LENGTH: 20
```

```
<212> TYPE: RNA
<213> ORGANISM: Artificial Sequence
<220> FEATURE:
<223> OTHER INFORMATION: synthesized

<400> SEQUENCE: 556
caaucagguc agccugugag                                               20

<210> SEQ ID NO 557
<211> LENGTH: 20
<212> TYPE: RNA
<213> ORGANISM: Artificial Sequence
<220> FEATURE:
<223> OTHER INFORMATION: synthesized

<400> SEQUENCE: 557
ccaaucaggu cagccuguga                                               20

<210> SEQ ID NO 558
<211> LENGTH: 20
<212> TYPE: RNA
<213> ORGANISM: Artificial Sequence
<220> FEATURE:
<223> OTHER INFORMATION: synthesized

<400> SEQUENCE: 558
cuucccucug augcuagagg                                               20

<210> SEQ ID NO 559
<211> LENGTH: 20
<212> TYPE: RNA
<213> ORGANISM: Artificial Sequence
<220> FEATURE:
<223> OTHER INFORMATION: synthesized

<400> SEQUENCE: 559
gaccaaucag gucagccugu                                               20

<210> SEQ ID NO 560
<211> LENGTH: 20
<212> TYPE: RNA
<213> ORGANISM: Artificial Sequence
<220> FEATURE:
<223> OTHER INFORMATION: synthesized

<400> SEQUENCE: 560
aagucuuggg uucuuugcua                                               20

<210> SEQ ID NO 561
<211> LENGTH: 20
<212> TYPE: RNA
<213> ORGANISM: Artificial Sequence
<220> FEATURE:
<223> OTHER INFORMATION: synthesized

<400> SEQUENCE: 561
aaucagguac ccugcaaaau                                               20

<210> SEQ ID NO 562
<211> LENGTH: 20
<212> TYPE: RNA
<213> ORGANISM: Artificial Sequence
<220> FEATURE:
<223> OTHER INFORMATION: synthesized

<400> SEQUENCE: 562
```

-continued cuaagucuug gguucuuugc                                              20

<210> SEQ ID NO 563
<211> LENGTH: 20
<212> TYPE: RNA
<213> ORGANISM: Artificial Sequence
<220> FEATURE:
<223> OTHER INFORMATION: synthesized

<400> SEQUENCE: 563
gaaucaggua cccugcaaaa                                              20

<210> SEQ ID NO 564
<211> LENGTH: 20
<212> TYPE: RNA
<213> ORGANISM: Artificial Sequence
<220> FEATURE:
<223> OTHER INFORMATION: synthesized

<400> SEQUENCE: 564
ucagguaccc ugcaaaaugu                                              20

<210> SEQ ID NO 565
<211> LENGTH: 20
<212> TYPE: RNA
<213> ORGANISM: Artificial Sequence
<220> FEATURE:
<223> OTHER INFORMATION: synthesized

<400> SEQUENCE: 565
aagccaacuu aucuggaaga                                              20

<210> SEQ ID NO 566
<211> LENGTH: 20
<212> TYPE: RNA
<213> ORGANISM: Artificial Sequence
<220> FEATURE:
<223> OTHER INFORMATION: synthesized

<400> SEQUENCE: 566
agccaacuua ucuggaagag                                              20

<210> SEQ ID NO 567
<211> LENGTH: 20
<212> TYPE: RNA
<213> ORGANISM: Artificial Sequence
<220> FEATURE:
<223> OTHER INFORMATION: synthesized

<400> SEQUENCE: 567
agcccccauu ucuuccuacc                                              20

<210> SEQ ID NO 568
<211> LENGTH: 20
<212> TYPE: RNA
<213> ORGANISM: Artificial Sequence
<220> FEATURE:
<223> OTHER INFORMATION: synthesized

<400> SEQUENCE: 568
cagcccccau uucuuccuac                                              20

<210> SEQ ID NO 569
<211> LENGTH: 20
<212> TYPE: RNA
<213> ORGANISM: Artificial Sequence

```
<220> FEATURE:
<223> OTHER INFORMATION: synthesized

<400> SEQUENCE: 569
cccccauuuc uuccuacccu                                          20

<210> SEQ ID NO 570
<211> LENGTH: 20
<212> TYPE: RNA
<213> ORGANISM: Artificial Sequence
<220> FEATURE:
<223> OTHER INFORMATION: synthesized

<400> SEQUENCE: 570 gccccauuu cuuccuaccc                                           20

<210> SEQ ID NO 571
<211> LENGTH: 20
<212> TYPE: RNA
<213> ORGANISM: Artificial Sequence
<220> FEATURE:
<223> OTHER INFORMATION: synthesized

<400> SEQUENCE: 571
acacagucuc acugacaaac                                          20

<210> SEQ ID NO 572
<211> LENGTH: 20
<212> TYPE: RNA
<213> ORGANISM: Artificial Sequence
<220> FEATURE:
<223> OTHER INFORMATION: synthesized

<400> SEQUENCE: 572
acagucucac ugacaaacuc                                          20

<210> SEQ ID NO 573
<211> LENGTH: 20
<212> TYPE: RNA
<213> ORGANISM: Artificial Sequence
<220> FEATURE:
<223> OTHER INFORMATION: synthesized

<400> SEQUENCE: 573
acucagucuc acugacaaac                                          20

<210> SEQ ID NO 574
<211> LENGTH: 20
<212> TYPE: RNA
<213> ORGANISM: Artificial Sequence
<220> FEATURE:
<223> OTHER INFORMATION: synthesized

<400> SEQUENCE: 574
acugagucua ggggcucaga                                          20

<210> SEQ ID NO 575
<211> LENGTH: 20
<212> TYPE: RNA
<213> ORGANISM: Artificial Sequence
<220> FEATURE:
<223> OTHER INFORMATION: synthesized

<400> SEQUENCE: 575
acugugucua ggggcucaga                                          20
```

<210> SEQ ID NO 576
<211> LENGTH: 20
<212> TYPE: RNA
<213> ORGANISM: Artificial Sequence
<220> FEATURE:
<223> OTHER INFORMATION: synthesized

<400> SEQUENCE: 576
agacacaguc ucacugacaa                                               20

<210> SEQ ID NO 577
<211> LENGTH: 20
<212> TYPE: RNA
<213> ORGANISM: Artificial Sequence
<220> FEATURE:
<223> OTHER INFORMATION: synthesized

<400> SEQUENCE: 577
agacucaguc ucacugacaa                                               20

<210> SEQ ID NO 578
<211> LENGTH: 20
<212> TYPE: RNA
<213> ORGANISM: Artificial Sequence
<220> FEATURE:
<223> OTHER INFORMATION: synthesized

<400> SEQUENCE: 578
agacugaguc uagggggcuca                                              20

<210> SEQ ID NO 579
<211> LENGTH: 20
<212> TYPE: RNA
<213> ORGANISM: Artificial Sequence
<220> FEATURE:
<223> OTHER INFORMATION: synthesized

<400> SEQUENCE: 579
agacuguguc uagggggcuca                                              20

<210> SEQ ID NO 580
<211> LENGTH: 20
<212> TYPE: RNA
<213> ORGANISM: Artificial Sequence
<220> FEATURE:
<223> OTHER INFORMATION: synthesized

<400> SEQUENCE: 580
agauucugag ccccuagaca                                               20

<210> SEQ ID NO 581
<211> LENGTH: 20
<212> TYPE: RNA
<213> ORGANISM: Artificial Sequence
<220> FEATURE:
<223> OTHER INFORMATION: synthesized

<400> SEQUENCE: 581
agauucugag ccccuagacu                                               20

<210> SEQ ID NO 582
<211> LENGTH: 20
<212> TYPE: RNA
<213> ORGANISM: Artificial Sequence
<220> FEATURE:
<223> OTHER INFORMATION: synthesized -continued

<400> SEQUENCE: 582
agccccuaga cacagucuca                                             20

<210> SEQ ID NO 583
<211> LENGTH: 20
<212> TYPE: RNA
<213> ORGANISM: Artificial Sequence
<220> FEATURE:
<223> OTHER INFORMATION: synthesized

<400> SEQUENCE: 583
agccccuaga cucagucuca                                             20

<210> SEQ ID NO 584
<211> LENGTH: 20
<212> TYPE: RNA
<213> ORGANISM: Artificial Sequence
<220> FEATURE:
<223> OTHER INFORMATION: synthesized

<400> SEQUENCE: 584
agucuagggg cucagaaucu                                             20

<210> SEQ ID NO 585
<211> LENGTH: 20
<212> TYPE: RNA
<213> ORGANISM: Artificial Sequence
<220> FEATURE:
<223> OTHER INFORMATION: synthesized

<400> SEQUENCE: 585
agugagacug agucuagggg                                             20

<210> SEQ ID NO 586
<211> LENGTH: 20
<212> TYPE: RNA
<213> ORGANISM: Artificial Sequence
<220> FEATURE:
<223> OTHER INFORMATION: synthesized

<400> SEQUENCE: 586
agugagacug ugucuagggg                                             20

<210> SEQ ID NO 587
<211> LENGTH: 20
<212> TYPE: RNA
<213> ORGANISM: Artificial Sequence
<220> FEATURE:
<223> OTHER INFORMATION: synthesized

<400> SEQUENCE: 587
aguuugucag ugagacugag                                             20

<210> SEQ ID NO 588
<211> LENGTH: 20
<212> TYPE: RNA
<213> ORGANISM: Artificial Sequence
<220> FEATURE:
<223> OTHER INFORMATION: synthesized

<400> SEQUENCE: 588
aguuugucag ugagacugug                                             20

<210> SEQ ID NO 589

```
<211> LENGTH: 20
<212> TYPE: RNA
<213> ORGANISM: Artificial Sequence
<220> FEATURE:
<223> OTHER INFORMATION: synthesized

<400> SEQUENCE: 589
auucugagcc ccuagacaca                                              20

<210> SEQ ID NO 590
<211> LENGTH: 20
<212> TYPE: RNA
<213> ORGANISM: Artificial Sequence
<220> FEATURE:
<223> OTHER INFORMATION: synthesized

<400> SEQUENCE: 590
auucugagcc ccuagacuca                                              20

<210> SEQ ID NO 591
<211> LENGTH: 20
<212> TYPE: RNA
<213> ORGANISM: Artificial Sequence
<220> FEATURE:
<223> OTHER INFORMATION: synthesized

<400> SEQUENCE: 591
cacagucuca cugacaaacu                                              20

<210> SEQ ID NO 592
<211> LENGTH: 20
<212> TYPE: RNA
<213> ORGANISM: Artificial Sequence
<220> FEATURE:
<223> OTHER INFORMATION: synthesized

<400> SEQUENCE: 592
cagugagacu gagucuaggg                                              20

<210> SEQ ID NO 593
<211> LENGTH: 20
<212> TYPE: RNA
<213> ORGANISM: Artificial Sequence
<220> FEATURE:
<223> OTHER INFORMATION: synthesized

<400> SEQUENCE: 593
cagugagacu gugucuaggg                                              20

<210> SEQ ID NO 594
<211> LENGTH: 20
<212> TYPE: RNA
<213> ORGANISM: Artificial Sequence
<220> FEATURE:
<223> OTHER INFORMATION: synthesized

<400> SEQUENCE: 594
ccccuagaca cagucucacu                                              20

<210> SEQ ID NO 595
<211> LENGTH: 20
<212> TYPE: RNA
<213> ORGANISM: Artificial Sequence
<220> FEATURE:
<223> OTHER INFORMATION: synthesized

<400> SEQUENCE: 595
```
ccccuagacu cagucucacu                                              20

<210> SEQ ID NO 596
<211> LENGTH: 20
<212> TYPE: RNA
<213> ORGANISM: Artificial Sequence
<220> FEATURE:
<223> OTHER INFORMATION: synthesized

<400> SEQUENCE: 596
cccuagacac agucucacug                                              20

<210> SEQ ID NO 597
<211> LENGTH: 20
<212> TYPE: RNA
<213> ORGANISM: Artificial Sequence
<220> FEATURE:
<223> OTHER INFORMATION: synthesized

<400> SEQUENCE: 597
cccuagacuc agucucacug                                              20

<210> SEQ ID NO 598
<211> LENGTH: 20
<212> TYPE: RNA
<213> ORGANISM: Artificial Sequence
<220> FEATURE:
<223> OTHER INFORMATION: synthesized

<400> SEQUENCE: 598
ccuagacaca gucucacuga                                              20

<210> SEQ ID NO 599
<211> LENGTH: 20
<212> TYPE: RNA
<213> ORGANISM: Artificial Sequence
<220> FEATURE:
<223> OTHER INFORMATION: synthesized

<400> SEQUENCE: 599
ccuagacuca gucucacuga                                              20

<210> SEQ ID NO 600
<211> LENGTH: 20
<212> TYPE: RNA
<213> ORGANISM: Artificial Sequence
<220> FEATURE:
<223> OTHER INFORMATION: synthesized

<400> SEQUENCE: 600
cuagacacag ucucacugac                                              20

<210> SEQ ID NO 601
<211> LENGTH: 20
<212> TYPE: RNA
<213> ORGANISM: Artificial Sequence
<220> FEATURE:
<223> OTHER INFORMATION: synthesized

<400> SEQUENCE: 601
cuagacucag ucucacugac                                              20

<210> SEQ ID NO 602
<211> LENGTH: 20
<212> TYPE: RNA

```
<213> ORGANISM: Artificial Sequence
<220> FEATURE:
<223> OTHER INFORMATION: synthesized

<400> SEQUENCE: 602
cucagucuca cugacaaacu                                               20

<210> SEQ ID NO 603
<211> LENGTH: 20
<212> TYPE: RNA
<213> ORGANISM: Artificial Sequence
<220> FEATURE:
<223> OTHER INFORMATION: synthesized

<400> SEQUENCE: 603
cugagccccu agacacaguc                                               20

<210> SEQ ID NO 604
<211> LENGTH: 20
<212> TYPE: RNA
<213> ORGANISM: Artificial Sequence
<220> FEATURE:
<223> OTHER INFORMATION: synthesized

<400> SEQUENCE: 604
cugagccccu agacucaguc                                               20

<210> SEQ ID NO 605
<211> LENGTH: 20
<212> TYPE: RNA
<213> ORGANISM: Artificial Sequence
<220> FEATURE:
<223> OTHER INFORMATION: synthesized

<400> SEQUENCE: 605
gacacagucu cacugacaaa                                               20

<210> SEQ ID NO 606
<211> LENGTH: 20
<212> TYPE: RNA
<213> ORGANISM: Artificial Sequence
<220> FEATURE:
<223> OTHER INFORMATION: synthesized

<400> SEQUENCE: 606
gacucagucu cacugacaaa                                               20

<210> SEQ ID NO 607
<211> LENGTH: 20
<212> TYPE: RNA
<213> ORGANISM: Artificial Sequence
<220> FEATURE:
<223> OTHER INFORMATION: synthesized

<400> SEQUENCE: 607
gacugagucu agggcucag                                                20

<210> SEQ ID NO 608
<211> LENGTH: 20
<212> TYPE: RNA
<213> ORGANISM: Artificial Sequence
<220> FEATURE:
<223> OTHER INFORMATION: synthesized

<400> SEQUENCE: 608
gacugugucu agggcucag                                                20
```

<210> SEQ ID NO 609
<211> LENGTH: 20
<212> TYPE: RNA
<213> ORGANISM: Artificial Sequence
<220> FEATURE:
<223> OTHER INFORMATION: synthesized

<400> SEQUENCE: 609
gaguuuguca gugagacuga                                               20

<210> SEQ ID NO 610
<211> LENGTH: 20
<212> TYPE: RNA
<213> ORGANISM: Artificial Sequence
<220> FEATURE:
<223> OTHER INFORMATION: synthesized

<400> SEQUENCE: 610
gaguuuguca gugagacugu                                               20

<210> SEQ ID NO 611
<211> LENGTH: 20
<212> TYPE: RNA
<213> ORGANISM: Artificial Sequence
<220> FEATURE:
<223> OTHER INFORMATION: synthesized

<400> SEQUENCE: 611
gauucugagc cccuagacac                                               20

<210> SEQ ID NO 612
<211> LENGTH: 20
<212> TYPE: RNA
<213> ORGANISM: Artificial Sequence
<220> FEATURE:
<223> OTHER INFORMATION: synthesized

<400> SEQUENCE: 612
gauucugagc cccuagacuc                                               20

<210> SEQ ID NO 613
<211> LENGTH: 20
<212> TYPE: RNA
<213> ORGANISM: Artificial Sequence
<220> FEATURE:
<223> OTHER INFORMATION: synthesized

<400> SEQUENCE: 613
gugagacuga gucuaggggc                                               20

<210> SEQ ID NO 614
<211> LENGTH: 20
<212> TYPE: RNA
<213> ORGANISM: Artificial Sequence
<220> FEATURE:
<223> OTHER INFORMATION: synthesized

<400> SEQUENCE: 614
gugagacugu gucuaggggc                                               20

<210> SEQ ID NO 615
<211> LENGTH: 20
<212> TYPE: RNA
<213> ORGANISM: Artificial Sequence
<220> FEATURE:

-continued

<223> OTHER INFORMATION: synthesized

<400> SEQUENCE: 615
guuugucagu gagacugagu                                           20

<210> SEQ ID NO 616
<211> LENGTH: 20
<212> TYPE: RNA
<213> ORGANISM: Artificial Sequence
<220> FEATURE:
<223> OTHER INFORMATION: synthesized

<400> SEQUENCE: 616
guuugucagu gagacugugu                                           20

<210> SEQ ID NO 617
<211> LENGTH: 20
<212> TYPE: RNA
<213> ORGANISM: Artificial Sequence
<220> FEATURE:
<223> OTHER INFORMATION: synthesized

<400> SEQUENCE: 617
uagacacagu cucacugaca                                           20

<210> SEQ ID NO 618
<211> LENGTH: 20
<212> TYPE: RNA
<213> ORGANISM: Artificial Sequence
<220> FEATURE:
<223> OTHER INFORMATION: synthesized

<400> SEQUENCE: 618
uagacucagu cucacugaca                                           20

<210> SEQ ID NO 619
<211> LENGTH: 20
<212> TYPE: RNA
<213> ORGANISM: Artificial Sequence
<220> FEATURE:
<223> OTHER INFORMATION: synthesized

<400> SEQUENCE: 619
ucagucucac ugacaaacuc                                           20

<210> SEQ ID NO 620
<211> LENGTH: 20
<212> TYPE: RNA
<213> ORGANISM: Artificial Sequence
<220> FEATURE:
<223> OTHER INFORMATION: synthesized

<400> SEQUENCE: 620
ucagugagac ugagucuagg                                           20

<210> SEQ ID NO 621
<211> LENGTH: 20
<212> TYPE: RNA
<213> ORGANISM: Artificial Sequence
<220> FEATURE:
<223> OTHER INFORMATION: synthesized

<400> SEQUENCE: 621
ucagugagac ugugucuagg                                           20

```
<210> SEQ ID NO 622
<211> LENGTH: 20
<212> TYPE: RNA
<213> ORGANISM: Artificial Sequence
<220> FEATURE:
<223> OTHER INFORMATION: synthesized

<400> SEQUENCE: 622
ucugagcccc uagacacagu                                                   20

<210> SEQ ID NO 623
<211> LENGTH: 20
<212> TYPE: RNA
<213> ORGANISM: Artificial Sequence
<220> FEATURE:
<223> OTHER INFORMATION: synthesized

<400> SEQUENCE: 623
ucugagcccc uagacucagu                                                   20

<210> SEQ ID NO 624
<211> LENGTH: 20
<212> TYPE: RNA
<213> ORGANISM: Artificial Sequence
<220> FEATURE:
<223> OTHER INFORMATION: synthesized

<400> SEQUENCE: 624
ugagccccua gacacagucu                                                   20

<210> SEQ ID NO 625
<211> LENGTH: 20
<212> TYPE: RNA
<213> ORGANISM: Artificial Sequence
<220> FEATURE:
<223> OTHER INFORMATION: synthesized

<400> SEQUENCE: 625
ugagccccua gacucagucu                                                   20

<210> SEQ ID NO 626
<211> LENGTH: 20
<212> TYPE: RNA
<213> ORGANISM: Artificial Sequence
<220> FEATURE:
<223> OTHER INFORMATION: synthesized

<400> SEQUENCE: 626
ugagucuagg ggcucagaau                                                   20

<210> SEQ ID NO 627
<211> LENGTH: 20
<212> TYPE: RNA
<213> ORGANISM: Artificial Sequence
<220> FEATURE:
<223> OTHER INFORMATION: synthesized

<400> SEQUENCE: 627
ugucuagggg cucagaaucu                                                   20

<210> SEQ ID NO 628
<211> LENGTH: 20
<212> TYPE: RNA
<213> ORGANISM: Artificial Sequence
<220> FEATURE:
<223> OTHER INFORMATION: synthesized
```

```
<400> SEQUENCE: 628
ugugucuagg ggcucagaau                                                      20

<210> SEQ ID NO 629
<211> LENGTH: 20
<212> TYPE: RNA
<213> ORGANISM: Artificial Sequence
<220> FEATURE:
<223> OTHER INFORMATION: synthesized

<400> SEQUENCE: 629
uucugagccc cuagacacag                                                      20

<210> SEQ ID NO 630
<211> LENGTH: 20
<212> TYPE: RNA
<213> ORGANISM: Artificial Sequence
<220> FEATURE:
<223> OTHER INFORMATION: synthesized

<400> SEQUENCE: 630
uucugagccc cuagacucag                                                      20

<210> SEQ ID NO 631
<211> LENGTH: 20
<212> TYPE: RNA
<213> ORGANISM: Artificial Sequence
<220> FEATURE:
<223> OTHER INFORMATION: synthesized

<400> SEQUENCE: 631
uuugucagug agacugaguc                                                      20

<210> SEQ ID NO 632
<211> LENGTH: 20
<212> TYPE: RNA
<213> ORGANISM: Artificial Sequence
<220> FEATURE:
<223> OTHER INFORMATION: synthesized

<400> SEQUENCE: 632
uuugucagug agacuguguc                                                      20

<210> SEQ ID NO 633
<211> LENGTH: 20
<212> TYPE: RNA
<213> ORGANISM: Artificial Sequence
<220> FEATURE:
<223> OTHER INFORMATION: synthesized

<400> SEQUENCE: 633
aaaaagauag auauaucaaa                                                      20

<210> SEQ ID NO 634
<211> LENGTH: 20
<212> TYPE: RNA
<213> ORGANISM: Artificial Sequence
<220> FEATURE:
<223> OTHER INFORMATION: synthesized

<400> SEQUENCE: 634
aaaagauaga uauaucaaac                                                      20

<210> SEQ ID NO 635
<211> LENGTH: 20
```

```
<212> TYPE: RNA
<213> ORGANISM: Artificial Sequence
<220> FEATURE:
<223> OTHER INFORMATION: synthesized

<400> SEQUENCE: 635
aaaagcaugu gacaauaagc                                                    20

<210> SEQ ID NO 636
<211> LENGTH: 20
<212> TYPE: RNA
<213> ORGANISM: Artificial Sequence
<220> FEATURE:
<223> OTHER INFORMATION: synthesized

<400> SEQUENCE: 636
aaaagcaugu gacaauaagg                                                    20

<210> SEQ ID NO 637
<211> LENGTH: 20
<212> TYPE: RNA
<213> ORGANISM: Artificial Sequence
<220> FEATURE:
<223> OTHER INFORMATION: synthesized

<400> SEQUENCE: 637
aaaaggauag auauaucaaa                                                    20

<210> SEQ ID NO 638
<211> LENGTH: 20
<212> TYPE: RNA
<213> ORGANISM: Artificial Sequence
<220> FEATURE:
<223> OTHER INFORMATION: synthesized

<400> SEQUENCE: 638
aaagauaccc uuauugucac                                                    20

<210> SEQ ID NO 639
<211> LENGTH: 20
<212> TYPE: RNA
<213> ORGANISM: Artificial Sequence
<220> FEATURE:
<223> OTHER INFORMATION: synthesized

<400> SEQUENCE: 639
aaagauacgc uuauugucac                                                    20

<210> SEQ ID NO 640
<211> LENGTH: 20
<212> TYPE: RNA
<213> ORGANISM: Artificial Sequence
<220> FEATURE:
<223> OTHER INFORMATION: synthesized

<400> SEQUENCE: 640
aaagauagau auaucaaaca                                                    20

<210> SEQ ID NO 641
<211> LENGTH: 20
<212> TYPE: RNA
<213> ORGANISM: Artificial Sequence
<220> FEATURE:
<223> OTHER INFORMATION: synthesized

<400> SEQUENCE: 641
```

```
aaagcaugug acaauaagcg                                              20

<210> SEQ ID NO 642
<211> LENGTH: 20
<212> TYPE: RNA
<213> ORGANISM: Artificial Sequence
<220> FEATURE:
<223> OTHER INFORMATION: synthesized

<400> SEQUENCE: 642
aaagcaugug acaauaaggg                                              20

<210> SEQ ID NO 643
<211> LENGTH: 20
<212> TYPE: RNA
<213> ORGANISM: Artificial Sequence
<220> FEATURE:
<223> OTHER INFORMATION: synthesized

<400> SEQUENCE: 643
aaaggauaga uauaucaaac                                              20

<210> SEQ ID NO 644
<211> LENGTH: 20
<212> TYPE: RNA
<213> ORGANISM: Artificial Sequence
<220> FEATURE:
<223> OTHER INFORMATION: synthesized

<400> SEQUENCE: 644
aacuucaaaa agauagauau                                              20

<210> SEQ ID NO 645
<211> LENGTH: 20
<212> TYPE: RNA
<213> ORGANISM: Artificial Sequence
<220> FEATURE:
<223> OTHER INFORMATION: synthesized

<400> SEQUENCE: 645
aacuucaaaa ggauagauau                                              20

<210> SEQ ID NO 646
<211> LENGTH: 20
<212> TYPE: RNA
<213> ORGANISM: Artificial Sequence
<220> FEATURE:
<223> OTHER INFORMATION: synthesized

<400> SEQUENCE: 646
aagacaaaua cugcuuagcu                                              20

<210> SEQ ID NO 647
<211> LENGTH: 20
<212> TYPE: RNA
<213> ORGANISM: Artificial Sequence
<220> FEATURE:
<223> OTHER INFORMATION: synthesized

<400> SEQUENCE: 647
aagauacccu uauugucaca                                              20

<210> SEQ ID NO 648
<211> LENGTH: 20
<212> TYPE: RNA
<213> ORGANISM: Artificial Sequence
```

```
<220> FEATURE:
<223> OTHER INFORMATION: synthesized

<400> SEQUENCE: 648
aagauacgcu uauugucaca                                              20

<210> SEQ ID NO 649
<211> LENGTH: 20
<212> TYPE: RNA
<213> ORGANISM: Artificial Sequence
<220> FEATURE:
<223> OTHER INFORMATION: synthesized

<400> SEQUENCE: 649
aagauagaua uaucaaacau                                              20

<210> SEQ ID NO 650
<211> LENGTH: 20
<212> TYPE: RNA
<213> ORGANISM: Artificial Sequence
<220> FEATURE:
<223> OTHER INFORMATION: synthesized

<400> SEQUENCE: 650
aagcaguauu ugucugucua                                              20

<210> SEQ ID NO 651
<211> LENGTH: 20
<212> TYPE: RNA
<213> ORGANISM: Artificial Sequence
<220> FEATURE:
<223> OTHER INFORMATION: synthesized

<400> SEQUENCE: 651
aagcaguauu ugucuuucua                                              20

<210> SEQ ID NO 652
<211> LENGTH: 20
<212> TYPE: RNA
<213> ORGANISM: Artificial Sequence
<220> FEATURE:
<223> OTHER INFORMATION: synthesized

<400> SEQUENCE: 652
aagcauguga caauaagcgu                                              20

<210> SEQ ID NO 653
<211> LENGTH: 20
<212> TYPE: RNA
<213> ORGANISM: Artificial Sequence
<220> FEATURE:
<223> OTHER INFORMATION: synthesized

<400> SEQUENCE: 653
aagcauguga caauaagggu                                              20

<210> SEQ ID NO 654
<211> LENGTH: 20
<212> TYPE: RNA
<213> ORGANISM: Artificial Sequence
<220> FEATURE:
<223> OTHER INFORMATION: synthesized

<400> SEQUENCE: 654
aagcguaucu uuaaaugugc                                              20
```

```
<210> SEQ ID NO 655
<211> LENGTH: 20
<212> TYPE: RNA
<213> ORGANISM: Artificial Sequence
<220> FEATURE:
<223> OTHER INFORMATION: synthesized

<400> SEQUENCE: 655
aaggauagau auaucaaaca                                              20

<210> SEQ ID NO 656
<211> LENGTH: 20
<212> TYPE: RNA
<213> ORGANISM: Artificial Sequence
<220> FEATURE:
<223> OTHER INFORMATION: synthesized

<400> SEQUENCE: 656
aaggguaucu uuaaaugugc                                              20

<210> SEQ ID NO 657
<211> LENGTH: 20
<212> TYPE: RNA
<213> ORGANISM: Artificial Sequence
<220> FEATURE:
<223> OTHER INFORMATION: synthesized

<400> SEQUENCE: 657
aauaagcgua ucuuuaaaug                                              20

<210> SEQ ID NO 658
<211> LENGTH: 20
<212> TYPE: RNA
<213> ORGANISM: Artificial Sequence
<220> FEATURE:
<223> OTHER INFORMATION: synthesized

<400> SEQUENCE: 658
aauaagggua ucuuuaaaug                                              20

<210> SEQ ID NO 659
<211> LENGTH: 20
<212> TYPE: RNA
<213> ORGANISM: Artificial Sequence
<220> FEATURE:
<223> OTHER INFORMATION: synthesized

<400> SEQUENCE: 659
aaugagcaga uauagaaaga                                              20

<210> SEQ ID NO 660
<211> LENGTH: 20
<212> TYPE: RNA
<213> ORGANISM: Artificial Sequence
<220> FEATURE:
<223> OTHER INFORMATION: synthesized

<400> SEQUENCE: 660
aaugagcaga uauagacaga                                              20

<210> SEQ ID NO 661
<211> LENGTH: 20
<212> TYPE: RNA
<213> ORGANISM: Artificial Sequence
<220> FEATURE:
<223> OTHER INFORMATION: synthesized
```

```
<400> SEQUENCE: 661
acauuaacuu caaaaagaua                                              20

<210> SEQ ID NO 662
<211> LENGTH: 20
<212> TYPE: RNA
<213> ORGANISM: Artificial Sequence
<220> FEATURE:
<223> OTHER INFORMATION: synthesized

<400> SEQUENCE: 662
acauuaacuu caaaaggaua                                              20

<210> SEQ ID NO 663
<211> LENGTH: 20
<212> TYPE: RNA
<213> ORGANISM: Artificial Sequence
<220> FEATURE:
<223> OTHER INFORMATION: synthesized

<400> SEQUENCE: 663
acccuuauug ucacaugcuu                                              20

<210> SEQ ID NO 664
<211> LENGTH: 20
<212> TYPE: RNA
<213> ORGANISM: Artificial Sequence
<220> FEATURE:
<223> OTHER INFORMATION: synthesized

<400> SEQUENCE: 664
acgcuuauug ucacaugcuu                                              20

<210> SEQ ID NO 665
<211> LENGTH: 20
<212> TYPE: RNA
<213> ORGANISM: Artificial Sequence
<220> FEATURE:
<223> OTHER INFORMATION: synthesized

<400> SEQUENCE: 665
agauacccuu auugucacau                                              20

<210> SEQ ID NO 666
<211> LENGTH: 20
<212> TYPE: RNA
<213> ORGANISM: Artificial Sequence
<220> FEATURE:
<223> OTHER INFORMATION: synthesized

<400> SEQUENCE: 666
agauacgcuu auugucacau                                              20

<210> SEQ ID NO 667
<211> LENGTH: 20
<212> TYPE: RNA
<213> ORGANISM: Artificial Sequence
<220> FEATURE:
<223> OTHER INFORMATION: synthesized

<400> SEQUENCE: 667
agauagauau aucaaacauc                                              20

<210> SEQ ID NO 668
```

```
<211> LENGTH: 20
<212> TYPE: RNA
<213> ORGANISM: Artificial Sequence
<220> FEATURE:
<223> OTHER INFORMATION: synthesized

<400> SEQUENCE: 668
agauauagaa agacaaauac                                              20

<210> SEQ ID NO 669
<211> LENGTH: 20
<212> TYPE: RNA
<213> ORGANISM: Artificial Sequence
<220> FEATURE:
<223> OTHER INFORMATION: synthesized

<400> SEQUENCE: 669
agauauagac agacaaauac                                              20

<210> SEQ ID NO 670
<211> LENGTH: 20
<212> TYPE: RNA
<213> ORGANISM: Artificial Sequence
<220> FEATURE:
<223> OTHER INFORMATION: synthesized

<400> SEQUENCE: 670
agcagauaua gaaagacaaa                                              20

<210> SEQ ID NO 671
<211> LENGTH: 20
<212> TYPE: RNA
<213> ORGANISM: Artificial Sequence
<220> FEATURE:
<223> OTHER INFORMATION: synthesized

<400> SEQUENCE: 671
agcagauaua gacagacaaa                                              20

<210> SEQ ID NO 672
<211> LENGTH: 20
<212> TYPE: RNA
<213> ORGANISM: Artificial Sequence
<220> FEATURE:
<223> OTHER INFORMATION: synthesized

<400> SEQUENCE: 672
agcaguauuu gucugucuau                                              20

<210> SEQ ID NO 673
<211> LENGTH: 20
<212> TYPE: RNA
<213> ORGANISM: Artificial Sequence
<220> FEATURE:
<223> OTHER INFORMATION: synthesized

<400> SEQUENCE: 673
agcaguauuu gucuuucuau                                              20

<210> SEQ ID NO 674
<211> LENGTH: 20
<212> TYPE: RNA
<213> ORGANISM: Artificial Sequence
<220> FEATURE:
<223> OTHER INFORMATION: synthesized

<400> SEQUENCE: 674
```
agcaugugac aauaagcgua                                              20

<210> SEQ ID NO 675
<211> LENGTH: 20
<212> TYPE: RNA
<213> ORGANISM: Artificial Sequence
<220> FEATURE:
<223> OTHER INFORMATION: synthesized

<400> SEQUENCE: 675
agcaugugac aauagggua                                               20

<210> SEQ ID NO 676
<211> LENGTH: 20
<212> TYPE: RNA
<213> ORGANISM: Artificial Sequence
<220> FEATURE:
<223> OTHER INFORMATION: synthesized

<400> SEQUENCE: 676
agcguaucuu uaaaugugca                                              20

<210> SEQ ID NO 677
<211> LENGTH: 20
<212> TYPE: RNA
<213> ORGANISM: Artificial Sequence
<220> FEATURE:
<223> OTHER INFORMATION: synthesized

<400> SEQUENCE: 677
agcuaagcag uauuugucug                                              20

<210> SEQ ID NO 678
<211> LENGTH: 20
<212> TYPE: RNA
<213> ORGANISM: Artificial Sequence
<220> FEATURE:
<223> OTHER INFORMATION: synthesized

<400> SEQUENCE: 678
agcuaagcag uauuugucuu                                              20

<210> SEQ ID NO 679
<211> LENGTH: 20
<212> TYPE: RNA
<213> ORGANISM: Artificial Sequence
<220> FEATURE:
<223> OTHER INFORMATION: synthesized

<400> SEQUENCE: 679
aggauagaua uaucaaacau                                              20

<210> SEQ ID NO 680
<211> LENGTH: 20
<212> TYPE: RNA
<213> ORGANISM: Artificial Sequence
<220> FEATURE:
<223> OTHER INFORMATION: synthesized

<400> SEQUENCE: 680
aggguaucuu uaaaugugca                                              20

<210> SEQ ID NO 681
<211> LENGTH: 20
<212> TYPE: RNA

```
<213> ORGANISM: Artificial Sequence
<220> FEATURE:
<223> OTHER INFORMATION: synthesized

<400> SEQUENCE: 681
aguauuuguc ugucuauauc                                              20

<210> SEQ ID NO 682
<211> LENGTH: 20
<212> TYPE: RNA
<213> ORGANISM: Artificial Sequence
<220> FEATURE:
<223> OTHER INFORMATION: synthesized

<400> SEQUENCE: 682
aguauuuguc uuucuauauc                                              20

<210> SEQ ID NO 683
<211> LENGTH: 20
<212> TYPE: RNA
<213> ORGANISM: Artificial Sequence
<220> FEATURE:
<223> OTHER INFORMATION: synthesized

<400> SEQUENCE: 683
auaagcguau cuuuaaaugu                                              20

<210> SEQ ID NO 684
<211> LENGTH: 20
<212> TYPE: RNA
<213> ORGANISM: Artificial Sequence
<220> FEATURE:
<223> OTHER INFORMATION: synthesized

<400> SEQUENCE: 684
auaaggguau cuuuaaaugu                                              20

<210> SEQ ID NO 685
<211> LENGTH: 20
<212> TYPE: RNA
<213> ORGANISM: Artificial Sequence
<220> FEATURE:
<223> OTHER INFORMATION: synthesized

<400> SEQUENCE: 685
auacccuuau ugucacaugc                                              20

<210> SEQ ID NO 686
<211> LENGTH: 20
<212> TYPE: RNA
<213> ORGANISM: Artificial Sequence
<220> FEATURE:
<223> OTHER INFORMATION: synthesized

<400> SEQUENCE: 686
auacgcuuau ugucacaugc                                              20

<210> SEQ ID NO 687
<211> LENGTH: 20
<212> TYPE: RNA
<213> ORGANISM: Artificial Sequence
<220> FEATURE:
<223> OTHER INFORMATION: synthesized

<400> SEQUENCE: 687
auagaaagac aaauacugcu                                              20
```

```
<210> SEQ ID NO 688
<211> LENGTH: 20
<212> TYPE: RNA
<213> ORGANISM: Artificial Sequence
<220> FEATURE:
<223> OTHER INFORMATION: synthesized

<400> SEQUENCE: 688
auagacagac aaauacugcu                                                20

<210> SEQ ID NO 689
<211> LENGTH: 20
<212> TYPE: RNA
<213> ORGANISM: Artificial Sequence
<220> FEATURE:
<223> OTHER INFORMATION: synthesized

<400> SEQUENCE: 689
auauagaaag acaaauacug                                                20

<210> SEQ ID NO 690
<211> LENGTH: 20
<212> TYPE: RNA
<213> ORGANISM: Artificial Sequence
<220> FEATURE:
<223> OTHER INFORMATION: synthesized

<400> SEQUENCE: 690
auauagacag acaaauacug                                                20

<210> SEQ ID NO 691
<211> LENGTH: 20
<212> TYPE: RNA
<213> ORGANISM: Artificial Sequence
<220> FEATURE:
<223> OTHER INFORMATION: synthesized

<400> SEQUENCE: 691
auauaucuau ccuuuugaag                                                20

<210> SEQ ID NO 692
<211> LENGTH: 20
<212> TYPE: RNA
<213> ORGANISM: Artificial Sequence
<220> FEATURE:
<223> OTHER INFORMATION: synthesized

<400> SEQUENCE: 692
auauaucuau cuuuuugaag                                                20

<210> SEQ ID NO 693
<211> LENGTH: 20
<212> TYPE: RNA
<213> ORGANISM: Artificial Sequence
<220> FEATURE:
<223> OTHER INFORMATION: synthesized

<400> SEQUENCE: 693
auaucuaucc uuuugaaguu                                                20

<210> SEQ ID NO 694
<211> LENGTH: 20
<212> TYPE: RNA
<213> ORGANISM: Artificial Sequence
<220> FEATURE:
```

<223> OTHER INFORMATION: synthesized

<400> SEQUENCE: 694
auaucuaucu uuuugaaguu                                           20

<210> SEQ ID NO 695
<211> LENGTH: 20
<212> TYPE: RNA
<213> ORGANISM: Artificial Sequence
<220> FEATURE:
<223> OTHER INFORMATION: synthesized

<400> SEQUENCE: 695
auccuuuuga aguuaaugua                                           20

<210> SEQ ID NO 696
<211> LENGTH: 20
<212> TYPE: RNA
<213> ORGANISM: Artificial Sequence
<220> FEATURE:
<223> OTHER INFORMATION: synthesized

<400> SEQUENCE: 696
aucuuuuuga aguuaaugua                                           20

<210> SEQ ID NO 697
<211> LENGTH: 20
<212> TYPE: RNA
<213> ORGANISM: Artificial Sequence
<220> FEATURE:
<223> OTHER INFORMATION: synthesized

<400> SEQUENCE: 697
augagcagau auagaaagac                                           20

<210> SEQ ID NO 698
<211> LENGTH: 20
<212> TYPE: RNA
<213> ORGANISM: Artificial Sequence
<220> FEATURE:
<223> OTHER INFORMATION: synthesized

<400> SEQUENCE: 698
augagcagau auagacagac                                           20

<210> SEQ ID NO 699
<211> LENGTH: 20
<212> TYPE: RNA
<213> ORGANISM: Artificial Sequence
<220> FEATURE:
<223> OTHER INFORMATION: synthesized

<400> SEQUENCE: 699
augugacaau aagcguaucu                                           20

<210> SEQ ID NO 700
<211> LENGTH: 20
<212> TYPE: RNA
<213> ORGANISM: Artificial Sequence
<220> FEATURE:
<223> OTHER INFORMATION: synthesized

<400> SEQUENCE: 700
augugacaau aagggunucu                                           20

```
<210> SEQ ID NO 701
<211> LENGTH: 20
<212> TYPE: RNA
<213> ORGANISM: Artificial Sequence
<220> FEATURE:
<223> OTHER INFORMATION: synthesized

<400> SEQUENCE: 701
auguuugaua uaucuauccu                                               20

<210> SEQ ID NO 702
<211> LENGTH: 20
<212> TYPE: RNA
<213> ORGANISM: Artificial Sequence
<220> FEATURE:
<223> OTHER INFORMATION: synthesized

<400> SEQUENCE: 702
auguuugaua uaucuaucuu                                               20

<210> SEQ ID NO 703
<211> LENGTH: 20
<212> TYPE: RNA
<213> ORGANISM: Artificial Sequence
<220> FEATURE:
<223> OTHER INFORMATION: synthesized

<400> SEQUENCE: 703
auuaacuuca aaagauaga                                                20

<210> SEQ ID NO 704
<211> LENGTH: 20
<212> TYPE: RNA
<213> ORGANISM: Artificial Sequence
<220> FEATURE:
<223> OTHER INFORMATION: synthesized

<400> SEQUENCE: 704
auuaacuuca aaaggauaga                                               20

<210> SEQ ID NO 705
<211> LENGTH: 20
<212> TYPE: RNA
<213> ORGANISM: Artificial Sequence
<220> FEATURE:
<223> OTHER INFORMATION: synthesized

<400> SEQUENCE: 705
auuuaaagau acccuuauug                                               20

<210> SEQ ID NO 706
<211> LENGTH: 20
<212> TYPE: RNA
<213> ORGANISM: Artificial Sequence
<220> FEATURE:
<223> OTHER INFORMATION: synthesized

<400> SEQUENCE: 706
auuuaaagau acgcuuauug                                               20

<210> SEQ ID NO 707
<211> LENGTH: 20
<212> TYPE: RNA
<213> ORGANISM: Artificial Sequence
<220> FEATURE:
<223> OTHER INFORMATION: synthesized
```

```
<400> SEQUENCE: 707
auuugucugu cuauaucugc                                               20

<210> SEQ ID NO 708
<211> LENGTH: 20
<212> TYPE: RNA
<213> ORGANISM: Artificial Sequence
<220> FEATURE:
<223> OTHER INFORMATION: synthesized

<400> SEQUENCE: 708
auuugucuuu cuauaucugc                                               20

<210> SEQ ID NO 709
<211> LENGTH: 20
<212> TYPE: RNA
<213> ORGANISM: Artificial Sequence
<220> FEATURE:
<223> OTHER INFORMATION: synthesized

<400> SEQUENCE: 709
caaaaagaua gauauaucaa                                               20

<210> SEQ ID NO 710
<211> LENGTH: 20
<212> TYPE: RNA
<213> ORGANISM: Artificial Sequence
<220> FEATURE:
<223> OTHER INFORMATION: synthesized

<400> SEQUENCE: 710
caaaaggaua gauauaucaa                                               20

<210> SEQ ID NO 711
<211> LENGTH: 20
<212> TYPE: RNA
<213> ORGANISM: Artificial Sequence
<220> FEATURE:
<223> OTHER INFORMATION: synthesized

<400> SEQUENCE: 711
caauaagcgu aucuuuaaau                                               20

<210> SEQ ID NO 712
<211> LENGTH: 20
<212> TYPE: RNA
<213> ORGANISM: Artificial Sequence
<220> FEATURE:
<223> OTHER INFORMATION: synthesized

<400> SEQUENCE: 712
caauaagggu aucuuuaaau                                               20

<210> SEQ ID NO 713
<211> LENGTH: 20
<212> TYPE: RNA
<213> ORGANISM: Artificial Sequence
<220> FEATURE:
<223> OTHER INFORMATION: synthesized

<400> SEQUENCE: 713
cacauuuaaa gauacccuua                                               20

<210> SEQ ID NO 714
<211> LENGTH: 20
```

```
<212> TYPE: RNA
<213> ORGANISM: Artificial Sequence
<220> FEATURE:
<223> OTHER INFORMATION: synthesized

<400> SEQUENCE: 714
cacauuuaaa gauacgcuua                                                    20

<210> SEQ ID NO 715
<211> LENGTH: 20
<212> TYPE: RNA
<213> ORGANISM: Artificial Sequence
<220> FEATURE:
<223> OTHER INFORMATION: synthesized

<400> SEQUENCE: 715
cagacaaaua cugcuuagcu                                                    20

<210> SEQ ID NO 716
<211> LENGTH: 20
<212> TYPE: RNA
<213> ORGANISM: Artificial Sequence
<220> FEATURE:
<223> OTHER INFORMATION: synthesized

<400> SEQUENCE: 716
cagauauaga aagacaaaua                                                    20

<210> SEQ ID NO 717
<211> LENGTH: 20
<212> TYPE: RNA
<213> ORGANISM: Artificial Sequence
<220> FEATURE:
<223> OTHER INFORMATION: synthesized

<400> SEQUENCE: 717
cagauauaga cagacaaaua                                                    20

<210> SEQ ID NO 718
<211> LENGTH: 20
<212> TYPE: RNA
<213> ORGANISM: Artificial Sequence
<220> FEATURE:
<223> OTHER INFORMATION: synthesized

<400> SEQUENCE: 718
caguauuugu cugucuauau                                                    20

<210> SEQ ID NO 719
<211> LENGTH: 20
<212> TYPE: RNA
<213> ORGANISM: Artificial Sequence
<220> FEATURE:
<223> OTHER INFORMATION: synthesized

<400> SEQUENCE: 719
caguauuugu cuuucuauau                                                    20

<210> SEQ ID NO 720
<211> LENGTH: 20
<212> TYPE: RNA
<213> ORGANISM: Artificial Sequence
<220> FEATURE:
<223> OTHER INFORMATION: synthesized

<400> SEQUENCE: 720
```

-continued caugugacaa uaagcguauc                                            20

<210> SEQ ID NO 721
<211> LENGTH: 20
<212> TYPE: RNA
<213> ORGANISM: Artificial Sequence
<220> FEATURE:
<223> OTHER INFORMATION: synthesized

<400> SEQUENCE: 721
caugugacaa uaaggguauc                                            20

<210> SEQ ID NO 722
<211> LENGTH: 20
<212> TYPE: RNA
<213> ORGANISM: Artificial Sequence
<220> FEATURE:
<223> OTHER INFORMATION: synthesized

<400> SEQUENCE: 722
cauuaacuuc aaaaagauag                                            20

<210> SEQ ID NO 723
<211> LENGTH: 20
<212> TYPE: RNA
<213> ORGANISM: Artificial Sequence
<220> FEATURE:
<223> OTHER INFORMATION: synthesized

<400> SEQUENCE: 723
cauuaacuuc aaaaggauag                                            20

<210> SEQ ID NO 724
<211> LENGTH: 20
<212> TYPE: RNA
<213> ORGANISM: Artificial Sequence
<220> FEATURE:
<223> OTHER INFORMATION: synthesized

<400> SEQUENCE: 724
cauuuaaaga uacccuuauu                                            20

<210> SEQ ID NO 725
<211> LENGTH: 20
<212> TYPE: RNA
<213> ORGANISM: Artificial Sequence
<220> FEATURE:
<223> OTHER INFORMATION: synthesized

<400> SEQUENCE: 725
cauuuaaaga uacgcuuauu                                            20

<210> SEQ ID NO 726
<211> LENGTH: 20
<212> TYPE: RNA
<213> ORGANISM: Artificial Sequence
<220> FEATURE:
<223> OTHER INFORMATION: synthesized

<400> SEQUENCE: 726
cccuuauugu cacaugcuuu                                            20

<210> SEQ ID NO 727
<211> LENGTH: 20
<212> TYPE: RNA
<213> ORGANISM: Artificial Sequence

```
<220> FEATURE:
<223> OTHER INFORMATION: synthesized

<400> SEQUENCE: 727
ccuuauuguc acaugcuuuu                                              20

<210> SEQ ID NO 728
<211> LENGTH: 20
<212> TYPE: RNA
<213> ORGANISM: Artificial Sequence
<220> FEATURE:
<223> OTHER INFORMATION: synthesized

<400> SEQUENCE: 728
cgcuuauugu cacaugcuuu                                              20

<210> SEQ ID NO 729
<211> LENGTH: 20
<212> TYPE: RNA
<213> ORGANISM: Artificial Sequence
<220> FEATURE:
<223> OTHER INFORMATION: synthesized

<400> SEQUENCE: 729
cguaucuuua aaugugcaaa                                              20

<210> SEQ ID NO 730
<211> LENGTH: 20
<212> TYPE: RNA
<213> ORGANISM: Artificial Sequence
<220> FEATURE:
<223> OTHER INFORMATION: synthesized

<400> SEQUENCE: 730
cuaagcagua uuugucuguc                                              20

<210> SEQ ID NO 731
<211> LENGTH: 20
<212> TYPE: RNA
<213> ORGANISM: Artificial Sequence
<220> FEATURE:
<223> OTHER INFORMATION: synthesized

<400> SEQUENCE: 731
cuaagcagua uuugucuuuc                                              20

<210> SEQ ID NO 732
<211> LENGTH: 20
<212> TYPE: RNA
<213> ORGANISM: Artificial Sequence
<220> FEATURE:
<223> OTHER INFORMATION: synthesized

<400> SEQUENCE: 732
cuauccuuuu gaaguuaaug                                              20

<210> SEQ ID NO 733
<211> LENGTH: 20
<212> TYPE: RNA
<213> ORGANISM: Artificial Sequence
<220> FEATURE:
<223> OTHER INFORMATION: synthesized

<400> SEQUENCE: 733
cuaucuuuuu gaaguuaaug                                              20
```

```
<210> SEQ ID NO 734
<211> LENGTH: 20
<212> TYPE: RNA
<213> ORGANISM: Artificial Sequence
<220> FEATURE:
<223> OTHER INFORMATION: synthesized

<400> SEQUENCE: 734
cugucuauau cugcucauuu                                               20

<210> SEQ ID NO 735
<211> LENGTH: 20
<212> TYPE: RNA
<213> ORGANISM: Artificial Sequence
<220> FEATURE:
<223> OTHER INFORMATION: synthesized

<400> SEQUENCE: 735
cuucaaaaag auagauauau                                               20

<210> SEQ ID NO 736
<211> LENGTH: 20
<212> TYPE: RNA
<213> ORGANISM: Artificial Sequence
<220> FEATURE:
<223> OTHER INFORMATION: synthesized

<400> SEQUENCE: 736
cuucaaaagg auagauauau                                               20

<210> SEQ ID NO 737
<211> LENGTH: 20
<212> TYPE: RNA
<213> ORGANISM: Artificial Sequence
<220> FEATURE:
<223> OTHER INFORMATION: synthesized

<400> SEQUENCE: 737
cuuucuauau cugcucauuu                                               20

<210> SEQ ID NO 738
<211> LENGTH: 20
<212> TYPE: RNA
<213> ORGANISM: Artificial Sequence
<220> FEATURE:
<223> OTHER INFORMATION: synthesized

<400> SEQUENCE: 738
cuuuugaagu uaauguaaua                                               20

<210> SEQ ID NO 739
<211> LENGTH: 20
<212> TYPE: RNA
<213> ORGANISM: Artificial Sequence
<220> FEATURE:
<223> OTHER INFORMATION: synthesized

<400> SEQUENCE: 739
gaaagacaaa uacugcuuag                                               20

<210> SEQ ID NO 740
<211> LENGTH: 20
<212> TYPE: RNA
<213> ORGANISM: Artificial Sequence
<220> FEATURE:
<223> OTHER INFORMATION: synthesized
```

<400> SEQUENCE: 740
gaaaugagca gauauagaaa                                          20

<210> SEQ ID NO 741
<211> LENGTH: 20
<212> TYPE: RNA
<213> ORGANISM: Artificial Sequence
<220> FEATURE:
<223> OTHER INFORMATION: synthesized

<400> SEQUENCE: 741
gaaaugagca gauauagaca                                          20

<210> SEQ ID NO 742
<211> LENGTH: 20
<212> TYPE: RNA
<213> ORGANISM: Artificial Sequence
<220> FEATURE:
<223> OTHER INFORMATION: synthesized

<400> SEQUENCE: 742
gacaauaagc guaucuuuaa                                          20

<210> SEQ ID NO 743
<211> LENGTH: 20
<212> TYPE: RNA
<213> ORGANISM: Artificial Sequence
<220> FEATURE:
<223> OTHER INFORMATION: synthesized

<400> SEQUENCE: 743
gacaauaagg guaucuuuaa                                          20

<210> SEQ ID NO 744
<211> LENGTH: 20
<212> TYPE: RNA
<213> ORGANISM: Artificial Sequence
<220> FEATURE:
<223> OTHER INFORMATION: synthesized

<400> SEQUENCE: 744
gacagacaaa uacugcuuag                                          20

<210> SEQ ID NO 745
<211> LENGTH: 20
<212> TYPE: RNA
<213> ORGANISM: Artificial Sequence
<220> FEATURE:
<223> OTHER INFORMATION: synthesized

<400> SEQUENCE: 745
gagcagauau agaaagacaa                                          20

<210> SEQ ID NO 746
<211> LENGTH: 20
<212> TYPE: RNA
<213> ORGANISM: Artificial Sequence
<220> FEATURE:
<223> OTHER INFORMATION: synthesized

<400> SEQUENCE: 746
gagcagauau agacagacaa                                          20

<210> SEQ ID NO 747

```
<210> SEQ ID NO 747
<211> LENGTH: 20
<212> TYPE: RNA
<213> ORGANISM: Artificial Sequence
<220> FEATURE:
<223> OTHER INFORMATION: synthesized

<400> SEQUENCE: 747
gauacccuua uugucacaug                                               20

<210> SEQ ID NO 748
<211> LENGTH: 20
<212> TYPE: RNA
<213> ORGANISM: Artificial Sequence
<220> FEATURE:
<223> OTHER INFORMATION: synthesized

<400> SEQUENCE: 748
gauacgcuua uugucacaug                                               20

<210> SEQ ID NO 749
<211> LENGTH: 20
<212> TYPE: RNA
<213> ORGANISM: Artificial Sequence
<220> FEATURE:
<223> OTHER INFORMATION: synthesized

<400> SEQUENCE: 749
gauauagaaa gacaaauacu                                               20

<210> SEQ ID NO 750
<211> LENGTH: 20
<212> TYPE: RNA
<213> ORGANISM: Artificial Sequence
<220> FEATURE:
<223> OTHER INFORMATION: synthesized

<400> SEQUENCE: 750
gauauagaca gacaaauacu                                               20

<210> SEQ ID NO 751
<211> LENGTH: 20
<212> TYPE: RNA
<213> ORGANISM: Artificial Sequence
<220> FEATURE:
<223> OTHER INFORMATION: synthesized

<400> SEQUENCE: 751
gauauaucua uccuuuugaa                                               20

<210> SEQ ID NO 752
<211> LENGTH: 20
<212> TYPE: RNA
<213> ORGANISM: Artificial Sequence
<220> FEATURE:
<223> OTHER INFORMATION: synthesized

<400> SEQUENCE: 752
gauauaucua ucuuuugaa                                                20

<210> SEQ ID NO 753
<211> LENGTH: 20
<212> TYPE: RNA
<213> ORGANISM: Artificial Sequence
<220> FEATURE:
<223> OTHER INFORMATION: synthesized

<400> SEQUENCE: 753
```

-continued gauguuugau auaucuaucc                                                  20

<210> SEQ ID NO 754
<211> LENGTH: 20
<212> TYPE: RNA
<213> ORGANISM: Artificial Sequence
<220> FEATURE:
<223> OTHER INFORMATION: synthesized

<400> SEQUENCE: 754
gauguuugau auaucuaucu                                                  20

<210> SEQ ID NO 755
<211> LENGTH: 20
<212> TYPE: RNA
<213> ORGANISM: Artificial Sequence
<220> FEATURE:
<223> OTHER INFORMATION: synthesized

<400> SEQUENCE: 755
gcacauuuaa agauacccuu                                                  20

<210> SEQ ID NO 756
<211> LENGTH: 20
<212> TYPE: RNA
<213> ORGANISM: Artificial Sequence
<220> FEATURE:
<223> OTHER INFORMATION: synthesized

<400> SEQUENCE: 756
gcacauuuaa agauacgcuu                                                  20

<210> SEQ ID NO 757
<211> LENGTH: 20
<212> TYPE: RNA
<213> ORGANISM: Artificial Sequence
<220> FEATURE:
<223> OTHER INFORMATION: synthesized

<400> SEQUENCE: 757
gcagauauag aaagacaaau                                                  20

<210> SEQ ID NO 758
<211> LENGTH: 20
<212> TYPE: RNA
<213> ORGANISM: Artificial Sequence
<220> FEATURE:
<223> OTHER INFORMATION: synthesized

<400> SEQUENCE: 758
gcagauauag acagacaaau                                                  20

<210> SEQ ID NO 759
<211> LENGTH: 20
<212> TYPE: RNA
<213> ORGANISM: Artificial Sequence
<220> FEATURE:
<223> OTHER INFORMATION: synthesized

<400> SEQUENCE: 759
gcaguauuug ucugucuaua                                                  20

<210> SEQ ID NO 760
<211> LENGTH: 20
<212> TYPE: RNA

```
<213> ORGANISM: Artificial Sequence
<220> FEATURE:
<223> OTHER INFORMATION: synthesized

<400> SEQUENCE: 760
gcaguauuug ucuuucuaua                                              20

<210> SEQ ID NO 761
<211> LENGTH: 20
<212> TYPE: RNA
<213> ORGANISM: Artificial Sequence
<220> FEATURE:
<223> OTHER INFORMATION: synthesized

<400> SEQUENCE: 761
gcaugugaca auaagcguau                                              20

<210> SEQ ID NO 762
<211> LENGTH: 20
<212> TYPE: RNA
<213> ORGANISM: Artificial Sequence
<220> FEATURE:
<223> OTHER INFORMATION: synthesized

<400> SEQUENCE: 762
gcaugugaca auaaggguau                                              20

<210> SEQ ID NO 763
<211> LENGTH: 20
<212> TYPE: RNA
<213> ORGANISM: Artificial Sequence
<220> FEATURE:
<223> OTHER INFORMATION: synthesized

<400> SEQUENCE: 763
gcguaucuuu aaaugugcaa                                              20

<210> SEQ ID NO 764
<211> LENGTH: 20
<212> TYPE: RNA
<213> ORGANISM: Artificial Sequence
<220> FEATURE:
<223> OTHER INFORMATION: synthesized

<400> SEQUENCE: 764
gcuaagcagu auuugucugu                                              20

<210> SEQ ID NO 765
<211> LENGTH: 20
<212> TYPE: RNA
<213> ORGANISM: Artificial Sequence
<220> FEATURE:
<223> OTHER INFORMATION: synthesized

<400> SEQUENCE: 765
gcuaagcagu auuugucuuu                                              20

<210> SEQ ID NO 766
<211> LENGTH: 20
<212> TYPE: RNA
<213> ORGANISM: Artificial Sequence
<220> FEATURE:
<223> OTHER INFORMATION: synthesized

<400> SEQUENCE: 766
gcuuauuguc acaugcuuuu                                              20
```

```
<210> SEQ ID NO 767
<211> LENGTH: 20
<212> TYPE: RNA
<213> ORGANISM: Artificial Sequence
<220> FEATURE:
<223> OTHER INFORMATION: synthesized

<400> SEQUENCE: 767
ggauagauau aucaaacauc                                                   20

<210> SEQ ID NO 768
<211> LENGTH: 20
<212> TYPE: RNA
<213> ORGANISM: Artificial Sequence
<220> FEATURE:
<223> OTHER INFORMATION: synthesized

<400> SEQUENCE: 768
ggguaucuuu aaaugugcaa                                                   20

<210> SEQ ID NO 769
<211> LENGTH: 20
<212> TYPE: RNA
<213> ORGANISM: Artificial Sequence
<220> FEATURE:
<223> OTHER INFORMATION: synthesized

<400> SEQUENCE: 769
gguaucuuua aaugugcaaa                                                   20

<210> SEQ ID NO 770
<211> LENGTH: 20
<212> TYPE: RNA
<213> ORGANISM: Artificial Sequence
<220> FEATURE:
<223> OTHER INFORMATION: synthesized

<400> SEQUENCE: 770
guauuugucu gucuauaucu                                                   20

<210> SEQ ID NO 771
<211> LENGTH: 20
<212> TYPE: RNA
<213> ORGANISM: Artificial Sequence
<220> FEATURE:
<223> OTHER INFORMATION: synthesized

<400> SEQUENCE: 771
guauuugucu uucuauaucu                                                   20

<210> SEQ ID NO 772
<211> LENGTH: 20
<212> TYPE: RNA
<213> ORGANISM: Artificial Sequence
<220> FEATURE:
<223> OTHER INFORMATION: synthesized

<400> SEQUENCE: 772
gucuauaucu gcucauuuca                                                   20

<210> SEQ ID NO 773
<211> LENGTH: 20
<212> TYPE: RNA
<213> ORGANISM: Artificial Sequence
<220> FEATURE:
```

<223> OTHER INFORMATION: synthesized

<400> SEQUENCE: 773
gucugucuau aucugcucau                     20

<210> SEQ ID NO 774
<211> LENGTH: 20
<212> TYPE: RNA
<213> ORGANISM: Artificial Sequence
<220> FEATURE:
<223> OTHER INFORMATION: synthesized

<400> SEQUENCE: 774
gucuuucuau aucugcucau                     20

<210> SEQ ID NO 775
<211> LENGTH: 20
<212> TYPE: RNA
<213> ORGANISM: Artificial Sequence
<220> FEATURE:
<223> OTHER INFORMATION: synthesized

<400> SEQUENCE: 775
gugacaauaa gcguaucuuu                     20

<210> SEQ ID NO 776
<211> LENGTH: 20
<212> TYPE: RNA
<213> ORGANISM: Artificial Sequence
<220> FEATURE:
<223> OTHER INFORMATION: synthesized

<400> SEQUENCE: 776
gugacaauaa ggguaucuuu                     20

<210> SEQ ID NO 777
<211> LENGTH: 20
<212> TYPE: RNA
<213> ORGANISM: Artificial Sequence
<220> FEATURE:
<223> OTHER INFORMATION: synthesized

<400> SEQUENCE: 777
uaaagauacc cuuauuguca                     20

<210> SEQ ID NO 778
<211> LENGTH: 20
<212> TYPE: RNA
<213> ORGANISM: Artificial Sequence
<220> FEATURE:
<223> OTHER INFORMATION: synthesized

<400> SEQUENCE: 778
uaaagauacg cuuauuguca                     20

<210> SEQ ID NO 779
<211> LENGTH: 20
<212> TYPE: RNA
<213> ORGANISM: Artificial Sequence
<220> FEATURE:
<223> OTHER INFORMATION: synthesized

<400> SEQUENCE: 779
uaacuucaaa aagauagaua                     20

-continued

<210> SEQ ID NO 780
<211> LENGTH: 20
<212> TYPE: RNA
<213> ORGANISM: Artificial Sequence
<220> FEATURE:
<223> OTHER INFORMATION: synthesized

<400> SEQUENCE: 780
uaacuucaaa aggauagaua                                                   20

<210> SEQ ID NO 781
<211> LENGTH: 20
<212> TYPE: RNA
<213> ORGANISM: Artificial Sequence
<220> FEATURE:
<223> OTHER INFORMATION: synthesized

<400> SEQUENCE: 781
uaagcaguau uugucugucu                                                   20

<210> SEQ ID NO 782
<211> LENGTH: 20
<212> TYPE: RNA
<213> ORGANISM: Artificial Sequence
<220> FEATURE:
<223> OTHER INFORMATION: synthesized

<400> SEQUENCE: 782
uaagcaguau uugucuuucu                                                   20

<210> SEQ ID NO 783
<211> LENGTH: 20
<212> TYPE: RNA
<213> ORGANISM: Artificial Sequence
<220> FEATURE:
<223> OTHER INFORMATION: synthesized

<400> SEQUENCE: 783
uaagcguauc uuuaaaugug                                                   20

<210> SEQ ID NO 784
<211> LENGTH: 20
<212> TYPE: RNA
<213> ORGANISM: Artificial Sequence
<220> FEATURE:
<223> OTHER INFORMATION: synthesized

<400> SEQUENCE: 784
uaaggguauc uuuaaaugug                                                   20

<210> SEQ ID NO 785
<211> LENGTH: 20
<212> TYPE: RNA
<213> ORGANISM: Artificial Sequence
<220> FEATURE:
<223> OTHER INFORMATION: synthesized

<400> SEQUENCE: 785
uacccuuauu gucacaugcu                                                   20

<210> SEQ ID NO 786
<211> LENGTH: 20
<212> TYPE: RNA
<213> ORGANISM: Artificial Sequence
<220> FEATURE:
<223> OTHER INFORMATION: synthesized

<400> SEQUENCE: 786
uacgcuuauu gucacaugcu                                              20

<210> SEQ ID NO 787
<211> LENGTH: 20
<212> TYPE: RNA
<213> ORGANISM: Artificial Sequence
<220> FEATURE:
<223> OTHER INFORMATION: synthesized

<400> SEQUENCE: 787
uagaaagaca aauacugcuu                                              20

<210> SEQ ID NO 788
<211> LENGTH: 20
<212> TYPE: RNA
<213> ORGANISM: Artificial Sequence
<220> FEATURE:
<223> OTHER INFORMATION: synthesized

<400> SEQUENCE: 788
uagacagaca aauacugcuu                                              20

<210> SEQ ID NO 789
<211> LENGTH: 20
<212> TYPE: RNA
<213> ORGANISM: Artificial Sequence
<220> FEATURE:
<223> OTHER INFORMATION: synthesized

<400> SEQUENCE: 789
uauagaaaga caaauacugc                                              20

<210> SEQ ID NO 790
<211> LENGTH: 20
<212> TYPE: RNA
<213> ORGANISM: Artificial Sequence
<220> FEATURE:
<223> OTHER INFORMATION: synthesized

<400> SEQUENCE: 790
uauagacaga caaauacugc                                              20

<210> SEQ ID NO 791
<211> LENGTH: 20
<212> TYPE: RNA
<213> ORGANISM: Artificial Sequence
<220> FEATURE:
<223> OTHER INFORMATION: synthesized

<400> SEQUENCE: 791
uauaucuauc cuuugaagu                                               20

<210> SEQ ID NO 792
<211> LENGTH: 20
<212> TYPE: RNA
<213> ORGANISM: Artificial Sequence
<220> FEATURE:
<223> OTHER INFORMATION: synthesized

<400> SEQUENCE: 792
uauaucuauc uuuugaagu                                               20

<210> SEQ ID NO 793
<211> LENGTH: 20

```
<212> TYPE: RNA
<213> ORGANISM: Artificial Sequence
<220> FEATURE:
<223> OTHER INFORMATION: synthesized

<400> SEQUENCE: 793
uauccuuuug aaguuaaugu                                                      20

<210> SEQ ID NO 794
<211> LENGTH: 20
<212> TYPE: RNA
<213> ORGANISM: Artificial Sequence
<220> FEATURE:
<223> OTHER INFORMATION: synthesized

<400> SEQUENCE: 794
uaucuauccu uuugaaguua                                                      20

<210> SEQ ID NO 795
<211> LENGTH: 20
<212> TYPE: RNA
<213> ORGANISM: Artificial Sequence
<220> FEATURE:
<223> OTHER INFORMATION: synthesized

<400> SEQUENCE: 795
uaucuaucuu uuugaaguua                                                      20

<210> SEQ ID NO 796
<211> LENGTH: 20
<212> TYPE: RNA
<213> ORGANISM: Artificial Sequence
<220> FEATURE:
<223> OTHER INFORMATION: synthesized

<400> SEQUENCE: 796
uaucuuuuug aaguuaaugu                                                      20

<210> SEQ ID NO 797
<211> LENGTH: 20
<212> TYPE: RNA
<213> ORGANISM: Artificial Sequence
<220> FEATURE:
<223> OTHER INFORMATION: synthesized

<400> SEQUENCE: 797
uauuacauua acuucaaaaa                                                      20

<210> SEQ ID NO 798
<211> LENGTH: 20
<212> TYPE: RNA
<213> ORGANISM: Artificial Sequence
<220> FEATURE:
<223> OTHER INFORMATION: synthesized

<400> SEQUENCE: 798
uauuacauua acuucaaaag                                                      20

<210> SEQ ID NO 799
<211> LENGTH: 20
<212> TYPE: RNA
<213> ORGANISM: Artificial Sequence
<220> FEATURE:
<223> OTHER INFORMATION: synthesized

<400> SEQUENCE: 799
```

-continued uauuugucug ucuauaucug                                    20

<210> SEQ ID NO 800
<211> LENGTH: 20
<212> TYPE: RNA
<213> ORGANISM: Artificial Sequence
<220> FEATURE:
<223> OTHER INFORMATION: synthesized

<400> SEQUENCE: 800
uauuugucuu ucuauaucug                                    20

<210> SEQ ID NO 801
<211> LENGTH: 20
<212> TYPE: RNA
<213> ORGANISM: Artificial Sequence
<220> FEATURE:
<223> OTHER INFORMATION: synthesized

<400> SEQUENCE: 801
ucaaaaagau agauauauca                                    20

<210> SEQ ID NO 802
<211> LENGTH: 20
<212> TYPE: RNA
<213> ORGANISM: Artificial Sequence
<220> FEATURE:
<223> OTHER INFORMATION: synthesized

<400> SEQUENCE: 802
ucaaaaggau agauauauca                                    20

<210> SEQ ID NO 803
<211> LENGTH: 20
<212> TYPE: RNA
<213> ORGANISM: Artificial Sequence
<220> FEATURE:
<223> OTHER INFORMATION: synthesized

<400> SEQUENCE: 803
uccuuuugaa guuaauguaa                                    20

<210> SEQ ID NO 804
<211> LENGTH: 20
<212> TYPE: RNA
<213> ORGANISM: Artificial Sequence
<220> FEATURE:
<223> OTHER INFORMATION: synthesized

<400> SEQUENCE: 804
ucuauccuuu ugaaguuaau                                    20

<210> SEQ ID NO 805
<211> LENGTH: 20
<212> TYPE: RNA
<213> ORGANISM: Artificial Sequence
<220> FEATURE:
<223> OTHER INFORMATION: synthesized

<400> SEQUENCE: 805
ucuaucuuuu ugaaguuaau                                    20

<210> SEQ ID NO 806
<211> LENGTH: 20
<212> TYPE: RNA
<213> ORGANISM: Artificial Sequence

```
<220> FEATURE:
<223> OTHER INFORMATION: synthesized

<400> SEQUENCE: 806
ucugucuaua ucugcucauu                                        20

<210> SEQ ID NO 807
<211> LENGTH: 20
<212> TYPE: RNA
<213> ORGANISM: Artificial Sequence
<220> FEATURE:
<223> OTHER INFORMATION: synthesized

<400> SEQUENCE: 807
ucuuucuaua ucugcucauu                                        20

<210> SEQ ID NO 808
<211> LENGTH: 20
<212> TYPE: RNA
<213> ORGANISM: Artificial Sequence
<220> FEATURE:
<223> OTHER INFORMATION: synthesized

<400> SEQUENCE: 808
ucuuuuugaa guuaauguaa                                        20

<210> SEQ ID NO 809
<211> LENGTH: 20
<212> TYPE: RNA
<213> ORGANISM: Artificial Sequence
<220> FEATURE:
<223> OTHER INFORMATION: synthesized

<400> SEQUENCE: 809
ugacaauaag cguaucuuua                                        20

<210> SEQ ID NO 810
<211> LENGTH: 20
<212> TYPE: RNA
<213> ORGANISM: Artificial Sequence
<220> FEATURE:
<223> OTHER INFORMATION: synthesized

<400> SEQUENCE: 810
ugacaauaag gguaucuuua                                        20

<210> SEQ ID NO 811
<211> LENGTH: 20
<212> TYPE: RNA
<213> ORGANISM: Artificial Sequence
<220> FEATURE:
<223> OTHER INFORMATION: synthesized

<400> SEQUENCE: 811
ugagcagaua uagaaagaca                                        20

<210> SEQ ID NO 812
<211> LENGTH: 20
<212> TYPE: RNA
<213> ORGANISM: Artificial Sequence
<220> FEATURE:
<223> OTHER INFORMATION: synthesized

<400> SEQUENCE: 812
ugagcagaua uagacagaca                                        20
```

<210> SEQ ID NO 813
<211> LENGTH: 20
<212> TYPE: RNA
<213> ORGANISM: Artificial Sequence
<220> FEATURE:
<223> OTHER INFORMATION: synthesized

<400> SEQUENCE: 813
ugauauaucu auccuuuuga                                               20

<210> SEQ ID NO 814
<211> LENGTH: 20
<212> TYPE: RNA
<213> ORGANISM: Artificial Sequence
<220> FEATURE:
<223> OTHER INFORMATION: synthesized

<400> SEQUENCE: 814
ugauauaucu aucuuuuuga                                               20

<210> SEQ ID NO 815
<211> LENGTH: 20
<212> TYPE: RNA
<213> ORGANISM: Artificial Sequence
<220> FEATURE:
<223> OTHER INFORMATION: synthesized

<400> SEQUENCE: 815
ugcacauuua aagauacccu                                               20

<210> SEQ ID NO 816
<211> LENGTH: 20
<212> TYPE: RNA
<213> ORGANISM: Artificial Sequence
<220> FEATURE:
<223> OTHER INFORMATION: synthesized

<400> SEQUENCE: 816
ugcacauuua aagauacgcu                                               20

<210> SEQ ID NO 817
<211> LENGTH: 20
<212> TYPE: RNA
<213> ORGANISM: Artificial Sequence
<220> FEATURE:
<223> OTHER INFORMATION: synthesized

<400> SEQUENCE: 817 ugcuauauc ugcucauuuc                                                20

<210> SEQ ID NO 818
<211> LENGTH: 20
<212> TYPE: RNA
<213> ORGANISM: Artificial Sequence
<220> FEATURE:
<223> OTHER INFORMATION: synthesized

<400> SEQUENCE: 818
ugucugucua uaucugcuca                                               20

<210> SEQ ID NO 819
<211> LENGTH: 20
<212> TYPE: RNA
<213> ORGANISM: Artificial Sequence
<220> FEATURE:
<223> OTHER INFORMATION: synthesized -continued

<400> SEQUENCE: 819
ugucuuucua uaucugcuca                                                    20

<210> SEQ ID NO 820
<211> LENGTH: 20
<212> TYPE: RNA
<213> ORGANISM: Artificial Sequence
<220> FEATURE:
<223> OTHER INFORMATION: synthesized

<400> SEQUENCE: 820
ugugacaaua agcguaucuu                                                    20

<210> SEQ ID NO 821
<211> LENGTH: 20
<212> TYPE: RNA
<213> ORGANISM: Artificial Sequence
<220> FEATURE:
<223> OTHER INFORMATION: synthesized

<400> SEQUENCE: 821
ugugacaaua aggguaucuu                                                    20

<210> SEQ ID NO 822
<211> LENGTH: 20
<212> TYPE: RNA
<213> ORGANISM: Artificial Sequence
<220> FEATURE:
<223> OTHER INFORMATION: synthesized

<400> SEQUENCE: 822
uguuugauau aucuauccuu                                                    20

<210> SEQ ID NO 823
<211> LENGTH: 20
<212> TYPE: RNA
<213> ORGANISM: Artificial Sequence
<220> FEATURE:
<223> OTHER INFORMATION: synthesized

<400> SEQUENCE: 823
uguuugauau aucuaucuuu                                                    20

<210> SEQ ID NO 824
<211> LENGTH: 20
<212> TYPE: RNA
<213> ORGANISM: Artificial Sequence
<220> FEATURE:
<223> OTHER INFORMATION: synthesized

<400> SEQUENCE: 824
uuaaagauac ccuuauuguc                                                    20

<210> SEQ ID NO 825
<211> LENGTH: 20
<212> TYPE: RNA
<213> ORGANISM: Artificial Sequence
<220> FEATURE:
<223> OTHER INFORMATION: synthesized

<400> SEQUENCE: 825
uuaaagauac gcuuauuguc                                                    20

<210> SEQ ID NO 826

```
<211> LENGTH: 20
<212> TYPE: RNA
<213> ORGANISM: Artificial Sequence
<220> FEATURE:
<223> OTHER INFORMATION: synthesized

<400> SEQUENCE: 826
uuaacuucaa aaagauagau                                               20

<210> SEQ ID NO 827
<211> LENGTH: 20
<212> TYPE: RNA
<213> ORGANISM: Artificial Sequence
<220> FEATURE:
<223> OTHER INFORMATION: synthesized

<400> SEQUENCE: 827
uuaacuucaa aaggauagau                                               20

<210> SEQ ID NO 828
<211> LENGTH: 20
<212> TYPE: RNA
<213> ORGANISM: Artificial Sequence
<220> FEATURE:
<223> OTHER INFORMATION: synthesized

<400> SEQUENCE: 828
uuacauuaac uucaaaaaga                                               20

<210> SEQ ID NO 829
<211> LENGTH: 20
<212> TYPE: RNA
<213> ORGANISM: Artificial Sequence
<220> FEATURE:
<223> OTHER INFORMATION: synthesized

<400> SEQUENCE: 829
uuacauuaac uucaaaagga                                               20

<210> SEQ ID NO 830
<211> LENGTH: 20
<212> TYPE: RNA
<213> ORGANISM: Artificial Sequence
<220> FEATURE:
<223> OTHER INFORMATION: synthesized

<400> SEQUENCE: 830
uucuauaucu gcucauuuca                                               20

<210> SEQ ID NO 831
<211> LENGTH: 20
<212> TYPE: RNA
<213> ORGANISM: Artificial Sequence
<220> FEATURE:
<223> OTHER INFORMATION: synthesized

<400> SEQUENCE: 831
uugauauauc uauccuuuug                                               20

<210> SEQ ID NO 832
<211> LENGTH: 20
<212> TYPE: RNA
<213> ORGANISM: Artificial Sequence
<220> FEATURE:
<223> OTHER INFORMATION: synthesized

<400> SEQUENCE: 832
```

-continued uugauauauc uaucuuuug    20

<210> SEQ ID NO 833
<211> LENGTH: 20
<212> TYPE: RNA
<213> ORGANISM: Artificial Sequence
<220> FEATURE:
<223> OTHER INFORMATION: synthesized

<400> SEQUENCE: 833
uugcacauuu aaagauaccc    20

<210> SEQ ID NO 834
<211> LENGTH: 20
<212> TYPE: RNA
<213> ORGANISM: Artificial Sequence
<220> FEATURE:
<223> OTHER INFORMATION: synthesized

<400> SEQUENCE: 834
uugcacauuu aaagauacgc    20

<210> SEQ ID NO 835
<211> LENGTH: 20
<212> TYPE: RNA
<213> ORGANISM: Artificial Sequence
<220> FEATURE:
<223> OTHER INFORMATION: synthesized

<400> SEQUENCE: 835
uugucugucu auaucugcuc    20

<210> SEQ ID NO 836
<211> LENGTH: 20
<212> TYPE: RNA
<213> ORGANISM: Artificial Sequence
<220> FEATURE:
<223> OTHER INFORMATION: synthesized

<400> SEQUENCE: 836
uugucuuucu auaucugcuc    20

<210> SEQ ID NO 837
<211> LENGTH: 20
<212> TYPE: RNA
<213> ORGANISM: Artificial Sequence
<220> FEATURE:
<223> OTHER INFORMATION: synthesized

<400> SEQUENCE: 837
uuuaaagaua cccuuauugu    20

<210> SEQ ID NO 838
<211> LENGTH: 20
<212> TYPE: RNA
<213> ORGANISM: Artificial Sequence
<220> FEATURE:
<223> OTHER INFORMATION: synthesized

<400> SEQUENCE: 838
uuuaaagaua cgcuuauugu    20

<210> SEQ ID NO 839
<211> LENGTH: 20
<212> TYPE: RNA

```
<213> ORGANISM: Artificial Sequence
<220> FEATURE:
<223> OTHER INFORMATION: synthesized

<400> SEQUENCE: 839
uuucuauauc ugcucauuuc                                                    20

<210> SEQ ID NO 840
<211> LENGTH: 20
<212> TYPE: RNA
<213> ORGANISM: Artificial Sequence
<220> FEATURE:
<223> OTHER INFORMATION: synthesized

<400> SEQUENCE: 840
uuugauauau cuauccuuuu                                                    20

<210> SEQ ID NO 841
<211> LENGTH: 20
<212> TYPE: RNA
<213> ORGANISM: Artificial Sequence
<220> FEATURE:
<223> OTHER INFORMATION: synthesized

<400> SEQUENCE: 841
uuugauauau cuaucuuuuu                                                    20

<210> SEQ ID NO 842
<211> LENGTH: 20
<212> TYPE: RNA
<213> ORGANISM: Artificial Sequence
<220> FEATURE:
<223> OTHER INFORMATION: synthesized

<400> SEQUENCE: 842
uuugcacauu uaaagauacc                                                    20

<210> SEQ ID NO 843
<211> LENGTH: 20
<212> TYPE: RNA
<213> ORGANISM: Artificial Sequence
<220> FEATURE:
<223> OTHER INFORMATION: synthesized

<400> SEQUENCE: 843
uuugcacauu uaaagauacg                                                    20

<210> SEQ ID NO 844
<211> LENGTH: 20
<212> TYPE: RNA
<213> ORGANISM: Artificial Sequence
<220> FEATURE:
<223> OTHER INFORMATION: synthesized

<400> SEQUENCE: 844
uuugucuguc uauaucugcu                                                    20

<210> SEQ ID NO 845
<211> LENGTH: 20
<212> TYPE: RNA
<213> ORGANISM: Artificial Sequence
<220> FEATURE:
<223> OTHER INFORMATION: synthesized

<400> SEQUENCE: 845
uuugucuuuc uauaucugcu                                                    20
```

```
<210> SEQ ID NO 846
<211> LENGTH: 20
<212> TYPE: RNA
<213> ORGANISM: Artificial Sequence
<220> FEATURE:
<223> OTHER INFORMATION: synthesized

<400> SEQUENCE: 846
uuuuugaagu uaauguaaua                                               20

<210> SEQ ID NO 847
<211> LENGTH: 20
<212> TYPE: RNA
<213> ORGANISM: Artificial Sequence
<220> FEATURE:
<223> OTHER INFORMATION: synthesized

<400> SEQUENCE: 847
aaacauucaa uacacauuag                                               20

<210> SEQ ID NO 848
<211> LENGTH: 20
<212> TYPE: RNA
<213> ORGANISM: Artificial Sequence
<220> FEATURE:
<223> OTHER INFORMATION: synthesized

<400> SEQUENCE: 848
aaacauucag uacacauuag                                               20

<210> SEQ ID NO 849
<211> LENGTH: 20
<212> TYPE: RNA
<213> ORGANISM: Artificial Sequence
<220> FEATURE:
<223> OTHER INFORMATION: synthesized

<400> SEQUENCE: 849
aacauucaau acacauuagc                                               20

<210> SEQ ID NO 850
<211> LENGTH: 20
<212> TYPE: RNA
<213> ORGANISM: Artificial Sequence
<220> FEATURE:
<223> OTHER INFORMATION: synthesized

<400> SEQUENCE: 850
aacauucagu acacauuagc                                               20

<210> SEQ ID NO 851
<211> LENGTH: 20
<212> TYPE: RNA
<213> ORGANISM: Artificial Sequence
<220> FEATURE:
<223> OTHER INFORMATION: synthesized

<400> SEQUENCE: 851
aagacuuagu aaacauucaa                                               20

<210> SEQ ID NO 852
<211> LENGTH: 20
<212> TYPE: RNA
<213> ORGANISM: Artificial Sequence
<220> FEATURE:
```

<223> OTHER INFORMATION: synthesized

<400> SEQUENCE: 852
aagacuuagu aaacauucag                                       20

<210> SEQ ID NO 853
<211> LENGTH: 20
<212> TYPE: RNA
<213> ORGANISM: Artificial Sequence
<220> FEATURE:
<223> OTHER INFORMATION: synthesized

<400> SEQUENCE: 853
aauacacauu agcuauuacu                                       20

<210> SEQ ID NO 854
<211> LENGTH: 20
<212> TYPE: RNA
<213> ORGANISM: Artificial Sequence
<220> FEATURE:
<223> OTHER INFORMATION: synthesized

<400> SEQUENCE: 854
aauagcuaau guguacugaa                                       20

<210> SEQ ID NO 855
<211> LENGTH: 20
<212> TYPE: RNA
<213> ORGANISM: Artificial Sequence
<220> FEATURE:
<223> OTHER INFORMATION: synthesized

<400> SEQUENCE: 855
aauagcuaau guguauugaa                                       20

<210> SEQ ID NO 856
<211> LENGTH: 20
<212> TYPE: RNA
<213> ORGANISM: Artificial Sequence
<220> FEATURE:
<223> OTHER INFORMATION: synthesized

<400> SEQUENCE: 856
aauguguacu gaauguuuac                                       20

<210> SEQ ID NO 857
<211> LENGTH: 20
<212> TYPE: RNA
<213> ORGANISM: Artificial Sequence
<220> FEATURE:
<223> OTHER INFORMATION: synthesized

<400> SEQUENCE: 857
aauguguauu gaauguuuac                                       20

<210> SEQ ID NO 858
<211> LENGTH: 20
<212> TYPE: RNA
<213> ORGANISM: Artificial Sequence
<220> FEATURE:
<223> OTHER INFORMATION: synthesized

<400> SEQUENCE: 858
acauucaaua cacauuagcu                                       20

```
<210> SEQ ID NO 859
<211> LENGTH: 20
<212> TYPE: RNA
<213> ORGANISM: Artificial Sequence
<220> FEATURE:
<223> OTHER INFORMATION: synthesized

<400> SEQUENCE: 859
acauucagua cacauuagcu                                               20

<210> SEQ ID NO 860
<211> LENGTH: 20
<212> TYPE: RNA
<213> ORGANISM: Artificial Sequence
<220> FEATURE:
<223> OTHER INFORMATION: synthesized

<400> SEQUENCE: 860
acuuaguaaa cauucaauac                                               20

<210> SEQ ID NO 861
<211> LENGTH: 20
<212> TYPE: RNA
<213> ORGANISM: Artificial Sequence
<220> FEATURE:
<223> OTHER INFORMATION: synthesized

<400> SEQUENCE: 861
acuuaguaaa cauucaguac                                               20

<210> SEQ ID NO 862
<211> LENGTH: 20
<212> TYPE: RNA
<213> ORGANISM: Artificial Sequence
<220> FEATURE:
<223> OTHER INFORMATION: synthesized

<400> SEQUENCE: 862
agacuuagua aacauucaau                                               20

<210> SEQ ID NO 863
<211> LENGTH: 20
<212> TYPE: RNA
<213> ORGANISM: Artificial Sequence
<220> FEATURE:
<223> OTHER INFORMATION: synthesized

<400> SEQUENCE: 863
agacuuagua aacauucagu                                               20

<210> SEQ ID NO 864
<211> LENGTH: 20
<212> TYPE: RNA
<213> ORGANISM: Artificial Sequence
<220> FEATURE:
<223> OTHER INFORMATION: synthesized

<400> SEQUENCE: 864
agcuaaugug uacugaaugu                                               20

<210> SEQ ID NO 865
<211> LENGTH: 20
<212> TYPE: RNA
<213> ORGANISM: Artificial Sequence
<220> FEATURE:
<223> OTHER INFORMATION: synthesized
```

<400> SEQUENCE: 865
agcuaaugug uauugaaugu                                           20

<210> SEQ ID NO 866
<211> LENGTH: 20
<212> TYPE: RNA
<213> ORGANISM: Artificial Sequence
<220> FEATURE:
<223> OTHER INFORMATION: synthesized

<400> SEQUENCE: 866
aguaaacauu caauacacau                                           20

<210> SEQ ID NO 867
<211> LENGTH: 20
<212> TYPE: RNA
<213> ORGANISM: Artificial Sequence
<220> FEATURE:
<223> OTHER INFORMATION: synthesized

<400> SEQUENCE: 867
aguaaacauu caguacacau                                           20

<210> SEQ ID NO 868
<211> LENGTH: 20
<212> TYPE: RNA
<213> ORGANISM: Artificial Sequence
<220> FEATURE:
<223> OTHER INFORMATION: synthesized

<400> SEQUENCE: 868
aguaauagcu aauguguacu                                           20

<210> SEQ ID NO 869
<211> LENGTH: 20
<212> TYPE: RNA
<213> ORGANISM: Artificial Sequence
<220> FEATURE:
<223> OTHER INFORMATION: synthesized

<400> SEQUENCE: 869
aguaauagcu aauguguauu                                           20

<210> SEQ ID NO 870
<211> LENGTH: 20
<212> TYPE: RNA
<213> ORGANISM: Artificial Sequence
<220> FEATURE:
<223> OTHER INFORMATION: synthesized

<400> SEQUENCE: 870
aguacacauu agcuauuacu                                           20

<210> SEQ ID NO 871
<211> LENGTH: 20
<212> TYPE: RNA
<213> ORGANISM: Artificial Sequence
<220> FEATURE:
<223> OTHER INFORMATION: synthesized

<400> SEQUENCE: 871
auacacauua gcuauuacuc                                           20

<210> SEQ ID NO 872
<211> LENGTH: 20

```
-continued

<212> TYPE: RNA
<213> ORGANISM: Artificial Sequence
<220> FEATURE:
<223> OTHER INFORMATION: synthesized

<400> SEQUENCE: 872
auagcuaaug uguacugaau                                                      20

<210> SEQ ID NO 873
<211> LENGTH: 20
<212> TYPE: RNA
<213> ORGANISM: Artificial Sequence
<220> FEATURE:
<223> OTHER INFORMATION: synthesized

<400> SEQUENCE: 873
auagcuaaug uguauugaau                                                      20

<210> SEQ ID NO 874
<211> LENGTH: 20
<212> TYPE: RNA
<213> ORGANISM: Artificial Sequence
<220> FEATURE:
<223> OTHER INFORMATION: synthesized

<400> SEQUENCE: 874
auguguacug aauguuuacu                                                      20

<210> SEQ ID NO 875
<211> LENGTH: 20
<212> TYPE: RNA
<213> ORGANISM: Artificial Sequence
<220> FEATURE:
<223> OTHER INFORMATION: synthesized

<400> SEQUENCE: 875
auguguauug aauguuuacu                                                      20

<210> SEQ ID NO 876
<211> LENGTH: 20
<212> TYPE: RNA
<213> ORGANISM: Artificial Sequence
<220> FEATURE:
<223> OTHER INFORMATION: synthesized

<400> SEQUENCE: 876
auucaauaca cauuagcuau                                                      20

<210> SEQ ID NO 877
<211> LENGTH: 20
<212> TYPE: RNA
<213> ORGANISM: Artificial Sequence
<220> FEATURE:
<223> OTHER INFORMATION: synthesized

<400> SEQUENCE: 877
auucaguaca cauuagcuau                                                      20

<210> SEQ ID NO 878
<211> LENGTH: 20
<212> TYPE: RNA
<213> ORGANISM: Artificial Sequence
<220> FEATURE:
<223> OTHER INFORMATION: synthesized

<400> SEQUENCE: 878
```

| | |
|---|---|
| caauacacau uagcuauuac | 20 |

<210> SEQ ID NO 879
<211> LENGTH: 20
<212> TYPE: RNA
<213> ORGANISM: Artificial Sequence
<220> FEATURE:
<223> OTHER INFORMATION: synthesized

<400> SEQUENCE: 879

| | |
|---|---|
| caguacacau uagcuauuac | 20 |

<210> SEQ ID NO 880
<211> LENGTH: 20
<212> TYPE: RNA
<213> ORGANISM: Artificial Sequence
<220> FEATURE:
<223> OTHER INFORMATION: synthesized

<400> SEQUENCE: 880

| | |
|---|---|
| cauucaauac acauuagcua | 20 |

<210> SEQ ID NO 881
<211> LENGTH: 20
<212> TYPE: RNA
<213> ORGANISM: Artificial Sequence
<220> FEATURE:
<223> OTHER INFORMATION: synthesized

<400> SEQUENCE: 881

| | |
|---|---|
| cauucaguac acauuagcua | 20 |

<210> SEQ ID NO 882
<211> LENGTH: 20
<212> TYPE: RNA
<213> ORGANISM: Artificial Sequence
<220> FEATURE:
<223> OTHER INFORMATION: synthesized

<400> SEQUENCE: 882

| | |
|---|---|
| cuaaugugua cugaauguuu | 20 |

<210> SEQ ID NO 883
<211> LENGTH: 20
<212> TYPE: RNA
<213> ORGANISM: Artificial Sequence
<220> FEATURE:
<223> OTHER INFORMATION: synthesized

<400> SEQUENCE: 883

| | |
|---|---|
| cuaaugugua uugaauguuu | 20 |

<210> SEQ ID NO 884
<211> LENGTH: 20
<212> TYPE: RNA
<213> ORGANISM: Artificial Sequence
<220> FEATURE:
<223> OTHER INFORMATION: synthesized

<400> SEQUENCE: 884

| | |
|---|---|
| cuuaguaaac auucaauaca | 20 |

<210> SEQ ID NO 885
<211> LENGTH: 20
<212> TYPE: RNA
<213> ORGANISM: Artificial Sequence

```
<220> FEATURE:
<223> OTHER INFORMATION: synthesized

<400> SEQUENCE: 885
cuuaguaaac auucaguaca                                               20

<210> SEQ ID NO 886
<211> LENGTH: 20
<212> TYPE: RNA
<213> ORGANISM: Artificial Sequence
<220> FEATURE:
<223> OTHER INFORMATION: synthesized

<400> SEQUENCE: 886
gacuuaguaa acauucaaua                                               20

<210> SEQ ID NO 887
<211> LENGTH: 20
<212> TYPE: RNA
<213> ORGANISM: Artificial Sequence
<220> FEATURE:
<223> OTHER INFORMATION: synthesized

<400> SEQUENCE: 887
gacuuaguaa acauucagua                                               20

<210> SEQ ID NO 888
<211> LENGTH: 20
<212> TYPE: RNA
<213> ORGANISM: Artificial Sequence
<220> FEATURE:
<223> OTHER INFORMATION: synthesized

<400> SEQUENCE: 888
gcuaaugugu acugaauguu                                               20

<210> SEQ ID NO 889
<211> LENGTH: 20
<212> TYPE: RNA
<213> ORGANISM: Artificial Sequence
<220> FEATURE:
<223> OTHER INFORMATION: synthesized

<400> SEQUENCE: 889
gcuaaugugu auugaauguu                                               20

<210> SEQ ID NO 890
<211> LENGTH: 20
<212> TYPE: RNA
<213> ORGANISM: Artificial Sequence
<220> FEATURE:
<223> OTHER INFORMATION: synthesized

<400> SEQUENCE: 890
guaaacauuc aauacacauu                                               20

<210> SEQ ID NO 891
<211> LENGTH: 20
<212> TYPE: RNA
<213> ORGANISM: Artificial Sequence
<220> FEATURE:
<223> OTHER INFORMATION: synthesized

<400> SEQUENCE: 891
guaaacauuc aguacacauu                                               20
```

```
<210> SEQ ID NO 892
<211> LENGTH: 20
<212> TYPE: RNA
<213> ORGANISM: Artificial Sequence
<220> FEATURE:
<223> OTHER INFORMATION: synthesized

<400> SEQUENCE: 892
guaauagcua auguguacug                                                     20

<210> SEQ ID NO 893
<211> LENGTH: 20
<212> TYPE: RNA
<213> ORGANISM: Artificial Sequence
<220> FEATURE:
<223> OTHER INFORMATION: synthesized

<400> SEQUENCE: 893
guaauagcua auguguauug                                                     20

<210> SEQ ID NO 894
<211> LENGTH: 20
<212> TYPE: RNA
<213> ORGANISM: Artificial Sequence
<220> FEATURE:
<223> OTHER INFORMATION: synthesized

<400> SEQUENCE: 894
guacacauua gcuauuacuc                                                     20

<210> SEQ ID NO 895
<211> LENGTH: 20
<212> TYPE: RNA
<213> ORGANISM: Artificial Sequence
<220> FEATURE:
<223> OTHER INFORMATION: synthesized

<400> SEQUENCE: 895
guacugaaug uuuacuaagu                                                     20

<210> SEQ ID NO 896
<211> LENGTH: 20
<212> TYPE: RNA
<213> ORGANISM: Artificial Sequence
<220> FEATURE:
<223> OTHER INFORMATION: synthesized

<400> SEQUENCE: 896
guauugaaug uuuacuaagu                                                     20

<210> SEQ ID NO 897
<211> LENGTH: 20
<212> TYPE: RNA
<213> ORGANISM: Artificial Sequence
<220> FEATURE:
<223> OTHER INFORMATION: synthesized

<400> SEQUENCE: 897
guguacugaa uguuuacuaa                                                     20

<210> SEQ ID NO 898
<211> LENGTH: 20
<212> TYPE: RNA
<213> ORGANISM: Artificial Sequence
<220> FEATURE:
<223> OTHER INFORMATION: synthesized
```

<400> SEQUENCE: 898
guguauugaa uguuuacuaa                                              20

<210> SEQ ID NO 899
<211> LENGTH: 20
<212> TYPE: RNA
<213> ORGANISM: Artificial Sequence
<220> FEATURE:
<223> OTHER INFORMATION: synthesized

<400> SEQUENCE: 899
uaaacauuca auacacauua                                              20

<210> SEQ ID NO 900
<211> LENGTH: 20
<212> TYPE: RNA
<213> ORGANISM: Artificial Sequence
<220> FEATURE:
<223> OTHER INFORMATION: synthesized

<400> SEQUENCE: 900
uaaacauuca guacacauua                                              20

<210> SEQ ID NO 901
<211> LENGTH: 20
<212> TYPE: RNA
<213> ORGANISM: Artificial Sequence
<220> FEATURE:
<223> OTHER INFORMATION: synthesized

<400> SEQUENCE: 901
uaauagcuaa uguguacuga                                              20

<210> SEQ ID NO 902
<211> LENGTH: 20
<212> TYPE: RNA
<213> ORGANISM: Artificial Sequence
<220> FEATURE:
<223> OTHER INFORMATION: synthesized

<400> SEQUENCE: 902
uaauagcuaa uguguauuga                                              20

<210> SEQ ID NO 903
<211> LENGTH: 20
<212> TYPE: RNA
<213> ORGANISM: Artificial Sequence
<220> FEATURE:
<223> OTHER INFORMATION: synthesized

<400> SEQUENCE: 903
uacugaaugu uuacuaaguc                                              20

<210> SEQ ID NO 904
<211> LENGTH: 20
<212> TYPE: RNA
<213> ORGANISM: Artificial Sequence
<220> FEATURE:
<223> OTHER INFORMATION: synthesized

<400> SEQUENCE: 904
uagcuaaugu guacugaaug                                              20

<210> SEQ ID NO 905

```
<211> LENGTH: 20
<212> TYPE: RNA
<213> ORGANISM: Artificial Sequence
<220> FEATURE:
<223> OTHER INFORMATION: synthesized

<400> SEQUENCE: 905
uagcuaaugu guauugaaug                                              20

<210> SEQ ID NO 906
<211> LENGTH: 20
<212> TYPE: RNA
<213> ORGANISM: Artificial Sequence
<220> FEATURE:
<223> OTHER INFORMATION: synthesized

<400> SEQUENCE: 906
uaguaaacau ucaauacaca                                              20

<210> SEQ ID NO 907
<211> LENGTH: 20
<212> TYPE: RNA
<213> ORGANISM: Artificial Sequence
<220> FEATURE:
<223> OTHER INFORMATION: synthesized

<400> SEQUENCE: 907
uaguaaacau ucaguacaca                                              20

<210> SEQ ID NO 908
<211> LENGTH: 20
<212> TYPE: RNA
<213> ORGANISM: Artificial Sequence
<220> FEATURE:
<223> OTHER INFORMATION: synthesized

<400> SEQUENCE: 908
uauugaaugu uuacuaaguc                                              20

<210> SEQ ID NO 909
<211> LENGTH: 20
<212> TYPE: RNA
<213> ORGANISM: Artificial Sequence
<220> FEATURE:
<223> OTHER INFORMATION: synthesized

<400> SEQUENCE: 909
ucaauacaca uuagcuauua                                              20

<210> SEQ ID NO 910
<211> LENGTH: 20
<212> TYPE: RNA
<213> ORGANISM: Artificial Sequence
<220> FEATURE:
<223> OTHER INFORMATION: synthesized

<400> SEQUENCE: 910
ucaguacaca uuagcuauua                                              20

<210> SEQ ID NO 911
<211> LENGTH: 20
<212> TYPE: RNA
<213> ORGANISM: Artificial Sequence
<220> FEATURE:
<223> OTHER INFORMATION: synthesized

<400> SEQUENCE: 911
```

```
uguacugaau guuuacuaag                                              20

<210> SEQ ID NO 912
<211> LENGTH: 20
<212> TYPE: RNA
<213> ORGANISM: Artificial Sequence
<220> FEATURE:
<223> OTHER INFORMATION: synthesized

<400> SEQUENCE: 912
uguauugaau guuuacuaag                                              20

<210> SEQ ID NO 913
<211> LENGTH: 20
<212> TYPE: RNA
<213> ORGANISM: Artificial Sequence
<220> FEATURE:
<223> OTHER INFORMATION: synthesized

<400> SEQUENCE: 913
uguguacuga auguuuacua                                              20

<210> SEQ ID NO 914
<211> LENGTH: 20
<212> TYPE: RNA
<213> ORGANISM: Artificial Sequence
<220> FEATURE:
<223> OTHER INFORMATION: synthesized

<400> SEQUENCE: 914
uguguauuga auguuuacua                                              20

<210> SEQ ID NO 915
<211> LENGTH: 20
<212> TYPE: RNA
<213> ORGANISM: Artificial Sequence
<220> FEATURE:
<223> OTHER INFORMATION: synthesized

<400> SEQUENCE: 915
uuaguaaaca uucaauacac                                              20

<210> SEQ ID NO 916
<211> LENGTH: 20
<212> TYPE: RNA
<213> ORGANISM: Artificial Sequence
<220> FEATURE:
<223> OTHER INFORMATION: synthesized

<400> SEQUENCE: 916
uuaguaaaca uucaguacac                                              20

<210> SEQ ID NO 917
<211> LENGTH: 20
<212> TYPE: RNA
<213> ORGANISM: Artificial Sequence
<220> FEATURE:
<223> OTHER INFORMATION: synthesized

<400> SEQUENCE: 917
uucaauacac auuagcuauu                                              20

<210> SEQ ID NO 918
<211> LENGTH: 20
<212> TYPE: RNA
```

```
<213> ORGANISM: Artificial Sequence
<220> FEATURE:
<223> OTHER INFORMATION: synthesized

<400> SEQUENCE: 918
uucaguacac auuagcuauu                                              20

<210> SEQ ID NO 919
<211> LENGTH: 20
<212> TYPE: RNA
<213> ORGANISM: Artificial Sequence
<220> FEATURE:
<223> OTHER INFORMATION: synthesized

<400> SEQUENCE: 919
aaagaaagga uugccgccac                                              20

<210> SEQ ID NO 920
<211> LENGTH: 20
<212> TYPE: RNA
<213> ORGANISM: Artificial Sequence
<220> FEATURE:
<223> OTHER INFORMATION: synthesized

<400> SEQUENCE: 920
aaagaaagga uugcugccac                                              20

<210> SEQ ID NO 921
<211> LENGTH: 20
<212> TYPE: RNA
<213> ORGANISM: Artificial Sequence
<220> FEATURE:
<223> OTHER INFORMATION: synthesized

<400> SEQUENCE: 921
aaaggauugc cgccacuccu                                              20

<210> SEQ ID NO 922
<211> LENGTH: 20
<212> TYPE: RNA
<213> ORGANISM: Artificial Sequence
<220> FEATURE:
<223> OTHER INFORMATION: synthesized

<400> SEQUENCE: 922
aaaggauugc ugccacuccu                                              20

<210> SEQ ID NO 923
<211> LENGTH: 20
<212> TYPE: RNA
<213> ORGANISM: Artificial Sequence
<220> FEATURE:
<223> OTHER INFORMATION: synthesized

<400> SEQUENCE: 923
aacuaggagu ggcagcaauc                                              20

<210> SEQ ID NO 924
<211> LENGTH: 20
<212> TYPE: RNA
<213> ORGANISM: Artificial Sequence
<220> FEATURE:
<223> OTHER INFORMATION: synthesized

<400> SEQUENCE: 924
aacuaggagu ggcggcaauc                                              20
```

```
<210> SEQ ID NO 925
<211> LENGTH: 20
<212> TYPE: RNA
<213> ORGANISM: Artificial Sequence
<220> FEATURE:
<223> OTHER INFORMATION: synthesized

<400> SEQUENCE: 925
aagaaaggau ugccgccacu                                              20

<210> SEQ ID NO 926
<211> LENGTH: 20
<212> TYPE: RNA
<213> ORGANISM: Artificial Sequence
<220> FEATURE:
<223> OTHER INFORMATION: synthesized

<400> SEQUENCE: 926
aagaaaggau ugcugccacu                                              20

<210> SEQ ID NO 927
<211> LENGTH: 20
<212> TYPE: RNA
<213> ORGANISM: Artificial Sequence
<220> FEATURE:
<223> OTHER INFORMATION: synthesized

<400> SEQUENCE: 927
aaggauugcc gccacuccua                                              20

<210> SEQ ID NO 928
<211> LENGTH: 20
<212> TYPE: RNA
<213> ORGANISM: Artificial Sequence
<220> FEATURE:
<223> OTHER INFORMATION: synthesized

<400> SEQUENCE: 928
aaggauugcu gccacuccua                                              20

<210> SEQ ID NO 929
<211> LENGTH: 20
<212> TYPE: RNA
<213> ORGANISM: Artificial Sequence
<220> FEATURE:
<223> OTHER INFORMATION: synthesized

<400> SEQUENCE: 929
acuaggagug gcagcaaucc                                              20

<210> SEQ ID NO 930
<211> LENGTH: 20
<212> TYPE: RNA
<213> ORGANISM: Artificial Sequence
<220> FEATURE:
<223> OTHER INFORMATION: synthesized

<400> SEQUENCE: 930
acuaggagug gcggcaaucc                                              20

<210> SEQ ID NO 931
<211> LENGTH: 20
<212> TYPE: RNA
<213> ORGANISM: Artificial Sequence
<220> FEATURE:
```

<223> OTHER INFORMATION: synthesized

<400> SEQUENCE: 931
agaaaggauu gccgccacuc                          20

<210> SEQ ID NO 932
<211> LENGTH: 20
<212> TYPE: RNA
<213> ORGANISM: Artificial Sequence
<220> FEATURE:
<223> OTHER INFORMATION: synthesized

<400> SEQUENCE: 932
agaaaggauu gcugccacuc                          20

<210> SEQ ID NO 933
<211> LENGTH: 20
<212> TYPE: RNA
<213> ORGANISM: Artificial Sequence
<220> FEATURE:
<223> OTHER INFORMATION: synthesized

<400> SEQUENCE: 933
agcugaaaga aaggauugcc                          20

<210> SEQ ID NO 934
<211> LENGTH: 20
<212> TYPE: RNA
<213> ORGANISM: Artificial Sequence
<220> FEATURE:
<223> OTHER INFORMATION: synthesized

<400> SEQUENCE: 934
agcugaaaga aaggauugcu                          20

<210> SEQ ID NO 935
<211> LENGTH: 20
<212> TYPE: RNA
<213> ORGANISM: Artificial Sequence
<220> FEATURE:
<223> OTHER INFORMATION: synthesized

<400> SEQUENCE: 935
aggaguggca gcaauccuuu                          20

<210> SEQ ID NO 936
<211> LENGTH: 20
<212> TYPE: RNA
<213> ORGANISM: Artificial Sequence
<220> FEATURE:
<223> OTHER INFORMATION: synthesized

<400> SEQUENCE: 936
aggaguggcg gcaauccuuu                          20

<210> SEQ ID NO 937
<211> LENGTH: 20
<212> TYPE: RNA
<213> ORGANISM: Artificial Sequence
<220> FEATURE:
<223> OTHER INFORMATION: synthesized

<400> SEQUENCE: 937
aggauugccg ccacuccuag                          20

```
<210> SEQ ID NO 938
<211> LENGTH: 20
<212> TYPE: RNA
<213> ORGANISM: Artificial Sequence
<220> FEATURE:
<223> OTHER INFORMATION: synthesized

<400> SEQUENCE: 938
aggauugcug ccacuccuag                                                   20

<210> SEQ ID NO 939
<211> LENGTH: 20
<212> TYPE: RNA
<213> ORGANISM: Artificial Sequence
<220> FEATURE:
<223> OTHER INFORMATION: synthesized

<400> SEQUENCE: 939
aguggcagca auccuuucuu                                                   20

<210> SEQ ID NO 940
<211> LENGTH: 20
<212> TYPE: RNA
<213> ORGANISM: Artificial Sequence
<220> FEATURE:
<223> OTHER INFORMATION: synthesized

<400> SEQUENCE: 940
aguggcggca auccuuucuu                                                   20

<210> SEQ ID NO 941
<211> LENGTH: 20
<212> TYPE: RNA
<213> ORGANISM: Artificial Sequence
<220> FEATURE:
<223> OTHER INFORMATION: synthesized

<400> SEQUENCE: 941
augggaacua ggaguggcag                                                   20

<210> SEQ ID NO 942
<211> LENGTH: 20
<212> TYPE: RNA
<213> ORGANISM: Artificial Sequence
<220> FEATURE:
<223> OTHER INFORMATION: synthesized

<400> SEQUENCE: 942
augggaacua ggaguggcgg                                                   20

<210> SEQ ID NO 943
<211> LENGTH: 20
<212> TYPE: RNA
<213> ORGANISM: Artificial Sequence
<220> FEATURE:
<223> OTHER INFORMATION: synthesized

<400> SEQUENCE: 943
auugccgcca cuccuaguuc                                                   20

<210> SEQ ID NO 944
<211> LENGTH: 20
<212> TYPE: RNA
<213> ORGANISM: Artificial Sequence
<220> FEATURE:
<223> OTHER INFORMATION: synthesized
```

-continued

<400> SEQUENCE: 944
auugcugcca cuccuaguuc                                                    20

<210> SEQ ID NO 945
<211> LENGTH: 20
<212> TYPE: RNA
<213> ORGANISM: Artificial Sequence
<220> FEATURE:
<223> OTHER INFORMATION: synthesized

<400> SEQUENCE: 945
ccgccacucc uaguucccau                                                    20

<210> SEQ ID NO 946
<211> LENGTH: 20
<212> TYPE: RNA
<213> ORGANISM: Artificial Sequence
<220> FEATURE:
<223> OTHER INFORMATION: synthesized

<400> SEQUENCE: 946
cgccacuccu aguucccauc                                                    20

<210> SEQ ID NO 947
<211> LENGTH: 20
<212> TYPE: RNA
<213> ORGANISM: Artificial Sequence
<220> FEATURE:
<223> OTHER INFORMATION: synthesized

<400> SEQUENCE: 947
cuaggagugg cagcaauccu                                                    20

<210> SEQ ID NO 948
<211> LENGTH: 20
<212> TYPE: RNA
<213> ORGANISM: Artificial Sequence
<220> FEATURE:
<223> OTHER INFORMATION: synthesized

<400> SEQUENCE: 948
cuaggagugg cggcaauccu                                                    20

<210> SEQ ID NO 949
<211> LENGTH: 20
<212> TYPE: RNA
<213> ORGANISM: Artificial Sequence
<220> FEATURE:
<223> OTHER INFORMATION: synthesized

<400> SEQUENCE: 949
cugaaagaaa ggauugccgc                                                    20

<210> SEQ ID NO 950
<211> LENGTH: 20
<212> TYPE: RNA
<213> ORGANISM: Artificial Sequence
<220> FEATURE:
<223> OTHER INFORMATION: synthesized

<400> SEQUENCE: 950
cugaaagaaa ggauugcugc                                                    20

<210> SEQ ID NO 951
<211> LENGTH: 20

```
<212> TYPE: RNA
<213> ORGANISM: Artificial Sequence
<220> FEATURE:
<223> OTHER INFORMATION: synthesized

<400> SEQUENCE: 951
cugccacucc uaguucccau                                               20

<210> SEQ ID NO 952
<211> LENGTH: 20
<212> TYPE: RNA
<213> ORGANISM: Artificial Sequence
<220> FEATURE:
<223> OTHER INFORMATION: synthesized

<400> SEQUENCE: 952
gaaagaaagg auugccgcca                                               20

<210> SEQ ID NO 953
<211> LENGTH: 20
<212> TYPE: RNA
<213> ORGANISM: Artificial Sequence
<220> FEATURE:
<223> OTHER INFORMATION: synthesized

<400> SEQUENCE: 953
gaaagaaagg auugcugcca                                               20

<210> SEQ ID NO 954
<211> LENGTH: 20
<212> TYPE: RNA
<213> ORGANISM: Artificial Sequence
<220> FEATURE:
<223> OTHER INFORMATION: synthesized

<400> SEQUENCE: 954
gaaaggauug ccgccacucc                                               20

<210> SEQ ID NO 955
<211> LENGTH: 20
<212> TYPE: RNA
<213> ORGANISM: Artificial Sequence
<220> FEATURE:
<223> OTHER INFORMATION: synthesized

<400> SEQUENCE: 955
gaaaggauug cugccacucc                                               20

<210> SEQ ID NO 956
<211> LENGTH: 20
<212> TYPE: RNA
<213> ORGANISM: Artificial Sequence
<220> FEATURE:
<223> OTHER INFORMATION: synthesized

<400> SEQUENCE: 956
gaacuaggag uggcagcaau                                               20

<210> SEQ ID NO 957
<211> LENGTH: 20
<212> TYPE: RNA
<213> ORGANISM: Artificial Sequence
<220> FEATURE:
<223> OTHER INFORMATION: synthesized

<400> SEQUENCE: 957
```
gaacuaggag uggcggcaau                                    20

<210> SEQ ID NO 958
<211> LENGTH: 20
<212> TYPE: RNA
<213> ORGANISM: Artificial Sequence
<220> FEATURE:
<223> OTHER INFORMATION: synthesized

<400> SEQUENCE: 958
gaguggcagc aauccuuucu                                    20

<210> SEQ ID NO 959
<211> LENGTH: 20
<212> TYPE: RNA
<213> ORGANISM: Artificial Sequence
<220> FEATURE:
<223> OTHER INFORMATION: synthesized

<400> SEQUENCE: 959
gaguggcggc aauccuuucu                                    20

<210> SEQ ID NO 960
<211> LENGTH: 20
<212> TYPE: RNA
<213> ORGANISM: Artificial Sequence
<220> FEATURE:
<223> OTHER INFORMATION: synthesized

<400> SEQUENCE: 960
gaugggaacu aggaguggca                                    20

<210> SEQ ID NO 961
<211> LENGTH: 20
<212> TYPE: RNA
<213> ORGANISM: Artificial Sequence
<220> FEATURE:
<223> OTHER INFORMATION: synthesized

<400> SEQUENCE: 961
gaugggaacu aggaguggcg                                    20

<210> SEQ ID NO 962
<211> LENGTH: 20
<212> TYPE: RNA
<213> ORGANISM: Artificial Sequence
<220> FEATURE:
<223> OTHER INFORMATION: synthesized

<400> SEQUENCE: 962
gauugccgcc acuccuaguu                                    20

<210> SEQ ID NO 963
<211> LENGTH: 20
<212> TYPE: RNA
<213> ORGANISM: Artificial Sequence
<220> FEATURE:
<223> OTHER INFORMATION: synthesized

<400> SEQUENCE: 963
gauugcugcc acuccuaguu                                    20

<210> SEQ ID NO 964
<211> LENGTH: 20
<212> TYPE: RNA
<213> ORGANISM: Artificial Sequence

```
<220> FEATURE:
<223> OTHER INFORMATION: synthesized

<400> SEQUENCE: 964
gcagcaaucc uuucuuucag                                                    20

<210> SEQ ID NO 965
<211> LENGTH: 20
<212> TYPE: RNA
<213> ORGANISM: Artificial Sequence
<220> FEATURE:
<223> OTHER INFORMATION: synthesized

<400> SEQUENCE: 965
gccgccacuc cuaguuccca                                                    20

<210> SEQ ID NO 966
<211> LENGTH: 20
<212> TYPE: RNA
<213> ORGANISM: Artificial Sequence
<220> FEATURE:
<223> OTHER INFORMATION: synthesized

<400> SEQUENCE: 966
gcggcaaucc uuucuuucag                                                    20

<210> SEQ ID NO 967
<211> LENGTH: 20
<212> TYPE: RNA
<213> ORGANISM: Artificial Sequence
<220> FEATURE:
<223> OTHER INFORMATION: synthesized

<400> SEQUENCE: 967
gcugaaagaa aggauugccg                                                    20

<210> SEQ ID NO 968
<211> LENGTH: 20
<212> TYPE: RNA
<213> ORGANISM: Artificial Sequence
<220> FEATURE:
<223> OTHER INFORMATION: synthesized

<400> SEQUENCE: 968
gcugaaagaa aggauugcug                                                    20

<210> SEQ ID NO 969
<211> LENGTH: 20
<212> TYPE: RNA
<213> ORGANISM: Artificial Sequence
<220> FEATURE:
<223> OTHER INFORMATION: synthesized

<400> SEQUENCE: 969
gcugccacuc cuaguuccca                                                    20

<210> SEQ ID NO 970
<211> LENGTH: 20
<212> TYPE: RNA
<213> ORGANISM: Artificial Sequence
<220> FEATURE:
<223> OTHER INFORMATION: synthesized

<400> SEQUENCE: 970
ggaacuagga guggcagcaa                                                    20
```

<210> SEQ ID NO 971
<211> LENGTH: 20
<212> TYPE: RNA
<213> ORGANISM: Artificial Sequence
<220> FEATURE:
<223> OTHER INFORMATION: synthesized

<400> SEQUENCE: 971
ggaacuagga guggcggcaa                                               20

<210> SEQ ID NO 972
<211> LENGTH: 20
<212> TYPE: RNA
<213> ORGANISM: Artificial Sequence
<220> FEATURE:
<223> OTHER INFORMATION: synthesized

<400> SEQUENCE: 972
ggaguggcag caauccuuuc                                               20

<210> SEQ ID NO 973
<211> LENGTH: 20
<212> TYPE: RNA
<213> ORGANISM: Artificial Sequence
<220> FEATURE:
<223> OTHER INFORMATION: synthesized

<400> SEQUENCE: 973
ggaguggcgg caauccuuuc                                               20

<210> SEQ ID NO 974
<211> LENGTH: 20
<212> TYPE: RNA
<213> ORGANISM: Artificial Sequence
<220> FEATURE:
<223> OTHER INFORMATION: synthesized

<400> SEQUENCE: 974
ggcagcaauc cuuucuuuca                                               20

<210> SEQ ID NO 975
<211> LENGTH: 20
<212> TYPE: RNA
<213> ORGANISM: Artificial Sequence
<220> FEATURE:
<223> OTHER INFORMATION: synthesized

<400> SEQUENCE: 975
ggcggcaauc cuuucuuuca                                               20

<210> SEQ ID NO 976
<211> LENGTH: 20
<212> TYPE: RNA
<213> ORGANISM: Artificial Sequence
<220> FEATURE:
<223> OTHER INFORMATION: synthesized

<400> SEQUENCE: 976
gggaacuagg aguggcagca                                               20

<210> SEQ ID NO 977
<211> LENGTH: 20
<212> TYPE: RNA
<213> ORGANISM: Artificial Sequence
<220> FEATURE:
<223> OTHER INFORMATION: synthesized

```
<400> SEQUENCE: 977
gggaacuagg aguggcggca                                              20

<210> SEQ ID NO 978
<211> LENGTH: 20
<212> TYPE: RNA
<213> ORGANISM: Artificial Sequence
<220> FEATURE:
<223> OTHER INFORMATION: synthesized

<400> SEQUENCE: 978
guggcagcaa uccuuucuuu                                              20

<210> SEQ ID NO 979
<211> LENGTH: 20
<212> TYPE: RNA
<213> ORGANISM: Artificial Sequence
<220> FEATURE:
<223> OTHER INFORMATION: synthesized

<400> SEQUENCE: 979
guggcggcaa uccuuucuuu                                              20

<210> SEQ ID NO 980
<211> LENGTH: 20
<212> TYPE: RNA
<213> ORGANISM: Artificial Sequence
<220> FEATURE:
<223> OTHER INFORMATION: synthesized

<400> SEQUENCE: 980
uaggaguggc agcaauccuu                                              20

<210> SEQ ID NO 981
<211> LENGTH: 20
<212> TYPE: RNA
<213> ORGANISM: Artificial Sequence
<220> FEATURE:
<223> OTHER INFORMATION: synthesized

<400> SEQUENCE: 981
uaggaguggc ggcaauccuu                                              20

<210> SEQ ID NO 982
<211> LENGTH: 20
<212> TYPE: RNA
<213> ORGANISM: Artificial Sequence
<220> FEATURE:
<223> OTHER INFORMATION: synthesized

<400> SEQUENCE: 982
ugaaagaaag gauugccgcc                                              20

<210> SEQ ID NO 983
<211> LENGTH: 20
<212> TYPE: RNA
<213> ORGANISM: Artificial Sequence
<220> FEATURE:
<223> OTHER INFORMATION: synthesized

<400> SEQUENCE: 983
ugaaagaaag gauugcugcc                                              20

<210> SEQ ID NO 984
```

```
<211> LENGTH: 20
<212> TYPE: RNA
<213> ORGANISM: Artificial Sequence
<220> FEATURE:
<223> OTHER INFORMATION: synthesized

<400> SEQUENCE: 984
ugccacuccu aguucccauc                                                 20

<210> SEQ ID NO 985
<211> LENGTH: 20
<212> TYPE: RNA
<213> ORGANISM: Artificial Sequence
<220> FEATURE:
<223> OTHER INFORMATION: synthesized

<400> SEQUENCE: 985
ugccgccacu ccuaguuccc                                                 20

<210> SEQ ID NO 986
<211> LENGTH: 20
<212> TYPE: RNA
<213> ORGANISM: Artificial Sequence
<220> FEATURE:
<223> OTHER INFORMATION: synthesized

<400> SEQUENCE: 986
ugcugccacu ccuaguuccc                                                 20

<210> SEQ ID NO 987
<211> LENGTH: 20
<212> TYPE: RNA
<213> ORGANISM: Artificial Sequence
<220> FEATURE:
<223> OTHER INFORMATION: synthesized

<400> SEQUENCE: 987
uggcagcaau ccuuucuuuc                                                 20

<210> SEQ ID NO 988
<211> LENGTH: 20
<212> TYPE: RNA
<213> ORGANISM: Artificial Sequence
<220> FEATURE:
<223> OTHER INFORMATION: synthesized

<400> SEQUENCE: 988
uggcggcaau ccuuucuuuc                                                 20

<210> SEQ ID NO 989
<211> LENGTH: 20
<212> TYPE: RNA
<213> ORGANISM: Artificial Sequence
<220> FEATURE:
<223> OTHER INFORMATION: synthesized

<400> SEQUENCE: 989
ugggaacuag gaguggcagc                                                 20

<210> SEQ ID NO 990
<211> LENGTH: 20
<212> TYPE: RNA
<213> ORGANISM: Artificial Sequence
<220> FEATURE:
<223> OTHER INFORMATION: synthesized

<400> SEQUENCE: 990
```
ugggaacuag gaguggcggc                                         20

<210> SEQ ID NO 991
<211> LENGTH: 20
<212> TYPE: RNA
<213> ORGANISM: Artificial Sequence
<220> FEATURE:
<223> OTHER INFORMATION: synthesized

<400> SEQUENCE: 991
uugccgccac uccuaguucc                                         20

<210> SEQ ID NO 992
<211> LENGTH: 20
<212> TYPE: RNA
<213> ORGANISM: Artificial Sequence
<220> FEATURE:
<223> OTHER INFORMATION: synthesized

<400> SEQUENCE: 992
uugcugccac uccuaguucc                                         20

<210> SEQ ID NO 993
<211> LENGTH: 20
<212> TYPE: RNA
<213> ORGANISM: Artificial Sequence
<220> FEATURE:
<223> OTHER INFORMATION: synthesized

<400> SEQUENCE: 993
aaguacugga agcuggaacu                                         20

<210> SEQ ID NO 994
<211> LENGTH: 20
<212> TYPE: RNA
<213> ORGANISM: Artificial Sequence
<220> FEATURE:
<223> OTHER INFORMATION: synthesized

<400> SEQUENCE: 994
aagugcugga agcuggaacu                                         20

<210> SEQ ID NO 995
<211> LENGTH: 20
<212> TYPE: RNA
<213> ORGANISM: Artificial Sequence
<220> FEATURE:
<223> OTHER INFORMATION: synthesized

<400> SEQUENCE: 995
acuggaagcu ggaacucugg                                         20

<210> SEQ ID NO 996
<211> LENGTH: 20
<212> TYPE: RNA
<213> ORGANISM: Artificial Sequence
<220> FEATURE:
<223> OTHER INFORMATION: synthesized

<400> SEQUENCE: 996
agaguuccag cuuccagcac                                         20

<210> SEQ ID NO 997
<211> LENGTH: 20
<212> TYPE: RNA

```
<213> ORGANISM: Artificial Sequence
<220> FEATURE:
<223> OTHER INFORMATION: synthesized

<400> SEQUENCE: 997
agaguuccag cuuccaguac                                                    20

<210> SEQ ID NO 998
<211> LENGTH: 20
<212> TYPE: RNA
<213> ORGANISM: Artificial Sequence
<220> FEATURE:
<223> OTHER INFORMATION: synthesized

<400> SEQUENCE: 998
agcacuucca gguccagagc                                                    20

<210> SEQ ID NO 999
<211> LENGTH: 20
<212> TYPE: RNA
<213> ORGANISM: Artificial Sequence
<220> FEATURE:
<223> OTHER INFORMATION: synthesized

<400> SEQUENCE: 999
agcuuccagc acuuccaggu                                                    20

<210> SEQ ID NO 1000
<211> LENGTH: 20
<212> TYPE: RNA
<213> ORGANISM: Artificial Sequence
<220> FEATURE:
<223> OTHER INFORMATION: synthesized

<400> SEQUENCE: 1000
agcuuccagu acuuccaggu                                                    20

<210> SEQ ID NO 1001
<211> LENGTH: 20
<212> TYPE: RNA
<213> ORGANISM: Artificial Sequence
<220> FEATURE:
<223> OTHER INFORMATION: synthesized

<400> SEQUENCE: 1001
aguacuucca gguccagagc                                                    20

<210> SEQ ID NO 1002
<211> LENGTH: 20
<212> TYPE: RNA
<213> ORGANISM: Artificial Sequence
<220> FEATURE:
<223> OTHER INFORMATION: synthesized

<400> SEQUENCE: 1002
cacuuccagg uccagagcuc                                                    20

<210> SEQ ID NO 1003
<211> LENGTH: 20
<212> TYPE: RNA
<213> ORGANISM: Artificial Sequence
<220> FEATURE:
<223> OTHER INFORMATION: synthesized

<400> SEQUENCE: 1003
cagaguucca gcuuccagca                                                    20
```

-continued

<210> SEQ ID NO 1004
<211> LENGTH: 20
<212> TYPE: RNA
<213> ORGANISM: Artificial Sequence
<220> FEATURE:
<223> OTHER INFORMATION: synthesized

<400> SEQUENCE: 1004
cagaguucca gcuuccagua                                               20

<210> SEQ ID NO 1005
<211> LENGTH: 20
<212> TYPE: RNA
<213> ORGANISM: Artificial Sequence
<220> FEATURE:
<223> OTHER INFORMATION: synthesized

<400> SEQUENCE: 1005
cagcacuucc agguccagag                                               20

<210> SEQ ID NO 1006
<211> LENGTH: 20
<212> TYPE: RNA
<213> ORGANISM: Artificial Sequence
<220> FEATURE:
<223> OTHER INFORMATION: synthesized

<400> SEQUENCE: 1006
cagcuuccag cacuuccagg                                               20

<210> SEQ ID NO 1007
<211> LENGTH: 20
<212> TYPE: RNA
<213> ORGANISM: Artificial Sequence
<220> FEATURE:
<223> OTHER INFORMATION: synthesized

<400> SEQUENCE: 1007
cagcuuccag uacuuccagg                                               20

<210> SEQ ID NO 1008
<211> LENGTH: 20
<212> TYPE: RNA
<213> ORGANISM: Artificial Sequence
<220> FEATURE:
<223> OTHER INFORMATION: synthesized

<400> SEQUENCE: 1008
caguacuucc agguccagag                                               20

<210> SEQ ID NO 1009
<211> LENGTH: 20
<212> TYPE: RNA
<213> ORGANISM: Artificial Sequence
<220> FEATURE:
<223> OTHER INFORMATION: synthesized

<400> SEQUENCE: 1009
ccagaguucc agcuuccagc                                               20

<210> SEQ ID NO 1010
<211> LENGTH: 20
<212> TYPE: RNA
<213> ORGANISM: Artificial Sequence
<220> FEATURE:

<223> OTHER INFORMATION: synthesized

<400> SEQUENCE: 1010
ccagaguucc agcuuccagu                                            20

<210> SEQ ID NO 1011
<211> LENGTH: 20
<212> TYPE: RNA
<213> ORGANISM: Artificial Sequence
<220> FEATURE:
<223> OTHER INFORMATION: synthesized

<400> SEQUENCE: 1011
ccagcacuuc cagguccaga                                            20

<210> SEQ ID NO 1012
<211> LENGTH: 20
<212> TYPE: RNA
<213> ORGANISM: Artificial Sequence
<220> FEATURE:
<223> OTHER INFORMATION: synthesized

<400> SEQUENCE: 1012
ccagcuucca gcacuuccag                                            20

<210> SEQ ID NO 1013
<211> LENGTH: 20
<212> TYPE: RNA
<213> ORGANISM: Artificial Sequence
<220> FEATURE:
<223> OTHER INFORMATION: synthesized

<400> SEQUENCE: 1013
ccagcuucca guacuuccag                                            20

<210> SEQ ID NO 1014
<211> LENGTH: 20
<212> TYPE: RNA
<213> ORGANISM: Artificial Sequence
<220> FEATURE:
<223> OTHER INFORMATION: synthesized

<400> SEQUENCE: 1014
ccaguacuuc cagguccaga                                            20

<210> SEQ ID NO 1015
<211> LENGTH: 20
<212> TYPE: RNA
<213> ORGANISM: Artificial Sequence
<220> FEATURE:
<223> OTHER INFORMATION: synthesized

<400> SEQUENCE: 1015
ccuggaagua cuggaagcug                                            20

<210> SEQ ID NO 1016
<211> LENGTH: 20
<212> TYPE: RNA
<213> ORGANISM: Artificial Sequence
<220> FEATURE:
<223> OTHER INFORMATION: synthesized

<400> SEQUENCE: 1016
ccuggaagug cuggaagcug                                            20

```
<210> SEQ ID NO 1017
<211> LENGTH: 20
<212> TYPE: RNA
<213> ORGANISM: Artificial Sequence
<220> FEATURE:
<223> OTHER INFORMATION: synthesized

<400> SEQUENCE: 1017
cucuggaccu ggaaguacug                                                  20

<210> SEQ ID NO 1018
<211> LENGTH: 20
<212> TYPE: RNA
<213> ORGANISM: Artificial Sequence
<220> FEATURE:
<223> OTHER INFORMATION: synthesized

<400> SEQUENCE: 1018
cucuggaccu ggaagugcug                                                  20

<210> SEQ ID NO 1019
<211> LENGTH: 20
<212> TYPE: RNA
<213> ORGANISM: Artificial Sequence
<220> FEATURE:
<223> OTHER INFORMATION: synthesized

<400> SEQUENCE: 1019
cuggaaguac uggaagcugg                                                  20

<210> SEQ ID NO 1020
<211> LENGTH: 20
<212> TYPE: RNA
<213> ORGANISM: Artificial Sequence
<220> FEATURE:
<223> OTHER INFORMATION: synthesized

<400> SEQUENCE: 1020
cuggaagugc uggaagcugg                                                  20

<210> SEQ ID NO 1021
<211> LENGTH: 20
<212> TYPE: RNA
<213> ORGANISM: Artificial Sequence
<220> FEATURE:
<223> OTHER INFORMATION: synthesized

<400> SEQUENCE: 1021
cuggaccugg aaguacugga                                                  20

<210> SEQ ID NO 1022
<211> LENGTH: 20
<212> TYPE: RNA
<213> ORGANISM: Artificial Sequence
<220> FEATURE:
<223> OTHER INFORMATION: synthesized

<400> SEQUENCE: 1022
cuggaccugg aagugcugga                                                  20

<210> SEQ ID NO 1023
<211> LENGTH: 20
<212> TYPE: RNA
<213> ORGANISM: Artificial Sequence
<220> FEATURE:
<223> OTHER INFORMATION: synthesized
```

```
<400> SEQUENCE: 1023
gaaguacugg aagcuggaac                                              20

<210> SEQ ID NO 1024
<211> LENGTH: 20
<212> TYPE: RNA
<213> ORGANISM: Artificial Sequence
<220> FEATURE:
<223> OTHER INFORMATION: synthesized

<400> SEQUENCE: 1024
gaagugcugg aagcuggaac                                              20

<210> SEQ ID NO 1025
<211> LENGTH: 20
<212> TYPE: RNA
<213> ORGANISM: Artificial Sequence
<220> FEATURE:
<223> OTHER INFORMATION: synthesized

<400> SEQUENCE: 1025
gagcucugga ccuggaagua                                              20

<210> SEQ ID NO 1026
<211> LENGTH: 20
<212> TYPE: RNA
<213> ORGANISM: Artificial Sequence
<220> FEATURE:
<223> OTHER INFORMATION: synthesized

<400> SEQUENCE: 1026
gagcucugga ccuggaagug                                              20

<210> SEQ ID NO 1027
<211> LENGTH: 20
<212> TYPE: RNA
<213> ORGANISM: Artificial Sequence
<220> FEATURE:
<223> OTHER INFORMATION: synthesized

<400> SEQUENCE: 1027
gaguuccagc uuccagcacu                                              20

<210> SEQ ID NO 1028
<211> LENGTH: 20
<212> TYPE: RNA
<213> ORGANISM: Artificial Sequence
<220> FEATURE:
<223> OTHER INFORMATION: synthesized

<400> SEQUENCE: 1028
gaguuccagc uuccaguacu                                              20

<210> SEQ ID NO 1029
<211> LENGTH: 20
<212> TYPE: RNA
<213> ORGANISM: Artificial Sequence
<220> FEATURE:
<223> OTHER INFORMATION: synthesized

<400> SEQUENCE: 1029
gcacuuccag guccagagcu                                              20

<210> SEQ ID NO 1030
<211> LENGTH: 20
```

```
<212> TYPE: RNA
<213> ORGANISM: Artificial Sequence
<220> FEATURE:
<223> OTHER INFORMATION: synthesized

<400> SEQUENCE: 1030
gcuggaagcu ggaacucugg                                               20

<210> SEQ ID NO 1031
<211> LENGTH: 20
<212> TYPE: RNA
<213> ORGANISM: Artificial Sequence
<220> FEATURE:
<223> OTHER INFORMATION: synthesized

<400> SEQUENCE: 1031
gcuuccagca cuuccagguc                                               20

<210> SEQ ID NO 1032
<211> LENGTH: 20
<212> TYPE: RNA
<213> ORGANISM: Artificial Sequence
<220> FEATURE:
<223> OTHER INFORMATION: synthesized

<400> SEQUENCE: 1032
gcuuccagua cuuccagguc                                               20

<210> SEQ ID NO 1033
<211> LENGTH: 20
<212> TYPE: RNA
<213> ORGANISM: Artificial Sequence
<220> FEATURE:
<223> OTHER INFORMATION: synthesized

<400> SEQUENCE: 1033
ggaaguacug gaagcuggaa                                               20

<210> SEQ ID NO 1034
<211> LENGTH: 20
<212> TYPE: RNA
<213> ORGANISM: Artificial Sequence
<220> FEATURE:
<223> OTHER INFORMATION: synthesized

<400> SEQUENCE: 1034
ggaagugcug gaagcuggaa                                               20

<210> SEQ ID NO 1035
<211> LENGTH: 20
<212> TYPE: RNA
<213> ORGANISM: Artificial Sequence
<220> FEATURE:
<223> OTHER INFORMATION: synthesized

<400> SEQUENCE: 1035
ggaccuggaa guacuggaag                                               20

<210> SEQ ID NO 1036
<211> LENGTH: 20
<212> TYPE: RNA
<213> ORGANISM: Artificial Sequence
<220> FEATURE:
<223> OTHER INFORMATION: synthesized

<400> SEQUENCE: 1036
```

-continued

```
ggaccuggaa gugcuggaag                                              20

<210> SEQ ID NO 1037
<211> LENGTH: 20
<212> TYPE: RNA
<213> ORGANISM: Artificial Sequence
<220> FEATURE:
<223> OTHER INFORMATION: synthesized

<400> SEQUENCE: 1037
guacuuccag guccagagcu                                              20

<210> SEQ ID NO 1038
<211> LENGTH: 20
<212> TYPE: RNA
<213> ORGANISM: Artificial Sequence
<220> FEATURE:
<223> OTHER INFORMATION: synthesized

<400> SEQUENCE: 1038
guuccagcuu ccagcacuuc                                              20

<210> SEQ ID NO 1039
<211> LENGTH: 20
<212> TYPE: RNA
<213> ORGANISM: Artificial Sequence
<220> FEATURE:
<223> OTHER INFORMATION: synthesized

<400> SEQUENCE: 1039
guuccagcuu ccaguacuuc                                              20

<210> SEQ ID NO 1040
<211> LENGTH: 20
<212> TYPE: RNA
<213> ORGANISM: Artificial Sequence
<220> FEATURE:
<223> OTHER INFORMATION: synthesized

<400> SEQUENCE: 1040
uacuuccagg uccagagcuc                                              20

<210> SEQ ID NO 1041
<211> LENGTH: 20
<212> TYPE: RNA
<213> ORGANISM: Artificial Sequence
<220> FEATURE:
<223> OTHER INFORMATION: synthesized

<400> SEQUENCE: 1041
uccagcacuu ccagguccag                                              20

<210> SEQ ID NO 1042
<211> LENGTH: 20
<212> TYPE: RNA
<213> ORGANISM: Artificial Sequence
<220> FEATURE:
<223> OTHER INFORMATION: synthesized

<400> SEQUENCE: 1042
uccagcuucc agcacuucca                                              20

<210> SEQ ID NO 1043
<211> LENGTH: 20
<212> TYPE: RNA
<213> ORGANISM: Artificial Sequence
```

-continued

<220> FEATURE:
<223> OTHER INFORMATION: synthesized

<400> SEQUENCE: 1043
uccagcuucc aguacuucca                                          20

<210> SEQ ID NO 1044
<211> LENGTH: 20
<212> TYPE: RNA
<213> ORGANISM: Artificial Sequence
<220> FEATURE:
<223> OTHER INFORMATION: synthesized

<400> SEQUENCE: 1044
uccaguacuu ccagguccag                                          20

<210> SEQ ID NO 1045
<211> LENGTH: 20
<212> TYPE: RNA
<213> ORGANISM: Artificial Sequence
<220> FEATURE:
<223> OTHER INFORMATION: synthesized

<400> SEQUENCE: 1045
ucuggaccug gaaguacugg                                          20

<210> SEQ ID NO 1046
<211> LENGTH: 20
<212> TYPE: RNA
<213> ORGANISM: Artificial Sequence
<220> FEATURE:
<223> OTHER INFORMATION: synthesized

<400> SEQUENCE: 1046
ucuggaccug gaagugcugg                                          20

<210> SEQ ID NO 1047
<211> LENGTH: 20
<212> TYPE: RNA
<213> ORGANISM: Artificial Sequence
<220> FEATURE:
<223> OTHER INFORMATION: synthesized

<400> SEQUENCE: 1047
uggaaguacu ggaagcugga                                          20

<210> SEQ ID NO 1048
<211> LENGTH: 20
<212> TYPE: RNA
<213> ORGANISM: Artificial Sequence
<220> FEATURE:
<223> OTHER INFORMATION: synthesized

<400> SEQUENCE: 1048
uggaagugcu ggaagcugga                                          20

<210> SEQ ID NO 1049
<211> LENGTH: 20
<212> TYPE: RNA
<213> ORGANISM: Artificial Sequence
<220> FEATURE:
<223> OTHER INFORMATION: synthesized

<400> SEQUENCE: 1049
uggaccugga aguacuggaa                                          20

```
<210> SEQ ID NO 1050
<211> LENGTH: 20
<212> TYPE: RNA
<213> ORGANISM: Artificial Sequence
<220> FEATURE:
<223> OTHER INFORMATION: synthesized

<400> SEQUENCE: 1050
uggaccugga agugcuggaa                                                    20

<210> SEQ ID NO 1051
<211> LENGTH: 20
<212> TYPE: RNA
<213> ORGANISM: Artificial Sequence
<220> FEATURE:
<223> OTHER INFORMATION: synthesized

<400> SEQUENCE: 1051
uuccagcacu uccaggucca                                                    20

<210> SEQ ID NO 1052
<211> LENGTH: 20
<212> TYPE: RNA
<213> ORGANISM: Artificial Sequence
<220> FEATURE:
<223> OTHER INFORMATION: synthesized

<400> SEQUENCE: 1052
uuccaguacu uccaggucca                                                    20

<210> SEQ ID NO 1053
<211> LENGTH: 20
<212> TYPE: RNA
<213> ORGANISM: Artificial Sequence
<220> FEATURE:
<223> OTHER INFORMATION: synthesized

<400> SEQUENCE: 1053
aaagcuuccu gaggccaaga                                                    20

<210> SEQ ID NO 1054
<211> LENGTH: 20
<212> TYPE: RNA
<213> ORGANISM: Artificial Sequence
<220> FEATURE:
<223> OTHER INFORMATION: synthesized

<400> SEQUENCE: 1054
aaagcuuccu gaggccaagg                                                    20

<210> SEQ ID NO 1055
<211> LENGTH: 20
<212> TYPE: RNA
<213> ORGANISM: Artificial Sequence
<220> FEATURE:
<223> OTHER INFORMATION: synthesized

<400> SEQUENCE: 1055
aagacacaag gacuggcaca                                                    20

<210> SEQ ID NO 1056
<211> LENGTH: 20
<212> TYPE: RNA
<213> ORGANISM: Artificial Sequence
<220> FEATURE:
<223> OTHER INFORMATION: synthesized
```

<400> SEQUENCE: 1056
aagcuuccug aggccaagac                                              20

<210> SEQ ID NO 1057
<211> LENGTH: 20
<212> TYPE: RNA
<213> ORGANISM: Artificial Sequence
<220> FEATURE:
<223> OTHER INFORMATION: synthesized

<400> SEQUENCE: 1057
aagcuuccug aggccaaggc                                              20

<210> SEQ ID NO 1058
<211> LENGTH: 20
<212> TYPE: RNA
<213> ORGANISM: Artificial Sequence
<220> FEATURE:
<223> OTHER INFORMATION: synthesized

<400> SEQUENCE: 1058
aaggcacaag gacuggcaca                                              20

<210> SEQ ID NO 1059
<211> LENGTH: 20
<212> TYPE: RNA
<213> ORGANISM: Artificial Sequence
<220> FEATURE:
<223> OTHER INFORMATION: synthesized

<400> SEQUENCE: 1059
acacaaggac uggcacaaau                                              20

<210> SEQ ID NO 1060
<211> LENGTH: 20
<212> TYPE: RNA
<213> ORGANISM: Artificial Sequence
<220> FEATURE:
<223> OTHER INFORMATION: synthesized

<400> SEQUENCE: 1060
agacacaagg acuggcacaa                                              20

<210> SEQ ID NO 1061
<211> LENGTH: 20
<212> TYPE: RNA
<213> ORGANISM: Artificial Sequence
<220> FEATURE:
<223> OTHER INFORMATION: synthesized

<400> SEQUENCE: 1061
agcuuccuga ggccaagaca                                              20

<210> SEQ ID NO 1062
<211> LENGTH: 20
<212> TYPE: RNA
<213> ORGANISM: Artificial Sequence
<220> FEATURE:
<223> OTHER INFORMATION: synthesized

<400> SEQUENCE: 1062
agcuuccuga ggccaaggca                                              20

<210> SEQ ID NO 1063

```
<211> LENGTH: 20
<212> TYPE: RNA
<213> ORGANISM: Artificial Sequence
<220> FEATURE:
<223> OTHER INFORMATION: synthesized

<400> SEQUENCE: 1063
aggcacaagg acuggcacaa                                               20

<210> SEQ ID NO 1064
<211> LENGTH: 20
<212> TYPE: RNA
<213> ORGANISM: Artificial Sequence
<220> FEATURE:
<223> OTHER INFORMATION: synthesized

<400> SEQUENCE: 1064
aggccaagac acaaggacug                                               20

<210> SEQ ID NO 1065
<211> LENGTH: 20
<212> TYPE: RNA
<213> ORGANISM: Artificial Sequence
<220> FEATURE:
<223> OTHER INFORMATION: synthesized

<400> SEQUENCE: 1065
aggccaaggc acaaggacug                                               20

<210> SEQ ID NO 1066
<211> LENGTH: 20
<212> TYPE: RNA
<213> ORGANISM: Artificial Sequence
<220> FEATURE:
<223> OTHER INFORMATION: synthesized

<400> SEQUENCE: 1066
caagacacaa ggacuggcac                                               20

<210> SEQ ID NO 1067
<211> LENGTH: 20
<212> TYPE: RNA
<213> ORGANISM: Artificial Sequence
<220> FEATURE:
<223> OTHER INFORMATION: synthesized

<400> SEQUENCE: 1067
caaggcacaa ggacuggcac                                               20

<210> SEQ ID NO 1068
<211> LENGTH: 20
<212> TYPE: RNA
<213> ORGANISM: Artificial Sequence
<220> FEATURE:
<223> OTHER INFORMATION: synthesized

<400> SEQUENCE: 1068
caguccuugu gccuuggccu                                               20

<210> SEQ ID NO 1069
<211> LENGTH: 20
<212> TYPE: RNA
<213> ORGANISM: Artificial Sequence
<220> FEATURE:
<223> OTHER INFORMATION: synthesized

<400> SEQUENCE: 1069
```
caguccuugu gucuuggccu                                        20

<210> SEQ ID NO 1070
<211> LENGTH: 20
<212> TYPE: RNA
<213> ORGANISM: Artificial Sequence
<220> FEATURE:
<223> OTHER INFORMATION: synthesized

<400> SEQUENCE: 1070
ccaagacaca aggacuggca                                        20

<210> SEQ ID NO 1071
<211> LENGTH: 20
<212> TYPE: RNA
<213> ORGANISM: Artificial Sequence
<220> FEATURE:
<223> OTHER INFORMATION: synthesized

<400> SEQUENCE: 1071
ccaaggcaca aggacuggca                                        20

<210> SEQ ID NO 1072
<211> LENGTH: 20
<212> TYPE: RNA
<213> ORGANISM: Artificial Sequence
<220> FEATURE:
<223> OTHER INFORMATION: synthesized

<400> SEQUENCE: 1072
ccaguccuug ugccuuggcc                                        20

<210> SEQ ID NO 1073
<211> LENGTH: 20
<212> TYPE: RNA
<213> ORGANISM: Artificial Sequence
<220> FEATURE:
<223> OTHER INFORMATION: synthesized

<400> SEQUENCE: 1073
ccaguccuug ugucuuggcc                                        20

<210> SEQ ID NO 1074
<211> LENGTH: 20
<212> TYPE: RNA
<213> ORGANISM: Artificial Sequence
<220> FEATURE:
<223> OTHER INFORMATION: synthesized

<400> SEQUENCE: 1074
ccuuggccuc aggaagcuuu                                        20

<210> SEQ ID NO 1075
<211> LENGTH: 20
<212> TYPE: RNA
<213> ORGANISM: Artificial Sequence
<220> FEATURE:
<223> OTHER INFORMATION: synthesized

<400> SEQUENCE: 1075
ccuugugccu uggccucagg                                        20

<210> SEQ ID NO 1076
<211> LENGTH: 20
<212> TYPE: RNA

```
<213> ORGANISM: Artificial Sequence
<220> FEATURE:
<223> OTHER INFORMATION: synthesized

<400> SEQUENCE: 1076
ccuugugucu uggccucagg                                               20

<210> SEQ ID NO 1077
<211> LENGTH: 20
<212> TYPE: RNA
<213> ORGANISM: Artificial Sequence
<220> FEATURE:
<223> OTHER INFORMATION: synthesized

<400> SEQUENCE: 1077
cugaggccaa gacacaagga                                               20

<210> SEQ ID NO 1078
<211> LENGTH: 20
<212> TYPE: RNA
<213> ORGANISM: Artificial Sequence
<220> FEATURE:
<223> OTHER INFORMATION: synthesized

<400> SEQUENCE: 1078
cugaggccaa ggcacaagga                                               20

<210> SEQ ID NO 1079
<211> LENGTH: 20
<212> TYPE: RNA
<213> ORGANISM: Artificial Sequence
<220> FEATURE:
<223> OTHER INFORMATION: synthesized

<400> SEQUENCE: 1079
cuugugccuu ggccucagga                                               20

<210> SEQ ID NO 1080
<211> LENGTH: 20
<212> TYPE: RNA
<213> ORGANISM: Artificial Sequence
<220> FEATURE:
<223> OTHER INFORMATION: synthesized

<400> SEQUENCE: 1080
cuugugucuu ggccucagga                                               20

<210> SEQ ID NO 1081
<211> LENGTH: 20
<212> TYPE: RNA
<213> ORGANISM: Artificial Sequence
<220> FEATURE:
<223> OTHER INFORMATION: synthesized

<400> SEQUENCE: 1081
gacacaagga cuggcacaaa                                               20

<210> SEQ ID NO 1082
<211> LENGTH: 20
<212> TYPE: RNA
<213> ORGANISM: Artificial Sequence
<220> FEATURE:
<223> OTHER INFORMATION: synthesized

<400> SEQUENCE: 1082
gaggccaaga cacaaggacu                                               20
```

<210> SEQ ID NO 1083
<211> LENGTH: 20
<212> TYPE: RNA
<213> ORGANISM: Artificial Sequence
<220> FEATURE:
<223> OTHER INFORMATION: synthesized

<400> SEQUENCE: 1083
gaggccaagg cacaaggacu                                          20

<210> SEQ ID NO 1084
<211> LENGTH: 20
<212> TYPE: RNA
<213> ORGANISM: Artificial Sequence
<220> FEATURE:
<223> OTHER INFORMATION: synthesized

<400> SEQUENCE: 1084
gcacaaggac uggcacaaau                                          20

<210> SEQ ID NO 1085
<211> LENGTH: 20
<212> TYPE: RNA
<213> ORGANISM: Artificial Sequence
<220> FEATURE:
<223> OTHER INFORMATION: synthesized

<400> SEQUENCE: 1085
gccaagacac aaggacuggc                                          20

<210> SEQ ID NO 1086
<211> LENGTH: 20
<212> TYPE: RNA
<213> ORGANISM: Artificial Sequence
<220> FEATURE:
<223> OTHER INFORMATION: synthesized

<400> SEQUENCE: 1086
gccaaggcac aaggacuggc                                          20

<210> SEQ ID NO 1087
<211> LENGTH: 20
<212> TYPE: RNA
<213> ORGANISM: Artificial Sequence
<220> FEATURE:
<223> OTHER INFORMATION: synthesized

<400> SEQUENCE: 1087
gccaguccuu gugccuuggc                                          20

<210> SEQ ID NO 1088
<211> LENGTH: 20
<212> TYPE: RNA
<213> ORGANISM: Artificial Sequence
<220> FEATURE:
<223> OTHER INFORMATION: synthesized

<400> SEQUENCE: 1088
gccaguccuu gugucuuggc                                          20

<210> SEQ ID NO 1089
<211> LENGTH: 20
<212> TYPE: RNA
<213> ORGANISM: Artificial Sequence
<220> FEATURE:

```
<223> OTHER INFORMATION: synthesized

<400> SEQUENCE: 1089
gcuuccugag gccaagacac                                              20

<210> SEQ ID NO 1090
<211> LENGTH: 20
<212> TYPE: RNA
<213> ORGANISM: Artificial Sequence
<220> FEATURE:
<223> OTHER INFORMATION: synthesized

<400> SEQUENCE: 1090
gcuuccugag gccaaggcac                                              20

<210> SEQ ID NO 1091
<211> LENGTH: 20
<212> TYPE: RNA
<213> ORGANISM: Artificial Sequence
<220> FEATURE:
<223> OTHER INFORMATION: synthesized

<400> SEQUENCE: 1091
ggcacaagga cuggcacaaa                                              20

<210> SEQ ID NO 1092
<211> LENGTH: 20
<212> TYPE: RNA
<213> ORGANISM: Artificial Sequence
<220> FEATURE:
<223> OTHER INFORMATION: synthesized

<400> SEQUENCE: 1092
ggccaagaca caaggacugg                                              20

<210> SEQ ID NO 1093
<211> LENGTH: 20
<212> TYPE: RNA
<213> ORGANISM: Artificial Sequence
<220> FEATURE:
<223> OTHER INFORMATION: synthesized

<400> SEQUENCE: 1093
ggccaaggca caaggacugg                                              20

<210> SEQ ID NO 1094
<211> LENGTH: 20
<212> TYPE: RNA
<213> ORGANISM: Artificial Sequence
<220> FEATURE:
<223> OTHER INFORMATION: synthesized

<400> SEQUENCE: 1094
gugccagucc uugugccuug                                              20

<210> SEQ ID NO 1095
<211> LENGTH: 20
<212> TYPE: RNA
<213> ORGANISM: Artificial Sequence
<220> FEATURE:
<223> OTHER INFORMATION: synthesized

<400> SEQUENCE: 1095
gugccagucc uugugucuug                                              20
```

<210> SEQ ID NO 1096
<211> LENGTH: 20
<212> TYPE: RNA
<213> ORGANISM: Artificial Sequence
<220> FEATURE:
<223> OTHER INFORMATION: synthesized

<400> SEQUENCE: 1096
gugccuuggc cucaggaagc                                                 20

<210> SEQ ID NO 1097
<211> LENGTH: 20
<212> TYPE: RNA
<213> ORGANISM: Artificial Sequence
<220> FEATURE:
<223> OTHER INFORMATION: synthesized

<400> SEQUENCE: 1097
gugucuuggc cucaggaagc                                                 20

<210> SEQ ID NO 1098
<211> LENGTH: 20
<212> TYPE: RNA
<213> ORGANISM: Artificial Sequence
<220> FEATURE:
<223> OTHER INFORMATION: synthesized

<400> SEQUENCE: 1098
uccugaggcc aagacacaag                                                 20

<210> SEQ ID NO 1099
<211> LENGTH: 20
<212> TYPE: RNA
<213> ORGANISM: Artificial Sequence
<220> FEATURE:
<223> OTHER INFORMATION: synthesized

<400> SEQUENCE: 1099
uccugaggcc aaggcacaag                                                 20

<210> SEQ ID NO 1100
<211> LENGTH: 20
<212> TYPE: RNA
<213> ORGANISM: Artificial Sequence
<220> FEATURE:
<223> OTHER INFORMATION: synthesized

<400> SEQUENCE: 1100
uccuugugcc uuggccucag                                                 20

<210> SEQ ID NO 1101
<211> LENGTH: 20
<212> TYPE: RNA
<213> ORGANISM: Artificial Sequence
<220> FEATURE:
<223> OTHER INFORMATION: synthesized

<400> SEQUENCE: 1101
uccuuguguc uuggccucag                                                 20

<210> SEQ ID NO 1102
<211> LENGTH: 20
<212> TYPE: RNA
<213> ORGANISM: Artificial Sequence
<220> FEATURE:
<223> OTHER INFORMATION: synthesized

```
<400> SEQUENCE: 1102
ucuuggccuc aggaagcuuu                                              20

<210> SEQ ID NO 1103
<211> LENGTH: 20
<212> TYPE: RNA
<213> ORGANISM: Artificial Sequence
<220> FEATURE:
<223> OTHER INFORMATION: synthesized

<400> SEQUENCE: 1103
ugccaguccu ugugccuugg                                              20

<210> SEQ ID NO 1104
<211> LENGTH: 20
<212> TYPE: RNA
<213> ORGANISM: Artificial Sequence
<220> FEATURE:
<223> OTHER INFORMATION: synthesized

<400> SEQUENCE: 1104
ugccaguccu ugugucuugg                                              20

<210> SEQ ID NO 1105
<211> LENGTH: 20
<212> TYPE: RNA
<213> ORGANISM: Artificial Sequence
<220> FEATURE:
<223> OTHER INFORMATION: synthesized

<400> SEQUENCE: 1105
ugccuuggcc ucaggaagcu                                              20

<210> SEQ ID NO 1106
<211> LENGTH: 20
<212> TYPE: RNA
<213> ORGANISM: Artificial Sequence
<220> FEATURE:
<223> OTHER INFORMATION: synthesized

<400> SEQUENCE: 1106
ugucuuggcc ucaggaagcu                                              20

<210> SEQ ID NO 1107
<211> LENGTH: 20
<212> TYPE: RNA
<213> ORGANISM: Artificial Sequence
<220> FEATURE:
<223> OTHER INFORMATION: synthesized

<400> SEQUENCE: 1107
ugugccaguc cuugugccuu                                              20

<210> SEQ ID NO 1108
<211> LENGTH: 20
<212> TYPE: RNA
<213> ORGANISM: Artificial Sequence
<220> FEATURE:
<223> OTHER INFORMATION: synthesized

<400> SEQUENCE: 1108
ugugccaguc cuugugucuu                                              20

<210> SEQ ID NO 1109
<211> LENGTH: 20
```

```
<212> TYPE: RNA
<213> ORGANISM: Artificial Sequence
<220> FEATURE:
<223> OTHER INFORMATION: synthesized

<400> SEQUENCE: 1109
ugugccuugg ccucaggaag                                               20

<210> SEQ ID NO 1110
<211> LENGTH: 20
<212> TYPE: RNA
<213> ORGANISM: Artificial Sequence
<220> FEATURE:
<223> OTHER INFORMATION: synthesized

<400> SEQUENCE: 1110
ugugucuugg ccucaggaag                                               20

<210> SEQ ID NO 1111
<211> LENGTH: 20
<212> TYPE: RNA
<213> ORGANISM: Artificial Sequence
<220> FEATURE:
<223> OTHER INFORMATION: synthesized

<400> SEQUENCE: 1111
uugugccuug gccucaggaa                                               20

<210> SEQ ID NO 1112
<211> LENGTH: 20
<212> TYPE: RNA
<213> ORGANISM: Artificial Sequence
<220> FEATURE:
<223> OTHER INFORMATION: synthesized

<400> SEQUENCE: 1112
uugugucuug gccucaggaa                                               20

<210> SEQ ID NO 1113
<211> LENGTH: 20
<212> TYPE: RNA
<213> ORGANISM: Artificial Sequence
<220> FEATURE:
<223> OTHER INFORMATION: synthesized

<400> SEQUENCE: 1113
uuugugccag uccuugugcc                                               20

<210> SEQ ID NO 1114
<211> LENGTH: 20
<212> TYPE: RNA
<213> ORGANISM: Artificial Sequence
<220> FEATURE:
<223> OTHER INFORMATION: synthesized

<400> SEQUENCE: 1114
uuugugccag uccuuguguc                                               20

<210> SEQ ID NO 1115
<211> LENGTH: 20
<212> TYPE: RNA
<213> ORGANISM: Artificial Sequence
<220> FEATURE:
<223> OTHER INFORMATION: synthesized

<400> SEQUENCE: 1115
```

```
aacaaauaaa gaaaaggaac                                              20

<210> SEQ ID NO 1116
<211> LENGTH: 20
<212> TYPE: RNA
<213> ORGANISM: Artificial Sequence
<220> FEATURE:
<223> OTHER INFORMATION: synthesized

<400> SEQUENCE: 1116
aauaguuacc uacauaacaa                                              20

<210> SEQ ID NO 1117
<211> LENGTH: 20
<212> TYPE: RNA
<213> ORGANISM: Artificial Sequence
<220> FEATURE:
<223> OTHER INFORMATION: synthesized

<400> SEQUENCE: 1117
aauaguuacc uacauagcaa                                              20

<210> SEQ ID NO 1118
<211> LENGTH: 20
<212> TYPE: RNA
<213> ORGANISM: Artificial Sequence
<220> FEATURE:
<223> OTHER INFORMATION: synthesized

<400> SEQUENCE: 1118
acaaauaaag aaaaggaacc                                              20

<210> SEQ ID NO 1119
<211> LENGTH: 20
<212> TYPE: RNA
<213> ORGANISM: Artificial Sequence
<220> FEATURE:
<223> OTHER INFORMATION: synthesized

<400> SEQUENCE: 1119
acauaacaaa uaaagaaaag                                              20

<210> SEQ ID NO 1120
<211> LENGTH: 20
<212> TYPE: RNA
<213> ORGANISM: Artificial Sequence
<220> FEATURE:
<223> OTHER INFORMATION: synthesized

<400> SEQUENCE: 1120
acauagcaaa uaaagaaaag                                              20

<210> SEQ ID NO 1121
<211> LENGTH: 20
<212> TYPE: RNA
<213> ORGANISM: Artificial Sequence
<220> FEATURE:
<223> OTHER INFORMATION: synthesized

<400> SEQUENCE: 1121
accuacauaa caaauaaaga                                              20

<210> SEQ ID NO 1122
<211> LENGTH: 20
<212> TYPE: RNA
<213> ORGANISM: Artificial Sequence
```

```
<220> FEATURE:
<223> OTHER INFORMATION: synthesized

<400> SEQUENCE: 1122
accuacauag caaauaaaga                                               20

<210> SEQ ID NO 1123
<211> LENGTH: 20
<212> TYPE: RNA
<213> ORGANISM: Artificial Sequence
<220> FEATURE:
<223> OTHER INFORMATION: synthesized

<400> SEQUENCE: 1123
agcaaauaaa gaaaggaac                                                20

<210> SEQ ID NO 1124
<211> LENGTH: 20
<212> TYPE: RNA
<213> ORGANISM: Artificial Sequence
<220> FEATURE:
<223> OTHER INFORMATION: synthesized

<400> SEQUENCE: 1124
aguuaccuac auaacaaaua                                               20

<210> SEQ ID NO 1125
<211> LENGTH: 20
<212> TYPE: RNA
<213> ORGANISM: Artificial Sequence
<220> FEATURE:
<223> OTHER INFORMATION: synthesized

<400> SEQUENCE: 1125
aguuaccuac auagcaaaua                                               20

<210> SEQ ID NO 1126
<211> LENGTH: 20
<212> TYPE: RNA
<213> ORGANISM: Artificial Sequence
<220> FEATURE:
<223> OTHER INFORMATION: synthesized

<400> SEQUENCE: 1126
auaacaaaua aagaaaagga                                               20

<210> SEQ ID NO 1127
<211> LENGTH: 20
<212> TYPE: RNA
<213> ORGANISM: Artificial Sequence
<220> FEATURE:
<223> OTHER INFORMATION: synthesized

<400> SEQUENCE: 1127
auagcaaaua aagaaaagga                                               20

<210> SEQ ID NO 1128
<211> LENGTH: 20
<212> TYPE: RNA
<213> ORGANISM: Artificial Sequence
<220> FEATURE:
<223> OTHER INFORMATION: synthesized

<400> SEQUENCE: 1128
auaguuaccu acauaacaaa                                               20
```

```
<210> SEQ ID NO 1129
<211> LENGTH: 20
<212> TYPE: RNA
<213> ORGANISM: Artificial Sequence
<220> FEATURE:
<223> OTHER INFORMATION: synthesized

<400> SEQUENCE: 1129
auaguuaccu acauagcaaa                                                   20

<210> SEQ ID NO 1130
<211> LENGTH: 20
<212> TYPE: RNA
<213> ORGANISM: Artificial Sequence
<220> FEATURE:
<223> OTHER INFORMATION: synthesized

<400> SEQUENCE: 1130
auuugcuaug uagguaacua                                                   20

<210> SEQ ID NO 1131
<211> LENGTH: 20
<212> TYPE: RNA
<213> ORGANISM: Artificial Sequence
<220> FEATURE:
<223> OTHER INFORMATION: synthesized

<400> SEQUENCE: 1131
auuuguuaug uagguaacua                                                   20

<210> SEQ ID NO 1132
<211> LENGTH: 20
<212> TYPE: RNA
<213> ORGANISM: Artificial Sequence
<220> FEATURE:
<223> OTHER INFORMATION: synthesized

<400> SEQUENCE: 1132
cauaacaaau aaagaaaagg                                                   20

<210> SEQ ID NO 1133
<211> LENGTH: 20
<212> TYPE: RNA
<213> ORGANISM: Artificial Sequence
<220> FEATURE:
<223> OTHER INFORMATION: synthesized

<400> SEQUENCE: 1133
cauagcaaau aaagaaaagg                                                   20

<210> SEQ ID NO 1134
<211> LENGTH: 20
<212> TYPE: RNA
<213> ORGANISM: Artificial Sequence
<220> FEATURE:
<223> OTHER INFORMATION: synthesized

<400> SEQUENCE: 1134
ccuacauaac aaauaaagaa                                                   20

<210> SEQ ID NO 1135
<211> LENGTH: 20
<212> TYPE: RNA
<213> ORGANISM: Artificial Sequence
<220> FEATURE:
<223> OTHER INFORMATION: synthesized
```

<400> SEQUENCE: 1135
ccuacauagc aaauaaagaa					20

<210> SEQ ID NO 1136
<211> LENGTH: 20
<212> TYPE: RNA
<213> ORGANISM: Artificial Sequence
<220> FEATURE:
<223> OTHER INFORMATION: synthesized

<400> SEQUENCE: 1136
ccuuuucuuu auuugcuaug					20

<210> SEQ ID NO 1137
<211> LENGTH: 20
<212> TYPE: RNA
<213> ORGANISM: Artificial Sequence
<220> FEATURE:
<223> OTHER INFORMATION: synthesized

<400> SEQUENCE: 1137
ccuuuucuuu auuuguuaug					20

<210> SEQ ID NO 1138
<211> LENGTH: 20
<212> TYPE: RNA
<213> ORGANISM: Artificial Sequence
<220> FEATURE:
<223> OTHER INFORMATION: synthesized

<400> SEQUENCE: 1138
cuauguaggu aacuauucaa					20

<210> SEQ ID NO 1139
<211> LENGTH: 20
<212> TYPE: RNA
<213> ORGANISM: Artificial Sequence
<220> FEATURE:
<223> OTHER INFORMATION: synthesized

<400> SEQUENCE: 1139
cuuuauuugc uauguaggua					20

<210> SEQ ID NO 1140
<211> LENGTH: 20
<212> TYPE: RNA
<213> ORGANISM: Artificial Sequence
<220> FEATURE:
<223> OTHER INFORMATION: synthesized

<400> SEQUENCE: 1140
cuuuauuugu uauguaggua					20

<210> SEQ ID NO 1141
<211> LENGTH: 20
<212> TYPE: RNA
<213> ORGANISM: Artificial Sequence
<220> FEATURE:
<223> OTHER INFORMATION: synthesized

<400> SEQUENCE: 1141
gaauaguuac cuacauaaca					20

<210> SEQ ID NO 1142

```
<211> LENGTH: 20
<212> TYPE: RNA
<213> ORGANISM: Artificial Sequence
<220> FEATURE:
<223> OTHER INFORMATION: synthesized

<400> SEQUENCE: 1142
gaauaguuac cuacauagca                                              20

<210> SEQ ID NO 1143
<211> LENGTH: 20
<212> TYPE: RNA
<213> ORGANISM: Artificial Sequence
<220> FEATURE:
<223> OTHER INFORMATION: synthesized

<400> SEQUENCE: 1143
gcaaauaaag aaaaggaacc                                              20

<210> SEQ ID NO 1144
<211> LENGTH: 20
<212> TYPE: RNA
<213> ORGANISM: Artificial Sequence
<220> FEATURE:
<223> OTHER INFORMATION: synthesized

<400> SEQUENCE: 1144
gcuauguagg uaacuauuca                                              20

<210> SEQ ID NO 1145
<211> LENGTH: 20
<212> TYPE: RNA
<213> ORGANISM: Artificial Sequence
<220> FEATURE:
<223> OTHER INFORMATION: synthesized

<400> SEQUENCE: 1145
gguuccuuuu cuuuauuugc                                              20

<210> SEQ ID NO 1146
<211> LENGTH: 20
<212> TYPE: RNA
<213> ORGANISM: Artificial Sequence
<220> FEATURE:
<223> OTHER INFORMATION: synthesized

<400> SEQUENCE: 1146
gguuccuuuu cuuuauuugu                                              20

<210> SEQ ID NO 1147
<211> LENGTH: 20
<212> TYPE: RNA
<213> ORGANISM: Artificial Sequence
<220> FEATURE:
<223> OTHER INFORMATION: synthesized

<400> SEQUENCE: 1147
guuauguagg uaacuauuca                                              20

<210> SEQ ID NO 1148
<211> LENGTH: 20
<212> TYPE: RNA
<213> ORGANISM: Artificial Sequence
<220> FEATURE:
<223> OTHER INFORMATION: synthesized

<400> SEQUENCE: 1148
```
guuccuuuuc uuuauuugcu                                              20

<210> SEQ ID NO 1149
<211> LENGTH: 20
<212> TYPE: RNA
<213> ORGANISM: Artificial Sequence
<220> FEATURE:
<223> OTHER INFORMATION: synthesized

<400> SEQUENCE: 1149
guuccuuuuc uuuauuuguu                                              20

<210> SEQ ID NO 1150
<211> LENGTH: 20
<212> TYPE: RNA
<213> ORGANISM: Artificial Sequence
<220> FEATURE:
<223> OTHER INFORMATION: synthesized

<400> SEQUENCE: 1150
uaacaaauaa agaaaaggaa                                              20

<210> SEQ ID NO 1151
<211> LENGTH: 20
<212> TYPE: RNA
<213> ORGANISM: Artificial Sequence
<220> FEATURE:
<223> OTHER INFORMATION: synthesized

<400> SEQUENCE: 1151
uacauaacaa auaaagaaaa                                              20

<210> SEQ ID NO 1152
<211> LENGTH: 20
<212> TYPE: RNA
<213> ORGANISM: Artificial Sequence
<220> FEATURE:
<223> OTHER INFORMATION: synthesized

<400> SEQUENCE: 1152
uaccuacaua acaaauaaag                                              20

<210> SEQ ID NO 1153
<211> LENGTH: 20
<212> TYPE: RNA
<213> ORGANISM: Artificial Sequence
<220> FEATURE:
<223> OTHER INFORMATION: synthesized

<400> SEQUENCE: 1153
uaccuacaua gcaaauaaag                                              20

<210> SEQ ID NO 1154
<211> LENGTH: 20
<212> TYPE: RNA
<213> ORGANISM: Artificial Sequence
<220> FEATURE:
<223> OTHER INFORMATION: synthesized

<400> SEQUENCE: 1154
uagcaaauaa agaaaaggaa                                              20

<210> SEQ ID NO 1155
<211> LENGTH: 20
<212> TYPE: RNA

```
<213> ORGANISM: Artificial Sequence
<220> FEATURE:
<223> OTHER INFORMATION: synthesized

<400> SEQUENCE: 1155
uaguuaccua cauaacaaau                                                   20

<210> SEQ ID NO 1156
<211> LENGTH: 20
<212> TYPE: RNA
<213> ORGANISM: Artificial Sequence
<220> FEATURE:
<223> OTHER INFORMATION: synthesized

<400> SEQUENCE: 1156
uaguuaccua cauagcaaau                                                   20

<210> SEQ ID NO 1157
<211> LENGTH: 20
<212> TYPE: RNA
<213> ORGANISM: Artificial Sequence
<220> FEATURE:
<223> OTHER INFORMATION: synthesized

<400> SEQUENCE: 1157
uauuugcuau guagguaacu                                                   20

<210> SEQ ID NO 1158
<211> LENGTH: 20
<212> TYPE: RNA
<213> ORGANISM: Artificial Sequence
<220> FEATURE:
<223> OTHER INFORMATION: synthesized

<400> SEQUENCE: 1158
uauuuguuau guagguaacu                                                   20

<210> SEQ ID NO 1159
<211> LENGTH: 20
<212> TYPE: RNA
<213> ORGANISM: Artificial Sequence
<220> FEATURE:
<223> OTHER INFORMATION: synthesized

<400> SEQUENCE: 1159
ucuuuauuug cuauguaggu                                                   20

<210> SEQ ID NO 1160
<211> LENGTH: 20
<212> TYPE: RNA
<213> ORGANISM: Artificial Sequence
<220> FEATURE:
<223> OTHER INFORMATION: synthesized

<400> SEQUENCE: 1160
ucuuuauuug uuauguaggu                                                   20

<210> SEQ ID NO 1161
<211> LENGTH: 20
<212> TYPE: RNA
<213> ORGANISM: Artificial Sequence
<220> FEATURE:
<223> OTHER INFORMATION: synthesized

<400> SEQUENCE: 1161
ugaauaguua ccuacauaac                                                   20
```

<210> SEQ ID NO 1162
<211> LENGTH: 20
<212> TYPE: RNA
<213> ORGANISM: Artificial Sequence
<220> FEATURE:
<223> OTHER INFORMATION: synthesized

<400> SEQUENCE: 1162
ugaauaguua ccuacauagc                                              20

<210> SEQ ID NO 1163
<211> LENGTH: 20
<212> TYPE: RNA
<213> ORGANISM: Artificial Sequence
<220> FEATURE:
<223> OTHER INFORMATION: synthesized

<400> SEQUENCE: 1163
ugcuauguag guaacuauuc                                              20

<210> SEQ ID NO 1164
<211> LENGTH: 20
<212> TYPE: RNA
<213> ORGANISM: Artificial Sequence
<220> FEATURE:
<223> OTHER INFORMATION: synthesized

<400> SEQUENCE: 1164
uguuauguag guaacuauuc                                              20

<210> SEQ ID NO 1165
<211> LENGTH: 20
<212> TYPE: RNA
<213> ORGANISM: Artificial Sequence
<220> FEATURE:
<223> OTHER INFORMATION: synthesized

<400> SEQUENCE: 1165
uuaccuacau aacaaauaaa                                              20

<210> SEQ ID NO 1166
<211> LENGTH: 20
<212> TYPE: RNA
<213> ORGANISM: Artificial Sequence
<220> FEATURE:
<223> OTHER INFORMATION: synthesized

<400> SEQUENCE: 1166
uuaccuacau agcaaauaaa                                              20

<210> SEQ ID NO 1167
<211> LENGTH: 20
<212> TYPE: RNA
<213> ORGANISM: Artificial Sequence
<220> FEATURE:
<223> OTHER INFORMATION: synthesized

<400> SEQUENCE: 1167
uuauguaggu aacuauucaa                                              20

<210> SEQ ID NO 1168
<211> LENGTH: 20
<212> TYPE: RNA
<213> ORGANISM: Artificial Sequence
<220> FEATURE:

<223> OTHER INFORMATION: synthesized

<400> SEQUENCE: 1168
uuauuugcua uguagguaac                                               20

<210> SEQ ID NO 1169
<211> LENGTH: 20
<212> TYPE: RNA
<213> ORGANISM: Artificial Sequence
<220> FEATURE:
<223> OTHER INFORMATION: synthesized

<400> SEQUENCE: 1169
uuauuuguua uguagguaac                                               20

<210> SEQ ID NO 1170
<211> LENGTH: 20
<212> TYPE: RNA
<213> ORGANISM: Artificial Sequence
<220> FEATURE:
<223> OTHER INFORMATION: synthesized

<400> SEQUENCE: 1170
uuccuuuucu uuauuugcua                                               20

<210> SEQ ID NO 1171
<211> LENGTH: 20
<212> TYPE: RNA
<213> ORGANISM: Artificial Sequence
<220> FEATURE:
<223> OTHER INFORMATION: synthesized

<400> SEQUENCE: 1171
uuccuuuucu uuauuuguua                                               20

<210> SEQ ID NO 1172
<211> LENGTH: 20
<212> TYPE: RNA
<213> ORGANISM: Artificial Sequence
<220> FEATURE:
<223> OTHER INFORMATION: synthesized

<400> SEQUENCE: 1172
uucuuuauuu gcuauguagg                                               20

<210> SEQ ID NO 1173
<211> LENGTH: 20
<212> TYPE: RNA
<213> ORGANISM: Artificial Sequence
<220> FEATURE:
<223> OTHER INFORMATION: synthesized

<400> SEQUENCE: 1173
uucuuuauuu guuauguagg                                               20

<210> SEQ ID NO 1174
<211> LENGTH: 20
<212> TYPE: RNA
<213> ORGANISM: Artificial Sequence
<220> FEATURE:
<223> OTHER INFORMATION: synthesized

<400> SEQUENCE: 1174
uugaauaguu accuacauaa                                               20

```
<210> SEQ ID NO 1175
<211> LENGTH: 20
<212> TYPE: RNA
<213> ORGANISM: Artificial Sequence
<220> FEATURE:
<223> OTHER INFORMATION: synthesized

<400> SEQUENCE: 1175
uugaauaguu accuacauag                                               20

<210> SEQ ID NO 1176
<211> LENGTH: 20
<212> TYPE: RNA
<213> ORGANISM: Artificial Sequence
<220> FEATURE:
<223> OTHER INFORMATION: synthesized

<400> SEQUENCE: 1176
uugcuaugua gguaacuauu                                               20

<210> SEQ ID NO 1177
<211> LENGTH: 20
<212> TYPE: RNA
<213> ORGANISM: Artificial Sequence
<220> FEATURE:
<223> OTHER INFORMATION: synthesized

<400> SEQUENCE: 1177
uuguuaugua gguaacuauu                                               20

<210> SEQ ID NO 1178
<211> LENGTH: 20
<212> TYPE: RNA
<213> ORGANISM: Artificial Sequence
<220> FEATURE:
<223> OTHER INFORMATION: synthesized

<400> SEQUENCE: 1178
uuuauuugcu auguagguaa                                               20

<210> SEQ ID NO 1179
<211> LENGTH: 20
<212> TYPE: RNA
<213> ORGANISM: Artificial Sequence
<220> FEATURE:
<223> OTHER INFORMATION: synthesized

<400> SEQUENCE: 1179
uuuauuuguu auguagguaa                                               20

<210> SEQ ID NO 1180
<211> LENGTH: 20
<212> TYPE: RNA
<213> ORGANISM: Artificial Sequence
<220> FEATURE:
<223> OTHER INFORMATION: synthesized

<400> SEQUENCE: 1180
uuucuuuauu ugcuauguag                                               20

<210> SEQ ID NO 1181
<211> LENGTH: 20
<212> TYPE: RNA
<213> ORGANISM: Artificial Sequence
<220> FEATURE:
<223> OTHER INFORMATION: synthesized
```

```
<400> SEQUENCE: 1181
uuucuuuauu uguuauguag                                               20

<210> SEQ ID NO 1182
<211> LENGTH: 20
<212> TYPE: RNA
<213> ORGANISM: Artificial Sequence
<220> FEATURE:
<223> OTHER INFORMATION: synthesized

<400> SEQUENCE: 1182
uuugcuaugu agguaacuau                                               20

<210> SEQ ID NO 1183
<211> LENGTH: 20
<212> TYPE: RNA
<213> ORGANISM: Artificial Sequence
<220> FEATURE:
<223> OTHER INFORMATION: synthesized

<400> SEQUENCE: 1183
uuuguuaugu agguaacuau                                               20

<210> SEQ ID NO 1184
<211> LENGTH: 20
<212> TYPE: RNA
<213> ORGANISM: Artificial Sequence
<220> FEATURE:
<223> OTHER INFORMATION: synthesized

<400> SEQUENCE: 1184
uuuucuuuau uugcuaugua                                               20

<210> SEQ ID NO 1185
<211> LENGTH: 20
<212> TYPE: RNA
<213> ORGANISM: Artificial Sequence
<220> FEATURE:
<223> OTHER INFORMATION: synthesized

<400> SEQUENCE: 1185
uuuucuuuau uuguuaugua                                               20

<210> SEQ ID NO 1186
<211> LENGTH: 20
<212> TYPE: RNA
<213> ORGANISM: Artificial Sequence
<220> FEATURE:
<223> OTHER INFORMATION: synthesized

<400> SEQUENCE: 1186
aacuucucuu cccauaccac                                               20

<210> SEQ ID NO 1187
<211> LENGTH: 20
<212> TYPE: RNA
<213> ORGANISM: Artificial Sequence
<220> FEATURE:
<223> OTHER INFORMATION: synthesized

<400> SEQUENCE: 1187
aacuucucuu ccuauaccac                                               20

<210> SEQ ID NO 1188
<211> LENGTH: 20
```

```
<212> TYPE: RNA
<213> ORGANISM: Artificial Sequence
<220> FEATURE:
<223> OTHER INFORMATION: synthesized

<400> SEQUENCE: 1188
agaacuucuc uucccauacc                                              20

<210> SEQ ID NO 1189
<211> LENGTH: 20
<212> TYPE: RNA
<213> ORGANISM: Artificial Sequence
<220> FEATURE:
<223> OTHER INFORMATION: synthesized

<400> SEQUENCE: 1189
agaacuucuc uuccuauacc                                              20

<210> SEQ ID NO 1190
<211> LENGTH: 20
<212> TYPE: RNA
<213> ORGANISM: Artificial Sequence
<220> FEATURE:
<223> OTHER INFORMATION: synthesized

<400> SEQUENCE: 1190
aggaagagaa guucucaaac                                              20

<210> SEQ ID NO 1191
<211> LENGTH: 20
<212> TYPE: RNA
<213> ORGANISM: Artificial Sequence
<220> FEATURE:
<223> OTHER INFORMATION: synthesized

<400> SEQUENCE: 1191
augauuuugg gugguauagg                                              20

<210> SEQ ID NO 1192
<211> LENGTH: 20
<212> TYPE: RNA
<213> ORGANISM: Artificial Sequence
<220> FEATURE:
<223> OTHER INFORMATION: synthesized

<400> SEQUENCE: 1192
augauuuugg gugguauggg                                              20

<210> SEQ ID NO 1193
<211> LENGTH: 20
<212> TYPE: RNA
<213> ORGANISM: Artificial Sequence
<220> FEATURE:
<223> OTHER INFORMATION: synthesized

<400> SEQUENCE: 1193
cauaccaccc aaaaucauaa                                              20

<210> SEQ ID NO 1194
<211> LENGTH: 20
<212> TYPE: RNA
<213> ORGANISM: Artificial Sequence
<220> FEATURE:
<223> OTHER INFORMATION: synthesized

<400> SEQUENCE: 1194
```
ccauaccacc caaaaucaua                                    20

<210> SEQ ID NO 1195
<211> LENGTH: 20
<212> TYPE: RNA
<213> ORGANISM: Artificial Sequence
<220> FEATURE:
<223> OTHER INFORMATION: synthesized

<400> SEQUENCE: 1195
cccauaccac ccaaaaucau                                    20

<210> SEQ ID NO 1196
<211> LENGTH: 20
<212> TYPE: RNA
<213> ORGANISM: Artificial Sequence
<220> FEATURE:
<223> OTHER INFORMATION: synthesized

<400> SEQUENCE: 1196
ccuauaccac ccaaaaucau                                    20

<210> SEQ ID NO 1197
<211> LENGTH: 20
<212> TYPE: RNA
<213> ORGANISM: Artificial Sequence
<220> FEATURE:
<223> OTHER INFORMATION: synthesized

<400> SEQUENCE: 1197
cuauaccacc caaaaucaua                                    20

<210> SEQ ID NO 1198
<211> LENGTH: 20
<212> TYPE: RNA
<213> ORGANISM: Artificial Sequence
<220> FEATURE:
<223> OTHER INFORMATION: synthesized

<400> SEQUENCE: 1198
cucuucccau accacccaaa                                    20

<210> SEQ ID NO 1199
<211> LENGTH: 20
<212> TYPE: RNA
<213> ORGANISM: Artificial Sequence
<220> FEATURE:
<223> OTHER INFORMATION: synthesized

<400> SEQUENCE: 1199
cucuuccuau accacccaaa                                    20

<210> SEQ ID NO 1200
<211> LENGTH: 20
<212> TYPE: RNA
<213> ORGANISM: Artificial Sequence
<220> FEATURE:
<223> OTHER INFORMATION: synthesized

<400> SEQUENCE: 1200
cuucccauac cacccaaaau                                    20

<210> SEQ ID NO 1201
<211> LENGTH: 20
<212> TYPE: RNA
<213> ORGANISM: Artificial Sequence

```
<220> FEATURE:
<223> OTHER INFORMATION: synthesized

<400> SEQUENCE: 1201
cuuccuauac cacccaaaau                                              20

<210> SEQ ID NO 1202
<211> LENGTH: 20
<212> TYPE: RNA
<213> ORGANISM: Artificial Sequence
<220> FEATURE:
<223> OTHER INFORMATION: synthesized

<400> SEQUENCE: 1202
cuucucuucc cauaccaccc                                              20

<210> SEQ ID NO 1203
<211> LENGTH: 20
<212> TYPE: RNA
<213> ORGANISM: Artificial Sequence
<220> FEATURE:
<223> OTHER INFORMATION: synthesized

<400> SEQUENCE: 1203
cuucucuucc uauaccaccc                                              20

<210> SEQ ID NO 1204
<211> LENGTH: 20
<212> TYPE: RNA
<213> ORGANISM: Artificial Sequence
<220> FEATURE:
<223> OTHER INFORMATION: synthesized

<400> SEQUENCE: 1204
gaacuucucu ucccauacca                                              20

<210> SEQ ID NO 1205
<211> LENGTH: 20
<212> TYPE: RNA
<213> ORGANISM: Artificial Sequence
<220> FEATURE:
<223> OTHER INFORMATION: synthesized

<400> SEQUENCE: 1205
gaacuucucu uccuauacca                                              20

<210> SEQ ID NO 1206
<211> LENGTH: 20
<212> TYPE: RNA
<213> ORGANISM: Artificial Sequence
<220> FEATURE:
<223> OTHER INFORMATION: synthesized

<400> SEQUENCE: 1206
gagaacuucu cuucccauac                                              20

<210> SEQ ID NO 1207
<211> LENGTH: 20
<212> TYPE: RNA
<213> ORGANISM: Artificial Sequence
<220> FEATURE:
<223> OTHER INFORMATION: synthesized

<400> SEQUENCE: 1207
gagaacuucu cuuccuauac                                              20
```

```
<210> SEQ ID NO 1208
<211> LENGTH: 20
<212> TYPE: RNA
<213> ORGANISM: Artificial Sequence
<220> FEATURE:
<223> OTHER INFORMATION: synthesized

<400> SEQUENCE: 1208 gauuugggu gguauaggaa                                                      20

<210> SEQ ID NO 1209
<211> LENGTH: 20
<212> TYPE: RNA
<213> ORGANISM: Artificial Sequence
<220> FEATURE:
<223> OTHER INFORMATION: synthesized

<400> SEQUENCE: 1209 gauuugggu gguaugggaa                                                      20

<210> SEQ ID NO 1210
<211> LENGTH: 20
<212> TYPE: RNA
<213> ORGANISM: Artificial Sequence
<220> FEATURE:
<223> OTHER INFORMATION: synthesized

<400> SEQUENCE: 1210
gggaagagaa guucucaaac                                                     20

<210> SEQ ID NO 1211
<211> LENGTH: 20
<212> TYPE: RNA
<213> ORGANISM: Artificial Sequence
<220> FEATURE:
<223> OTHER INFORMATION: synthesized

<400> SEQUENCE: 1211
gggugguaua ggaagagaag                                                     20

<210> SEQ ID NO 1212
<211> LENGTH: 20
<212> TYPE: RNA
<213> ORGANISM: Artificial Sequence
<220> FEATURE:
<223> OTHER INFORMATION: synthesized

<400> SEQUENCE: 1212
gggugguaug ggaagagaag                                                     20

<210> SEQ ID NO 1213
<211> LENGTH: 20
<212> TYPE: RNA
<213> ORGANISM: Artificial Sequence
<220> FEATURE:
<223> OTHER INFORMATION: synthesized

<400> SEQUENCE: 1213
gguauaggaa gagaaguucu                                                     20

<210> SEQ ID NO 1214
<211> LENGTH: 20
<212> TYPE: RNA
<213> ORGANISM: Artificial Sequence
<220> FEATURE:
<223> OTHER INFORMATION: synthesized
```

<400> SEQUENCE: 1214
gguaugggaa gagaaguucu                                            20

<210> SEQ ID NO 1215
<211> LENGTH: 20
<212> TYPE: RNA
<213> ORGANISM: Artificial Sequence
<220> FEATURE:
<223> OTHER INFORMATION: synthesized

<400> SEQUENCE: 1215
ggugguauag gaagagaagu                                            20

<210> SEQ ID NO 1216
<211> LENGTH: 20
<212> TYPE: RNA
<213> ORGANISM: Artificial Sequence
<220> FEATURE:
<223> OTHER INFORMATION: synthesized

<400> SEQUENCE: 1216
ggugguaugg gaagagaagu                                            20

<210> SEQ ID NO 1217
<211> LENGTH: 20
<212> TYPE: RNA
<213> ORGANISM: Artificial Sequence
<220> FEATURE:
<223> OTHER INFORMATION: synthesized

<400> SEQUENCE: 1217
guauaggaag agaaguucuc                                            20

<210> SEQ ID NO 1218
<211> LENGTH: 20
<212> TYPE: RNA
<213> ORGANISM: Artificial Sequence
<220> FEATURE:
<223> OTHER INFORMATION: synthesized

<400> SEQUENCE: 1218
guaugggaag agaaguucuc                                            20

<210> SEQ ID NO 1219
<211> LENGTH: 20
<212> TYPE: RNA
<213> ORGANISM: Artificial Sequence
<220> FEATURE:
<223> OTHER INFORMATION: synthesized

<400> SEQUENCE: 1219
gugguauagg aagagaaguu                                            20

<210> SEQ ID NO 1220
<211> LENGTH: 20
<212> TYPE: RNA
<213> ORGANISM: Artificial Sequence
<220> FEATURE:
<223> OTHER INFORMATION: synthesized

<400> SEQUENCE: 1220
gugguauggg aagagaaguu                                            20

<210> SEQ ID NO 1221

```
<211> LENGTH: 20
<212> TYPE: RNA
<213> ORGANISM: Artificial Sequence
<220> FEATURE:
<223> OTHER INFORMATION: synthesized

<400> SEQUENCE: 1221
guuugagaac uucucuuccc                                              20

<210> SEQ ID NO 1222
<211> LENGTH: 20
<212> TYPE: RNA
<213> ORGANISM: Artificial Sequence
<220> FEATURE:
<223> OTHER INFORMATION: synthesized

<400> SEQUENCE: 1222
guuugagaac uucucuuccu                                              20

<210> SEQ ID NO 1223
<211> LENGTH: 20
<212> TYPE: RNA
<213> ORGANISM: Artificial Sequence
<220> FEATURE:
<223> OTHER INFORMATION: synthesized

<400> SEQUENCE: 1223
uaggaagaga aguucucaaa                                              20

<210> SEQ ID NO 1224
<211> LENGTH: 20
<212> TYPE: RNA
<213> ORGANISM: Artificial Sequence
<220> FEATURE:
<223> OTHER INFORMATION: synthesized

<400> SEQUENCE: 1224
uauaccaccc aaaaucauaa                                              20

<210> SEQ ID NO 1225
<211> LENGTH: 20
<212> TYPE: RNA
<213> ORGANISM: Artificial Sequence
<220> FEATURE:
<223> OTHER INFORMATION: synthesized

<400> SEQUENCE: 1225
uauaggaaga gaaguucuca                                              20

<210> SEQ ID NO 1226
<211> LENGTH: 20
<212> TYPE: RNA
<213> ORGANISM: Artificial Sequence
<220> FEATURE:
<223> OTHER INFORMATION: synthesized

<400> SEQUENCE: 1226
uaugauuuug ggugguauag                                              20

<210> SEQ ID NO 1227
<211> LENGTH: 20
<212> TYPE: RNA
<213> ORGANISM: Artificial Sequence
<220> FEATURE:
<223> OTHER INFORMATION: synthesized

<400> SEQUENCE: 1227
```

```
uaugauuuug ggugguaugg                                                   20

<210> SEQ ID NO 1228
<211> LENGTH: 20
<212> TYPE: RNA
<213> ORGANISM: Artificial Sequence
<220> FEATURE:
<223> OTHER INFORMATION: synthesized

<400> SEQUENCE: 1228
uaugggaaga gaaguucuca                                                   20

<210> SEQ ID NO 1229
<211> LENGTH: 20
<212> TYPE: RNA
<213> ORGANISM: Artificial Sequence
<220> FEATURE:
<223> OTHER INFORMATION: synthesized

<400> SEQUENCE: 1229
ucccauacca cccaaaauca                                                   20

<210> SEQ ID NO 1230
<211> LENGTH: 20
<212> TYPE: RNA
<213> ORGANISM: Artificial Sequence
<220> FEATURE:
<223> OTHER INFORMATION: synthesized

<400> SEQUENCE: 1230
uccuauacca cccaaaauca                                                   20

<210> SEQ ID NO 1231
<211> LENGTH: 20
<212> TYPE: RNA
<213> ORGANISM: Artificial Sequence
<220> FEATURE:
<223> OTHER INFORMATION: synthesized

<400> SEQUENCE: 1231
ucuucccaua ccacccaaaa                                                   20

<210> SEQ ID NO 1232
<211> LENGTH: 20
<212> TYPE: RNA
<213> ORGANISM: Artificial Sequence
<220> FEATURE:
<223> OTHER INFORMATION: synthesized

<400> SEQUENCE: 1232
ucuuccuaua ccacccaaaa                                                   20

<210> SEQ ID NO 1233
<211> LENGTH: 20
<212> TYPE: RNA
<213> ORGANISM: Artificial Sequence
<220> FEATURE:
<223> OTHER INFORMATION: synthesized

<400> SEQUENCE: 1233
ugagaacuuc ucuucccaua                                                   20

<210> SEQ ID NO 1234
<211> LENGTH: 20
<212> TYPE: RNA
```

```
<213> ORGANISM: Artificial Sequence
<220> FEATURE:
<223> OTHER INFORMATION: synthesized

<400> SEQUENCE: 1234
ugagaacuuc ucuuccuaua                                           20

<210> SEQ ID NO 1235
<211> LENGTH: 20
<212> TYPE: RNA
<213> ORGANISM: Artificial Sequence
<220> FEATURE:
<223> OTHER INFORMATION: synthesized

<400> SEQUENCE: 1235
ugggaagaga aguucucaaa                                           20

<210> SEQ ID NO 1236
<211> LENGTH: 20
<212> TYPE: RNA
<213> ORGANISM: Artificial Sequence
<220> FEATURE:
<223> OTHER INFORMATION: synthesized

<400> SEQUENCE: 1236
ugggugguau aggaagagaa                                           20

<210> SEQ ID NO 1237
<211> LENGTH: 20
<212> TYPE: RNA
<213> ORGANISM: Artificial Sequence
<220> FEATURE:
<223> OTHER INFORMATION: synthesized

<400> SEQUENCE: 1237
ugggugguau gggaagagaa                                           20

<210> SEQ ID NO 1238
<211> LENGTH: 20
<212> TYPE: RNA
<213> ORGANISM: Artificial Sequence
<220> FEATURE:
<223> OTHER INFORMATION: synthesized

<400> SEQUENCE: 1238
uucccauacc acccaaaauc                                           20

<210> SEQ ID NO 1239
<211> LENGTH: 20
<212> TYPE: RNA
<213> ORGANISM: Artificial Sequence
<220> FEATURE:
<223> OTHER INFORMATION: synthesized

<400> SEQUENCE: 1239
uuccuauacc acccaaaauc                                           20

<210> SEQ ID NO 1240
<211> LENGTH: 20
<212> TYPE: RNA
<213> ORGANISM: Artificial Sequence
<220> FEATURE:
<223> OTHER INFORMATION: synthesized

<400> SEQUENCE: 1240
uucucuuccc auaccaccca                                           20
```

<210> SEQ ID NO 1241
<211> LENGTH: 20
<212> TYPE: RNA
<213> ORGANISM: Artificial Sequence
<220> FEATURE:
<223> OTHER INFORMATION: synthesized

<400> SEQUENCE: 1241
uucucuuccu auaccaccca                                               20

<210> SEQ ID NO 1242
<211> LENGTH: 20
<212> TYPE: RNA
<213> ORGANISM: Artificial Sequence
<220> FEATURE:
<223> OTHER INFORMATION: synthesized

<400> SEQUENCE: 1242
uugagaacuu cucuucccau                                               20

<210> SEQ ID NO 1243
<211> LENGTH: 20
<212> TYPE: RNA
<213> ORGANISM: Artificial Sequence
<220> FEATURE:
<223> OTHER INFORMATION: synthesized

<400> SEQUENCE: 1243
uugagaacuu cucuuccuau                                               20

<210> SEQ ID NO 1244
<211> LENGTH: 20
<212> TYPE: RNA
<213> ORGANISM: Artificial Sequence
<220> FEATURE:
<223> OTHER INFORMATION: synthesized

<400> SEQUENCE: 1244
uuggguggua uaggaagaga                                               20

<210> SEQ ID NO 1245
<211> LENGTH: 20
<212> TYPE: RNA
<213> ORGANISM: Artificial Sequence
<220> FEATURE:
<223> OTHER INFORMATION: synthesized

<400> SEQUENCE: 1245
uuggguggua ugggaagaga                                               20

<210> SEQ ID NO 1246
<211> LENGTH: 20
<212> TYPE: RNA
<213> ORGANISM: Artificial Sequence
<220> FEATURE:
<223> OTHER INFORMATION: synthesized

<400> SEQUENCE: 1246
uuuggguggu auaggaagag                                               20

<210> SEQ ID NO 1247
<211> LENGTH: 20
<212> TYPE: RNA
<213> ORGANISM: Artificial Sequence
<220> FEATURE:

<223> OTHER INFORMATION: synthesized

<400> SEQUENCE: 1247 uuugggugu augggaagag                                                    20

<210> SEQ ID NO 1248
<211> LENGTH: 20
<212> TYPE: RNA
<213> ORGANISM: Artificial Sequence
<220> FEATURE:
<223> OTHER INFORMATION: synthesized

<400> SEQUENCE: 1248
uuuugggugg uauaggaaga                                                   20

<210> SEQ ID NO 1249
<211> LENGTH: 20
<212> TYPE: RNA
<213> ORGANISM: Artificial Sequence
<220> FEATURE:
<223> OTHER INFORMATION: synthesized

<400> SEQUENCE: 1249
uuuugggugg uaugggaaga                                                   20

<210> SEQ ID NO 1250
<211> LENGTH: 20
<212> TYPE: RNA
<213> ORGANISM: Artificial Sequence
<220> FEATURE:
<223> OTHER INFORMATION: synthesized

<400> SEQUENCE: 1250
aaaaagccaa ugcacggcag                                                   20

<210> SEQ ID NO 1251
<211> LENGTH: 20
<212> TYPE: RNA
<213> ORGANISM: Artificial Sequence
<220> FEATURE:
<223> OTHER INFORMATION: synthesized

<400> SEQUENCE: 1251
aaaaagccaa ugcauggcag                                                   20

<210> SEQ ID NO 1252
<211> LENGTH: 20
<212> TYPE: RNA
<213> ORGANISM: Artificial Sequence
<220> FEATURE:
<223> OTHER INFORMATION: synthesized

<400> SEQUENCE: 1252
aaaagccaau gcacggcaga                                                   20

<210> SEQ ID NO 1253
<211> LENGTH: 20
<212> TYPE: RNA
<213> ORGANISM: Artificial Sequence
<220> FEATURE:
<223> OTHER INFORMATION: synthesized

<400> SEQUENCE: 1253
aaaagccaau gcauggcaga                                                   20

```
<210> SEQ ID NO 1254
<211> LENGTH: 20
<212> TYPE: RNA
<213> ORGANISM: Artificial Sequence
<220> FEATURE:
<223> OTHER INFORMATION: synthesized

<400> SEQUENCE: 1254
aaagaaaaag ccaaugcacg                                              20

<210> SEQ ID NO 1255
<211> LENGTH: 20
<212> TYPE: RNA
<213> ORGANISM: Artificial Sequence
<220> FEATURE:
<223> OTHER INFORMATION: synthesized

<400> SEQUENCE: 1255
aaagaaaaag ccaaugcaug                                              20

<210> SEQ ID NO 1256
<211> LENGTH: 20
<212> TYPE: RNA
<213> ORGANISM: Artificial Sequence
<220> FEATURE:
<223> OTHER INFORMATION: synthesized

<400> SEQUENCE: 1256
aaagccaaug cacggcagau                                              20

<210> SEQ ID NO 1257
<211> LENGTH: 20
<212> TYPE: RNA
<213> ORGANISM: Artificial Sequence
<220> FEATURE:
<223> OTHER INFORMATION: synthesized

<400> SEQUENCE: 1257
aaagccaaug cauggcagau                                              20

<210> SEQ ID NO 1258
<211> LENGTH: 20
<212> TYPE: RNA
<213> ORGANISM: Artificial Sequence
<220> FEATURE:
<223> OTHER INFORMATION: synthesized

<400> SEQUENCE: 1258
aaauuauaau cugccaugca                                              20

<210> SEQ ID NO 1259
<211> LENGTH: 20
<212> TYPE: RNA
<213> ORGANISM: Artificial Sequence
<220> FEATURE:
<223> OTHER INFORMATION: synthesized

<400> SEQUENCE: 1259
aaauuauaau cugccgugca                                              20

<210> SEQ ID NO 1260
<211> LENGTH: 20
<212> TYPE: RNA
<213> ORGANISM: Artificial Sequence
<220> FEATURE:
<223> OTHER INFORMATION: synthesized
```

```
<400> SEQUENCE: 1260
aagaaaaagc caaugcacgg                                               20

<210> SEQ ID NO 1261
<211> LENGTH: 20
<212> TYPE: RNA
<213> ORGANISM: Artificial Sequence
<220> FEATURE:
<223> OTHER INFORMATION: synthesized

<400> SEQUENCE: 1261
aagaaaaagc caaugcaugg                                               20

<210> SEQ ID NO 1262
<211> LENGTH: 20
<212> TYPE: RNA
<213> ORGANISM: Artificial Sequence
<220> FEATURE:
<223> OTHER INFORMATION: synthesized

<400> SEQUENCE: 1262
aagccaaugc acggcagauu                                               20

<210> SEQ ID NO 1263
<211> LENGTH: 20
<212> TYPE: RNA
<213> ORGANISM: Artificial Sequence
<220> FEATURE:
<223> OTHER INFORMATION: synthesized

<400> SEQUENCE: 1263
aagccaaugc auggcagauu                                               20

<210> SEQ ID NO 1264
<211> LENGTH: 20
<212> TYPE: RNA
<213> ORGANISM: Artificial Sequence
<220> FEATURE:
<223> OTHER INFORMATION: synthesized

<400> SEQUENCE: 1264
aaucugccau gcauuggcuu                                               20

<210> SEQ ID NO 1265
<211> LENGTH: 20
<212> TYPE: RNA
<213> ORGANISM: Artificial Sequence
<220> FEATURE:
<223> OTHER INFORMATION: synthesized

<400> SEQUENCE: 1265
aaucugccgu gcauuggcuu                                               20

<210> SEQ ID NO 1266
<211> LENGTH: 20
<212> TYPE: RNA
<213> ORGANISM: Artificial Sequence
<220> FEATURE:
<223> OTHER INFORMATION: synthesized

<400> SEQUENCE: 1266
acggcagauu auaauuuaag                                               20

<210> SEQ ID NO 1267
<211> LENGTH: 20
```

```
<212> TYPE: RNA
<213> ORGANISM: Artificial Sequence
<220> FEATURE:
<223> OTHER INFORMATION: synthesized

<400> SEQUENCE: 1267
agccaaugca cggcagauua                                               20

<210> SEQ ID NO 1268
<211> LENGTH: 20
<212> TYPE: RNA
<213> ORGANISM: Artificial Sequence
<220> FEATURE:
<223> OTHER INFORMATION: synthesized

<400> SEQUENCE: 1268
agccaaugca uggcagauua                                               20

<210> SEQ ID NO 1269
<211> LENGTH: 20
<212> TYPE: RNA
<213> ORGANISM: Artificial Sequence
<220> FEATURE:
<223> OTHER INFORMATION: synthesized

<400> SEQUENCE: 1269
auaaucugcc augcauuggc                                               20

<210> SEQ ID NO 1270
<211> LENGTH: 20
<212> TYPE: RNA
<213> ORGANISM: Artificial Sequence
<220> FEATURE:
<223> OTHER INFORMATION: synthesized

<400> SEQUENCE: 1270
auaaucugcc gugcauuggc                                               20

<210> SEQ ID NO 1271
<211> LENGTH: 20
<212> TYPE: RNA
<213> ORGANISM: Artificial Sequence
<220> FEATURE:
<223> OTHER INFORMATION: synthesized

<400> SEQUENCE: 1271
aucugccaug cauuggcuuu                                               20

<210> SEQ ID NO 1272
<211> LENGTH: 20
<212> TYPE: RNA
<213> ORGANISM: Artificial Sequence
<220> FEATURE:
<223> OTHER INFORMATION: synthesized

<400> SEQUENCE: 1272
aucugccgug cauuggcuuu                                               20

<210> SEQ ID NO 1273
<211> LENGTH: 20
<212> TYPE: RNA
<213> ORGANISM: Artificial Sequence
<220> FEATURE:
<223> OTHER INFORMATION: synthesized

<400> SEQUENCE: 1273
```

```
augcacggca gauuauaauu                                                    20

<210> SEQ ID NO 1274
<211> LENGTH: 20
<212> TYPE: RNA
<213> ORGANISM: Artificial Sequence
<220> FEATURE:
<223> OTHER INFORMATION: synthesized

<400> SEQUENCE: 1274
augcauggca gauuauaauu                                                    20

<210> SEQ ID NO 1275
<211> LENGTH: 20
<212> TYPE: RNA
<213> ORGANISM: Artificial Sequence
<220> FEATURE:
<223> OTHER INFORMATION: synthesized

<400> SEQUENCE: 1275
auggcagauu auaauuuaag                                                    20

<210> SEQ ID NO 1276
<211> LENGTH: 20
<212> TYPE: RNA
<213> ORGANISM: Artificial Sequence
<220> FEATURE:
<223> OTHER INFORMATION: synthesized

<400> SEQUENCE: 1276
auuauaaucu gccaugcauu                                                    20

<210> SEQ ID NO 1277
<211> LENGTH: 20
<212> TYPE: RNA
<213> ORGANISM: Artificial Sequence
<220> FEATURE:
<223> OTHER INFORMATION: synthesized

<400> SEQUENCE: 1277
auuauaaucu gccgugcauu                                                    20

<210> SEQ ID NO 1278
<211> LENGTH: 20
<212> TYPE: RNA
<213> ORGANISM: Artificial Sequence
<220> FEATURE:
<223> OTHER INFORMATION: synthesized

<400> SEQUENCE: 1278
caaugcacgg cagauuauaa                                                    20

<210> SEQ ID NO 1279
<211> LENGTH: 20
<212> TYPE: RNA
<213> ORGANISM: Artificial Sequence
<220> FEATURE:
<223> OTHER INFORMATION: synthesized

<400> SEQUENCE: 1279
caaugcaugg cagauuauaa                                                    20

<210> SEQ ID NO 1280
<211> LENGTH: 20
<212> TYPE: RNA
<213> ORGANISM: Artificial Sequence
```

<220> FEATURE:
<223> OTHER INFORMATION: synthesized

<400> SEQUENCE: 1280
cacggcagau uauaauuuaa                                              20

<210> SEQ ID NO 1281
<211> LENGTH: 20
<212> TYPE: RNA
<213> ORGANISM: Artificial Sequence
<220> FEATURE:
<223> OTHER INFORMATION: synthesized

<400> SEQUENCE: 1281
caugcauugg cuuuuucuuu                                              20

<210> SEQ ID NO 1282
<211> LENGTH: 20
<212> TYPE: RNA
<213> ORGANISM: Artificial Sequence
<220> FEATURE:
<223> OTHER INFORMATION: synthesized

<400> SEQUENCE: 1282
cauggcagau uauaauuuaa                                              20

<210> SEQ ID NO 1283
<211> LENGTH: 20
<212> TYPE: RNA
<213> ORGANISM: Artificial Sequence
<220> FEATURE:
<223> OTHER INFORMATION: synthesized

<400> SEQUENCE: 1283
ccaaugcacg gcagauuaua                                              20

<210> SEQ ID NO 1284
<211> LENGTH: 20
<212> TYPE: RNA
<213> ORGANISM: Artificial Sequence
<220> FEATURE:
<223> OTHER INFORMATION: synthesized

<400> SEQUENCE: 1284
ccaaugcaug gcagauuaua                                              20

<210> SEQ ID NO 1285
<211> LENGTH: 20
<212> TYPE: RNA
<213> ORGANISM: Artificial Sequence
<220> FEATURE:
<223> OTHER INFORMATION: synthesized

<400> SEQUENCE: 1285
ccaugcauug gcuuuuucuu                                              20

<210> SEQ ID NO 1286
<211> LENGTH: 20
<212> TYPE: RNA
<213> ORGANISM: Artificial Sequence
<220> FEATURE:
<223> OTHER INFORMATION: synthesized

<400> SEQUENCE: 1286
ccgugcauug gcuuuuucuu                                              20

```
<210> SEQ ID NO 1287
<211> LENGTH: 20
<212> TYPE: RNA
<213> ORGANISM: Artificial Sequence
<220> FEATURE:
<223> OTHER INFORMATION: synthesized

<400> SEQUENCE: 1287
cggcagauua uaauuuaagc                                               20

<210> SEQ ID NO 1288
<211> LENGTH: 20
<212> TYPE: RNA
<213> ORGANISM: Artificial Sequence
<220> FEATURE:
<223> OTHER INFORMATION: synthesized

<400> SEQUENCE: 1288
cgugcauugg cuuuuucuuu                                               20

<210> SEQ ID NO 1289
<211> LENGTH: 20
<212> TYPE: RNA
<213> ORGANISM: Artificial Sequence
<220> FEATURE:
<223> OTHER INFORMATION: synthesized

<400> SEQUENCE: 1289
cugccaugca uuggcuuuuu                                               20

<210> SEQ ID NO 1290
<211> LENGTH: 20
<212> TYPE: RNA
<213> ORGANISM: Artificial Sequence
<220> FEATURE:
<223> OTHER INFORMATION: synthesized

<400> SEQUENCE: 1290
cugccgugca uuggcuuuuu                                               20

<210> SEQ ID NO 1291
<211> LENGTH: 20
<212> TYPE: RNA
<213> ORGANISM: Artificial Sequence
<220> FEATURE:
<223> OTHER INFORMATION: synthesized

<400> SEQUENCE: 1291
cuuaaauuau aaucugccau                                               20

<210> SEQ ID NO 1292
<211> LENGTH: 20
<212> TYPE: RNA
<213> ORGANISM: Artificial Sequence
<220> FEATURE:
<223> OTHER INFORMATION: synthesized

<400> SEQUENCE: 1292
cuuaaauuau aaucugccgu                                               20

<210> SEQ ID NO 1293
<211> LENGTH: 20
<212> TYPE: RNA
<213> ORGANISM: Artificial Sequence
<220> FEATURE:
<223> OTHER INFORMATION: synthesized
```

```
<400> SEQUENCE: 1293
gaaaaagcca augcacggca                                               20

<210> SEQ ID NO 1294
<211> LENGTH: 20
<212> TYPE: RNA
<213> ORGANISM: Artificial Sequence
<220> FEATURE:
<223> OTHER INFORMATION: synthesized

<400> SEQUENCE: 1294
gaaaaagcca augcauggca                                               20

<210> SEQ ID NO 1295
<211> LENGTH: 20
<212> TYPE: RNA
<213> ORGANISM: Artificial Sequence
<220> FEATURE:
<223> OTHER INFORMATION: synthesized

<400> SEQUENCE: 1295
gcacggcaga uuauaauuua                                               20

<210> SEQ ID NO 1296
<211> LENGTH: 20
<212> TYPE: RNA
<213> ORGANISM: Artificial Sequence
<220> FEATURE:
<223> OTHER INFORMATION: synthesized

<400> SEQUENCE: 1296
gcauggcaga uuauaauuua                                               20

<210> SEQ ID NO 1297
<211> LENGTH: 20
<212> TYPE: RNA
<213> ORGANISM: Artificial Sequence
<220> FEATURE:
<223> OTHER INFORMATION: synthesized

<400> SEQUENCE: 1297
gccaaugcac ggcagauuau                                               20

<210> SEQ ID NO 1298
<211> LENGTH: 20
<212> TYPE: RNA
<213> ORGANISM: Artificial Sequence
<220> FEATURE:
<223> OTHER INFORMATION: synthesized

<400> SEQUENCE: 1298
gccaaugcau ggcagauuau                                               20

<210> SEQ ID NO 1299
<211> LENGTH: 20
<212> TYPE: RNA
<213> ORGANISM: Artificial Sequence
<220> FEATURE:
<223> OTHER INFORMATION: synthesized

<400> SEQUENCE: 1299
gccaugcauu ggcuuuuucu                                               20

<210> SEQ ID NO 1300
```

```
<211> LENGTH: 20
<212> TYPE: RNA
<213> ORGANISM: Artificial Sequence
<220> FEATURE:
<223> OTHER INFORMATION: synthesized

<400> SEQUENCE: 1300
gccgugcauu ggcuuuucu                                            20

<210> SEQ ID NO 1301
<211> LENGTH: 20
<212> TYPE: RNA
<213> ORGANISM: Artificial Sequence
<220> FEATURE:
<223> OTHER INFORMATION: synthesized

<400> SEQUENCE: 1301
gcuuaaauua uaaucugcca                                           20

<210> SEQ ID NO 1302
<211> LENGTH: 20
<212> TYPE: RNA
<213> ORGANISM: Artificial Sequence
<220> FEATURE:
<223> OTHER INFORMATION: synthesized

<400> SEQUENCE: 1302
gcuuaaauua uaaucugccg                                           20

<210> SEQ ID NO 1303
<211> LENGTH: 20
<212> TYPE: RNA
<213> ORGANISM: Artificial Sequence
<220> FEATURE:
<223> OTHER INFORMATION: synthesized

<400> SEQUENCE: 1303
uaaauuauaa ucugccaugc                                           20

<210> SEQ ID NO 1304
<211> LENGTH: 20
<212> TYPE: RNA
<213> ORGANISM: Artificial Sequence
<220> FEATURE:
<223> OTHER INFORMATION: synthesized

<400> SEQUENCE: 1304
uaaauuauaa ucugccgugc                                           20

<210> SEQ ID NO 1305
<211> LENGTH: 20
<212> TYPE: RNA
<213> ORGANISM: Artificial Sequence
<220> FEATURE:
<223> OTHER INFORMATION: synthesized

<400> SEQUENCE: 1305
uaaucugcca ugcauuggcu                                           20

<210> SEQ ID NO 1306
<211> LENGTH: 20
<212> TYPE: RNA
<213> ORGANISM: Artificial Sequence
<220> FEATURE:
<223> OTHER INFORMATION: synthesized

<400> SEQUENCE: 1306
```
uaaucugccg ugcauuggcu 20

<210> SEQ ID NO 1307
<211> LENGTH: 20
<212> TYPE: RNA
<213> ORGANISM: Artificial Sequence
<220> FEATURE:
<223> OTHER INFORMATION: synthesized

<400> SEQUENCE: 1307
uauaaucugc caugcauugg 20

<210> SEQ ID NO 1308
<211> LENGTH: 20
<212> TYPE: RNA
<213> ORGANISM: Artificial Sequence
<220> FEATURE:
<223> OTHER INFORMATION: synthesized

<400> SEQUENCE: 1308
uauaaucugc cgugcauugg 20

<210> SEQ ID NO 1309
<211> LENGTH: 20
<212> TYPE: RNA
<213> ORGANISM: Artificial Sequence
<220> FEATURE:
<223> OTHER INFORMATION: synthesized

<400> SEQUENCE: 1309
ucugccaugc auuggcuuuu 20

<210> SEQ ID NO 1310
<211> LENGTH: 20
<212> TYPE: RNA
<213> ORGANISM: Artificial Sequence
<220> FEATURE:
<223> OTHER INFORMATION: synthesized

<400> SEQUENCE: 1310
ucugccgugc auuggcuuuu 20

<210> SEQ ID NO 1311
<211> LENGTH: 20
<212> TYPE: RNA
<213> ORGANISM: Artificial Sequence
<220> FEATURE:
<223> OTHER INFORMATION: synthesized

<400> SEQUENCE: 1311
ugcacggcag auuauaauuu 20

<210> SEQ ID NO 1312
<211> LENGTH: 20
<212> TYPE: RNA
<213> ORGANISM: Artificial Sequence
<220> FEATURE:
<223> OTHER INFORMATION: synthesized

<400> SEQUENCE: 1312
ugcauggcag auuauaauuu 20

<210> SEQ ID NO 1313
<211> LENGTH: 20
<212> TYPE: RNA

```
<213> ORGANISM: Artificial Sequence
<220> FEATURE:
<223> OTHER INFORMATION: synthesized

<400> SEQUENCE: 1313
ugccaugcau uggcuuuuuc                                                    20

<210> SEQ ID NO 1314
<211> LENGTH: 20
<212> TYPE: RNA
<213> ORGANISM: Artificial Sequence
<220> FEATURE:
<223> OTHER INFORMATION: synthesized

<400> SEQUENCE: 1314
ugccgugcau uggcuuuuuc                                                    20

<210> SEQ ID NO 1315
<211> LENGTH: 20
<212> TYPE: RNA
<213> ORGANISM: Artificial Sequence
<220> FEATURE:
<223> OTHER INFORMATION: synthesized

<400> SEQUENCE: 1315
uggcagauua uaauuuaagc                                                    20

<210> SEQ ID NO 1316
<211> LENGTH: 20
<212> TYPE: RNA
<213> ORGANISM: Artificial Sequence
<220> FEATURE:
<223> OTHER INFORMATION: synthesized

<400> SEQUENCE: 1316
uuaaauuaua aucugccaug                                                    20

<210> SEQ ID NO 1317
<211> LENGTH: 20
<212> TYPE: RNA
<213> ORGANISM: Artificial Sequence
<220> FEATURE:
<223> OTHER INFORMATION: synthesized

<400> SEQUENCE: 1317
uuaaauuaua aucugccgug                                                    20

<210> SEQ ID NO 1318
<211> LENGTH: 20
<212> TYPE: RNA
<213> ORGANISM: Artificial Sequence
<220> FEATURE:
<223> OTHER INFORMATION: synthesized

<400> SEQUENCE: 1318
uuauaaucug ccaugcauug                                                    20

<210> SEQ ID NO 1319
<211> LENGTH: 20
<212> TYPE: RNA
<213> ORGANISM: Artificial Sequence
<220> FEATURE:
<223> OTHER INFORMATION: synthesized

<400> SEQUENCE: 1319
uuauaaucug ccgugcauug                                                    20
```

<210> SEQ ID NO 1320
<211> LENGTH: 20
<212> TYPE: RNA
<213> ORGANISM: Artificial Sequence
<220> FEATURE:
<223> OTHER INFORMATION: synthesized

<400> SEQUENCE: 1320
aaauuaggug ccaggaaauu                                              20

<210> SEQ ID NO 1321
<211> LENGTH: 20
<212> TYPE: RNA
<213> ORGANISM: Artificial Sequence
<220> FEATURE:
<223> OTHER INFORMATION: synthesized

<400> SEQUENCE: 1321
aaucuauggc uaaguggacc                                              20

<210> SEQ ID NO 1322
<211> LENGTH: 20
<212> TYPE: RNA
<213> ORGANISM: Artificial Sequence
<220> FEATURE:
<223> OTHER INFORMATION: synthesized

<400> SEQUENCE: 1322
aauuuauggc uaaguggacc                                              20

<210> SEQ ID NO 1323
<211> LENGTH: 20
<212> TYPE: RNA
<213> ORGANISM: Artificial Sequence
<220> FEATURE:
<223> OTHER INFORMATION: synthesized

<400> SEQUENCE: 1323
aauuuccugg caccuaaucu                                              20

<210> SEQ ID NO 1324
<211> LENGTH: 20
<212> TYPE: RNA
<213> ORGANISM: Artificial Sequence
<220> FEATURE:
<223> OTHER INFORMATION: synthesized

<400> SEQUENCE: 1324
aauuuccugg caccuaauuu                                              20

<210> SEQ ID NO 1325
<211> LENGTH: 20
<212> TYPE: RNA
<213> ORGANISM: Artificial Sequence
<220> FEATURE:
<223> OTHER INFORMATION: synthesized

<400> SEQUENCE: 1325
accuaaucua uggcuaagug                                              20

<210> SEQ ID NO 1326
<211> LENGTH: 20
<212> TYPE: RNA
<213> ORGANISM: Artificial Sequence
<220> FEATURE:

-continued

<223> OTHER INFORMATION: synthesized

<400> SEQUENCE: 1326
accuaauuua uggcuaagug                                          20

<210> SEQ ID NO 1327
<211> LENGTH: 20
<212> TYPE: RNA
<213> ORGANISM: Artificial Sequence
<220> FEATURE:
<223> OTHER INFORMATION: synthesized

<400> SEQUENCE: 1327
acuuagccau aaauuaggug                                          20

<210> SEQ ID NO 1328
<211> LENGTH: 20
<212> TYPE: RNA
<213> ORGANISM: Artificial Sequence
<220> FEATURE:
<223> OTHER INFORMATION: synthesized

<400> SEQUENCE: 1328
acuuagccau agauuaggug                                          20

<210> SEQ ID NO 1329
<211> LENGTH: 20
<212> TYPE: RNA
<213> ORGANISM: Artificial Sequence
<220> FEATURE:
<223> OTHER INFORMATION: synthesized

<400> SEQUENCE: 1329
agauuaggug ccaggaaauu                                          20

<210> SEQ ID NO 1330
<211> LENGTH: 20
<212> TYPE: RNA
<213> ORGANISM: Artificial Sequence
<220> FEATURE:
<223> OTHER INFORMATION: synthesized

<400> SEQUENCE: 1330
agccauaaau uaggugccag                                          20

<210> SEQ ID NO 1331
<211> LENGTH: 20
<212> TYPE: RNA
<213> ORGANISM: Artificial Sequence
<220> FEATURE:
<223> OTHER INFORMATION: synthesized

<400> SEQUENCE: 1331
agccauagau uaggugccag                                          20

<210> SEQ ID NO 1332
<211> LENGTH: 20
<212> TYPE: RNA
<213> ORGANISM: Artificial Sequence
<220> FEATURE:
<223> OTHER INFORMATION: synthesized

<400> SEQUENCE: 1332
aggguccacu uagccauaaa                                          20

```
<210> SEQ ID NO 1333
<211> LENGTH: 20
<212> TYPE: RNA
<213> ORGANISM: Artificial Sequence
<220> FEATURE:
<223> OTHER INFORMATION: synthesized

<400> SEQUENCE: 1333
aggguccacu uagccauaga                                               20

<210> SEQ ID NO 1334
<211> LENGTH: 20
<212> TYPE: RNA
<213> ORGANISM: Artificial Sequence
<220> FEATURE:
<223> OTHER INFORMATION: synthesized

<400> SEQUENCE: 1334
auaaauuagg ugccaggaaa                                               20

<210> SEQ ID NO 1335
<211> LENGTH: 20
<212> TYPE: RNA
<213> ORGANISM: Artificial Sequence
<220> FEATURE:
<223> OTHER INFORMATION: synthesized

<400> SEQUENCE: 1335
auagauuagg ugccaggaaa                                               20

<210> SEQ ID NO 1336
<211> LENGTH: 20
<212> TYPE: RNA
<213> ORGANISM: Artificial Sequence
<220> FEATURE:
<223> OTHER INFORMATION: synthesized

<400> SEQUENCE: 1336
aucuauggcu aaguggaccc                                               20

<210> SEQ ID NO 1337
<211> LENGTH: 20
<212> TYPE: RNA
<213> ORGANISM: Artificial Sequence
<220> FEATURE:
<223> OTHER INFORMATION: synthesized

<400> SEQUENCE: 1337
auuuauggcu aaguggaccc                                               20

<210> SEQ ID NO 1338
<211> LENGTH: 20
<212> TYPE: RNA
<213> ORGANISM: Artificial Sequence
<220> FEATURE:
<223> OTHER INFORMATION: synthesized

<400> SEQUENCE: 1338
caauuuccug gcaccuaauc                                               20

<210> SEQ ID NO 1339
<211> LENGTH: 20
<212> TYPE: RNA
<213> ORGANISM: Artificial Sequence
<220> FEATURE:
<223> OTHER INFORMATION: synthesized
```

```
<400> SEQUENCE: 1339
caauuuccug gcaccuaauu                                                    20

<210> SEQ ID NO 1340
<211> LENGTH: 20
<212> TYPE: RNA
<213> ORGANISM: Artificial Sequence
<220> FEATURE:
<223> OTHER INFORMATION: synthesized

<400> SEQUENCE: 1340
cacuuagcca uaaauuaggu                                                    20

<210> SEQ ID NO 1341
<211> LENGTH: 20
<212> TYPE: RNA
<213> ORGANISM: Artificial Sequence
<220> FEATURE:
<223> OTHER INFORMATION: synthesized

<400> SEQUENCE: 1341
cacuuagcca uagauuaggu                                                    20

<210> SEQ ID NO 1342
<211> LENGTH: 20
<212> TYPE: RNA
<213> ORGANISM: Artificial Sequence
<220> FEATURE:
<223> OTHER INFORMATION: synthesized

<400> SEQUENCE: 1342
cauaaauuag gugccaggaa                                                    20

<210> SEQ ID NO 1343
<211> LENGTH: 20
<212> TYPE: RNA
<213> ORGANISM: Artificial Sequence
<220> FEATURE:
<223> OTHER INFORMATION: synthesized

<400> SEQUENCE: 1343
cauagauuag gugccaggaa                                                    20

<210> SEQ ID NO 1344
<211> LENGTH: 20
<212> TYPE: RNA
<213> ORGANISM: Artificial Sequence
<220> FEATURE:
<223> OTHER INFORMATION: synthesized

<400> SEQUENCE: 1344
ccacuuagcc auaaauuagg                                                    20

<210> SEQ ID NO 1345
<211> LENGTH: 20
<212> TYPE: RNA
<213> ORGANISM: Artificial Sequence
<220> FEATURE:
<223> OTHER INFORMATION: synthesized

<400> SEQUENCE: 1345
ccacuuagcc auagauuagg                                                    20

<210> SEQ ID NO 1346
<211> LENGTH: 20
```

-continued

```
<212> TYPE: RNA
<213> ORGANISM: Artificial Sequence
<220> FEATURE:
<223> OTHER INFORMATION: synthesized

<400> SEQUENCE: 1346
ccauaaauua ggugccagga                                              20

<210> SEQ ID NO 1347
<211> LENGTH: 20
<212> TYPE: RNA
<213> ORGANISM: Artificial Sequence
<220> FEATURE:
<223> OTHER INFORMATION: synthesized

<400> SEQUENCE: 1347
ccauagauua ggugccagga                                              20

<210> SEQ ID NO 1348
<211> LENGTH: 20
<212> TYPE: RNA
<213> ORGANISM: Artificial Sequence
<220> FEATURE:
<223> OTHER INFORMATION: synthesized

<400> SEQUENCE: 1348
ccuaaucuau ggcuaagugg                                              20

<210> SEQ ID NO 1349
<211> LENGTH: 20
<212> TYPE: RNA
<213> ORGANISM: Artificial Sequence
<220> FEATURE:
<223> OTHER INFORMATION: synthesized

<400> SEQUENCE: 1349
ccuaauuuau ggcuaagugg                                              20

<210> SEQ ID NO 1350
<211> LENGTH: 20
<212> TYPE: RNA
<213> ORGANISM: Artificial Sequence
<220> FEATURE:
<223> OTHER INFORMATION: synthesized

<400> SEQUENCE: 1350
ccuggcaccu aaucuauggc                                              20

<210> SEQ ID NO 1351
<211> LENGTH: 20
<212> TYPE: RNA
<213> ORGANISM: Artificial Sequence
<220> FEATURE:
<223> OTHER INFORMATION: synthesized

<400> SEQUENCE: 1351
ccuggcaccu aauuuauggc                                              20

<210> SEQ ID NO 1352
<211> LENGTH: 20
<212> TYPE: RNA
<213> ORGANISM: Artificial Sequence
<220> FEATURE:
<223> OTHER INFORMATION: synthesized

<400> SEQUENCE: 1352
```
cuaaucuaug gcuaagugga 20

<210> SEQ ID NO 1353
<211> LENGTH: 20
<212> TYPE: RNA
<213> ORGANISM: Artificial Sequence
<220> FEATURE:
<223> OTHER INFORMATION: synthesized

<400> SEQUENCE: 1353
cuaauuuaug gcuaagugga 20

<210> SEQ ID NO 1354
<211> LENGTH: 20
<212> TYPE: RNA
<213> ORGANISM: Artificial Sequence
<220> FEATURE:
<223> OTHER INFORMATION: synthesized

<400> SEQUENCE: 1354
cuauggcuaa guggacccuc 20

<210> SEQ ID NO 1355
<211> LENGTH: 20
<212> TYPE: RNA
<213> ORGANISM: Artificial Sequence
<220> FEATURE:
<223> OTHER INFORMATION: synthesized

<400> SEQUENCE: 1355
cuggcaccua aucuauggcu 20

<210> SEQ ID NO 1356
<211> LENGTH: 20
<212> TYPE: RNA
<213> ORGANISM: Artificial Sequence
<220> FEATURE:
<223> OTHER INFORMATION: synthesized

<400> SEQUENCE: 1356
cuggcaccua auuuauggcu 20

<210> SEQ ID NO 1357
<211> LENGTH: 20
<212> TYPE: RNA
<213> ORGANISM: Artificial Sequence
<220> FEATURE:
<223> OTHER INFORMATION: synthesized

<400> SEQUENCE: 1357
cuuagccaua aauuaggugc 20

<210> SEQ ID NO 1358
<211> LENGTH: 20
<212> TYPE: RNA
<213> ORGANISM: Artificial Sequence
<220> FEATURE:
<223> OTHER INFORMATION: synthesized

<400> SEQUENCE: 1358
cuuagccaua gauuaggugc 20

<210> SEQ ID NO 1359
<211> LENGTH: 20
<212> TYPE: RNA
<213> ORGANISM: Artificial Sequence

```
<220> FEATURE:
<223> OTHER INFORMATION: synthesized

<400> SEQUENCE: 1359
gagggtccac uuagccauaa                                              20

<210> SEQ ID NO 1360
<211> LENGTH: 20
<212> TYPE: RNA
<213> ORGANISM: Artificial Sequence
<220> FEATURE:
<223> OTHER INFORMATION: synthesized

<400> SEQUENCE: 1360
gagggtccac uuagccauag                                              20

<210> SEQ ID NO 1361
<211> LENGTH: 20
<212> TYPE: RNA
<213> ORGANISM: Artificial Sequence
<220> FEATURE:
<223> OTHER INFORMATION: synthesized

<400> SEQUENCE: 1361
gccauaaauu aggugccagg                                              20

<210> SEQ ID NO 1362
<211> LENGTH: 20
<212> TYPE: RNA
<213> ORGANISM: Artificial Sequence
<220> FEATURE:
<223> OTHER INFORMATION: synthesized

<400> SEQUENCE: 1362
gccauagauu aggugccagg                                              20

<210> SEQ ID NO 1363
<211> LENGTH: 20
<212> TYPE: RNA
<213> ORGANISM: Artificial Sequence
<220> FEATURE:
<223> OTHER INFORMATION: synthesized

<400> SEQUENCE: 1363
ggguccacuu agccauaaau                                              20

<210> SEQ ID NO 1364
<211> LENGTH: 20
<212> TYPE: RNA
<213> ORGANISM: Artificial Sequence
<220> FEATURE:
<223> OTHER INFORMATION: synthesized

<400> SEQUENCE: 1364
ggguccacuu agccauagau                                              20

<210> SEQ ID NO 1365
<211> LENGTH: 20
<212> TYPE: RNA
<213> ORGANISM: Artificial Sequence
<220> FEATURE:
<223> OTHER INFORMATION: synthesized

<400> SEQUENCE: 1365
uaaucuaugg cuaaguggac                                              20
```

```
<210> SEQ ID NO 1366
<211> LENGTH: 20
<212> TYPE: RNA
<213> ORGANISM: Artificial Sequence
<220> FEATURE:
<223> OTHER INFORMATION: synthesized

<400> SEQUENCE: 1366
uaauuuaugg cuaaguggac                                               20

<210> SEQ ID NO 1367
<211> LENGTH: 20
<212> TYPE: RNA
<213> ORGANISM: Artificial Sequence
<220> FEATURE:
<223> OTHER INFORMATION: synthesized

<400> SEQUENCE: 1367
uccacuuagc cauaaauuag                                               20

<210> SEQ ID NO 1368
<211> LENGTH: 20
<212> TYPE: RNA
<213> ORGANISM: Artificial Sequence
<220> FEATURE:
<223> OTHER INFORMATION: synthesized

<400> SEQUENCE: 1368
uccacuuagc cauagauuag                                               20

<210> SEQ ID NO 1369
<211> LENGTH: 20
<212> TYPE: RNA
<213> ORGANISM: Artificial Sequence
<220> FEATURE:
<223> OTHER INFORMATION: synthesized

<400> SEQUENCE: 1369
uccuggcacc uaaucuaugg                                               20

<210> SEQ ID NO 1370
<211> LENGTH: 20
<212> TYPE: RNA
<213> ORGANISM: Artificial Sequence
<220> FEATURE:
<223> OTHER INFORMATION: synthesized

<400> SEQUENCE: 1370
uccuggcacc uaauuuaugg                                               20

<210> SEQ ID NO 1371
<211> LENGTH: 20
<212> TYPE: RNA
<213> ORGANISM: Artificial Sequence
<220> FEATURE:
<223> OTHER INFORMATION: synthesized

<400> SEQUENCE: 1371
ucuauggcua aguggacccu                                               20

<210> SEQ ID NO 1372
<211> LENGTH: 20
<212> TYPE: RNA
<213> ORGANISM: Artificial Sequence
<220> FEATURE:
<223> OTHER INFORMATION: synthesized
```

```
<400> SEQUENCE: 1372
uuauggcuaa guggacccuc                                              20

<210> SEQ ID NO 1373
<211> LENGTH: 20
<212> TYPE: RNA
<213> ORGANISM: Artificial Sequence
<220> FEATURE:
<223> OTHER INFORMATION: synthesized

<400> SEQUENCE: 1373
uuccuggcac cuaaucuaug                                              20

<210> SEQ ID NO 1374
<211> LENGTH: 20
<212> TYPE: RNA
<213> ORGANISM: Artificial Sequence
<220> FEATURE:
<223> OTHER INFORMATION: synthesized

<400> SEQUENCE: 1374
uuccuggcac cuaauuuaug                                              20

<210> SEQ ID NO 1375
<211> LENGTH: 20
<212> TYPE: RNA
<213> ORGANISM: Artificial Sequence
<220> FEATURE:
<223> OTHER INFORMATION: synthesized

<400> SEQUENCE: 1375
uuuauggcua aguggacccu                                              20

<210> SEQ ID NO 1376
<211> LENGTH: 20
<212> TYPE: RNA
<213> ORGANISM: Artificial Sequence
<220> FEATURE:
<223> OTHER INFORMATION: synthesized

<400> SEQUENCE: 1376
uuuccuggca ccuaaucuau                                              20

<210> SEQ ID NO 1377
<211> LENGTH: 20
<212> TYPE: RNA
<213> ORGANISM: Artificial Sequence
<220> FEATURE:
<223> OTHER INFORMATION: synthesized

<400> SEQUENCE: 1377
uuuccuggca ccuaauuuau                                              20

<210> SEQ ID NO 1378
<211> LENGTH: 20
<212> TYPE: RNA
<213> ORGANISM: Artificial Sequence
<220> FEATURE:
<223> OTHER INFORMATION: synthesized

<400> SEQUENCE: 1378
aaaaacaagg acaucuggga                                              20

<210> SEQ ID NO 1379
```

```
<211> LENGTH: 20
<212> TYPE: RNA
<213> ORGANISM: Artificial Sequence
<220> FEATURE:
<223> OTHER INFORMATION: synthesized

<400> SEQUENCE: 1379
agaaacaagg acaucuggga                                           20

<210> SEQ ID NO 1380
<211> LENGTH: 20
<212> TYPE: RNA
<213> ORGANISM: Artificial Sequence
<220> FEATURE:
<223> OTHER INFORMATION: synthesized

<400> SEQUENCE: 1380
caaaaacaag gacaucuggg                                           20

<210> SEQ ID NO 1381
<211> LENGTH: 20
<212> TYPE: RNA
<213> ORGANISM: Artificial Sequence
<220> FEATURE:
<223> OTHER INFORMATION: synthesized

<400> SEQUENCE: 1381
cagaaacaag gacaucuggg                                           20

<210> SEQ ID NO 1382
<211> LENGTH: 20
<212> TYPE: RNA
<213> ORGANISM: Artificial Sequence
<220> FEATURE:
<223> OTHER INFORMATION: synthesized

<400> SEQUENCE: 1382
cagauguccu uguuucugag                                           20

<210> SEQ ID NO 1383
<211> LENGTH: 20
<212> TYPE: RNA
<213> ORGANISM: Artificial Sequence
<220> FEATURE:
<223> OTHER INFORMATION: synthesized

<400> SEQUENCE: 1383
cagauguccu uguuuugag                                            20

<210> SEQ ID NO 1384
<211> LENGTH: 20
<212> TYPE: RNA
<213> ORGANISM: Artificial Sequence
<220> FEATURE:
<223> OTHER INFORMATION: synthesized

<400> SEQUENCE: 1384
ccagaugucc uuguuucuga                                           20

<210> SEQ ID NO 1385
<211> LENGTH: 20
<212> TYPE: RNA
<213> ORGANISM: Artificial Sequence
<220> FEATURE:
<223> OTHER INFORMATION: synthesized

<400> SEQUENCE: 1385
```
ccagaugucc uuguuuuga                                              20

<210> SEQ ID NO 1386
<211> LENGTH: 20
<212> TYPE: RNA
<213> ORGANISM: Artificial Sequence
<220> FEATURE:
<223> OTHER INFORMATION: synthesized

<400> SEQUENCE: 1386
cccagauguc cuuguuucug                                             20

<210> SEQ ID NO 1387
<211> LENGTH: 20
<212> TYPE: RNA
<213> ORGANISM: Artificial Sequence
<220> FEATURE:
<223> OTHER INFORMATION: synthesized

<400> SEQUENCE: 1387
cccagauguc cuuguuuug                                              20

<210> SEQ ID NO 1388
<211> LENGTH: 20
<212> TYPE: RNA
<213> ORGANISM: Artificial Sequence
<220> FEATURE:
<223> OTHER INFORMATION: synthesized

<400> SEQUENCE: 1388
cccucuacuc aaaaacaagg                                             20

<210> SEQ ID NO 1389
<211> LENGTH: 20
<212> TYPE: RNA
<213> ORGANISM: Artificial Sequence
<220> FEATURE:
<223> OTHER INFORMATION: synthesized

<400> SEQUENCE: 1389
cccucuacuc agaaacaagg                                             20

<210> SEQ ID NO 1390
<211> LENGTH: 20
<212> TYPE: RNA
<213> ORGANISM: Artificial Sequence
<220> FEATURE:
<223> OTHER INFORMATION: synthesized

<400> SEQUENCE: 1390
ccucuacuca aaacaagga                                              20

<210> SEQ ID NO 1391
<211> LENGTH: 20
<212> TYPE: RNA
<213> ORGANISM: Artificial Sequence
<220> FEATURE:
<223> OTHER INFORMATION: synthesized

<400> SEQUENCE: 1391
ccucuacuca gaaacaagga                                             20

<210> SEQ ID NO 1392
<211> LENGTH: 20
<212> TYPE: RNA

```
<213> ORGANISM: Artificial Sequence
<220> FEATURE:
<223> OTHER INFORMATION: synthesized

<400> SEQUENCE: 1392
ccuuguuucu gaguagaggg                                              20

<210> SEQ ID NO 1393
<211> LENGTH: 20
<212> TYPE: RNA
<213> ORGANISM: Artificial Sequence
<220> FEATURE:
<223> OTHER INFORMATION: synthesized

<400> SEQUENCE: 1393
ccuuguuuuu gaguagaggg                                              20

<210> SEQ ID NO 1394
<211> LENGTH: 20
<212> TYPE: RNA
<213> ORGANISM: Artificial Sequence
<220> FEATURE:
<223> OTHER INFORMATION: synthesized

<400> SEQUENCE: 1394
ccuuuucccu cuacucaaaa                                              20

<210> SEQ ID NO 1395
<211> LENGTH: 20
<212> TYPE: RNA
<213> ORGANISM: Artificial Sequence
<220> FEATURE:
<223> OTHER INFORMATION: synthesized

<400> SEQUENCE: 1395
ccuuuucccu cuacucagaa                                              20

<210> SEQ ID NO 1396
<211> LENGTH: 20
<212> TYPE: RNA
<213> ORGANISM: Artificial Sequence
<220> FEATURE:
<223> OTHER INFORMATION: synthesized

<400> SEQUENCE: 1396
cuacucaaaa acaaggacau                                              20

<210> SEQ ID NO 1397
<211> LENGTH: 20
<212> TYPE: RNA
<213> ORGANISM: Artificial Sequence
<220> FEATURE:
<223> OTHER INFORMATION: synthesized

<400> SEQUENCE: 1397
cuacucagaa acaaggacau                                              20

<210> SEQ ID NO 1398
<211> LENGTH: 20
<212> TYPE: RNA
<213> ORGANISM: Artificial Sequence
<220> FEATURE:
<223> OTHER INFORMATION: synthesized

<400> SEQUENCE: 1398
cucuacucaa aaacaaggac                                              20
```

```
<210> SEQ ID NO 1399
<211> LENGTH: 20
<212> TYPE: RNA
<213> ORGANISM: Artificial Sequence
<220> FEATURE:
<223> OTHER INFORMATION: synthesized

<400> SEQUENCE: 1399
cucuacucag aaacaaggac                                              20

<210> SEQ ID NO 1400
<211> LENGTH: 20
<212> TYPE: RNA
<213> ORGANISM: Artificial Sequence
<220> FEATURE:
<223> OTHER INFORMATION: synthesized

<400> SEQUENCE: 1400
cuuguuucug aguagaggga                                              20

<210> SEQ ID NO 1401
<211> LENGTH: 20
<212> TYPE: RNA
<213> ORGANISM: Artificial Sequence
<220> FEATURE:
<223> OTHER INFORMATION: synthesized

<400> SEQUENCE: 1401
cuuguuuuug aguagaggga                                              20

<210> SEQ ID NO 1402
<211> LENGTH: 20
<212> TYPE: RNA
<213> ORGANISM: Artificial Sequence
<220> FEATURE:
<223> OTHER INFORMATION: synthesized

<400> SEQUENCE: 1402
cuuuucccuc uacucaaaaa                                              20

<210> SEQ ID NO 1403
<211> LENGTH: 20
<212> TYPE: RNA
<213> ORGANISM: Artificial Sequence
<220> FEATURE:
<223> OTHER INFORMATION: synthesized

<400> SEQUENCE: 1403
cuuuucccuc uacucagaaa                                              20

<210> SEQ ID NO 1404
<211> LENGTH: 20
<212> TYPE: RNA
<213> ORGANISM: Artificial Sequence
<220> FEATURE:
<223> OTHER INFORMATION: synthesized

<400> SEQUENCE: 1404
gauguccuug uuucugagua                                              20

<210> SEQ ID NO 1405
<211> LENGTH: 20
<212> TYPE: RNA
<213> ORGANISM: Artificial Sequence
<220> FEATURE:
```

<223> OTHER INFORMATION: synthesized

<400> SEQUENCE: 1405
gauguccuug uuuuugagua                                           20

<210> SEQ ID NO 1406
<211> LENGTH: 20
<212> TYPE: RNA
<213> ORGANISM: Artificial Sequence
<220> FEATURE:
<223> OTHER INFORMATION: synthesized

<400> SEQUENCE: 1406
ucccagaugu ccuuguuucu                                           20

<210> SEQ ID NO 1407
<211> LENGTH: 20
<212> TYPE: RNA
<213> ORGANISM: Artificial Sequence
<220> FEATURE:
<223> OTHER INFORMATION: synthesized

<400> SEQUENCE: 1407
ucccagaugu ccuuguuuuu                                           20

<210> SEQ ID NO 1408
<211> LENGTH: 20
<212> TYPE: RNA
<213> ORGANISM: Artificial Sequence
<220> FEATURE:
<223> OTHER INFORMATION: synthesized

<400> SEQUENCE: 1408
ucccucuacu caaaaacaag                                           20

<210> SEQ ID NO 1409
<211> LENGTH: 20
<212> TYPE: RNA
<213> ORGANISM: Artificial Sequence
<220> FEATURE:
<223> OTHER INFORMATION: synthesized

<400> SEQUENCE: 1409
ucccucuacu cagaaacaag                                           20

<210> SEQ ID NO 1410
<211> LENGTH: 20
<212> TYPE: RNA
<213> ORGANISM: Artificial Sequence
<220> FEATURE:
<223> OTHER INFORMATION: synthesized

<400> SEQUENCE: 1410
uccuuguuuc ugaguagagg                                           20

<210> SEQ ID NO 1411
<211> LENGTH: 20
<212> TYPE: RNA
<213> ORGANISM: Artificial Sequence
<220> FEATURE:
<223> OTHER INFORMATION: synthesized

<400> SEQUENCE: 1411
uccuuguuuu ugaguagagg                                           20

```
<210> SEQ ID NO 1412
<211> LENGTH: 20
<212> TYPE: RNA
<213> ORGANISM: Artificial Sequence
<220> FEATURE:
<223> OTHER INFORMATION: synthesized

<400> SEQUENCE: 1412
uccuuuuccc ucuacucaaa                                                20

<210> SEQ ID NO 1413
<211> LENGTH: 20
<212> TYPE: RNA
<213> ORGANISM: Artificial Sequence
<220> FEATURE:
<223> OTHER INFORMATION: synthesized

<400> SEQUENCE: 1413
uccuuuuccc ucuacucaga                                                20

<210> SEQ ID NO 1414
<211> LENGTH: 20
<212> TYPE: RNA
<213> ORGANISM: Artificial Sequence
<220> FEATURE:
<223> OTHER INFORMATION: synthesized

<400> SEQUENCE: 1414
ucuacucaaa aacaaggaca                                                20

<210> SEQ ID NO 1415
<211> LENGTH: 20
<212> TYPE: RNA
<213> ORGANISM: Artificial Sequence
<220> FEATURE:
<223> OTHER INFORMATION: synthesized

<400> SEQUENCE: 1415
ucuacucaga aacaaggaca                                                20

<210> SEQ ID NO 1416
<211> LENGTH: 20
<212> TYPE: RNA
<213> ORGANISM: Artificial Sequence
<220> FEATURE:
<223> OTHER INFORMATION: synthesized

<400> SEQUENCE: 1416
uuccuuuucc cucuacucaa                                                20

<210> SEQ ID NO 1417
<211> LENGTH: 20
<212> TYPE: RNA
<213> ORGANISM: Artificial Sequence
<220> FEATURE:
<223> OTHER INFORMATION: synthesized

<400> SEQUENCE: 1417
uuccuuuucc cucuacucag                                                20

<210> SEQ ID NO 1418
<211> LENGTH: 20
<212> TYPE: RNA
<213> ORGANISM: Artificial Sequence
<220> FEATURE:
<223> OTHER INFORMATION: synthesized
```

```
<400> SEQUENCE: 1418
uucugaguag agggaaaagg                                                  20

<210> SEQ ID NO 1419
<211> LENGTH: 20
<212> TYPE: RNA
<213> ORGANISM: Artificial Sequence
<220> FEATURE:
<223> OTHER INFORMATION: synthesized

<400> SEQUENCE: 1419
uuguuucuga guagagggaa                                                  20

<210> SEQ ID NO 1420
<211> LENGTH: 20
<212> TYPE: RNA
<213> ORGANISM: Artificial Sequence
<220> FEATURE:
<223> OTHER INFORMATION: synthesized

<400> SEQUENCE: 1420
uuguuuuuga guagagggaa                                                  20

<210> SEQ ID NO 1421
<211> LENGTH: 20
<212> TYPE: RNA
<213> ORGANISM: Artificial Sequence
<220> FEATURE:
<223> OTHER INFORMATION: synthesized

<400> SEQUENCE: 1421
uuuugaguag agggaaaagg                                                  20

<210> SEQ ID NO 1422
<211> LENGTH: 20
<212> TYPE: RNA
<213> ORGANISM: Artificial Sequence
<220> FEATURE:
<223> OTHER INFORMATION: synthesized

<400> SEQUENCE: 1422
uuuuugagua gagggaaaag                                                  20

<210> SEQ ID NO 1423
<211> LENGTH: 20
<212> TYPE: RNA
<213> ORGANISM: Artificial Sequence
<220> FEATURE:
<223> OTHER INFORMATION: synthesized

<400> SEQUENCE: 1423
aagguacugc auggaaaaac                                                  20

<210> SEQ ID NO 1424
<211> LENGTH: 20
<212> TYPE: RNA
<213> ORGANISM: Artificial Sequence
<220> FEATURE:
<223> OTHER INFORMATION: synthesized

<400> SEQUENCE: 1424
aagguacugc guggaaaaac                                                  20

<210> SEQ ID NO 1425
<211> LENGTH: 20
```

```
<212> TYPE: RNA
<213> ORGANISM: Artificial Sequence
<220> FEATURE:
<223> OTHER INFORMATION: synthesized

<400> SEQUENCE: 1425
acucugcuug guuuuccac                                                20

<210> SEQ ID NO 1426
<211> LENGTH: 20
<212> TYPE: RNA
<213> ORGANISM: Artificial Sequence
<220> FEATURE:
<223> OTHER INFORMATION: synthesized

<400> SEQUENCE: 1426
acucugcuug guuuuccau                                                20

<210> SEQ ID NO 1427
<211> LENGTH: 20
<212> TYPE: RNA
<213> ORGANISM: Artificial Sequence
<220> FEATURE:
<223> OTHER INFORMATION: synthesized

<400> SEQUENCE: 1427
agguacugca uggaaaaacc                                               20

<210> SEQ ID NO 1428
<211> LENGTH: 20
<212> TYPE: RNA
<213> ORGANISM: Artificial Sequence
<220> FEATURE:
<223> OTHER INFORMATION: synthesized

<400> SEQUENCE: 1428
agguacugcg uggaaaaacc                                               20

<210> SEQ ID NO 1429
<211> LENGTH: 20
<212> TYPE: RNA
<213> ORGANISM: Artificial Sequence
<220> FEATURE:
<223> OTHER INFORMATION: synthesized

<400> SEQUENCE: 1429
auaagguacu gcauggaaaa                                               20

<210> SEQ ID NO 1430
<211> LENGTH: 20
<212> TYPE: RNA
<213> ORGANISM: Artificial Sequence
<220> FEATURE:
<223> OTHER INFORMATION: synthesized

<400> SEQUENCE: 1430
auaagguacu gcguggaaaa                                               20

<210> SEQ ID NO 1431
<211> LENGTH: 20
<212> TYPE: RNA
<213> ORGANISM: Artificial Sequence
<220> FEATURE:
<223> OTHER INFORMATION: synthesized

<400> SEQUENCE: 1431
```
auggaaaaac caagcagagu                                          20

<210> SEQ ID NO 1432
<211> LENGTH: 20
<212> TYPE: RNA
<213> ORGANISM: Artificial Sequence
<220> FEATURE:
<223> OTHER INFORMATION: synthesized

<400> SEQUENCE: 1432
cauggaaaaa ccaagcagag                                          20

<210> SEQ ID NO 1433
<211> LENGTH: 20
<212> TYPE: RNA
<213> ORGANISM: Artificial Sequence
<220> FEATURE:
<223> OTHER INFORMATION: synthesized

<400> SEQUENCE: 1433
ccacgcagua ccuuauaacu                                          20

<210> SEQ ID NO 1434
<211> LENGTH: 20
<212> TYPE: RNA
<213> ORGANISM: Artificial Sequence
<220> FEATURE:
<223> OTHER INFORMATION: synthesized

<400> SEQUENCE: 1434
ccaugcagua ccuuauaacu                                          20

<210> SEQ ID NO 1435
<211> LENGTH: 20
<212> TYPE: RNA
<213> ORGANISM: Artificial Sequence
<220> FEATURE:
<223> OTHER INFORMATION: synthesized

<400> SEQUENCE: 1435
cguggaaaaa ccaagcagag                                          20

<210> SEQ ID NO 1436
<211> LENGTH: 20
<212> TYPE: RNA
<213> ORGANISM: Artificial Sequence
<220> FEATURE:
<223> OTHER INFORMATION: synthesized

<400> SEQUENCE: 1436
cucugcuugg uuuuuccacg                                          20

<210> SEQ ID NO 1437
<211> LENGTH: 20
<212> TYPE: RNA
<213> ORGANISM: Artificial Sequence
<220> FEATURE:
<223> OTHER INFORMATION: synthesized

<400> SEQUENCE: 1437
cucugcuugg uuuuuccaug                                          20

<210> SEQ ID NO 1438
<211> LENGTH: 20
<212> TYPE: RNA
<213> ORGANISM: Artificial Sequence

```
<220> FEATURE:
<223> OTHER INFORMATION: synthesized

<400> SEQUENCE: 1438
cugcauggaa aaaccaagca                                                  20

<210> SEQ ID NO 1439
<211> LENGTH: 20
<212> TYPE: RNA
<213> ORGANISM: Artificial Sequence
<220> FEATURE:
<223> OTHER INFORMATION: synthesized

<400> SEQUENCE: 1439
cugcguggaa aaaccaagca                                                  20

<210> SEQ ID NO 1440
<211> LENGTH: 20
<212> TYPE: RNA
<213> ORGANISM: Artificial Sequence
<220> FEATURE:
<223> OTHER INFORMATION: synthesized

<400> SEQUENCE: 1440
cugcuugguu uuuccacgca                                                  20

<210> SEQ ID NO 1441
<211> LENGTH: 20
<212> TYPE: RNA
<213> ORGANISM: Artificial Sequence
<220> FEATURE:
<223> OTHER INFORMATION: synthesized

<400> SEQUENCE: 1441
cugcuugguu uuuccaugca                                                  20

<210> SEQ ID NO 1442
<211> LENGTH: 20
<212> TYPE: RNA
<213> ORGANISM: Artificial Sequence
<220> FEATURE:
<223> OTHER INFORMATION: synthesized

<400> SEQUENCE: 1442
cuugguuuuu ccacgcagua                                                  20

<210> SEQ ID NO 1443
<211> LENGTH: 20
<212> TYPE: RNA
<213> ORGANISM: Artificial Sequence
<220> FEATURE:
<223> OTHER INFORMATION: synthesized

<400> SEQUENCE: 1443
cuugguuuuu ccaugcagua                                                  20

<210> SEQ ID NO 1444
<211> LENGTH: 20
<212> TYPE: RNA
<213> ORGANISM: Artificial Sequence
<220> FEATURE:
<223> OTHER INFORMATION: synthesized

<400> SEQUENCE: 1444
gaguuauaag guacugcaug                                                  20
```

```
<210> SEQ ID NO 1445
<211> LENGTH: 20
<212> TYPE: RNA
<213> ORGANISM: Artificial Sequence
<220> FEATURE:
<223> OTHER INFORMATION: synthesized

<400> SEQUENCE: 1445
gaguuauaag guacugcgug                                                 20

<210> SEQ ID NO 1446
<211> LENGTH: 20
<212> TYPE: RNA
<213> ORGANISM: Artificial Sequence
<220> FEATURE:
<223> OTHER INFORMATION: synthesized

<400> SEQUENCE: 1446
gcauggaaaa accaagcaga                                                 20

<210> SEQ ID NO 1447
<211> LENGTH: 20
<212> TYPE: RNA
<213> ORGANISM: Artificial Sequence
<220> FEATURE:
<223> OTHER INFORMATION: synthesized

<400> SEQUENCE: 1447
gcguggaaaa accaagcaga                                                 20

<210> SEQ ID NO 1448
<211> LENGTH: 20
<212> TYPE: RNA
<213> ORGANISM: Artificial Sequence
<220> FEATURE:
<223> OTHER INFORMATION: synthesized

<400> SEQUENCE: 1448
gcuugguuuu uccacgcagu                                                 20

<210> SEQ ID NO 1449
<211> LENGTH: 20
<212> TYPE: RNA
<213> ORGANISM: Artificial Sequence
<220> FEATURE:
<223> OTHER INFORMATION: synthesized

<400> SEQUENCE: 1449
gcuugguuuu uccaugcagu                                                 20

<210> SEQ ID NO 1450
<211> LENGTH: 20
<212> TYPE: RNA
<213> ORGANISM: Artificial Sequence
<220> FEATURE:
<223> OTHER INFORMATION: synthesized

<400> SEQUENCE: 1450
gguacugcau ggaaaaacca                                                 20

<210> SEQ ID NO 1451
<211> LENGTH: 20
<212> TYPE: RNA
<213> ORGANISM: Artificial Sequence
<220> FEATURE:
<223> OTHER INFORMATION: synthesized
```

```
<400> SEQUENCE: 1451
gguacugcgu ggaaaaacca                                              20

<210> SEQ ID NO 1452
<211> LENGTH: 20
<212> TYPE: RNA
<213> ORGANISM: Artificial Sequence
<220> FEATURE:
<223> OTHER INFORMATION: synthesized

<400> SEQUENCE: 1452
gguuuuucca cgcaguaccu                                              20

<210> SEQ ID NO 1453
<211> LENGTH: 20
<212> TYPE: RNA
<213> ORGANISM: Artificial Sequence
<220> FEATURE:
<223> OTHER INFORMATION: synthesized

<400> SEQUENCE: 1453
gguuuuucca ugcaguaccu                                              20

<210> SEQ ID NO 1454
<211> LENGTH: 20
<212> TYPE: RNA
<213> ORGANISM: Artificial Sequence
<220> FEATURE:
<223> OTHER INFORMATION: synthesized

<400> SEQUENCE: 1454
guacugcaug gaaaaaccaa                                              20

<210> SEQ ID NO 1455
<211> LENGTH: 20
<212> TYPE: RNA
<213> ORGANISM: Artificial Sequence
<220> FEATURE:
<223> OTHER INFORMATION: synthesized

<400> SEQUENCE: 1455
guacugcgug gaaaaaccaa                                              20

<210> SEQ ID NO 1456
<211> LENGTH: 20
<212> TYPE: RNA
<213> ORGANISM: Artificial Sequence
<220> FEATURE:
<223> OTHER INFORMATION: synthesized

<400> SEQUENCE: 1456
guggaaaaac caagcagagu                                              20

<210> SEQ ID NO 1457
<211> LENGTH: 20
<212> TYPE: RNA
<213> ORGANISM: Artificial Sequence
<220> FEATURE:
<223> OTHER INFORMATION: synthesized

<400> SEQUENCE: 1457
guuauaaggu acugcaugga                                              20

<210> SEQ ID NO 1458
```

```
<211> LENGTH: 20
<212> TYPE: RNA
<213> ORGANISM: Artificial Sequence
<220> FEATURE:
<223> OTHER INFORMATION: synthesized

<400> SEQUENCE: 1458
guuauaaggu acugcgugga                                                       20

<210> SEQ ID NO 1459
<211> LENGTH: 20
<212> TYPE: RNA
<213> ORGANISM: Artificial Sequence
<220> FEATURE:
<223> OTHER INFORMATION: synthesized

<400> SEQUENCE: 1459 guuuuccac gcaguaccuu                                                        20

<210> SEQ ID NO 1460
<211> LENGTH: 20
<212> TYPE: RNA
<213> ORGANISM: Artificial Sequence
<220> FEATURE:
<223> OTHER INFORMATION: synthesized

<400> SEQUENCE: 1460 guuuuccau gcaguaccuu                                                        20

<210> SEQ ID NO 1461
<211> LENGTH: 20
<212> TYPE: RNA
<213> ORGANISM: Artificial Sequence
<220> FEATURE:
<223> OTHER INFORMATION: synthesized

<400> SEQUENCE: 1461
uauaagguac ugcauggaaa                                                       20

<210> SEQ ID NO 1462
<211> LENGTH: 20
<212> TYPE: RNA
<213> ORGANISM: Artificial Sequence
<220> FEATURE:
<223> OTHER INFORMATION: synthesized

<400> SEQUENCE: 1462
uauaagguac ugcguggaaa                                                       20

<210> SEQ ID NO 1463
<211> LENGTH: 20
<212> TYPE: RNA
<213> ORGANISM: Artificial Sequence
<220> FEATURE:
<223> OTHER INFORMATION: synthesized

<400> SEQUENCE: 1463
uccacgcagu accuuauaac                                                       20

<210> SEQ ID NO 1464
<211> LENGTH: 20
<212> TYPE: RNA
<213> ORGANISM: Artificial Sequence
<220> FEATURE:
<223> OTHER INFORMATION: synthesized

<400> SEQUENCE: 1464
```
uccaugcagu accuuauaac                                               20

<210> SEQ ID NO 1465
<211> LENGTH: 20
<212> TYPE: RNA
<213> ORGANISM: Artificial Sequence
<220> FEATURE:
<223> OTHER INFORMATION: synthesized

<400> SEQUENCE: 1465
ucugcuuggu uuuccacgc                                                20

<210> SEQ ID NO 1466
<211> LENGTH: 20
<212> TYPE: RNA
<213> ORGANISM: Artificial Sequence
<220> FEATURE:
<223> OTHER INFORMATION: synthesized

<400> SEQUENCE: 1466
ucugcuuggu uuuccaugc                                                20

<210> SEQ ID NO 1467
<211> LENGTH: 20
<212> TYPE: RNA
<213> ORGANISM: Artificial Sequence
<220> FEATURE:
<223> OTHER INFORMATION: synthesized

<400> SEQUENCE: 1467
ugcauggaaa aaccaagcag                                               20

<210> SEQ ID NO 1468
<211> LENGTH: 20
<212> TYPE: RNA
<213> ORGANISM: Artificial Sequence
<220> FEATURE:
<223> OTHER INFORMATION: synthesized

<400> SEQUENCE: 1468
ugcguggaaa aaccaagcag                                               20

<210> SEQ ID NO 1469
<211> LENGTH: 20
<212> TYPE: RNA
<213> ORGANISM: Artificial Sequence
<220> FEATURE:
<223> OTHER INFORMATION: synthesized

<400> SEQUENCE: 1469
ugcuugguuu uuccacgcag                                               20

<210> SEQ ID NO 1470
<211> LENGTH: 20
<212> TYPE: RNA
<213> ORGANISM: Artificial Sequence
<220> FEATURE:
<223> OTHER INFORMATION: synthesized

<400> SEQUENCE: 1470
ugcuugguuu uuccaugcag                                               20

<210> SEQ ID NO 1471
<211> LENGTH: 20
<212> TYPE: RNA

```
<213> ORGANISM: Artificial Sequence
<220> FEATURE:
<223> OTHER INFORMATION: synthesized

<400> SEQUENCE: 1471
ugguuuuucc acgcaguacc                                                     20

<210> SEQ ID NO 1472
<211> LENGTH: 20
<212> TYPE: RNA
<213> ORGANISM: Artificial Sequence
<220> FEATURE:
<223> OTHER INFORMATION: synthesized

<400> SEQUENCE: 1472
ugguuuuucc augcaguacc                                                     20

<210> SEQ ID NO 1473
<211> LENGTH: 20
<212> TYPE: RNA
<213> ORGANISM: Artificial Sequence
<220> FEATURE:
<223> OTHER INFORMATION: synthesized

<400> SEQUENCE: 1473
uuauaaggua cugcauggaa                                                     20

<210> SEQ ID NO 1474
<211> LENGTH: 20
<212> TYPE: RNA
<213> ORGANISM: Artificial Sequence
<220> FEATURE:
<223> OTHER INFORMATION: synthesized

<400> SEQUENCE: 1474
uuauaaggua cugcguggaa                                                     20

<210> SEQ ID NO 1475
<211> LENGTH: 20
<212> TYPE: RNA
<213> ORGANISM: Artificial Sequence
<220> FEATURE:
<223> OTHER INFORMATION: synthesized

<400> SEQUENCE: 1475
uuccacgcag uaccuuauaa                                                     20

<210> SEQ ID NO 1476
<211> LENGTH: 20
<212> TYPE: RNA
<213> ORGANISM: Artificial Sequence
<220> FEATURE:
<223> OTHER INFORMATION: synthesized

<400> SEQUENCE: 1476
uuccaugcag uaccuuauaa                                                     20

<210> SEQ ID NO 1477
<211> LENGTH: 20
<212> TYPE: RNA
<213> ORGANISM: Artificial Sequence
<220> FEATURE:
<223> OTHER INFORMATION: synthesized

<400> SEQUENCE: 1477
uugguuuuuc cacgcaguac                                                     20
```

<210> SEQ ID NO 1478
<211> LENGTH: 20
<212> TYPE: RNA
<213> ORGANISM: Artificial Sequence
<220> FEATURE:
<223> OTHER INFORMATION: synthesized

<400> SEQUENCE: 1478
uugguuuuuc caugcaguac                                               20

<210> SEQ ID NO 1479
<211> LENGTH: 20
<212> TYPE: RNA
<213> ORGANISM: Artificial Sequence
<220> FEATURE:
<223> OTHER INFORMATION: synthesized

<400> SEQUENCE: 1479
uuuccacgca guaccuuaua                                               20

<210> SEQ ID NO 1480
<211> LENGTH: 20
<212> TYPE: RNA
<213> ORGANISM: Artificial Sequence
<220> FEATURE:
<223> OTHER INFORMATION: synthesized

<400> SEQUENCE: 1480
uuuccaugca guaccuuaua                                               20

<210> SEQ ID NO 1481
<211> LENGTH: 20
<212> TYPE: RNA
<213> ORGANISM: Artificial Sequence
<220> FEATURE:
<223> OTHER INFORMATION: synthesized

<400> SEQUENCE: 1481
uuuuccacgc aguaccuuau                                               20

<210> SEQ ID NO 1482
<211> LENGTH: 20
<212> TYPE: RNA
<213> ORGANISM: Artificial Sequence
<220> FEATURE:
<223> OTHER INFORMATION: synthesized

<400> SEQUENCE: 1482
uuuuccaugc aguaccuuau                                               20

<210> SEQ ID NO 1483
<211> LENGTH: 20
<212> TYPE: RNA
<213> ORGANISM: Artificial Sequence
<220> FEATURE:
<223> OTHER INFORMATION: synthesized

<400> SEQUENCE: 1483
uuuuuccacg caguaccuua                                               20

<210> SEQ ID NO 1484
<211> LENGTH: 20
<212> TYPE: RNA
<213> ORGANISM: Artificial Sequence
<220> FEATURE:

-continued

<223> OTHER INFORMATION: synthesized

<400> SEQUENCE: 1484
uuuuuccaug caguaccuua                                                    20

<210> SEQ ID NO 1485
<211> LENGTH: 20
<212> TYPE: RNA
<213> ORGANISM: Artificial Sequence
<220> FEATURE:
<223> OTHER INFORMATION: synthesized

<400> SEQUENCE: 1485
aaaauuaggc cccuugugac                                                    20

<210> SEQ ID NO 1486
<211> LENGTH: 20
<212> TYPE: RNA
<213> ORGANISM: Artificial Sequence
<220> FEATURE:
<223> OTHER INFORMATION: synthesized

<400> SEQUENCE: 1486
aaaauuaggc cucuugugac                                                    20

<210> SEQ ID NO 1487
<211> LENGTH: 20
<212> TYPE: RNA
<213> ORGANISM: Artificial Sequence
<220> FEATURE:
<223> OTHER INFORMATION: synthesized

<400> SEQUENCE: 1487
aaauuaggcc ccuugugacc                                                    20

<210> SEQ ID NO 1488
<211> LENGTH: 20
<212> TYPE: RNA
<213> ORGANISM: Artificial Sequence
<220> FEATURE:
<223> OTHER INFORMATION: synthesized

<400> SEQUENCE: 1488
aaauuaggcc ucuugugacc                                                    20

<210> SEQ ID NO 1489
<211> LENGTH: 20
<212> TYPE: RNA
<213> ORGANISM: Artificial Sequence
<220> FEATURE:
<223> OTHER INFORMATION: synthesized

<400> SEQUENCE: 1489
aagaggccua auuuucaugc                                                    20

<210> SEQ ID NO 1490
<211> LENGTH: 20
<212> TYPE: RNA
<213> ORGANISM: Artificial Sequence
<220> FEATURE:
<223> OTHER INFORMATION: synthesized

<400> SEQUENCE: 1490
aaggggccua auuuucaugc                                                    20

```
<210> SEQ ID NO 1491
<211> LENGTH: 20
<212> TYPE: RNA
<213> ORGANISM: Artificial Sequence
<220> FEATURE:
<223> OTHER INFORMATION: synthesized

<400> SEQUENCE: 1491
aauuaggccc cuugugaccc                                                   20

<210> SEQ ID NO 1492
<211> LENGTH: 20
<212> TYPE: RNA
<213> ORGANISM: Artificial Sequence
<220> FEATURE:
<223> OTHER INFORMATION: synthesized

<400> SEQUENCE: 1492
aauuaggccu cuugugaccc                                                   20

<210> SEQ ID NO 1493
<211> LENGTH: 20
<212> TYPE: RNA
<213> ORGANISM: Artificial Sequence
<220> FEATURE:
<223> OTHER INFORMATION: synthesized

<400> SEQUENCE: 1493
agccuauugg gucacaagag                                                   20

<210> SEQ ID NO 1494
<211> LENGTH: 20
<212> TYPE: RNA
<213> ORGANISM: Artificial Sequence
<220> FEATURE:
<223> OTHER INFORMATION: synthesized

<400> SEQUENCE: 1494
agccuauugg gucacaaggg                                                   20

<210> SEQ ID NO 1495
<211> LENGTH: 20
<212> TYPE: RNA
<213> ORGANISM: Artificial Sequence
<220> FEATURE:
<223> OTHER INFORMATION: synthesized

<400> SEQUENCE: 1495
aggccccuug ugacccaaua                                                   20

<210> SEQ ID NO 1496
<211> LENGTH: 20
<212> TYPE: RNA
<213> ORGANISM: Artificial Sequence
<220> FEATURE:
<223> OTHER INFORMATION: synthesized

<400> SEQUENCE: 1496
aggccuaauu uucaugcgaa                                                   20

<210> SEQ ID NO 1497
<211> LENGTH: 20
<212> TYPE: RNA
<213> ORGANISM: Artificial Sequence
<220> FEATURE:
<223> OTHER INFORMATION: synthesized
```

-continued

<400> SEQUENCE: 1497
aggccucuug ugacccaaua                    20

<210> SEQ ID NO 1498
<211> LENGTH: 20
<212> TYPE: RNA
<213> ORGANISM: Artificial Sequence
<220> FEATURE:
<223> OTHER INFORMATION: synthesized

<400> SEQUENCE: 1498
augaaaauua ggccccuugu                    20

<210> SEQ ID NO 1499
<211> LENGTH: 20
<212> TYPE: RNA
<213> ORGANISM: Artificial Sequence
<220> FEATURE:
<223> OTHER INFORMATION: synthesized

<400> SEQUENCE: 1499
augaaaauua ggccucuugu                    20

<210> SEQ ID NO 1500
<211> LENGTH: 20
<212> TYPE: RNA
<213> ORGANISM: Artificial Sequence
<220> FEATURE:
<223> OTHER INFORMATION: synthesized

<400> SEQUENCE: 1500
auuaggcccc uugugaccca                    20

<210> SEQ ID NO 1501
<211> LENGTH: 20
<212> TYPE: RNA
<213> ORGANISM: Artificial Sequence
<220> FEATURE:
<223> OTHER INFORMATION: synthesized

<400> SEQUENCE: 1501
auuaggccuc uugugaccca                    20

<210> SEQ ID NO 1502
<211> LENGTH: 20
<212> TYPE: RNA
<213> ORGANISM: Artificial Sequence
<220> FEATURE:
<223> OTHER INFORMATION: synthesized

<400> SEQUENCE: 1502
auugggucac aagaggccua                    20

<210> SEQ ID NO 1503
<211> LENGTH: 20
<212> TYPE: RNA
<213> ORGANISM: Artificial Sequence
<220> FEATURE:
<223> OTHER INFORMATION: synthesized

<400> SEQUENCE: 1503
auugggucac aaggggccua                    20

<210> SEQ ID NO 1504
<211> LENGTH: 20

```
<212> TYPE: RNA
<213> ORGANISM: Artificial Sequence
<220> FEATURE:
<223> OTHER INFORMATION: synthesized

<400> SEQUENCE: 1504
cagccuauug ggucacaaga                                              20

<210> SEQ ID NO 1505
<211> LENGTH: 20
<212> TYPE: RNA
<213> ORGANISM: Artificial Sequence
<220> FEATURE:
<223> OTHER INFORMATION: synthesized

<400> SEQUENCE: 1505
cagccuauug ggucacaagg                                              20

<210> SEQ ID NO 1506
<211> LENGTH: 20
<212> TYPE: RNA
<213> ORGANISM: Artificial Sequence
<220> FEATURE:
<223> OTHER INFORMATION: synthesized

<400> SEQUENCE: 1506
cccuugugac ccauaggcu                                               20

<210> SEQ ID NO 1507
<211> LENGTH: 20
<212> TYPE: RNA
<213> ORGANISM: Artificial Sequence
<220> FEATURE:
<223> OTHER INFORMATION: synthesized

<400> SEQUENCE: 1507 ccuaugggu cacaagaggc                                               20

<210> SEQ ID NO 1508
<211> LENGTH: 20
<212> TYPE: RNA
<213> ORGANISM: Artificial Sequence
<220> FEATURE:
<223> OTHER INFORMATION: synthesized

<400> SEQUENCE: 1508 ccuaugggu cacaaggggc                                               20

<210> SEQ ID NO 1509
<211> LENGTH: 20
<212> TYPE: RNA
<213> ORGANISM: Artificial Sequence
<220> FEATURE:
<223> OTHER INFORMATION: synthesized

<400> SEQUENCE: 1509
ccuugugacc caauaggcug                                              20

<210> SEQ ID NO 1510
<211> LENGTH: 20
<212> TYPE: RNA
<213> ORGANISM: Artificial Sequence
<220> FEATURE:
<223> OTHER INFORMATION: synthesized

<400> SEQUENCE: 1510
```

| | |
|---|---|
| cuauugggc acaagaggcc | 20 |

<210> SEQ ID NO 1511
<211> LENGTH: 20
<212> TYPE: RNA
<213> ORGANISM: Artificial Sequence
<220> FEATURE:
<223> OTHER INFORMATION: synthesized

<400> SEQUENCE: 1511

| | |
|---|---|
| cuauugggc acaaggggcc | 20 |

<210> SEQ ID NO 1512
<211> LENGTH: 20
<212> TYPE: RNA
<213> ORGANISM: Artificial Sequence
<220> FEATURE:
<223> OTHER INFORMATION: synthesized

<400> SEQUENCE: 1512

| | |
|---|---|
| cucuugugac ccauaggcu | 20 |

<210> SEQ ID NO 1513
<211> LENGTH: 20
<212> TYPE: RNA
<213> ORGANISM: Artificial Sequence
<220> FEATURE:
<223> OTHER INFORMATION: synthesized

<400> SEQUENCE: 1513

| | |
|---|---|
| gaggccuaau uuucaugcga | 20 |

<210> SEQ ID NO 1514
<211> LENGTH: 20
<212> TYPE: RNA
<213> ORGANISM: Artificial Sequence
<220> FEATURE:
<223> OTHER INFORMATION: synthesized

<400> SEQUENCE: 1514

| | |
|---|---|
| gcaugaaaau uaggccccuu | 20 |

<210> SEQ ID NO 1515
<211> LENGTH: 20
<212> TYPE: RNA
<213> ORGANISM: Artificial Sequence
<220> FEATURE:
<223> OTHER INFORMATION: synthesized

<400> SEQUENCE: 1515

| | |
|---|---|
| gcaugaaaau uaggccucuu | 20 |

<210> SEQ ID NO 1516
<211> LENGTH: 20
<212> TYPE: RNA
<213> ORGANISM: Artificial Sequence
<220> FEATURE:
<223> OTHER INFORMATION: synthesized

<400> SEQUENCE: 1516

| | |
|---|---|
| gccccuugug acccauaggg | 20 |

<210> SEQ ID NO 1517
<211> LENGTH: 20
<212> TYPE: RNA
<213> ORGANISM: Artificial Sequence
<220> FEATURE:
<223> OTHER INFORMATION: synthesized

<400> SEQUENCE: 1517
gccuauuggg ucacaagagg				20

<210> SEQ ID NO 1518
<211> LENGTH: 20
<212> TYPE: RNA
<213> ORGANISM: Artificial Sequence
<220> FEATURE:
<223> OTHER INFORMATION: synthesized

<400> SEQUENCE: 1518
gccuauuggg ucacaagggg				20

<210> SEQ ID NO 1519
<211> LENGTH: 20
<212> TYPE: RNA
<213> ORGANISM: Artificial Sequence
<220> FEATURE:
<223> OTHER INFORMATION: synthesized

<400> SEQUENCE: 1519
gccucuugug acccaauagg				20

<210> SEQ ID NO 1520
<211> LENGTH: 20
<212> TYPE: RNA
<213> ORGANISM: Artificial Sequence
<220> FEATURE:
<223> OTHER INFORMATION: synthesized

<400> SEQUENCE: 1520
ggccccuugu gacccaauag				20

<210> SEQ ID NO 1521
<211> LENGTH: 20
<212> TYPE: RNA
<213> ORGANISM: Artificial Sequence
<220> FEATURE:
<223> OTHER INFORMATION: synthesized

<400> SEQUENCE: 1521
ggccucuugu gacccaauag				20

<210> SEQ ID NO 1522
<211> LENGTH: 20
<212> TYPE: RNA
<213> ORGANISM: Artificial Sequence
<220> FEATURE:
<223> OTHER INFORMATION: synthesized

<400> SEQUENCE: 1522
gggccuaauu uucaugcgaa				20

<210> SEQ ID NO 1523
<211> LENGTH: 20
<212> TYPE: RNA
<213> ORGANISM: Artificial Sequence
<220> FEATURE:
<223> OTHER INFORMATION: synthesized

<400> SEQUENCE: 1523
ggggccuaau uuucaugcga				20

<210> SEQ ID NO 1524
<211> LENGTH: 20
<212> TYPE: RNA
<213> ORGANISM: Artificial Sequence
<220> FEATURE:
<223> OTHER INFORMATION: synthesized

<400> SEQUENCE: 1524
gggucacaag aggccuaauu                    20

<210> SEQ ID NO 1525
<211> LENGTH: 20
<212> TYPE: RNA
<213> ORGANISM: Artificial Sequence
<220> FEATURE:
<223> OTHER INFORMATION: synthesized

<400> SEQUENCE: 1525
gggucacaag gggccuaauu                    20

<210> SEQ ID NO 1526
<211> LENGTH: 20
<212> TYPE: RNA
<213> ORGANISM: Artificial Sequence
<220> FEATURE:
<223> OTHER INFORMATION: synthesized

<400> SEQUENCE: 1526
ggucacaaga ggccuaauuu                    20

<210> SEQ ID NO 1527
<211> LENGTH: 20
<212> TYPE: RNA
<213> ORGANISM: Artificial Sequence
<220> FEATURE:
<223> OTHER INFORMATION: synthesized

<400> SEQUENCE: 1527
ggucacaagg ggccuaauuu                    20

<210> SEQ ID NO 1528
<211> LENGTH: 20
<212> TYPE: RNA
<213> ORGANISM: Artificial Sequence
<220> FEATURE:
<223> OTHER INFORMATION: synthesized

<400> SEQUENCE: 1528
gucacaagag gccuaauuuu                    20

<210> SEQ ID NO 1529
<211> LENGTH: 20
<212> TYPE: RNA
<213> ORGANISM: Artificial Sequence
<220> FEATURE:
<223> OTHER INFORMATION: synthesized

<400> SEQUENCE: 1529
gucacaaggg gccuaauuuu                    20

<210> SEQ ID NO 1530
<211> LENGTH: 20
<212> TYPE: RNA
<213> ORGANISM: Artificial Sequence
<220> FEATURE:
<223> OTHER INFORMATION: synthesized

<400> SEQUENCE: 1530
uauuggguca caagaggccu                                                20

<210> SEQ ID NO 1531
<211> LENGTH: 20
<212> TYPE: RNA
<213> ORGANISM: Artificial Sequence
<220> FEATURE:
<223> OTHER INFORMATION: synthesized

<400> SEQUENCE: 1531
uauuggguca caaggggccu                                                20

<210> SEQ ID NO 1532
<211> LENGTH: 20
<212> TYPE: RNA
<213> ORGANISM: Artificial Sequence
<220> FEATURE:
<223> OTHER INFORMATION: synthesized

<400> SEQUENCE: 1532
ucacaagagg ccuaauuuuc                                                20

<210> SEQ ID NO 1533
<211> LENGTH: 20
<212> TYPE: RNA
<213> ORGANISM: Artificial Sequence
<220> FEATURE:
<223> OTHER INFORMATION: synthesized

<400> SEQUENCE: 1533
ucacaagggg ccuaauuuuc                                                20

<210> SEQ ID NO 1534
<211> LENGTH: 20
<212> TYPE: RNA
<213> ORGANISM: Artificial Sequence
<220> FEATURE:
<223> OTHER INFORMATION: synthesized

<400> SEQUENCE: 1534
ucgcaugaaa auuaggcccc                                                20

<210> SEQ ID NO 1535
<211> LENGTH: 20
<212> TYPE: RNA
<213> ORGANISM: Artificial Sequence
<220> FEATURE:
<223> OTHER INFORMATION: synthesized

<400> SEQUENCE: 1535
ucgcaugaaa auuaggccuc                                                20

<210> SEQ ID NO 1536
<211> LENGTH: 20
<212> TYPE: RNA
<213> ORGANISM: Artificial Sequence
<220> FEATURE:
<223> OTHER INFORMATION: synthesized

<400> SEQUENCE: 1536
ucuugugacc caauaggcug                                                20

<210> SEQ ID NO 1537

```
<211> LENGTH: 20
<212> TYPE: RNA
<213> ORGANISM: Artificial Sequence
<220> FEATURE:
<223> OTHER INFORMATION: synthesized

<400> SEQUENCE: 1537
ugaaaauuag gccccuugug                                                  20

<210> SEQ ID NO 1538
<211> LENGTH: 20
<212> TYPE: RNA
<213> ORGANISM: Artificial Sequence
<220> FEATURE:
<223> OTHER INFORMATION: synthesized

<400> SEQUENCE: 1538
ugaaaauuag gcccucuugug                                                 20

<210> SEQ ID NO 1539
<211> LENGTH: 20
<212> TYPE: RNA
<213> ORGANISM: Artificial Sequence
<220> FEATURE:
<223> OTHER INFORMATION: synthesized

<400> SEQUENCE: 1539
ugggucacaa gaggccuaau                                                  20

<210> SEQ ID NO 1540
<211> LENGTH: 20
<212> TYPE: RNA
<213> ORGANISM: Artificial Sequence
<220> FEATURE:
<223> OTHER INFORMATION: synthesized

<400> SEQUENCE: 1540
ugggucacaa ggggccuaau                                                  20

<210> SEQ ID NO 1541
<211> LENGTH: 20
<212> TYPE: RNA
<213> ORGANISM: Artificial Sequence
<220> FEATURE:
<223> OTHER INFORMATION: synthesized

<400> SEQUENCE: 1541
uuaggccccu ugugacccaa                                                  20

<210> SEQ ID NO 1542
<211> LENGTH: 20
<212> TYPE: RNA
<213> ORGANISM: Artificial Sequence
<220> FEATURE:
<223> OTHER INFORMATION: synthesized

<400> SEQUENCE: 1542
uuaggccucu ugugacccaa                                                  20

<210> SEQ ID NO 1543
<211> LENGTH: 20
<212> TYPE: RNA
<213> ORGANISM: Artificial Sequence
<220> FEATURE:
<223> OTHER INFORMATION: synthesized

<400> SEQUENCE: 1543
```
uucgcaugaa aauuaggccc                                              20

<210> SEQ ID NO 1544
<211> LENGTH: 20
<212> TYPE: RNA
<213> ORGANISM: Artificial Sequence
<220> FEATURE:
<223> OTHER INFORMATION: synthesized

<400> SEQUENCE: 1544
uucgcaugaa aauuaggccu                                              20

<210> SEQ ID NO 1545
<211> LENGTH: 20
<212> TYPE: RNA
<213> ORGANISM: Artificial Sequence
<220> FEATURE:
<223> OTHER INFORMATION: synthesized

<400> SEQUENCE: 1545
uugggucaca agaggccuaa                                              20

<210> SEQ ID NO 1546
<211> LENGTH: 20
<212> TYPE: RNA
<213> ORGANISM: Artificial Sequence
<220> FEATURE:
<223> OTHER INFORMATION: synthesized

<400> SEQUENCE: 1546
uugggucaca aggggccuaa                                              20

<210> SEQ ID NO 1547
<211> LENGTH: 20
<212> TYPE: RNA
<213> ORGANISM: Artificial Sequence
<220> FEATURE:
<223> OTHER INFORMATION: synthesized

<400> SEQUENCE: 1547
aaccucuaac uaguccucuu                                              20

<210> SEQ ID NO 1548
<211> LENGTH: 20
<212> TYPE: RNA
<213> ORGANISM: Artificial Sequence
<220> FEATURE:
<223> OTHER INFORMATION: synthesized

<400> SEQUENCE: 1548
aagaggacua guuagagguc                                              20

<210> SEQ ID NO 1549
<211> LENGTH: 20
<212> TYPE: RNA
<213> ORGANISM: Artificial Sequence
<220> FEATURE:
<223> OTHER INFORMATION: synthesized

<400> SEQUENCE: 1549
aagaggacua guuagagguu                                              20

<210> SEQ ID NO 1550
<211> LENGTH: 20
<212> TYPE: RNA

```
<213> ORGANISM: Artificial Sequence
<220> FEATURE:
<223> OTHER INFORMATION: synthesized

<400> SEQUENCE: 1550
acuaguuaga ggucgcagag                                                    20

<210> SEQ ID NO 1551
<211> LENGTH: 20
<212> TYPE: RNA
<213> ORGANISM: Artificial Sequence
<220> FEATURE:
<223> OTHER INFORMATION: synthesized

<400> SEQUENCE: 1551
acuaguuaga gguugcagag                                                    20

<210> SEQ ID NO 1552
<211> LENGTH: 20
<212> TYPE: RNA
<213> ORGANISM: Artificial Sequence
<220> FEATURE:
<223> OTHER INFORMATION: synthesized

<400> SEQUENCE: 1552
agaggacuag uuagaggucg                                                    20

<210> SEQ ID NO 1553
<211> LENGTH: 20
<212> TYPE: RNA
<213> ORGANISM: Artificial Sequence
<220> FEATURE:
<223> OTHER INFORMATION: synthesized

<400> SEQUENCE: 1553
agaggacuag uuagagguug                                                    20

<210> SEQ ID NO 1554
<211> LENGTH: 20
<212> TYPE: RNA
<213> ORGANISM: Artificial Sequence
<220> FEATURE:
<223> OTHER INFORMATION: synthesized

<400> SEQUENCE: 1554
agaguuucuc ugcaaccucu                                                    20

<210> SEQ ID NO 1555
<211> LENGTH: 20
<212> TYPE: RNA
<213> ORGANISM: Artificial Sequence
<220> FEATURE:
<223> OTHER INFORMATION: synthesized

<400> SEQUENCE: 1555
agaguuucuc ugcgaccucu                                                    20

<210> SEQ ID NO 1556
<211> LENGTH: 20
<212> TYPE: RNA
<213> ORGANISM: Artificial Sequence
<220> FEATURE:
<223> OTHER INFORMATION: synthesized

<400> SEQUENCE: 1556
aggacuaguu agaggucgca                                                    20
```

<210> SEQ ID NO 1557
<211> LENGTH: 20
<212> TYPE: RNA
<213> ORGANISM: Artificial Sequence
<220> FEATURE:
<223> OTHER INFORMATION: synthesized

<400> SEQUENCE: 1557
aggacuaguu agagguugca                                               20

<210> SEQ ID NO 1558
<211> LENGTH: 20
<212> TYPE: RNA
<213> ORGANISM: Artificial Sequence
<220> FEATURE:
<223> OTHER INFORMATION: synthesized

<400> SEQUENCE: 1558
aggucgcaga gaaacucugg                                               20

<210> SEQ ID NO 1559
<211> LENGTH: 20
<212> TYPE: RNA
<213> ORGANISM: Artificial Sequence
<220> FEATURE:
<223> OTHER INFORMATION: synthesized

<400> SEQUENCE: 1559
agguugcaga gaaacucugg                                               20

<210> SEQ ID NO 1560
<211> LENGTH: 20
<212> TYPE: RNA
<213> ORGANISM: Artificial Sequence
<220> FEATURE:
<223> OTHER INFORMATION: synthesized

<400> SEQUENCE: 1560
aguuagaggu cgcagagaaa                                               20

<210> SEQ ID NO 1561
<211> LENGTH: 20
<212> TYPE: RNA
<213> ORGANISM: Artificial Sequence
<220> FEATURE:
<223> OTHER INFORMATION: synthesized

<400> SEQUENCE: 1561
aguuagaggu ugcagagaaa                                               20

<210> SEQ ID NO 1562
<211> LENGTH: 20
<212> TYPE: RNA
<213> ORGANISM: Artificial Sequence
<220> FEATURE:
<223> OTHER INFORMATION: synthesized

<400> SEQUENCE: 1562
aguuucucug caaccucuaa                                               20

<210> SEQ ID NO 1563
<211> LENGTH: 20
<212> TYPE: RNA
<213> ORGANISM: Artificial Sequence
<220> FEATURE:

<223> OTHER INFORMATION: synthesized

<400> SEQUENCE: 1563
aguuucucug cgaccucuaa                                           20

<210> SEQ ID NO 1564
<211> LENGTH: 20
<212> TYPE: RNA
<213> ORGANISM: Artificial Sequence
<220> FEATURE:
<223> OTHER INFORMATION: synthesized

<400> SEQUENCE: 1564
auuccagagu uucucugcaa                                           20

<210> SEQ ID NO 1565
<211> LENGTH: 20
<212> TYPE: RNA
<213> ORGANISM: Artificial Sequence
<220> FEATURE:
<223> OTHER INFORMATION: synthesized

<400> SEQUENCE: 1565
auuccagagu uucucugcga                                           20

<210> SEQ ID NO 1566
<211> LENGTH: 20
<212> TYPE: RNA
<213> ORGANISM: Artificial Sequence
<220> FEATURE:
<223> OTHER INFORMATION: synthesized

<400> SEQUENCE: 1566
caaccucuaa cuaguccucu                                           20

<210> SEQ ID NO 1567
<211> LENGTH: 20
<212> TYPE: RNA
<213> ORGANISM: Artificial Sequence
<220> FEATURE:
<223> OTHER INFORMATION: synthesized

<400> SEQUENCE: 1567
cagaguuucu cugcaaccuc                                           20

<210> SEQ ID NO 1568
<211> LENGTH: 20
<212> TYPE: RNA
<213> ORGANISM: Artificial Sequence
<220> FEATURE:
<223> OTHER INFORMATION: synthesized

<400> SEQUENCE: 1568
cagaguuucu cugcgaccuc                                           20

<210> SEQ ID NO 1569
<211> LENGTH: 20
<212> TYPE: RNA
<213> ORGANISM: Artificial Sequence
<220> FEATURE:
<223> OTHER INFORMATION: synthesized

<400> SEQUENCE: 1569
cauuccagag uuucucugca                                           20

-continued

```
<210> SEQ ID NO 1570
<211> LENGTH: 20
<212> TYPE: RNA
<213> ORGANISM: Artificial Sequence
<220> FEATURE:
<223> OTHER INFORMATION: synthesized

<400> SEQUENCE: 1570
cauuccagag uuucucugcg                                                 20

<210> SEQ ID NO 1571
<211> LENGTH: 20
<212> TYPE: RNA
<213> ORGANISM: Artificial Sequence
<220> FEATURE:
<223> OTHER INFORMATION: synthesized

<400> SEQUENCE: 1571
ccagaguuuc ucugcaaccu                                                 20

<210> SEQ ID NO 1572
<211> LENGTH: 20
<212> TYPE: RNA
<213> ORGANISM: Artificial Sequence
<220> FEATURE:
<223> OTHER INFORMATION: synthesized

<400> SEQUENCE: 1572
ccagaguuuc ucugcgaccu                                                 20

<210> SEQ ID NO 1573
<211> LENGTH: 20
<212> TYPE: RNA
<213> ORGANISM: Artificial Sequence
<220> FEATURE:
<223> OTHER INFORMATION: synthesized

<400> SEQUENCE: 1573
cgaccucuaa cuaguccucu                                                 20

<210> SEQ ID NO 1574
<211> LENGTH: 20
<212> TYPE: RNA
<213> ORGANISM: Artificial Sequence
<220> FEATURE:
<223> OTHER INFORMATION: synthesized

<400> SEQUENCE: 1574
cuaguuagag gucgcagaga                                                 20

<210> SEQ ID NO 1575
<211> LENGTH: 20
<212> TYPE: RNA
<213> ORGANISM: Artificial Sequence
<220> FEATURE:
<223> OTHER INFORMATION: synthesized

<400> SEQUENCE: 1575
cuaguuagag guugcagaga                                                 20

<210> SEQ ID NO 1576
<211> LENGTH: 20
<212> TYPE: RNA
<213> ORGANISM: Artificial Sequence
<220> FEATURE:
<223> OTHER INFORMATION: synthesized
```

```
<400> SEQUENCE: 1576
cucugcaacc ucuaacuagu                                              20

<210> SEQ ID NO 1577
<211> LENGTH: 20
<212> TYPE: RNA
<213> ORGANISM: Artificial Sequence
<220> FEATURE:
<223> OTHER INFORMATION: synthesized

<400> SEQUENCE: 1577
cucugcgacc ucuaacuagu                                              20

<210> SEQ ID NO 1578
<211> LENGTH: 20
<212> TYPE: RNA
<213> ORGANISM: Artificial Sequence
<220> FEATURE:
<223> OTHER INFORMATION: synthesized

<400> SEQUENCE: 1578
cugcaaccuc uaacuagucc                                              20

<210> SEQ ID NO 1579
<211> LENGTH: 20
<212> TYPE: RNA
<213> ORGANISM: Artificial Sequence
<220> FEATURE:
<223> OTHER INFORMATION: synthesized

<400> SEQUENCE: 1579
cugcgaccuc uaacuagucc                                              20

<210> SEQ ID NO 1580
<211> LENGTH: 20
<212> TYPE: RNA
<213> ORGANISM: Artificial Sequence
<220> FEATURE:
<223> OTHER INFORMATION: synthesized

<400> SEQUENCE: 1580
gaccucuaac uaguccucuu                                              20

<210> SEQ ID NO 1581
<211> LENGTH: 20
<212> TYPE: RNA
<213> ORGANISM: Artificial Sequence
<220> FEATURE:
<223> OTHER INFORMATION: synthesized

<400> SEQUENCE: 1581
gacuaguuag aggucgcaga                                              20

<210> SEQ ID NO 1582
<211> LENGTH: 20
<212> TYPE: RNA
<213> ORGANISM: Artificial Sequence
<220> FEATURE:
<223> OTHER INFORMATION: synthesized

<400> SEQUENCE: 1582
gacuaguuag agguugcaga                                              20

<210> SEQ ID NO 1583
<211> LENGTH: 20
```

```
<212> TYPE: RNA
<213> ORGANISM: Artificial Sequence
<220> FEATURE:
<223> OTHER INFORMATION: synthesized

<400> SEQUENCE: 1583
gaggucgcag agaaacucug                                               20

<210> SEQ ID NO 1584
<211> LENGTH: 20
<212> TYPE: RNA
<213> ORGANISM: Artificial Sequence
<220> FEATURE:
<223> OTHER INFORMATION: synthesized

<400> SEQUENCE: 1584
gagguugcag agaaacucug                                               20

<210> SEQ ID NO 1585
<211> LENGTH: 20
<212> TYPE: RNA
<213> ORGANISM: Artificial Sequence
<220> FEATURE:
<223> OTHER INFORMATION: synthesized

<400> SEQUENCE: 1585
gcaaccucua acuaguccuc                                               20

<210> SEQ ID NO 1586
<211> LENGTH: 20
<212> TYPE: RNA
<213> ORGANISM: Artificial Sequence
<220> FEATURE:
<223> OTHER INFORMATION: synthesized

<400> SEQUENCE: 1586
gcgaccucua acuaguccuc                                               20

<210> SEQ ID NO 1587
<211> LENGTH: 20
<212> TYPE: RNA
<213> ORGANISM: Artificial Sequence
<220> FEATURE:
<223> OTHER INFORMATION: synthesized

<400> SEQUENCE: 1587
ggucgcagag aaacucugga                                               20

<210> SEQ ID NO 1588
<211> LENGTH: 20
<212> TYPE: RNA
<213> ORGANISM: Artificial Sequence
<220> FEATURE:
<223> OTHER INFORMATION: synthesized

<400> SEQUENCE: 1588
gguugcagag aaacucugga                                               20

<210> SEQ ID NO 1589
<211> LENGTH: 20
<212> TYPE: RNA
<213> ORGANISM: Artificial Sequence
<220> FEATURE:
<223> OTHER INFORMATION: synthesized

<400> SEQUENCE: 1589
```
guuagagguc gcagagaaac						20

<210> SEQ ID NO 1590
<211> LENGTH: 20
<212> TYPE: RNA
<213> ORGANISM: Artificial Sequence
<220> FEATURE:
<223> OTHER INFORMATION: synthesized

<400> SEQUENCE: 1590
guuagagguu gcagagaaac						20

<210> SEQ ID NO 1591
<211> LENGTH: 20
<212> TYPE: RNA
<213> ORGANISM: Artificial Sequence
<220> FEATURE:
<223> OTHER INFORMATION: synthesized

<400> SEQUENCE: 1591
guuucucugc aaccucuaac						20

<210> SEQ ID NO 1592
<211> LENGTH: 20
<212> TYPE: RNA
<213> ORGANISM: Artificial Sequence
<220> FEATURE:
<223> OTHER INFORMATION: synthesized

<400> SEQUENCE: 1592
guuucucugc gaccucuaac						20

<210> SEQ ID NO 1593
<211> LENGTH: 20
<212> TYPE: RNA
<213> ORGANISM: Artificial Sequence
<220> FEATURE:
<223> OTHER INFORMATION: synthesized

<400> SEQUENCE: 1593
uaguuagagg ucgcagagaa						20

<210> SEQ ID NO 1594
<211> LENGTH: 20
<212> TYPE: RNA
<213> ORGANISM: Artificial Sequence
<220> FEATURE:
<223> OTHER INFORMATION: synthesized

<400> SEQUENCE: 1594
uaguuagagg uugcagagaa						20

<210> SEQ ID NO 1595
<211> LENGTH: 20
<212> TYPE: RNA
<213> ORGANISM: Artificial Sequence
<220> FEATURE:
<223> OTHER INFORMATION: synthesized

<400> SEQUENCE: 1595
uccagaguuu cucugcaacc						20

<210> SEQ ID NO 1596
<211> LENGTH: 20
<212> TYPE: RNA
<213> ORGANISM: Artificial Sequence

```
<220> FEATURE:
<223> OTHER INFORMATION: synthesized

<400> SEQUENCE: 1596
uccagaguuu cucugcgacc                                              20

<210> SEQ ID NO 1597
<211> LENGTH: 20
<212> TYPE: RNA
<213> ORGANISM: Artificial Sequence
<220> FEATURE:
<223> OTHER INFORMATION: synthesized

<400> SEQUENCE: 1597
ucucugcaac cucuaacuag                                              20

<210> SEQ ID NO 1598
<211> LENGTH: 20
<212> TYPE: RNA
<213> ORGANISM: Artificial Sequence
<220> FEATURE:
<223> OTHER INFORMATION: synthesized

<400> SEQUENCE: 1598
ucucugcgac cucuaacuag                                              20

<210> SEQ ID NO 1599
<211> LENGTH: 20
<212> TYPE: RNA
<213> ORGANISM: Artificial Sequence
<220> FEATURE:
<223> OTHER INFORMATION: synthesized

<400> SEQUENCE: 1599
ucugcaaccu cuaacuaguc                                              20

<210> SEQ ID NO 1600
<211> LENGTH: 20
<212> TYPE: RNA
<213> ORGANISM: Artificial Sequence
<220> FEATURE:
<223> OTHER INFORMATION: synthesized

<400> SEQUENCE: 1600
ucugcgaccu cuaacuaguc                                              20

<210> SEQ ID NO 1601
<211> LENGTH: 20
<212> TYPE: RNA
<213> ORGANISM: Artificial Sequence
<220> FEATURE:
<223> OTHER INFORMATION: synthesized

<400> SEQUENCE: 1601
ugcaaccucu aacuaguccu                                              20

<210> SEQ ID NO 1602
<211> LENGTH: 20
<212> TYPE: RNA
<213> ORGANISM: Artificial Sequence
<220> FEATURE:
<223> OTHER INFORMATION: synthesized

<400> SEQUENCE: 1602
ugcgaccucu aacuaguccu                                              20
```

```
<210> SEQ ID NO 1603
<211> LENGTH: 20
<212> TYPE: RNA
<213> ORGANISM: Artificial Sequence
<220> FEATURE:
<223> OTHER INFORMATION: synthesized

<400> SEQUENCE: 1603
uuagaggucg cagagaaacu                                               20

<210> SEQ ID NO 1604
<211> LENGTH: 20
<212> TYPE: RNA
<213> ORGANISM: Artificial Sequence
<220> FEATURE:
<223> OTHER INFORMATION: synthesized

<400> SEQUENCE: 1604
uuagagguug cagagaaacu                                               20

<210> SEQ ID NO 1605
<211> LENGTH: 20
<212> TYPE: RNA
<213> ORGANISM: Artificial Sequence
<220> FEATURE:
<223> OTHER INFORMATION: synthesized

<400> SEQUENCE: 1605
uuccagaguu ucucugcaac                                               20

<210> SEQ ID NO 1606
<211> LENGTH: 20
<212> TYPE: RNA
<213> ORGANISM: Artificial Sequence
<220> FEATURE:
<223> OTHER INFORMATION: synthesized

<400> SEQUENCE: 1606
uuccagaguu ucucugcgac                                               20

<210> SEQ ID NO 1607
<211> LENGTH: 20
<212> TYPE: RNA
<213> ORGANISM: Artificial Sequence
<220> FEATURE:
<223> OTHER INFORMATION: synthesized

<400> SEQUENCE: 1607
uucucugcaa ccucuaacua                                               20

<210> SEQ ID NO 1608
<211> LENGTH: 20
<212> TYPE: RNA
<213> ORGANISM: Artificial Sequence
<220> FEATURE:
<223> OTHER INFORMATION: synthesized

<400> SEQUENCE: 1608
uucucugcga ccucuaacua                                               20

<210> SEQ ID NO 1609
<211> LENGTH: 20
<212> TYPE: RNA
<213> ORGANISM: Artificial Sequence
<220> FEATURE:
<223> OTHER INFORMATION: synthesized
```

-continued

<400> SEQUENCE: 1609
uuucucugca accucuaacu                                              20

<210> SEQ ID NO 1610
<211> LENGTH: 20
<212> TYPE: RNA
<213> ORGANISM: Artificial Sequence
<220> FEATURE:
<223> OTHER INFORMATION: synthesized

<400> SEQUENCE: 1610
uuucucugcg accucuaacu                                              20

<210> SEQ ID NO 1611
<211> LENGTH: 20
<212> TYPE: RNA
<213> ORGANISM: Artificial Sequence
<220> FEATURE:
<223> OTHER INFORMATION: synthesized

<400> SEQUENCE: 1611
aacuucacau cucuggaacc                                              20

<210> SEQ ID NO 1612
<211> LENGTH: 20
<212> TYPE: RNA
<213> ORGANISM: Artificial Sequence
<220> FEATURE:
<223> OTHER INFORMATION: synthesized

<400> SEQUENCE: 1612
aacuucgcau cucuggaacc                                              20

<210> SEQ ID NO 1613
<211> LENGTH: 20
<212> TYPE: RNA
<213> ORGANISM: Artificial Sequence
<220> FEATURE:
<223> OTHER INFORMATION: synthesized

<400> SEQUENCE: 1613
aaguggguuc cagagaugcg                                              20

<210> SEQ ID NO 1614
<211> LENGTH: 20
<212> TYPE: RNA
<213> ORGANISM: Artificial Sequence
<220> FEATURE:
<223> OTHER INFORMATION: synthesized

<400> SEQUENCE: 1614
aaguggguuc cagagaugug                                              20

<210> SEQ ID NO 1615
<211> LENGTH: 20
<212> TYPE: RNA
<213> ORGANISM: Artificial Sequence
<220> FEATURE:
<223> OTHER INFORMATION: synthesized

<400> SEQUENCE: 1615
acaucucugg aacccacuua                                              20

<210> SEQ ID NO 1616

```
<211> LENGTH: 20
<212> TYPE: RNA
<213> ORGANISM: Artificial Sequence
<220> FEATURE:
<223> OTHER INFORMATION: synthesized

<400> SEQUENCE: 1616
acuucacauc ucuggaaccc                                           20

<210> SEQ ID NO 1617
<211> LENGTH: 20
<212> TYPE: RNA
<213> ORGANISM: Artificial Sequence
<220> FEATURE:
<223> OTHER INFORMATION: synthesized

<400> SEQUENCE: 1617
acuucgcauc ucuggaaccc                                           20

<210> SEQ ID NO 1618
<211> LENGTH: 20
<212> TYPE: RNA
<213> ORGANISM: Artificial Sequence
<220> FEATURE:
<223> OTHER INFORMATION: synthesized

<400> SEQUENCE: 1618
agagaugcga aguugccugg                                           20

<210> SEQ ID NO 1619
<211> LENGTH: 20
<212> TYPE: RNA
<213> ORGANISM: Artificial Sequence
<220> FEATURE:
<223> OTHER INFORMATION: synthesized

<400> SEQUENCE: 1619
agagauguga aguugccugg                                           20

<210> SEQ ID NO 1620
<211> LENGTH: 20
<212> TYPE: RNA
<213> ORGANISM: Artificial Sequence
<220> FEATURE:
<223> OTHER INFORMATION: synthesized

<400> SEQUENCE: 1620
agaugcgaag uugccuggcu                                           20

<210> SEQ ID NO 1621
<211> LENGTH: 20
<212> TYPE: RNA
<213> ORGANISM: Artificial Sequence
<220> FEATURE:
<223> OTHER INFORMATION: synthesized

<400> SEQUENCE: 1621
agaugugaag uugccuggcu                                           20

<210> SEQ ID NO 1622
<211> LENGTH: 20
<212> TYPE: RNA
<213> ORGANISM: Artificial Sequence
<220> FEATURE:
<223> OTHER INFORMATION: synthesized

<400> SEQUENCE: 1622
```
agccaggcaa cuucacaucu                                             20

<210> SEQ ID NO 1623
<211> LENGTH: 20
<212> TYPE: RNA
<213> ORGANISM: Artificial Sequence
<220> FEATURE:
<223> OTHER INFORMATION: synthesized

<400> SEQUENCE: 1623
agccaggcaa cuucgcaucu                                             20

<210> SEQ ID NO 1624
<211> LENGTH: 20
<212> TYPE: RNA
<213> ORGANISM: Artificial Sequence
<220> FEATURE:
<223> OTHER INFORMATION: synthesized

<400> SEQUENCE: 1624
aggcaacuuc acaucucugg                                             20

<210> SEQ ID NO 1625
<211> LENGTH: 20
<212> TYPE: RNA
<213> ORGANISM: Artificial Sequence
<220> FEATURE:
<223> OTHER INFORMATION: synthesized

<400> SEQUENCE: 1625
aggcaacuuc gcaucucugg                                             20

<210> SEQ ID NO 1626
<211> LENGTH: 20
<212> TYPE: RNA
<213> ORGANISM: Artificial Sequence
<220> FEATURE:
<223> OTHER INFORMATION: synthesized

<400> SEQUENCE: 1626
aggcagccag gcaacuucac                                             20

<210> SEQ ID NO 1627
<211> LENGTH: 20
<212> TYPE: RNA
<213> ORGANISM: Artificial Sequence
<220> FEATURE:
<223> OTHER INFORMATION: synthesized

<400> SEQUENCE: 1627
aggcagccag gcaacuucgc                                             20

<210> SEQ ID NO 1628
<211> LENGTH: 20
<212> TYPE: RNA
<213> ORGANISM: Artificial Sequence
<220> FEATURE:
<223> OTHER INFORMATION: synthesized

<400> SEQUENCE: 1628
aguggguucc agagaugcga                                             20

<210> SEQ ID NO 1629
<211> LENGTH: 20
<212> TYPE: RNA

```
<213> ORGANISM: Artificial Sequence
<220> FEATURE:
<223> OTHER INFORMATION: synthesized

<400> SEQUENCE: 1629
aguggguucc agagauguga                                               20

<210> SEQ ID NO 1630
<211> LENGTH: 20
<212> TYPE: RNA
<213> ORGANISM: Artificial Sequence
<220> FEATURE:
<223> OTHER INFORMATION: synthesized

<400> SEQUENCE: 1630
augcgaaguu gccuggcugc                                               20

<210> SEQ ID NO 1631
<211> LENGTH: 20
<212> TYPE: RNA
<213> ORGANISM: Artificial Sequence
<220> FEATURE:
<223> OTHER INFORMATION: synthesized

<400> SEQUENCE: 1631
augugaaguu gccuggcugc                                               20

<210> SEQ ID NO 1632
<211> LENGTH: 20
<212> TYPE: RNA
<213> ORGANISM: Artificial Sequence
<220> FEATURE:
<223> OTHER INFORMATION: synthesized

<400> SEQUENCE: 1632
caacuucaca ucucuggaac                                               20

<210> SEQ ID NO 1633
<211> LENGTH: 20
<212> TYPE: RNA
<213> ORGANISM: Artificial Sequence
<220> FEATURE:
<223> OTHER INFORMATION: synthesized

<400> SEQUENCE: 1633
caacuucgca ucucuggaac                                               20

<210> SEQ ID NO 1634
<211> LENGTH: 20
<212> TYPE: RNA
<213> ORGANISM: Artificial Sequence
<220> FEATURE:
<223> OTHER INFORMATION: synthesized

<400> SEQUENCE: 1634
cacaucucug gaacccacuu                                               20

<210> SEQ ID NO 1635
<211> LENGTH: 20
<212> TYPE: RNA
<213> ORGANISM: Artificial Sequence
<220> FEATURE:
<223> OTHER INFORMATION: synthesized

<400> SEQUENCE: 1635
cagagaugcg aaguugccug                                               20
```

```
<210> SEQ ID NO 1636
<211> LENGTH: 20
<212> TYPE: RNA
<213> ORGANISM: Artificial Sequence
<220> FEATURE:
<223> OTHER INFORMATION: synthesized

<400> SEQUENCE: 1636
cagagaugug aaguugccug                                               20

<210> SEQ ID NO 1637
<211> LENGTH: 20
<212> TYPE: RNA
<213> ORGANISM: Artificial Sequence
<220> FEATURE:
<223> OTHER INFORMATION: synthesized

<400> SEQUENCE: 1637
cagccaggca acuucacauc                                               20

<210> SEQ ID NO 1638
<211> LENGTH: 20
<212> TYPE: RNA
<213> ORGANISM: Artificial Sequence
<220> FEATURE:
<223> OTHER INFORMATION: synthesized

<400> SEQUENCE: 1638
cagccaggca acuucgcauc                                               20

<210> SEQ ID NO 1639
<211> LENGTH: 20
<212> TYPE: RNA
<213> ORGANISM: Artificial Sequence
<220> FEATURE:
<223> OTHER INFORMATION: synthesized

<400> SEQUENCE: 1639
caggcaacuu cacaucucug                                               20

<210> SEQ ID NO 1640
<211> LENGTH: 20
<212> TYPE: RNA
<213> ORGANISM: Artificial Sequence
<220> FEATURE:
<223> OTHER INFORMATION: synthesized

<400> SEQUENCE: 1640
caggcaacuu cgcaucucug                                               20

<210> SEQ ID NO 1641
<211> LENGTH: 20
<212> TYPE: RNA
<213> ORGANISM: Artificial Sequence
<220> FEATURE:
<223> OTHER INFORMATION: synthesized

<400> SEQUENCE: 1641
ccagagaugc gaaguugccu                                               20

<210> SEQ ID NO 1642
<211> LENGTH: 20
<212> TYPE: RNA
<213> ORGANISM: Artificial Sequence
<220> FEATURE:
```

<223> OTHER INFORMATION: synthesized

<400> SEQUENCE: 1642
ccagagaugu gaaguugccu                                                    20

<210> SEQ ID NO 1643
<211> LENGTH: 20
<212> TYPE: RNA
<213> ORGANISM: Artificial Sequence
<220> FEATURE:
<223> OTHER INFORMATION: synthesized

<400> SEQUENCE: 1643
cgaaguugcc uggcugccuc                                                    20

<210> SEQ ID NO 1644
<211> LENGTH: 20
<212> TYPE: RNA
<213> ORGANISM: Artificial Sequence
<220> FEATURE:
<223> OTHER INFORMATION: synthesized

<400> SEQUENCE: 1644
cgcaucucug gaacccacuu                                                    20

<210> SEQ ID NO 1645
<211> LENGTH: 20
<212> TYPE: RNA
<213> ORGANISM: Artificial Sequence
<220> FEATURE:
<223> OTHER INFORMATION: synthesized

<400> SEQUENCE: 1645
cuucacaucu cuggaaccca                                                    20

<210> SEQ ID NO 1646
<211> LENGTH: 20
<212> TYPE: RNA
<213> ORGANISM: Artificial Sequence
<220> FEATURE:
<223> OTHER INFORMATION: synthesized

<400> SEQUENCE: 1646
cuucgcaucu cuggaaccca                                                    20

<210> SEQ ID NO 1647
<211> LENGTH: 20
<212> TYPE: RNA
<213> ORGANISM: Artificial Sequence
<220> FEATURE:
<223> OTHER INFORMATION: synthesized

<400> SEQUENCE: 1647
gagaugcgaa guugccuggc                                                    20

<210> SEQ ID NO 1648
<211> LENGTH: 20
<212> TYPE: RNA
<213> ORGANISM: Artificial Sequence
<220> FEATURE:
<223> OTHER INFORMATION: synthesized

<400> SEQUENCE: 1648
gagaugugaa guugccuggc                                                    20

```
<210> SEQ ID NO 1649
<211> LENGTH: 20
<212> TYPE: RNA
<213> ORGANISM: Artificial Sequence
<220> FEATURE:
<223> OTHER INFORMATION: synthesized

<400> SEQUENCE: 1649
gaggcagcca ggcaacuuca                                               20

<210> SEQ ID NO 1650
<211> LENGTH: 20
<212> TYPE: RNA
<213> ORGANISM: Artificial Sequence
<220> FEATURE:
<223> OTHER INFORMATION: synthesized

<400> SEQUENCE: 1650
gaggcagcca ggcaacuucg                                               20

<210> SEQ ID NO 1651
<211> LENGTH: 20
<212> TYPE: RNA
<213> ORGANISM: Artificial Sequence
<220> FEATURE:
<223> OTHER INFORMATION: synthesized

<400> SEQUENCE: 1651
gaugcgaagu ugccuggcug                                               20

<210> SEQ ID NO 1652
<211> LENGTH: 20
<212> TYPE: RNA
<213> ORGANISM: Artificial Sequence
<220> FEATURE:
<223> OTHER INFORMATION: synthesized

<400> SEQUENCE: 1652
gaugugaagu ugccuggcug                                               20

<210> SEQ ID NO 1653
<211> LENGTH: 20
<212> TYPE: RNA
<213> ORGANISM: Artificial Sequence
<220> FEATURE:
<223> OTHER INFORMATION: synthesized

<400> SEQUENCE: 1653
gcaacuucac aucucuggaa                                               20

<210> SEQ ID NO 1654
<211> LENGTH: 20
<212> TYPE: RNA
<213> ORGANISM: Artificial Sequence
<220> FEATURE:
<223> OTHER INFORMATION: synthesized

<400> SEQUENCE: 1654
gcaacuucgc aucucuggaa                                               20

<210> SEQ ID NO 1655
<211> LENGTH: 20
<212> TYPE: RNA
<213> ORGANISM: Artificial Sequence
<220> FEATURE:
<223> OTHER INFORMATION: synthesized
```

<400> SEQUENCE: 1655
gcagccaggc aacuucacau                                              20

<210> SEQ ID NO 1656
<211> LENGTH: 20
<212> TYPE: RNA
<213> ORGANISM: Artificial Sequence
<220> FEATURE:
<223> OTHER INFORMATION: synthesized

<400> SEQUENCE: 1656
gcagccaggc aacuucgcau                                              20

<210> SEQ ID NO 1657
<211> LENGTH: 20
<212> TYPE: RNA
<213> ORGANISM: Artificial Sequence
<220> FEATURE:
<223> OTHER INFORMATION: synthesized

<400> SEQUENCE: 1657
gcaucucugg aacccacuua                                              20

<210> SEQ ID NO 1658
<211> LENGTH: 20
<212> TYPE: RNA
<213> ORGANISM: Artificial Sequence
<220> FEATURE:
<223> OTHER INFORMATION: synthesized

<400> SEQUENCE: 1658
gcgaaguugc cuggcugccu                                              20

<210> SEQ ID NO 1659
<211> LENGTH: 20
<212> TYPE: RNA
<213> ORGANISM: Artificial Sequence
<220> FEATURE:
<223> OTHER INFORMATION: synthesized

<400> SEQUENCE: 1659
ggcaacuuca caucucugga                                              20

<210> SEQ ID NO 1660
<211> LENGTH: 20
<212> TYPE: RNA
<213> ORGANISM: Artificial Sequence
<220> FEATURE:
<223> OTHER INFORMATION: synthesized

<400> SEQUENCE: 1660
ggcaacuucg caucucugga                                              20

<210> SEQ ID NO 1661
<211> LENGTH: 20
<212> TYPE: RNA
<213> ORGANISM: Artificial Sequence
<220> FEATURE:
<223> OTHER INFORMATION: synthesized

<400> SEQUENCE: 1661
ggcagccagg caacuucaca                                              20

<210> SEQ ID NO 1662
<211> LENGTH: 20

-continued

<212> TYPE: RNA
<213> ORGANISM: Artificial Sequence
<220> FEATURE:
<223> OTHER INFORMATION: synthesized

<400> SEQUENCE: 1662
ggcagccagg caacuucgca                                               20

<210> SEQ ID NO 1663
<211> LENGTH: 20
<212> TYPE: RNA
<213> ORGANISM: Artificial Sequence
<220> FEATURE:
<223> OTHER INFORMATION: synthesized

<400> SEQUENCE: 1663
ggguuccaga gaugcgaagu                                               20

<210> SEQ ID NO 1664
<211> LENGTH: 20
<212> TYPE: RNA
<213> ORGANISM: Artificial Sequence
<220> FEATURE:
<223> OTHER INFORMATION: synthesized

<400> SEQUENCE: 1664
ggguuccaga gaugugaagu                                               20

<210> SEQ ID NO 1665
<211> LENGTH: 20
<212> TYPE: RNA
<213> ORGANISM: Artificial Sequence
<220> FEATURE:
<223> OTHER INFORMATION: synthesized

<400> SEQUENCE: 1665
gguuccagag augcgaaguu                                               20

<210> SEQ ID NO 1666
<211> LENGTH: 20
<212> TYPE: RNA
<213> ORGANISM: Artificial Sequence
<220> FEATURE:
<223> OTHER INFORMATION: synthesized

<400> SEQUENCE: 1666
gguuccagag augugaaguu                                               20

<210> SEQ ID NO 1667
<211> LENGTH: 20
<212> TYPE: RNA
<213> ORGANISM: Artificial Sequence
<220> FEATURE:
<223> OTHER INFORMATION: synthesized

<400> SEQUENCE: 1667
gugaaguugc cuggcugccu                                               20

<210> SEQ ID NO 1668
<211> LENGTH: 20
<212> TYPE: RNA
<213> ORGANISM: Artificial Sequence
<220> FEATURE:
<223> OTHER INFORMATION: synthesized

<400> SEQUENCE: 1668

```
guggguucca gagaugcgaa                                                   20

<210> SEQ ID NO 1669
<211> LENGTH: 20
<212> TYPE: RNA
<213> ORGANISM: Artificial Sequence
<220> FEATURE:
<223> OTHER INFORMATION: synthesized

<400> SEQUENCE: 1669
guggguucca gagaugugaa                                                   20

<210> SEQ ID NO 1670
<211> LENGTH: 20
<212> TYPE: RNA
<213> ORGANISM: Artificial Sequence
<220> FEATURE:
<223> OTHER INFORMATION: synthesized

<400> SEQUENCE: 1670
guuccagaga ugcgaaguug                                                   20

<210> SEQ ID NO 1671
<211> LENGTH: 20
<212> TYPE: RNA
<213> ORGANISM: Artificial Sequence
<220> FEATURE:
<223> OTHER INFORMATION: synthesized

<400> SEQUENCE: 1671
guuccagaga ugugaaguug                                                   20

<210> SEQ ID NO 1672
<211> LENGTH: 20
<212> TYPE: RNA
<213> ORGANISM: Artificial Sequence
<220> FEATURE:
<223> OTHER INFORMATION: synthesized

<400> SEQUENCE: 1672
uaaguggguu ccagagaugc                                                   20

<210> SEQ ID NO 1673
<211> LENGTH: 20
<212> TYPE: RNA
<213> ORGANISM: Artificial Sequence
<220> FEATURE:
<223> OTHER INFORMATION: synthesized

<400> SEQUENCE: 1673
uaaguggguu ccagagaugu                                                   20

<210> SEQ ID NO 1674
<211> LENGTH: 20
<212> TYPE: RNA
<213> ORGANISM: Artificial Sequence
<220> FEATURE:
<223> OTHER INFORMATION: synthesized

<400> SEQUENCE: 1674
ucacaucucu ggaacccacu                                                   20

<210> SEQ ID NO 1675
<211> LENGTH: 20
<212> TYPE: RNA
<213> ORGANISM: Artificial Sequence
```

```
<220> FEATURE:
<223> OTHER INFORMATION: synthesized

<400> SEQUENCE: 1675
ucgcaucucu ggaacccacu                                               20

<210> SEQ ID NO 1676
<211> LENGTH: 20
<212> TYPE: RNA
<213> ORGANISM: Artificial Sequence
<220> FEATURE:
<223> OTHER INFORMATION: synthesized

<400> SEQUENCE: 1676
ugaaguugcc uggcugccuc                                               20

<210> SEQ ID NO 1677
<211> LENGTH: 20
<212> TYPE: RNA
<213> ORGANISM: Artificial Sequence
<220> FEATURE:
<223> OTHER INFORMATION: synthesized

<400> SEQUENCE: 1677
ugcgaaguug ccuggcugcc                                               20

<210> SEQ ID NO 1678
<211> LENGTH: 20
<212> TYPE: RNA
<213> ORGANISM: Artificial Sequence
<220> FEATURE:
<223> OTHER INFORMATION: synthesized

<400> SEQUENCE: 1678
uggguuccag agaugcgaag                                               20

<210> SEQ ID NO 1679
<211> LENGTH: 20
<212> TYPE: RNA
<213> ORGANISM: Artificial Sequence
<220> FEATURE:
<223> OTHER INFORMATION: synthesized

<400> SEQUENCE: 1679
uggguuccag agaugugaag                                               20

<210> SEQ ID NO 1680
<211> LENGTH: 20
<212> TYPE: RNA
<213> ORGANISM: Artificial Sequence
<220> FEATURE:
<223> OTHER INFORMATION: synthesized

<400> SEQUENCE: 1680
ugugaaguug ccuggcugcc                                               20

<210> SEQ ID NO 1681
<211> LENGTH: 20
<212> TYPE: RNA
<213> ORGANISM: Artificial Sequence
<220> FEATURE:
<223> OTHER INFORMATION: synthesized

<400> SEQUENCE: 1681
uucacaucuc uggaacccac                                               20
```

```
<210> SEQ ID NO 1682
<211> LENGTH: 20
<212> TYPE: RNA
<213> ORGANISM: Artificial Sequence
<220> FEATURE:
<223> OTHER INFORMATION: synthesized

<400> SEQUENCE: 1682
uuccagagau gcgaaguugc                                                     20

<210> SEQ ID NO 1683
<211> LENGTH: 20
<212> TYPE: RNA
<213> ORGANISM: Artificial Sequence
<220> FEATURE:
<223> OTHER INFORMATION: synthesized

<400> SEQUENCE: 1683
uuccagagau gugaaguugc                                                     20

<210> SEQ ID NO 1684
<211> LENGTH: 20
<212> TYPE: RNA
<213> ORGANISM: Artificial Sequence
<220> FEATURE:
<223> OTHER INFORMATION: synthesized

<400> SEQUENCE: 1684
uucgcaucuc uggaacccac                                                     20

<210> SEQ ID NO 1685
<211> LENGTH: 20
<212> TYPE: RNA
<213> ORGANISM: Artificial Sequence
<220> FEATURE:
<223> OTHER INFORMATION: synthesized

<400> SEQUENCE: 1685
aacugcauua ucccucaaag                                                     20

<210> SEQ ID NO 1686
<211> LENGTH: 20
<212> TYPE: RNA
<213> ORGANISM: Artificial Sequence
<220> FEATURE:
<223> OTHER INFORMATION: synthesized

<400> SEQUENCE: 1686
aacugcauua ucucucaaag                                                     20

<210> SEQ ID NO 1687
<211> LENGTH: 20
<212> TYPE: RNA
<213> ORGANISM: Artificial Sequence
<220> FEATURE:
<223> OTHER INFORMATION: synthesized

<400> SEQUENCE: 1687
agauaaugca guuauaucag                                                     20

<210> SEQ ID NO 1688
<211> LENGTH: 20
<212> TYPE: RNA
<213> ORGANISM: Artificial Sequence
<220> FEATURE:
<223> OTHER INFORMATION: synthesized
```

```
<400> SEQUENCE: 1688
auauaacugc auuaucccuc                                              20

<210> SEQ ID NO 1689
<211> LENGTH: 20
<212> TYPE: RNA
<213> ORGANISM: Artificial Sequence
<220> FEATURE:
<223> OTHER INFORMATION: synthesized

<400> SEQUENCE: 1689
auauaacugc auuaucucuc                                              20

<210> SEQ ID NO 1690
<211> LENGTH: 20
<212> TYPE: RNA
<213> ORGANISM: Artificial Sequence
<220> FEATURE:
<223> OTHER INFORMATION: synthesized

<400> SEQUENCE: 1690
aucccucaaa gaaggaagga                                              20

<210> SEQ ID NO 1691
<211> LENGTH: 20
<212> TYPE: RNA
<213> ORGANISM: Artificial Sequence
<220> FEATURE:
<223> OTHER INFORMATION: synthesized

<400> SEQUENCE: 1691
aucucucaaa gaaggaagga                                              20

<210> SEQ ID NO 1692
<211> LENGTH: 20
<212> TYPE: RNA
<213> ORGANISM: Artificial Sequence
<220> FEATURE:
<223> OTHER INFORMATION: synthesized

<400> SEQUENCE: 1692
cccucaaaga aggaaggaga                                              20

<210> SEQ ID NO 1693
<211> LENGTH: 20
<212> TYPE: RNA
<213> ORGANISM: Artificial Sequence
<220> FEATURE:
<223> OTHER INFORMATION: synthesized

<400> SEQUENCE: 1693
ccuuccuucu uugagagaua                                              20

<210> SEQ ID NO 1694
<211> LENGTH: 20
<212> TYPE: RNA
<213> ORGANISM: Artificial Sequence
<220> FEATURE:
<223> OTHER INFORMATION: synthesized

<400> SEQUENCE: 1694
ccuuccuucu uugagggaua                                              20

<210> SEQ ID NO 1695
```

<210> SEQ ID NO 1695
<211> LENGTH: 20
<212> TYPE: RNA
<213> ORGANISM: Artificial Sequence
<220> FEATURE:
<223> OTHER INFORMATION: synthesized

<400> SEQUENCE: 1695
ccuucuuuga gagauaaugc                                               20

<210> SEQ ID NO 1696
<211> LENGTH: 20
<212> TYPE: RNA
<213> ORGANISM: Artificial Sequence
<220> FEATURE:
<223> OTHER INFORMATION: synthesized

<400> SEQUENCE: 1696
ccuucuuuga gggauaaugc                                               20

<210> SEQ ID NO 1697
<211> LENGTH: 20
<212> TYPE: RNA
<213> ORGANISM: Artificial Sequence
<220> FEATURE:
<223> OTHER INFORMATION: synthesized

<400> SEQUENCE: 1697
cuccuuccuu cuuugagaga                                               20

<210> SEQ ID NO 1698
<211> LENGTH: 20
<212> TYPE: RNA
<213> ORGANISM: Artificial Sequence
<220> FEATURE:
<223> OTHER INFORMATION: synthesized

<400> SEQUENCE: 1698
cuccuuccuu cuuugaggga                                               20

<210> SEQ ID NO 1699
<211> LENGTH: 20
<212> TYPE: RNA
<213> ORGANISM: Artificial Sequence
<220> FEATURE:
<223> OTHER INFORMATION: synthesized

<400> SEQUENCE: 1699
cucucaaaga aggaaggaga                                               20

<210> SEQ ID NO 1700
<211> LENGTH: 20
<212> TYPE: RNA
<213> ORGANISM: Artificial Sequence
<220> FEATURE:
<223> OTHER INFORMATION: synthesized

<400> SEQUENCE: 1700
cucuccuucc uucuuugaga                                               20

<210> SEQ ID NO 1701
<211> LENGTH: 20
<212> TYPE: RNA
<213> ORGANISM: Artificial Sequence
<220> FEATURE:
<223> OTHER INFORMATION: synthesized

<400> SEQUENCE: 1701

```
cucuccuucc uucuuugagg                                                20

<210> SEQ ID NO 1702
<211> LENGTH: 20
<212> TYPE: RNA
<213> ORGANISM: Artificial Sequence
<220> FEATURE:
<223> OTHER INFORMATION: synthesized

<400> SEQUENCE: 1702
cugauauaac ugcauuaucc                                                20

<210> SEQ ID NO 1703
<211> LENGTH: 20
<212> TYPE: RNA
<213> ORGANISM: Artificial Sequence
<220> FEATURE:
<223> OTHER INFORMATION: synthesized

<400> SEQUENCE: 1703
cugauauaac ugcauuaucu                                                20

<210> SEQ ID NO 1704
<211> LENGTH: 20
<212> TYPE: RNA
<213> ORGANISM: Artificial Sequence
<220> FEATURE:
<223> OTHER INFORMATION: synthesized

<400> SEQUENCE: 1704
cuuccuucuu ugagagauaa                                                20

<210> SEQ ID NO 1705
<211> LENGTH: 20
<212> TYPE: RNA
<213> ORGANISM: Artificial Sequence
<220> FEATURE:
<223> OTHER INFORMATION: synthesized

<400> SEQUENCE: 1705
cuuccuucuu ugagggauaa                                                20

<210> SEQ ID NO 1706
<211> LENGTH: 20
<212> TYPE: RNA
<213> ORGANISM: Artificial Sequence
<220> FEATURE:
<223> OTHER INFORMATION: synthesized

<400> SEQUENCE: 1706
cuucuuugag agauaaugca                                                20

<210> SEQ ID NO 1707
<211> LENGTH: 20
<212> TYPE: RNA
<213> ORGANISM: Artificial Sequence
<220> FEATURE:
<223> OTHER INFORMATION: synthesized

<400> SEQUENCE: 1707
cuucuuugag ggauaaugca                                                20

<210> SEQ ID NO 1708
<211> LENGTH: 20
<212> TYPE: RNA
```

```
<213> ORGANISM: Artificial Sequence
<220> FEATURE:
<223> OTHER INFORMATION: synthesized

<400> SEQUENCE: 1708
cuuugagaga uaaugcaguu                                               20

<210> SEQ ID NO 1709
<211> LENGTH: 20
<212> TYPE: RNA
<213> ORGANISM: Artificial Sequence
<220> FEATURE:
<223> OTHER INFORMATION: synthesized

<400> SEQUENCE: 1709
cuuugaggga uaaugcaguu                                               20

<210> SEQ ID NO 1710
<211> LENGTH: 20
<212> TYPE: RNA
<213> ORGANISM: Artificial Sequence
<220> FEATURE:
<223> OTHER INFORMATION: synthesized

<400> SEQUENCE: 1710
gagauaaugc aguuauauca                                               20

<210> SEQ ID NO 1711
<211> LENGTH: 20
<212> TYPE: RNA
<213> ORGANISM: Artificial Sequence
<220> FEATURE:
<223> OTHER INFORMATION: synthesized

<400> SEQUENCE: 1711
gauauaacug cauuaucccu                                               20

<210> SEQ ID NO 1712
<211> LENGTH: 20
<212> TYPE: RNA
<213> ORGANISM: Artificial Sequence
<220> FEATURE:
<223> OTHER INFORMATION: synthesized

<400> SEQUENCE: 1712
gauauaacug cauuaucucu                                               20

<210> SEQ ID NO 1713
<211> LENGTH: 20
<212> TYPE: RNA
<213> ORGANISM: Artificial Sequence
<220> FEATURE:
<223> OTHER INFORMATION: synthesized

<400> SEQUENCE: 1713
gcauuauccc ucaaagaagg                                               20

<210> SEQ ID NO 1714
<211> LENGTH: 20
<212> TYPE: RNA
<213> ORGANISM: Artificial Sequence
<220> FEATURE:
<223> OTHER INFORMATION: synthesized

<400> SEQUENCE: 1714
gcauuaucuc ucaaagaagg                                               20
```

<210> SEQ ID NO 1715
<211> LENGTH: 20
<212> TYPE: RNA
<213> ORGANISM: Artificial Sequence
<220> FEATURE:
<223> OTHER INFORMATION: synthesized

<400> SEQUENCE: 1715
ggauaaugca guuauaucag                                              20

<210> SEQ ID NO 1716
<211> LENGTH: 20
<212> TYPE: RNA
<213> ORGANISM: Artificial Sequence
<220> FEATURE:
<223> OTHER INFORMATION: synthesized

<400> SEQUENCE: 1716
gggauaaugc aguuauauca                                              20

<210> SEQ ID NO 1717
<211> LENGTH: 20
<212> TYPE: RNA
<213> ORGANISM: Artificial Sequence
<220> FEATURE:
<223> OTHER INFORMATION: synthesized

<400> SEQUENCE: 1717
uaacugcauu aucccucaaa                                              20

<210> SEQ ID NO 1718
<211> LENGTH: 20
<212> TYPE: RNA
<213> ORGANISM: Artificial Sequence
<220> FEATURE:
<223> OTHER INFORMATION: synthesized

<400> SEQUENCE: 1718
uaacugcauu aucucucaaa                                              20

<210> SEQ ID NO 1719
<211> LENGTH: 20
<212> TYPE: RNA
<213> ORGANISM: Artificial Sequence
<220> FEATURE:
<223> OTHER INFORMATION: synthesized

<400> SEQUENCE: 1719
uauaacugca uuaucccuca                                              20

<210> SEQ ID NO 1720
<211> LENGTH: 20
<212> TYPE: RNA
<213> ORGANISM: Artificial Sequence
<220> FEATURE:
<223> OTHER INFORMATION: synthesized

<400> SEQUENCE: 1720
uauaacugca uuaucucuca                                              20

<210> SEQ ID NO 1721
<211> LENGTH: 20
<212> TYPE: RNA
<213> ORGANISM: Artificial Sequence
<220> FEATURE:

<223> OTHER INFORMATION: synthesized

<400> SEQUENCE: 1721
uccuuccuuc uuugagagau                                                    20

<210> SEQ ID NO 1722
<211> LENGTH: 20
<212> TYPE: RNA
<213> ORGANISM: Artificial Sequence
<220> FEATURE:
<223> OTHER INFORMATION: synthesized

<400> SEQUENCE: 1722
uccuuccuuc uuugagggau                                                    20

<210> SEQ ID NO 1723
<211> LENGTH: 20
<212> TYPE: RNA
<213> ORGANISM: Artificial Sequence
<220> FEATURE:
<223> OTHER INFORMATION: synthesized

<400> SEQUENCE: 1723
uccuucuuug agagauaaug                                                    20

<210> SEQ ID NO 1724
<211> LENGTH: 20
<212> TYPE: RNA
<213> ORGANISM: Artificial Sequence
<220> FEATURE:
<223> OTHER INFORMATION: synthesized

<400> SEQUENCE: 1724
uccuucuuug agggauaaug                                                    20

<210> SEQ ID NO 1725
<211> LENGTH: 20
<212> TYPE: RNA
<213> ORGANISM: Artificial Sequence
<220> FEATURE:
<223> OTHER INFORMATION: synthesized

<400> SEQUENCE: 1725
ucuccuuccu ucuuugagag                                                    20

<210> SEQ ID NO 1726
<211> LENGTH: 20
<212> TYPE: RNA
<213> ORGANISM: Artificial Sequence
<220> FEATURE:
<223> OTHER INFORMATION: synthesized

<400> SEQUENCE: 1726
ucuccuuccu ucuuugaggg                                                    20

<210> SEQ ID NO 1727
<211> LENGTH: 20
<212> TYPE: RNA
<213> ORGANISM: Artificial Sequence
<220> FEATURE:
<223> OTHER INFORMATION: synthesized

<400> SEQUENCE: 1727
ucuuugagag auaaugcagu                                                    20

```
<210> SEQ ID NO 1728
<211> LENGTH: 20
<212> TYPE: RNA
<213> ORGANISM: Artificial Sequence
<220> FEATURE:
<223> OTHER INFORMATION: synthesized

<400> SEQUENCE: 1728
ucuuugaggg auaaugcagu                                               20

<210> SEQ ID NO 1729
<211> LENGTH: 20
<212> TYPE: RNA
<213> ORGANISM: Artificial Sequence
<220> FEATURE:
<223> OTHER INFORMATION: synthesized

<400> SEQUENCE: 1729
ugagagauaa ugcaguuaua                                               20

<210> SEQ ID NO 1730
<211> LENGTH: 20
<212> TYPE: RNA
<213> ORGANISM: Artificial Sequence
<220> FEATURE:
<223> OTHER INFORMATION: synthesized

<400> SEQUENCE: 1730
ugagggauaa ugcaguuaua                                               20

<210> SEQ ID NO 1731
<211> LENGTH: 20
<212> TYPE: RNA
<213> ORGANISM: Artificial Sequence
<220> FEATURE:
<223> OTHER INFORMATION: synthesized

<400> SEQUENCE: 1731
ugauauaacu gcauuauccc                                               20

<210> SEQ ID NO 1732
<211> LENGTH: 20
<212> TYPE: RNA
<213> ORGANISM: Artificial Sequence
<220> FEATURE:
<223> OTHER INFORMATION: synthesized

<400> SEQUENCE: 1732
ugauauaacu gcauuaucuc                                               20

<210> SEQ ID NO 1733
<211> LENGTH: 20
<212> TYPE: RNA
<213> ORGANISM: Artificial Sequence
<220> FEATURE:
<223> OTHER INFORMATION: synthesized

<400> SEQUENCE: 1733
ugcauuaucc cucaaagaag                                               20

<210> SEQ ID NO 1734
<211> LENGTH: 20
<212> TYPE: RNA
<213> ORGANISM: Artificial Sequence
<220> FEATURE:
<223> OTHER INFORMATION: synthesized
```

```
<400> SEQUENCE: 1734
ugcauuaucu cucaaagaag                                               20

<210> SEQ ID NO 1735
<211> LENGTH: 20
<212> TYPE: RNA
<213> ORGANISM: Artificial Sequence
<220> FEATURE:
<223> OTHER INFORMATION: synthesized

<400> SEQUENCE: 1735
uuaucccuca aagaaggaag                                               20

<210> SEQ ID NO 1736
<211> LENGTH: 20
<212> TYPE: RNA
<213> ORGANISM: Artificial Sequence
<220> FEATURE:
<223> OTHER INFORMATION: synthesized

<400> SEQUENCE: 1736
uuaucucuca aagaaggaag                                               20

<210> SEQ ID NO 1737
<211> LENGTH: 20
<212> TYPE: RNA
<213> ORGANISM: Artificial Sequence
<220> FEATURE:
<223> OTHER INFORMATION: synthesized

<400> SEQUENCE: 1737
uuccuucuuu gagagauaau                                               20

<210> SEQ ID NO 1738
<211> LENGTH: 20
<212> TYPE: RNA
<213> ORGANISM: Artificial Sequence
<220> FEATURE:
<223> OTHER INFORMATION: synthesized

<400> SEQUENCE: 1738
uuccuucuuu gagggauaau                                               20

<210> SEQ ID NO 1739
<211> LENGTH: 20
<212> TYPE: RNA
<213> ORGANISM: Artificial Sequence
<220> FEATURE:
<223> OTHER INFORMATION: synthesized

<400> SEQUENCE: 1739
uucuuugaga gauaaugcag                                               20

<210> SEQ ID NO 1740
<211> LENGTH: 20
<212> TYPE: RNA
<213> ORGANISM: Artificial Sequence
<220> FEATURE:
<223> OTHER INFORMATION: synthesized

<400> SEQUENCE: 1740
uucuuugagg gauaaugcag                                               20

<210> SEQ ID NO 1741
<211> LENGTH: 20
```

```
<212> TYPE: RNA
<213> ORGANISM: Artificial Sequence
<220> FEATURE:
<223> OTHER INFORMATION: synthesized

<400> SEQUENCE: 1741
uugagagaua augcaguuau                                                   20

<210> SEQ ID NO 1742
<211> LENGTH: 20
<212> TYPE: RNA
<213> ORGANISM: Artificial Sequence
<220> FEATURE:
<223> OTHER INFORMATION: synthesized

<400> SEQUENCE: 1742
uugagggaua augcaguuau                                                   20

<210> SEQ ID NO 1743
<211> LENGTH: 20
<212> TYPE: RNA
<213> ORGANISM: Artificial Sequence
<220> FEATURE:
<223> OTHER INFORMATION: synthesized

<400> SEQUENCE: 1743
uuugagagau aaugcaguua                                                   20

<210> SEQ ID NO 1744
<211> LENGTH: 20
<212> TYPE: RNA
<213> ORGANISM: Artificial Sequence
<220> FEATURE:
<223> OTHER INFORMATION: synthesized

<400> SEQUENCE: 1744
uuugagggau aaugcaguua                                                   20

<210> SEQ ID NO 1745
<211> LENGTH: 20
<212> TYPE: RNA
<213> ORGANISM: Artificial Sequence
<220> FEATURE:
<223> OTHER INFORMATION: synthesized

<400> SEQUENCE: 1745
aaauccuguc uguucaccca                                                   20

<210> SEQ ID NO 1746
<211> LENGTH: 20
<212> TYPE: RNA
<213> ORGANISM: Artificial Sequence
<220> FEATURE:
<223> OTHER INFORMATION: synthesized

<400> SEQUENCE: 1746
aacagacagg acuucaguug                                                   20

<210> SEQ ID NO 1747
<211> LENGTH: 20
<212> TYPE: RNA
<213> ORGANISM: Artificial Sequence
<220> FEATURE:
<223> OTHER INFORMATION: synthesized

<400> SEQUENCE: 1747
```

-continued aacagacagg auuucaguug                                               20

<210> SEQ ID NO 1748
<211> LENGTH: 20
<212> TYPE: RNA
<213> ORGANISM: Artificial Sequence
<220> FEATURE:
<223> OTHER INFORMATION: synthesized

<400> SEQUENCE: 1748
aacugaaauc cugucuguuc                                               20

<210> SEQ ID NO 1749
<211> LENGTH: 20
<212> TYPE: RNA
<213> ORGANISM: Artificial Sequence
<220> FEATURE:
<223> OTHER INFORMATION: synthesized

<400> SEQUENCE: 1749
aacugaaguc cugucuguuc                                               20

<210> SEQ ID NO 1750
<211> LENGTH: 20
<212> TYPE: RNA
<213> ORGANISM: Artificial Sequence
<220> FEATURE:
<223> OTHER INFORMATION: synthesized

<400> SEQUENCE: 1750
aaguccuguc uguucaccca                                               20

<210> SEQ ID NO 1751
<211> LENGTH: 20
<212> TYPE: RNA
<213> ORGANISM: Artificial Sequence
<220> FEATURE:
<223> OTHER INFORMATION: synthesized

<400> SEQUENCE: 1751
aauccugucu guucacccac                                               20

<210> SEQ ID NO 1752
<211> LENGTH: 20
<212> TYPE: RNA
<213> ORGANISM: Artificial Sequence
<220> FEATURE:
<223> OTHER INFORMATION: synthesized

<400> SEQUENCE: 1752
acagacagga cuucaguugc                                               20

<210> SEQ ID NO 1753
<211> LENGTH: 20
<212> TYPE: RNA
<213> ORGANISM: Artificial Sequence
<220> FEATURE:
<223> OTHER INFORMATION: synthesized

<400> SEQUENCE: 1753
acagacagga uuucaguugc                                               20

<210> SEQ ID NO 1754
<211> LENGTH: 20
<212> TYPE: RNA
<213> ORGANISM: Artificial Sequence

```
<220> FEATURE:
<223> OTHER INFORMATION: synthesized

<400> SEQUENCE: 1754
acugaaaucc ugucuguuca                                              20

<210> SEQ ID NO 1755
<211> LENGTH: 20
<212> TYPE: RNA
<213> ORGANISM: Artificial Sequence
<220> FEATURE:
<223> OTHER INFORMATION: synthesized

<400> SEQUENCE: 1755
acugaagucc ugucuguuca                                              20

<210> SEQ ID NO 1756
<211> LENGTH: 20
<212> TYPE: RNA
<213> ORGANISM: Artificial Sequence
<220> FEATURE:
<223> OTHER INFORMATION: synthesized

<400> SEQUENCE: 1756
agacaggacu ucaguugcau                                              20

<210> SEQ ID NO 1757
<211> LENGTH: 20
<212> TYPE: RNA
<213> ORGANISM: Artificial Sequence
<220> FEATURE:
<223> OTHER INFORMATION: synthesized

<400> SEQUENCE: 1757
agacaggauu ucaguugcau                                              20

<210> SEQ ID NO 1758
<211> LENGTH: 20
<212> TYPE: RNA
<213> ORGANISM: Artificial Sequence
<220> FEATURE:
<223> OTHER INFORMATION: synthesized

<400> SEQUENCE: 1758
agcaugcaac ugaaauccug                                              20

<210> SEQ ID NO 1759
<211> LENGTH: 20
<212> TYPE: RNA
<213> ORGANISM: Artificial Sequence
<220> FEATURE:
<223> OTHER INFORMATION: synthesized

<400> SEQUENCE: 1759
agcaugcaac ugaaguccug                                              20

<210> SEQ ID NO 1760
<211> LENGTH: 20
<212> TYPE: RNA
<213> ORGANISM: Artificial Sequence
<220> FEATURE:
<223> OTHER INFORMATION: synthesized

<400> SEQUENCE: 1760
aguccugucu guucacccac                                              20
```

```
<210> SEQ ID NO 1761
<211> LENGTH: 20
<212> TYPE: RNA
<213> ORGANISM: Artificial Sequence
<220> FEATURE:
<223> OTHER INFORMATION: synthesized

<400> SEQUENCE: 1761
agugggugaa cagacaggac                                              20

<210> SEQ ID NO 1762
<211> LENGTH: 20
<212> TYPE: RNA
<213> ORGANISM: Artificial Sequence
<220> FEATURE:
<223> OTHER INFORMATION: synthesized

<400> SEQUENCE: 1762
agugggugaa cagacaggau                                              20

<210> SEQ ID NO 1763
<211> LENGTH: 20
<212> TYPE: RNA
<213> ORGANISM: Artificial Sequence
<220> FEATURE:
<223> OTHER INFORMATION: synthesized

<400> SEQUENCE: 1763
caacugaaau ccugucuguu                                              20

<210> SEQ ID NO 1764
<211> LENGTH: 20
<212> TYPE: RNA
<213> ORGANISM: Artificial Sequence
<220> FEATURE:
<223> OTHER INFORMATION: synthesized

<400> SEQUENCE: 1764
caacugaagu ccugucuguu                                              20

<210> SEQ ID NO 1765
<211> LENGTH: 20
<212> TYPE: RNA
<213> ORGANISM: Artificial Sequence
<220> FEATURE:
<223> OTHER INFORMATION: synthesized

<400> SEQUENCE: 1765
cagacaggac uucaguugca                                              20

<210> SEQ ID NO 1766
<211> LENGTH: 20
<212> TYPE: RNA
<213> ORGANISM: Artificial Sequence
<220> FEATURE:
<223> OTHER INFORMATION: synthesized

<400> SEQUENCE: 1766
cagacaggau uucaguugca                                              20

<210> SEQ ID NO 1767
<211> LENGTH: 20
<212> TYPE: RNA
<213> ORGANISM: Artificial Sequence
<220> FEATURE:
<223> OTHER INFORMATION: synthesized
```

```
<400> SEQUENCE: 1767
caggacuuca guugcaugcu                                                      20

<210> SEQ ID NO 1768
<211> LENGTH: 20
<212> TYPE: RNA
<213> ORGANISM: Artificial Sequence
<220> FEATURE:
<223> OTHER INFORMATION: synthesized

<400> SEQUENCE: 1768
caggauuuca guugcaugcu                                                      20

<210> SEQ ID NO 1769
<211> LENGTH: 20
<212> TYPE: RNA
<213> ORGANISM: Artificial Sequence
<220> FEATURE:
<223> OTHER INFORMATION: synthesized

<400> SEQUENCE: 1769
caugcaacug aaauccuguc                                                      20

<210> SEQ ID NO 1770
<211> LENGTH: 20
<212> TYPE: RNA
<213> ORGANISM: Artificial Sequence
<220> FEATURE:
<223> OTHER INFORMATION: synthesized

<400> SEQUENCE: 1770
caugcaacug aaguccuguc                                                      20

<210> SEQ ID NO 1771
<211> LENGTH: 20
<212> TYPE: RNA
<213> ORGANISM: Artificial Sequence
<220> FEATURE:
<223> OTHER INFORMATION: synthesized

<400> SEQUENCE: 1771
ccugagcaug caacugaaau                                                      20

<210> SEQ ID NO 1772
<211> LENGTH: 20
<212> TYPE: RNA
<213> ORGANISM: Artificial Sequence
<220> FEATURE:
<223> OTHER INFORMATION: synthesized

<400> SEQUENCE: 1772
ccugagcaug caacugaagu                                                      20

<210> SEQ ID NO 1773
<211> LENGTH: 20
<212> TYPE: RNA
<213> ORGANISM: Artificial Sequence
<220> FEATURE:
<223> OTHER INFORMATION: synthesized

<400> SEQUENCE: 1773
cugaaauccu gucuguucac                                                      20

<210> SEQ ID NO 1774
```

```
<211> LENGTH: 20
<212> TYPE: RNA
<213> ORGANISM: Artificial Sequence
<220> FEATURE:
<223> OTHER INFORMATION: synthesized

<400> SEQUENCE: 1774
cugaaguccu gucuguucac                                              20

<210> SEQ ID NO 1775
<211> LENGTH: 20
<212> TYPE: RNA
<213> ORGANISM: Artificial Sequence
<220> FEATURE:
<223> OTHER INFORMATION: synthesized

<400> SEQUENCE: 1775
cugagcaugc aacugaaauc                                              20

<210> SEQ ID NO 1776
<211> LENGTH: 20
<212> TYPE: RNA
<213> ORGANISM: Artificial Sequence
<220> FEATURE:
<223> OTHER INFORMATION: synthesized

<400> SEQUENCE: 1776
cugagcaugc aacugaaguc                                              20

<210> SEQ ID NO 1777
<211> LENGTH: 20
<212> TYPE: RNA
<213> ORGANISM: Artificial Sequence
<220> FEATURE:
<223> OTHER INFORMATION: synthesized

<400> SEQUENCE: 1777
cuucaguugc augcucaggc                                              20

<210> SEQ ID NO 1778
<211> LENGTH: 20
<212> TYPE: RNA
<213> ORGANISM: Artificial Sequence
<220> FEATURE:
<223> OTHER INFORMATION: synthesized

<400> SEQUENCE: 1778
gaaauccugu cuguucaccc                                              20

<210> SEQ ID NO 1779
<211> LENGTH: 20
<212> TYPE: RNA
<213> ORGANISM: Artificial Sequence
<220> FEATURE:
<223> OTHER INFORMATION: synthesized

<400> SEQUENCE: 1779
gaacagacag gacuucaguu                                              20

<210> SEQ ID NO 1780
<211> LENGTH: 20
<212> TYPE: RNA
<213> ORGANISM: Artificial Sequence
<220> FEATURE:
<223> OTHER INFORMATION: synthesized

<400> SEQUENCE: 1780
```

| | |
|---|---|
| gaacagacag gauuucaguu | 20 |

```
<210> SEQ ID NO 1781
<211> LENGTH: 20
<212> TYPE: RNA
<213> ORGANISM: Artificial Sequence
<220> FEATURE:
<223> OTHER INFORMATION: synthesized

<400> SEQUENCE: 1781
```

| | |
|---|---|
| gaaguccugu cuguucaccc | 20 |

```
<210> SEQ ID NO 1782
<211> LENGTH: 20
<212> TYPE: RNA
<213> ORGANISM: Artificial Sequence
<220> FEATURE:
<223> OTHER INFORMATION: synthesized

<400> SEQUENCE: 1782
```

| | |
|---|---|
| gacaggacuu caguugcaug | 20 |

```
<210> SEQ ID NO 1783
<211> LENGTH: 20
<212> TYPE: RNA
<213> ORGANISM: Artificial Sequence
<220> FEATURE:
<223> OTHER INFORMATION: synthesized

<400> SEQUENCE: 1783
```

| | |
|---|---|
| gacaggauuu caguugcaug | 20 |

```
<210> SEQ ID NO 1784
<211> LENGTH: 20
<212> TYPE: RNA
<213> ORGANISM: Artificial Sequence
<220> FEATURE:
<223> OTHER INFORMATION: synthesized

<400> SEQUENCE: 1784
```

| | |
|---|---|
| gacuucaguu gcaugcucag | 20 |

```
<210> SEQ ID NO 1785
<211> LENGTH: 20
<212> TYPE: RNA
<213> ORGANISM: Artificial Sequence
<220> FEATURE:
<223> OTHER INFORMATION: synthesized

<400> SEQUENCE: 1785
```

| | |
|---|---|
| gagcaugcaa cugaaauccu | 20 |

```
<210> SEQ ID NO 1786
<211> LENGTH: 20
<212> TYPE: RNA
<213> ORGANISM: Artificial Sequence
<220> FEATURE:
<223> OTHER INFORMATION: synthesized

<400> SEQUENCE: 1786
```

| | |
|---|---|
| gagcaugcaa cugaaguccu | 20 |

```
<210> SEQ ID NO 1787
<211> LENGTH: 20
<212> TYPE: RNA
```

```
<213> ORGANISM: Artificial Sequence
<220> FEATURE:
<223> OTHER INFORMATION: synthesized

<400> SEQUENCE: 1787
gauuucaguu gcaugcucag                                               20

<210> SEQ ID NO 1788
<211> LENGTH: 20
<212> TYPE: RNA
<213> ORGANISM: Artificial Sequence
<220> FEATURE:
<223> OTHER INFORMATION: synthesized

<400> SEQUENCE: 1788
gcaacugaaa uccugucugu                                               20

<210> SEQ ID NO 1789
<211> LENGTH: 20
<212> TYPE: RNA
<213> ORGANISM: Artificial Sequence
<220> FEATURE:
<223> OTHER INFORMATION: synthesized

<400> SEQUENCE: 1789
gcaacugaag uccugucugu                                               20

<210> SEQ ID NO 1790
<211> LENGTH: 20
<212> TYPE: RNA
<213> ORGANISM: Artificial Sequence
<220> FEATURE:
<223> OTHER INFORMATION: synthesized

<400> SEQUENCE: 1790
gcaugcaacu gaaauccugu                                               20

<210> SEQ ID NO 1791
<211> LENGTH: 20
<212> TYPE: RNA
<213> ORGANISM: Artificial Sequence
<220> FEATURE:
<223> OTHER INFORMATION: synthesized

<400> SEQUENCE: 1791
gcaugcaacu gaaguccugu                                               20

<210> SEQ ID NO 1792
<211> LENGTH: 20
<212> TYPE: RNA
<213> ORGANISM: Artificial Sequence
<220> FEATURE:
<223> OTHER INFORMATION: synthesized

<400> SEQUENCE: 1792
gccugagcau gcaacugaaa                                               20

<210> SEQ ID NO 1793
<211> LENGTH: 20
<212> TYPE: RNA
<213> ORGANISM: Artificial Sequence
<220> FEATURE:
<223> OTHER INFORMATION: synthesized

<400> SEQUENCE: 1793
gccugagcau gcaacugaag                                               20
```

<210> SEQ ID NO 1794
<211> LENGTH: 20
<212> TYPE: RNA
<213> ORGANISM: Artificial Sequence
<220> FEATURE:
<223> OTHER INFORMATION: synthesized

<400> SEQUENCE: 1794
ggacuucagu ugcaugcuca                                              20

<210> SEQ ID NO 1795
<211> LENGTH: 20
<212> TYPE: RNA
<213> ORGANISM: Artificial Sequence
<220> FEATURE:
<223> OTHER INFORMATION: synthesized

<400> SEQUENCE: 1795
ggauuucagu ugcaugcuca                                              20

<210> SEQ ID NO 1796
<211> LENGTH: 20
<212> TYPE: RNA
<213> ORGANISM: Artificial Sequence
<220> FEATURE:
<223> OTHER INFORMATION: synthesized

<400> SEQUENCE: 1796
gggugaacag acaggacuuc                                              20

<210> SEQ ID NO 1797
<211> LENGTH: 20
<212> TYPE: RNA
<213> ORGANISM: Artificial Sequence
<220> FEATURE:
<223> OTHER INFORMATION: synthesized

<400> SEQUENCE: 1797
gggugaacag acaggauuuc                                              20

<210> SEQ ID NO 1798
<211> LENGTH: 20
<212> TYPE: RNA
<213> ORGANISM: Artificial Sequence
<220> FEATURE:
<223> OTHER INFORMATION: synthesized

<400> SEQUENCE: 1798
ggugaacaga caggacuuca                                              20

<210> SEQ ID NO 1799
<211> LENGTH: 20
<212> TYPE: RNA
<213> ORGANISM: Artificial Sequence
<220> FEATURE:
<223> OTHER INFORMATION: synthesized

<400> SEQUENCE: 1799
ggugaacaga caggauuuca                                              20

<210> SEQ ID NO 1800
<211> LENGTH: 20
<212> TYPE: RNA
<213> ORGANISM: Artificial Sequence
<220> FEATURE:

<223> OTHER INFORMATION: synthesized

<400> SEQUENCE: 1800
gugaacagac aggacuucag                    20

<210> SEQ ID NO 1801
<211> LENGTH: 20
<212> TYPE: RNA
<213> ORGANISM: Artificial Sequence
<220> FEATURE:
<223> OTHER INFORMATION: synthesized

<400> SEQUENCE: 1801
gugaacagac aggauuucag                    20

<210> SEQ ID NO 1802
<211> LENGTH: 20
<212> TYPE: RNA
<213> ORGANISM: Artificial Sequence
<220> FEATURE:
<223> OTHER INFORMATION: synthesized

<400> SEQUENCE: 1802
gugggugaac agacaggacu                    20

<210> SEQ ID NO 1803
<211> LENGTH: 20
<212> TYPE: RNA
<213> ORGANISM: Artificial Sequence
<220> FEATURE:
<223> OTHER INFORMATION: synthesized

<400> SEQUENCE: 1803
gugggugaac agacaggauu                    20

<210> SEQ ID NO 1804
<211> LENGTH: 20
<212> TYPE: RNA
<213> ORGANISM: Artificial Sequence
<220> FEATURE:
<223> OTHER INFORMATION: synthesized

<400> SEQUENCE: 1804
ugaaauccug ucuguucacc                    20

<210> SEQ ID NO 1805
<211> LENGTH: 20
<212> TYPE: RNA
<213> ORGANISM: Artificial Sequence
<220> FEATURE:
<223> OTHER INFORMATION: synthesized

<400> SEQUENCE: 1805
ugaacagaca ggacuucagu                    20

<210> SEQ ID NO 1806
<211> LENGTH: 20
<212> TYPE: RNA
<213> ORGANISM: Artificial Sequence
<220> FEATURE:
<223> OTHER INFORMATION: synthesized

<400> SEQUENCE: 1806
ugaacagaca ggauuucagu                    20

```
<210> SEQ ID NO 1807
<211> LENGTH: 20
<212> TYPE: RNA
<213> ORGANISM: Artificial Sequence
<220> FEATURE:
<223> OTHER INFORMATION: synthesized

<400> SEQUENCE: 1807
ugaaguccug ucuguucacc                                                 20

<210> SEQ ID NO 1808
<211> LENGTH: 20
<212> TYPE: RNA
<213> ORGANISM: Artificial Sequence
<220> FEATURE:
<223> OTHER INFORMATION: synthesized

<400> SEQUENCE: 1808
ugagcaugca acugaaaucc                                                 20

<210> SEQ ID NO 1809
<211> LENGTH: 20
<212> TYPE: RNA
<213> ORGANISM: Artificial Sequence
<220> FEATURE:
<223> OTHER INFORMATION: synthesized

<400> SEQUENCE: 1809
ugagcaugca acugaagucc                                                 20

<210> SEQ ID NO 1810
<211> LENGTH: 20
<212> TYPE: RNA
<213> ORGANISM: Artificial Sequence
<220> FEATURE:
<223> OTHER INFORMATION: synthesized

<400> SEQUENCE: 1810
ugcaacugaa auccugucug                                                 20

<210> SEQ ID NO 1811
<211> LENGTH: 20
<212> TYPE: RNA
<213> ORGANISM: Artificial Sequence
<220> FEATURE:
<223> OTHER INFORMATION: synthesized

<400> SEQUENCE: 1811
ugcaacugaa guccugucug                                                 20

<210> SEQ ID NO 1812
<211> LENGTH: 20
<212> TYPE: RNA
<213> ORGANISM: Artificial Sequence
<220> FEATURE:
<223> OTHER INFORMATION: synthesized

<400> SEQUENCE: 1812
ugggugaaca gacaggacuu                                                 20

<210> SEQ ID NO 1813
<211> LENGTH: 20
<212> TYPE: RNA
<213> ORGANISM: Artificial Sequence
<220> FEATURE:
<223> OTHER INFORMATION: synthesized
```

```
<400> SEQUENCE: 1813
ugggugaaca gacaggauuu                                              20

<210> SEQ ID NO 1814
<211> LENGTH: 20
<212> TYPE: RNA
<213> ORGANISM: Artificial Sequence
<220> FEATURE:
<223> OTHER INFORMATION: synthesized

<400> SEQUENCE: 1814
uuucaguugc augcucaggc                                              20

<210> SEQ ID NO 1815
<211> LENGTH: 20
<212> TYPE: RNA
<213> ORGANISM: Artificial Sequence
<220> FEATURE:
<223> OTHER INFORMATION: synthesized

<400> SEQUENCE: 1815
aaucagguca gccugugagc                                              20

<210> SEQ ID NO 1816
<211> LENGTH: 20
<212> TYPE: RNA
<213> ORGANISM: Artificial Sequence
<220> FEATURE:
<223> OTHER INFORMATION: synthesized

<400> SEQUENCE: 1816
aaucagguca gccugugagu                                              20

<210> SEQ ID NO 1817
<211> LENGTH: 20
<212> TYPE: RNA
<213> ORGANISM: Artificial Sequence
<220> FEATURE:
<223> OTHER INFORMATION: synthesized

<400> SEQUENCE: 1817
acucacaggc ugaccugauu                                              20

<210> SEQ ID NO 1818
<211> LENGTH: 20
<212> TYPE: RNA
<213> ORGANISM: Artificial Sequence
<220> FEATURE:
<223> OTHER INFORMATION: synthesized

<400> SEQUENCE: 1818
agagggacuc acaggcugac                                              20

<210> SEQ ID NO 1819
<211> LENGTH: 20
<212> TYPE: RNA
<213> ORGANISM: Artificial Sequence
<220> FEATURE:
<223> OTHER INFORMATION: synthesized

<400> SEQUENCE: 1819
agaggggcuc acaggcugac                                              20

<210> SEQ ID NO 1820
<211> LENGTH: 20
```

```
<212> TYPE: RNA
<213> ORGANISM: Artificial Sequence
<220> FEATURE:
<223> OTHER INFORMATION: synthesized

<400> SEQUENCE: 1820
agccccucua gcaucagagg                                               20

<210> SEQ ID NO 1821
<211> LENGTH: 20
<212> TYPE: RNA
<213> ORGANISM: Artificial Sequence
<220> FEATURE:
<223> OTHER INFORMATION: synthesized

<400> SEQUENCE: 1821
agccugugag ccccucuagc                                               20

<210> SEQ ID NO 1822
<211> LENGTH: 20
<212> TYPE: RNA
<213> ORGANISM: Artificial Sequence
<220> FEATURE:
<223> OTHER INFORMATION: synthesized

<400> SEQUENCE: 1822
agccugugag ucccucuagc                                               20

<210> SEQ ID NO 1823
<211> LENGTH: 20
<212> TYPE: RNA
<213> ORGANISM: Artificial Sequence
<220> FEATURE:
<223> OTHER INFORMATION: synthesized

<400> SEQUENCE: 1823
agggacucac aggcugaccu                                               20

<210> SEQ ID NO 1824
<211> LENGTH: 20
<212> TYPE: RNA
<213> ORGANISM: Artificial Sequence
<220> FEATURE:
<223> OTHER INFORMATION: synthesized

<400> SEQUENCE: 1824
aggggcucac aggcugaccu                                               20

<210> SEQ ID NO 1825
<211> LENGTH: 20
<212> TYPE: RNA
<213> ORGANISM: Artificial Sequence
<220> FEATURE:
<223> OTHER INFORMATION: synthesized

<400> SEQUENCE: 1825
aggucagccu gugagccccu                                               20

<210> SEQ ID NO 1826
<211> LENGTH: 20
<212> TYPE: RNA
<213> ORGANISM: Artificial Sequence
<220> FEATURE:
<223> OTHER INFORMATION: synthesized

<400> SEQUENCE: 1826
```
aggucagccu gugagucccu                                          20

<210> SEQ ID NO 1827
<211> LENGTH: 20
<212> TYPE: RNA
<213> ORGANISM: Artificial Sequence
<220> FEATURE:
<223> OTHER INFORMATION: synthesized

<400> SEQUENCE: 1827
agucccucua gcaucagagg                                          20

<210> SEQ ID NO 1828
<211> LENGTH: 20
<212> TYPE: RNA
<213> ORGANISM: Artificial Sequence
<220> FEATURE:
<223> OTHER INFORMATION: synthesized

<400> SEQUENCE: 1828
aucaggucag ccugugagcc                                          20

<210> SEQ ID NO 1829
<211> LENGTH: 20
<212> TYPE: RNA
<213> ORGANISM: Artificial Sequence
<220> FEATURE:
<223> OTHER INFORMATION: synthesized

<400> SEQUENCE: 1829
aucaggucag ccugugaguc                                          20

<210> SEQ ID NO 1830
<211> LENGTH: 20
<212> TYPE: RNA
<213> ORGANISM: Artificial Sequence
<220> FEATURE:
<223> OTHER INFORMATION: synthesized

<400> SEQUENCE: 1830
augcuagagg gacucacagg                                          20

<210> SEQ ID NO 1831
<211> LENGTH: 20
<212> TYPE: RNA
<213> ORGANISM: Artificial Sequence
<220> FEATURE:
<223> OTHER INFORMATION: synthesized

<400> SEQUENCE: 1831
augcuagagg ggcucacagg                                          20

<210> SEQ ID NO 1832
<211> LENGTH: 20
<212> TYPE: RNA
<213> ORGANISM: Artificial Sequence
<220> FEATURE:
<223> OTHER INFORMATION: synthesized

<400> SEQUENCE: 1832
cagccuguga gccccucuag                                          20

<210> SEQ ID NO 1833
<211> LENGTH: 20
<212> TYPE: RNA
<213> ORGANISM: Artificial Sequence
<220> FEATURE:
<223> OTHER INFORMATION: synthesized

<400> SEQUENCE: 1833
cagccuguga gucccucuag                                              20

<210> SEQ ID NO 1834
<211> LENGTH: 20
<212> TYPE: RNA
<213> ORGANISM: Artificial Sequence
<220> FEATURE:
<223> OTHER INFORMATION: synthesized

<400> SEQUENCE: 1834
cccucugaug cuagagggac                                              20

<210> SEQ ID NO 1835
<211> LENGTH: 20
<212> TYPE: RNA
<213> ORGANISM: Artificial Sequence
<220> FEATURE:
<223> OTHER INFORMATION: synthesized

<400> SEQUENCE: 1835
cccucugaug cuagaggggc                                              20

<210> SEQ ID NO 1836
<211> LENGTH: 20
<212> TYPE: RNA
<213> ORGANISM: Artificial Sequence
<220> FEATURE:
<223> OTHER INFORMATION: synthesized

<400> SEQUENCE: 1836
ccucugaugc uagagggacu                                              20

<210> SEQ ID NO 1837
<211> LENGTH: 20
<212> TYPE: RNA
<213> ORGANISM: Artificial Sequence
<220> FEATURE:
<223> OTHER INFORMATION: synthesized

<400> SEQUENCE: 1837
ccucugaugc uagaggggcu                                              20

<210> SEQ ID NO 1838
<211> LENGTH: 20
<212> TYPE: RNA
<213> ORGANISM: Artificial Sequence
<220> FEATURE:
<223> OTHER INFORMATION: synthesized

<400> SEQUENCE: 1838
ccugugagcc ccucuagcau                                              20

<210> SEQ ID NO 1839
<211> LENGTH: 20
<212> TYPE: RNA
<213> ORGANISM: Artificial Sequence
<220> FEATURE:
<223> OTHER INFORMATION: synthesized

<400> SEQUENCE: 1839
ccugugaguc ccucuagcau                                              20

```
<210> SEQ ID NO 1840
<211> LENGTH: 20
<212> TYPE: RNA
<213> ORGANISM: Artificial Sequence
<220> FEATURE:
<223> OTHER INFORMATION: synthesized

<400> SEQUENCE: 1840
cucugaugcu agagggacuc                                                    20

<210> SEQ ID NO 1841
<211> LENGTH: 20
<212> TYPE: RNA
<213> ORGANISM: Artificial Sequence
<220> FEATURE:
<223> OTHER INFORMATION: synthesized

<400> SEQUENCE: 1841
cucugaugcu agaggggcuc                                                    20

<210> SEQ ID NO 1842
<211> LENGTH: 20
<212> TYPE: RNA
<213> ORGANISM: Artificial Sequence
<220> FEATURE:
<223> OTHER INFORMATION: synthesized

<400> SEQUENCE: 1842
gccccucuag caucagaggg                                                    20

<210> SEQ ID NO 1843
<211> LENGTH: 20
<212> TYPE: RNA
<213> ORGANISM: Artificial Sequence
<220> FEATURE:
<223> OTHER INFORMATION: synthesized

<400> SEQUENCE: 1843
gccugugagc cccucuagca                                                    20

<210> SEQ ID NO 1844
<211> LENGTH: 20
<212> TYPE: RNA
<213> ORGANISM: Artificial Sequence
<220> FEATURE:
<223> OTHER INFORMATION: synthesized

<400> SEQUENCE: 1844
gccugugagu cccucuagca                                                    20

<210> SEQ ID NO 1845
<211> LENGTH: 20
<212> TYPE: RNA
<213> ORGANISM: Artificial Sequence
<220> FEATURE:
<223> OTHER INFORMATION: synthesized

<400> SEQUENCE: 1845
gcuagaggga cucacaggcu                                                    20

<210> SEQ ID NO 1846
<211> LENGTH: 20
<212> TYPE: RNA
<213> ORGANISM: Artificial Sequence
<220> FEATURE:
<223> OTHER INFORMATION: synthesized
```

```
<400> SEQUENCE: 1846
gcuagagggg cucacaggcu                                                    20

<210> SEQ ID NO 1847
<211> LENGTH: 20
<212> TYPE: RNA
<213> ORGANISM: Artificial Sequence
<220> FEATURE:
<223> OTHER INFORMATION: synthesized

<400> SEQUENCE: 1847
gcucacaggc ugaccugauu                                                    20

<210> SEQ ID NO 1848
<211> LENGTH: 20
<212> TYPE: RNA
<213> ORGANISM: Artificial Sequence
<220> FEATURE:
<223> OTHER INFORMATION: synthesized

<400> SEQUENCE: 1848
ggacucacag gcugaccuga                                                    20

<210> SEQ ID NO 1849
<211> LENGTH: 20
<212> TYPE: RNA
<213> ORGANISM: Artificial Sequence
<220> FEATURE:
<223> OTHER INFORMATION: synthesized

<400> SEQUENCE: 1849
gggcucacag gcugaccuga                                                    20

<210> SEQ ID NO 1850
<211> LENGTH: 20
<212> TYPE: RNA
<213> ORGANISM: Artificial Sequence
<220> FEATURE:
<223> OTHER INFORMATION: synthesized

<400> SEQUENCE: 1850
gucagccugu gagccccucu                                                    20

<210> SEQ ID NO 1851
<211> LENGTH: 20
<212> TYPE: RNA
<213> ORGANISM: Artificial Sequence
<220> FEATURE:
<223> OTHER INFORMATION: synthesized

<400> SEQUENCE: 1851
gucagccugu gagucccucu                                                    20

<210> SEQ ID NO 1852
<211> LENGTH: 20
<212> TYPE: RNA
<213> ORGANISM: Artificial Sequence
<220> FEATURE:
<223> OTHER INFORMATION: synthesized

<400> SEQUENCE: 1852
gucccucuag caucagaggg                                                    20

<210> SEQ ID NO 1853
```

```
<211> LENGTH: 20
<212> TYPE: RNA
<213> ORGANISM: Artificial Sequence
<220> FEATURE:
<223> OTHER INFORMATION: synthesized

<400> SEQUENCE: 1853
uagagggacu cacaggcuga                                                     20

<210> SEQ ID NO 1854
<211> LENGTH: 20
<212> TYPE: RNA
<213> ORGANISM: Artificial Sequence
<220> FEATURE:
<223> OTHER INFORMATION: synthesized

<400> SEQUENCE: 1854
uagaggggcu cacaggcuga                                                     20

<210> SEQ ID NO 1855
<211> LENGTH: 20
<212> TYPE: RNA
<213> ORGANISM: Artificial Sequence
<220> FEATURE:
<223> OTHER INFORMATION: synthesized

<400> SEQUENCE: 1855
ucagccugug agccccucua                                                     20

<210> SEQ ID NO 1856
<211> LENGTH: 20
<212> TYPE: RNA
<213> ORGANISM: Artificial Sequence
<220> FEATURE:
<223> OTHER INFORMATION: synthesized

<400> SEQUENCE: 1856
ucagccugug agucccucua                                                     20

<210> SEQ ID NO 1857
<211> LENGTH: 20
<212> TYPE: RNA
<213> ORGANISM: Artificial Sequence
<220> FEATURE:
<223> OTHER INFORMATION: synthesized

<400> SEQUENCE: 1857
ucaggucagc cugugagccc                                                     20

<210> SEQ ID NO 1858
<211> LENGTH: 20
<212> TYPE: RNA
<213> ORGANISM: Artificial Sequence
<220> FEATURE:
<223> OTHER INFORMATION: synthesized

<400> SEQUENCE: 1858
ucaggucagc cugugagucc                                                     20

<210> SEQ ID NO 1859
<211> LENGTH: 20
<212> TYPE: RNA
<213> ORGANISM: Artificial Sequence
<220> FEATURE:
<223> OTHER INFORMATION: synthesized

<400> SEQUENCE: 1859
```
ucccucugau gcuagaggga                                       20

<210> SEQ ID NO 1860
<211> LENGTH: 20
<212> TYPE: RNA
<213> ORGANISM: Artificial Sequence
<220> FEATURE:
<223> OTHER INFORMATION: synthesized

<400> SEQUENCE: 1860
ucccucugau gcuagagggg                                       20

<210> SEQ ID NO 1861
<211> LENGTH: 20
<212> TYPE: RNA
<213> ORGANISM: Artificial Sequence
<220> FEATURE:
<223> OTHER INFORMATION: synthesized

<400> SEQUENCE: 1861
ucugaugcua gagggacuca                                       20

<210> SEQ ID NO 1862
<211> LENGTH: 20
<212> TYPE: RNA
<213> ORGANISM: Artificial Sequence
<220> FEATURE:
<223> OTHER INFORMATION: synthesized

<400> SEQUENCE: 1862
ucugaugcua gaggggcuca                                       20

<210> SEQ ID NO 1863
<211> LENGTH: 20
<212> TYPE: RNA
<213> ORGANISM: Artificial Sequence
<220> FEATURE:
<223> OTHER INFORMATION: synthesized

<400> SEQUENCE: 1863
ugaugcuaga gggacucaca                                       20

<210> SEQ ID NO 1864
<211> LENGTH: 20
<212> TYPE: RNA
<213> ORGANISM: Artificial Sequence
<220> FEATURE:
<223> OTHER INFORMATION: synthesized

<400> SEQUENCE: 1864
ugaugcuaga ggggcucaca                                       20

<210> SEQ ID NO 1865
<211> LENGTH: 20
<212> TYPE: RNA
<213> ORGANISM: Artificial Sequence
<220> FEATURE:
<223> OTHER INFORMATION: synthesized

<400> SEQUENCE: 1865
ugugagcccc ucuagcauca                                       20

<210> SEQ ID NO 1866
<211> LENGTH: 20
<212> TYPE: RNA

```
<213> ORGANISM: Artificial Sequence
<220> FEATURE:
<223> OTHER INFORMATION: synthesized

<400> SEQUENCE: 1866
ugugaguccc ucuagcauca                                               20

<210> SEQ ID NO 1867
<211> LENGTH: 20
<212> TYPE: RNA
<213> ORGANISM: Artificial Sequence
<220> FEATURE:
<223> OTHER INFORMATION: synthesized

<400> SEQUENCE: 1867
aaaaugucua gcaaagaacc                                               20

<210> SEQ ID NO 1868
<211> LENGTH: 20
<212> TYPE: RNA
<213> ORGANISM: Artificial Sequence
<220> FEATURE:
<223> OTHER INFORMATION: synthesized

<400> SEQUENCE: 1868
aaaauguuua gcaaagaacc                                               20

<210> SEQ ID NO 1869
<211> LENGTH: 20
<212> TYPE: RNA
<213> ORGANISM: Artificial Sequence
<220> FEATURE:
<223> OTHER INFORMATION: synthesized

<400> SEQUENCE: 1869
aaacauuuug caggguaccu                                               20

<210> SEQ ID NO 1870
<211> LENGTH: 20
<212> TYPE: RNA
<213> ORGANISM: Artificial Sequence
<220> FEATURE:
<223> OTHER INFORMATION: synthesized

<400> SEQUENCE: 1870
aaaugucuag caaagaaccc                                               20

<210> SEQ ID NO 1871
<211> LENGTH: 20
<212> TYPE: RNA
<213> ORGANISM: Artificial Sequence
<220> FEATURE:
<223> OTHER INFORMATION: synthesized

<400> SEQUENCE: 1871
aaauguuuag caaagaaccc                                               20

<210> SEQ ID NO 1872
<211> LENGTH: 20
<212> TYPE: RNA
<213> ORGANISM: Artificial Sequence
<220> FEATURE:
<223> OTHER INFORMATION: synthesized

<400> SEQUENCE: 1872
aacauuuugc aggguaccug                                               20
```

<210> SEQ ID NO 1873
<211> LENGTH: 20
<212> TYPE: RNA
<213> ORGANISM: Artificial Sequence
<220> FEATURE:
<223> OTHER INFORMATION: synthesized

<400> SEQUENCE: 1873
agacauuuug caggguaccu                                               20

<210> SEQ ID NO 1874
<211> LENGTH: 20
<212> TYPE: RNA
<213> ORGANISM: Artificial Sequence
<220> FEATURE:
<223> OTHER INFORMATION: synthesized

<400> SEQUENCE: 1874
agguacccug caaaaugucu                                               20

<210> SEQ ID NO 1875
<211> LENGTH: 20
<212> TYPE: RNA
<213> ORGANISM: Artificial Sequence
<220> FEATURE:
<223> OTHER INFORMATION: synthesized

<400> SEQUENCE: 1875
agguacccug caaaauguuu                                               20

<210> SEQ ID NO 1876
<211> LENGTH: 20
<212> TYPE: RNA
<213> ORGANISM: Artificial Sequence
<220> FEATURE:
<223> OTHER INFORMATION: synthesized

<400> SEQUENCE: 1876
agucuugggu ucuuugcuaa                                               20

<210> SEQ ID NO 1877
<211> LENGTH: 20
<212> TYPE: RNA
<213> ORGANISM: Artificial Sequence
<220> FEATURE:
<223> OTHER INFORMATION: synthesized

<400> SEQUENCE: 1877
agucuugggu ucuuugcuag                                               20

<210> SEQ ID NO 1878
<211> LENGTH: 20
<212> TYPE: RNA
<213> ORGANISM: Artificial Sequence
<220> FEATURE:
<223> OTHER INFORMATION: synthesized

<400> SEQUENCE: 1878
augucuagca aagaacccaa                                               20

<210> SEQ ID NO 1879
<211> LENGTH: 20
<212> TYPE: RNA
<213> ORGANISM: Artificial Sequence
<220> FEATURE:

<223> OTHER INFORMATION: synthesized

<400> SEQUENCE: 1879
auguuuagca aagaacccaa                                                      20

<210> SEQ ID NO 1880
<211> LENGTH: 20
<212> TYPE: RNA
<213> ORGANISM: Artificial Sequence
<220> FEATURE:
<223> OTHER INFORMATION: synthesized

<400> SEQUENCE: 1880
caaaaugucu agcaaagaac                                                      20

<210> SEQ ID NO 1881
<211> LENGTH: 20
<212> TYPE: RNA
<213> ORGANISM: Artificial Sequence
<220> FEATURE:
<223> OTHER INFORMATION: synthesized

<400> SEQUENCE: 1881
caaaauguuu agcaaagaac                                                      20

<210> SEQ ID NO 1882
<211> LENGTH: 20
<212> TYPE: RNA
<213> ORGANISM: Artificial Sequence
<220> FEATURE:
<223> OTHER INFORMATION: synthesized

<400> SEQUENCE: 1882
cagguacccu gcaaaauguc                                                      20

<210> SEQ ID NO 1883
<211> LENGTH: 20
<212> TYPE: RNA
<213> ORGANISM: Artificial Sequence
<220> FEATURE:
<223> OTHER INFORMATION: synthesized

<400> SEQUENCE: 1883
cagguacccu gcaaaauguu                                                      20

<210> SEQ ID NO 1884
<211> LENGTH: 20
<212> TYPE: RNA
<213> ORGANISM: Artificial Sequence
<220> FEATURE:
<223> OTHER INFORMATION: synthesized

<400> SEQUENCE: 1884
ccugcaaaau gucuagcaaa                                                      20

<210> SEQ ID NO 1885
<211> LENGTH: 20
<212> TYPE: RNA
<213> ORGANISM: Artificial Sequence
<220> FEATURE:
<223> OTHER INFORMATION: synthesized

<400> SEQUENCE: 1885
ccugcaaaau guuuagcaaa                                                      20

<210> SEQ ID NO 1886
<211> LENGTH: 20
<212> TYPE: RNA
<213> ORGANISM: Artificial Sequence
<220> FEATURE:
<223> OTHER INFORMATION: synthesized

<400> SEQUENCE: 1886
cuaaacauuu ugcaggguac                                          20

<210> SEQ ID NO 1887
<211> LENGTH: 20
<212> TYPE: RNA
<213> ORGANISM: Artificial Sequence
<220> FEATURE:
<223> OTHER INFORMATION: synthesized

<400> SEQUENCE: 1887
cuagacauuu ugcaggguac                                          20

<210> SEQ ID NO 1888
<211> LENGTH: 20
<212> TYPE: RNA
<213> ORGANISM: Artificial Sequence
<220> FEATURE:
<223> OTHER INFORMATION: synthesized

<400> SEQUENCE: 1888
cuagcaaaga acccaagacu                                          20

<210> SEQ ID NO 1889
<211> LENGTH: 20
<212> TYPE: RNA
<213> ORGANISM: Artificial Sequence
<220> FEATURE:
<223> OTHER INFORMATION: synthesized

<400> SEQUENCE: 1889
cugcaaaaug ucuagcaaag                                          20

<210> SEQ ID NO 1890
<211> LENGTH: 20
<212> TYPE: RNA
<213> ORGANISM: Artificial Sequence
<220> FEATURE:
<223> OTHER INFORMATION: synthesized

<400> SEQUENCE: 1890
cugcaaaaug uuuagcaaag                                          20

<210> SEQ ID NO 1891
<211> LENGTH: 20
<212> TYPE: RNA
<213> ORGANISM: Artificial Sequence
<220> FEATURE:
<223> OTHER INFORMATION: synthesized

<400> SEQUENCE: 1891
cuuggguucu uugcuaaaca                                          20

<210> SEQ ID NO 1892
<211> LENGTH: 20
<212> TYPE: RNA
<213> ORGANISM: Artificial Sequence
<220> FEATURE:
<223> OTHER INFORMATION: synthesized

```
<400> SEQUENCE: 1892 cuugguucu uugcuagaca                                              20

<210> SEQ ID NO 1893
<211> LENGTH: 20
<212> TYPE: RNA
<213> ORGANISM: Artificial Sequence
<220> FEATURE:
<223> OTHER INFORMATION: synthesized

<400> SEQUENCE: 1893 cuugcuaaa cauuuugcag                                              20

<210> SEQ ID NO 1894
<211> LENGTH: 20
<212> TYPE: RNA
<213> ORGANISM: Artificial Sequence
<220> FEATURE:
<223> OTHER INFORMATION: synthesized

<400> SEQUENCE: 1894 cuugcuaga cauuuugcag                                              20

<210> SEQ ID NO 1895
<211> LENGTH: 20
<212> TYPE: RNA
<213> ORGANISM: Artificial Sequence
<220> FEATURE:
<223> OTHER INFORMATION: synthesized

<400> SEQUENCE: 1895 gacauuugc aggguaccug                                              20

<210> SEQ ID NO 1896
<211> LENGTH: 20
<212> TYPE: RNA
<213> ORGANISM: Artificial Sequence
<220> FEATURE:
<223> OTHER INFORMATION: synthesized

<400> SEQUENCE: 1896
gcaaaauguc uagcaaagaa                                             20

<210> SEQ ID NO 1897
<211> LENGTH: 20
<212> TYPE: RNA
<213> ORGANISM: Artificial Sequence
<220> FEATURE:
<223> OTHER INFORMATION: synthesized

<400> SEQUENCE: 1897
gcaaaauguu uagcaaagaa                                             20

<210> SEQ ID NO 1898
<211> LENGTH: 20
<212> TYPE: RNA
<213> ORGANISM: Artificial Sequence
<220> FEATURE:
<223> OTHER INFORMATION: synthesized

<400> SEQUENCE: 1898
gcuaaacauu uugcagggua                                             20

<210> SEQ ID NO 1899
<211> LENGTH: 20
```

```
<212> TYPE: RNA
<213> ORGANISM: Artificial Sequence
<220> FEATURE:
<223> OTHER INFORMATION: synthesized

<400> SEQUENCE: 1899
gcuagacauu uugcagggua                                               20

<210> SEQ ID NO 1900
<211> LENGTH: 20
<212> TYPE: RNA
<213> ORGANISM: Artificial Sequence
<220> FEATURE:
<223> OTHER INFORMATION: synthesized

<400> SEQUENCE: 1900
ggguucuuug cuaaacauuu                                               20

<210> SEQ ID NO 1901
<211> LENGTH: 20
<212> TYPE: RNA
<213> ORGANISM: Artificial Sequence
<220> FEATURE:
<223> OTHER INFORMATION: synthesized

<400> SEQUENCE: 1901
ggguucuuug cuagacauuu                                               20

<210> SEQ ID NO 1902
<211> LENGTH: 20
<212> TYPE: RNA
<213> ORGANISM: Artificial Sequence
<220> FEATURE:
<223> OTHER INFORMATION: synthesized

<400> SEQUENCE: 1902
gguacccugc aaaaugucua                                               20

<210> SEQ ID NO 1903
<211> LENGTH: 20
<212> TYPE: RNA
<213> ORGANISM: Artificial Sequence
<220> FEATURE:
<223> OTHER INFORMATION: synthesized

<400> SEQUENCE: 1903
gguacccugc aaaauguuua                                               20

<210> SEQ ID NO 1904
<211> LENGTH: 20
<212> TYPE: RNA
<213> ORGANISM: Artificial Sequence
<220> FEATURE:
<223> OTHER INFORMATION: synthesized

<400> SEQUENCE: 1904
gguucuuugc uaaacauuuu                                               20

<210> SEQ ID NO 1905
<211> LENGTH: 20
<212> TYPE: RNA
<213> ORGANISM: Artificial Sequence
<220> FEATURE:
<223> OTHER INFORMATION: synthesized

<400> SEQUENCE: 1905
```
gguucuuugc uagacauuuu                                         20

<210> SEQ ID NO 1906
<211> LENGTH: 20
<212> TYPE: RNA
<213> ORGANISM: Artificial Sequence
<220> FEATURE:
<223> OTHER INFORMATION: synthesized

<400> SEQUENCE: 1906
guacccugca aaaugucuag                                         20

<210> SEQ ID NO 1907
<211> LENGTH: 20
<212> TYPE: RNA
<213> ORGANISM: Artificial Sequence
<220> FEATURE:
<223> OTHER INFORMATION: synthesized

<400> SEQUENCE: 1907
guacccugca aaauguuuag                                         20

<210> SEQ ID NO 1908
<211> LENGTH: 20
<212> TYPE: RNA
<213> ORGANISM: Artificial Sequence
<220> FEATURE:
<223> OTHER INFORMATION: synthesized

<400> SEQUENCE: 1908
gucuuggguu cuuugcuaaa                                         20

<210> SEQ ID NO 1909
<211> LENGTH: 20
<212> TYPE: RNA
<213> ORGANISM: Artificial Sequence
<220> FEATURE:
<223> OTHER INFORMATION: synthesized

<400> SEQUENCE: 1909
gucuuggguu cuuugcuaga                                         20

<210> SEQ ID NO 1910
<211> LENGTH: 20
<212> TYPE: RNA
<213> ORGANISM: Artificial Sequence
<220> FEATURE:
<223> OTHER INFORMATION: synthesized

<400> SEQUENCE: 1910
uacccugcaa aaugucuagc                                         20

<210> SEQ ID NO 1911
<211> LENGTH: 20
<212> TYPE: RNA
<213> ORGANISM: Artificial Sequence
<220> FEATURE:
<223> OTHER INFORMATION: synthesized

<400> SEQUENCE: 1911
uacccugcaa aauguuuagc                                         20

<210> SEQ ID NO 1912
<211> LENGTH: 20
<212> TYPE: RNA
<213> ORGANISM: Artificial Sequence

```
<220> FEATURE:
<223> OTHER INFORMATION: synthesized

<400> SEQUENCE: 1912
ucuagcaaag aacccaagac                                               20

<210> SEQ ID NO 1913
<211> LENGTH: 20
<212> TYPE: RNA
<213> ORGANISM: Artificial Sequence
<220> FEATURE:
<223> OTHER INFORMATION: synthesized

<400> SEQUENCE: 1913
ucuuggguuc uuugcuaaac                                               20

<210> SEQ ID NO 1914
<211> LENGTH: 20
<212> TYPE: RNA
<213> ORGANISM: Artificial Sequence
<220> FEATURE:
<223> OTHER INFORMATION: synthesized

<400> SEQUENCE: 1914
ucuuggguuc uuugcuagac                                               20

<210> SEQ ID NO 1915
<211> LENGTH: 20
<212> TYPE: RNA
<213> ORGANISM: Artificial Sequence
<220> FEATURE:
<223> OTHER INFORMATION: synthesized

<400> SEQUENCE: 1915
ugcaaaaugu cuagcaaaga                                               20

<210> SEQ ID NO 1916
<211> LENGTH: 20
<212> TYPE: RNA
<213> ORGANISM: Artificial Sequence
<220> FEATURE:
<223> OTHER INFORMATION: synthesized

<400> SEQUENCE: 1916
ugcaaaaugu uuagcaaaga                                               20

<210> SEQ ID NO 1917
<211> LENGTH: 20
<212> TYPE: RNA
<213> ORGANISM: Artificial Sequence
<220> FEATURE:
<223> OTHER INFORMATION: synthesized

<400> SEQUENCE: 1917
uggguucuuu gcuaaacauu                                               20

<210> SEQ ID NO 1918
<211> LENGTH: 20
<212> TYPE: RNA
<213> ORGANISM: Artificial Sequence
<220> FEATURE:
<223> OTHER INFORMATION: synthesized

<400> SEQUENCE: 1918
uggguucuuu gcuagacauu                                               20
```

```
<210> SEQ ID NO 1919
<211> LENGTH: 20
<212> TYPE: RNA
<213> ORGANISM: Artificial Sequence
<220> FEATURE:
<223> OTHER INFORMATION: synthesized

<400> SEQUENCE: 1919
ugucuagcaa agaacccaag                                               20

<210> SEQ ID NO 1920
<211> LENGTH: 20
<212> TYPE: RNA
<213> ORGANISM: Artificial Sequence
<220> FEATURE:
<223> OTHER INFORMATION: synthesized

<400> SEQUENCE: 1920
uguuuagcaa agaacccaag                                               20

<210> SEQ ID NO 1921
<211> LENGTH: 20
<212> TYPE: RNA
<213> ORGANISM: Artificial Sequence
<220> FEATURE:
<223> OTHER INFORMATION: synthesized

<400> SEQUENCE: 1921
uuagcaaaga acccaagacu                                               20

<210> SEQ ID NO 1922
<211> LENGTH: 20
<212> TYPE: RNA
<213> ORGANISM: Artificial Sequence
<220> FEATURE:
<223> OTHER INFORMATION: synthesized

<400> SEQUENCE: 1922
uugcuaaaca uuuugcaggg                                               20

<210> SEQ ID NO 1923
<211> LENGTH: 20
<212> TYPE: RNA
<213> ORGANISM: Artificial Sequence
<220> FEATURE:
<223> OTHER INFORMATION: synthesized

<400> SEQUENCE: 1923
uugcuagaca uuuugcaggg                                               20

<210> SEQ ID NO 1924
<211> LENGTH: 20
<212> TYPE: RNA
<213> ORGANISM: Artificial Sequence
<220> FEATURE:
<223> OTHER INFORMATION: synthesized

<400> SEQUENCE: 1924
uuggguucuu ugcuaaacau                                               20

<210> SEQ ID NO 1925
<211> LENGTH: 20
<212> TYPE: RNA
<213> ORGANISM: Artificial Sequence
<220> FEATURE:
<223> OTHER INFORMATION: synthesized
```

-continued

<400> SEQUENCE: 1925
uuggguucuu ugcuagacau                                           20

<210> SEQ ID NO 1926
<211> LENGTH: 20
<212> TYPE: RNA
<213> ORGANISM: Artificial Sequence
<220> FEATURE:
<223> OTHER INFORMATION: synthesized

<400> SEQUENCE: 1926
uuuagcaaag aacccaagac                                           20

<210> SEQ ID NO 1927
<211> LENGTH: 20
<212> TYPE: RNA
<213> ORGANISM: Artificial Sequence
<220> FEATURE:
<223> OTHER INFORMATION: synthesized

<400> SEQUENCE: 1927
uuugcuaaac auuuugcagg                                           20

<210> SEQ ID NO 1928
<211> LENGTH: 20
<212> TYPE: RNA
<213> ORGANISM: Artificial Sequence
<220> FEATURE:
<223> OTHER INFORMATION: synthesized

<400> SEQUENCE: 1928
uuugcuagac auuuugcagg                                           20

<210> SEQ ID NO 1929
<211> LENGTH: 20
<212> TYPE: RNA
<213> ORGANISM: Artificial Sequence
<220> FEATURE:
<223> OTHER INFORMATION: synthesized

<400> SEQUENCE: 1929
aaaggguagg aagaaauggg                                           20

<210> SEQ ID NO 1930
<211> LENGTH: 20
<212> TYPE: RNA
<213> ORGANISM: Artificial Sequence
<220> FEATURE:
<223> OTHER INFORMATION: synthesized

<400> SEQUENCE: 1930
aacuuaucug gaagagaaag                                           20

<210> SEQ ID NO 1931
<211> LENGTH: 20
<212> TYPE: RNA
<213> ORGANISM: Artificial Sequence
<220> FEATURE:
<223> OTHER INFORMATION: synthesized

<400> SEQUENCE: 1931
aacuuaucug gaagagauag                                           20

<210> SEQ ID NO 1932

```
<211> LENGTH: 20
<212> TYPE: RNA
<213> ORGANISM: Artificial Sequence
<220> FEATURE:
<223> OTHER INFORMATION: synthesized

<400> SEQUENCE: 1932
aagagaaagg guaggaagaa                                                     20

<210> SEQ ID NO 1933
<211> LENGTH: 20
<212> TYPE: RNA
<213> ORGANISM: Artificial Sequence
<220> FEATURE:
<223> OTHER INFORMATION: synthesized

<400> SEQUENCE: 1933
aagagauagg guaggaagaa                                                     20

<210> SEQ ID NO 1934
<211> LENGTH: 20
<212> TYPE: RNA
<213> ORGANISM: Artificial Sequence
<220> FEATURE:
<223> OTHER INFORMATION: synthesized

<400> SEQUENCE: 1934
aaggguagga agaaaugggg                                                     20

<210> SEQ ID NO 1935
<211> LENGTH: 20
<212> TYPE: RNA
<213> ORGANISM: Artificial Sequence
<220> FEATURE:
<223> OTHER INFORMATION: synthesized

<400> SEQUENCE: 1935
acccuaucuc uuccagauaa                                                     20

<210> SEQ ID NO 1936
<211> LENGTH: 20
<212> TYPE: RNA
<213> ORGANISM: Artificial Sequence
<220> FEATURE:
<223> OTHER INFORMATION: synthesized

<400> SEQUENCE: 1936
acccuuucuc uuccagauaa                                                     20

<210> SEQ ID NO 1937
<211> LENGTH: 20
<212> TYPE: RNA
<213> ORGANISM: Artificial Sequence
<220> FEATURE:
<223> OTHER INFORMATION: synthesized

<400> SEQUENCE: 1937
acuuaucugg aagagaaagg                                                     20

<210> SEQ ID NO 1938
<211> LENGTH: 20
<212> TYPE: RNA
<213> ORGANISM: Artificial Sequence
<220> FEATURE:
<223> OTHER INFORMATION: synthesized

<400> SEQUENCE: 1938
```

-continued acuuaucugg aagagauagg                                                    20

<210> SEQ ID NO 1939
<211> LENGTH: 20
<212> TYPE: RNA
<213> ORGANISM: Artificial Sequence
<220> FEATURE:
<223> OTHER INFORMATION: synthesized

<400> SEQUENCE: 1939 auagguagg aagaaauggg                                                     20

<210> SEQ ID NO 1940
<211> LENGTH: 20
<212> TYPE: RNA
<213> ORGANISM: Artificial Sequence
<220> FEATURE:
<223> OTHER INFORMATION: synthesized

<400> SEQUENCE: 1940
aucucuucca gauaaguugg                                                    20

<210> SEQ ID NO 1941
<211> LENGTH: 20
<212> TYPE: RNA
<213> ORGANISM: Artificial Sequence
<220> FEATURE:
<223> OTHER INFORMATION: synthesized

<400> SEQUENCE: 1941
aucuggaaga gaaaggguag                                                    20

<210> SEQ ID NO 1942
<211> LENGTH: 20
<212> TYPE: RNA
<213> ORGANISM: Artificial Sequence
<220> FEATURE:
<223> OTHER INFORMATION: synthesized

<400> SEQUENCE: 1942
aucuggaaga gauaggguag                                                    20

<210> SEQ ID NO 1943
<211> LENGTH: 20
<212> TYPE: RNA
<213> ORGANISM: Artificial Sequence
<220> FEATURE:
<223> OTHER INFORMATION: synthesized

<400> SEQUENCE: 1943
auuucuuccu acccuaucuc                                                    20

<210> SEQ ID NO 1944
<211> LENGTH: 20
<212> TYPE: RNA
<213> ORGANISM: Artificial Sequence
<220> FEATURE:
<223> OTHER INFORMATION: synthesized

<400> SEQUENCE: 1944
auuucuuccu acccuuucuc                                                    20

<210> SEQ ID NO 1945
<211> LENGTH: 20
<212> TYPE: RNA

```
<213> ORGANISM: Artificial Sequence
<220> FEATURE:
<223> OTHER INFORMATION: synthesized

<400> SEQUENCE: 1945
cauuucuucc uacccuaucu                                              20

<210> SEQ ID NO 1946
<211> LENGTH: 20
<212> TYPE: RNA
<213> ORGANISM: Artificial Sequence
<220> FEATURE:
<223> OTHER INFORMATION: synthesized

<400> SEQUENCE: 1946
cauuucuucc uacccuuucu                                              20

<210> SEQ ID NO 1947
<211> LENGTH: 20
<212> TYPE: RNA
<213> ORGANISM: Artificial Sequence
<220> FEATURE:
<223> OTHER INFORMATION: synthesized

<400> SEQUENCE: 1947
ccauuucuuc cuacccuauc                                              20

<210> SEQ ID NO 1948
<211> LENGTH: 20
<212> TYPE: RNA
<213> ORGANISM: Artificial Sequence
<220> FEATURE:
<223> OTHER INFORMATION: synthesized

<400> SEQUENCE: 1948
ccauuucuuc cuacccuuuc                                              20

<210> SEQ ID NO 1949
<211> LENGTH: 20
<212> TYPE: RNA
<213> ORGANISM: Artificial Sequence
<220> FEATURE:
<223> OTHER INFORMATION: synthesized

<400> SEQUENCE: 1949
cccauuucuu ccuacccuau                                              20

<210> SEQ ID NO 1950
<211> LENGTH: 20
<212> TYPE: RNA
<213> ORGANISM: Artificial Sequence
<220> FEATURE:
<223> OTHER INFORMATION: synthesized

<400> SEQUENCE: 1950
cccauuucuu ccuacccuuu                                              20

<210> SEQ ID NO 1951
<211> LENGTH: 20
<212> TYPE: RNA
<213> ORGANISM: Artificial Sequence
<220> FEATURE:
<223> OTHER INFORMATION: synthesized

<400> SEQUENCE: 1951
ccccauuucu uccuacccua                                              20
```

<210> SEQ ID NO 1952
<211> LENGTH: 20
<212> TYPE: RNA
<213> ORGANISM: Artificial Sequence
<220> FEATURE:
<223> OTHER INFORMATION: synthesized

<400> SEQUENCE: 1952
ccccauuucu uccuacccuu                                               20

<210> SEQ ID NO 1953
<211> LENGTH: 20
<212> TYPE: RNA
<213> ORGANISM: Artificial Sequence
<220> FEATURE:
<223> OTHER INFORMATION: synthesized

<400> SEQUENCE: 1953
cccuaucucu uccagauaag                                               20

<210> SEQ ID NO 1954
<211> LENGTH: 20
<212> TYPE: RNA
<213> ORGANISM: Artificial Sequence
<220> FEATURE:
<223> OTHER INFORMATION: synthesized

<400> SEQUENCE: 1954
cccuuucucu uccagauaag                                               20

<210> SEQ ID NO 1955
<211> LENGTH: 20
<212> TYPE: RNA
<213> ORGANISM: Artificial Sequence
<220> FEATURE:
<223> OTHER INFORMATION: synthesized

<400> SEQUENCE: 1955
ccuacccuau cucuuccaga                                               20

<210> SEQ ID NO 1956
<211> LENGTH: 20
<212> TYPE: RNA
<213> ORGANISM: Artificial Sequence
<220> FEATURE:
<223> OTHER INFORMATION: synthesized

<400> SEQUENCE: 1956
ccuacccuuu cucuuccaga                                               20

<210> SEQ ID NO 1957
<211> LENGTH: 20
<212> TYPE: RNA
<213> ORGANISM: Artificial Sequence
<220> FEATURE:
<223> OTHER INFORMATION: synthesized

<400> SEQUENCE: 1957
cuacccuauc ucuuccagau                                               20

<210> SEQ ID NO 1958
<211> LENGTH: 20
<212> TYPE: RNA
<213> ORGANISM: Artificial Sequence
<220> FEATURE:

<223> OTHER INFORMATION: synthesized

<400> SEQUENCE: 1958
cuacccuuuc ucuuccagau                                              20

<210> SEQ ID NO 1959
<211> LENGTH: 20
<212> TYPE: RNA
<213> ORGANISM: Artificial Sequence
<220> FEATURE:
<223> OTHER INFORMATION: synthesized

<400> SEQUENCE: 1959
cuaucucuuc cagauaaguu                                              20

<210> SEQ ID NO 1960
<211> LENGTH: 20
<212> TYPE: RNA
<213> ORGANISM: Artificial Sequence
<220> FEATURE:
<223> OTHER INFORMATION: synthesized

<400> SEQUENCE: 1960
cuuaucugga agagaaaggg                                              20

<210> SEQ ID NO 1961
<211> LENGTH: 20
<212> TYPE: RNA
<213> ORGANISM: Artificial Sequence
<220> FEATURE:
<223> OTHER INFORMATION: synthesized

<400> SEQUENCE: 1961
cuuaucugga agagauaggg                                              20

<210> SEQ ID NO 1962
<211> LENGTH: 20
<212> TYPE: RNA
<213> ORGANISM: Artificial Sequence
<220> FEATURE:
<223> OTHER INFORMATION: synthesized

<400> SEQUENCE: 1962
cuuucucuuc cagauaaguu                                              20

<210> SEQ ID NO 1963
<211> LENGTH: 20
<212> TYPE: RNA
<213> ORGANISM: Artificial Sequence
<220> FEATURE:
<223> OTHER INFORMATION: synthesized

<400> SEQUENCE: 1963
gaagagaaag gguaggaaga                                              20

<210> SEQ ID NO 1964
<211> LENGTH: 20
<212> TYPE: RNA
<213> ORGANISM: Artificial Sequence
<220> FEATURE:
<223> OTHER INFORMATION: synthesized

<400> SEQUENCE: 1964
gaagagauag gguaggaaga                                              20

```
<210> SEQ ID NO 1965
<211> LENGTH: 20
<212> TYPE: RNA
<213> ORGANISM: Artificial Sequence
<220> FEATURE:
<223> OTHER INFORMATION: synthesized

<400> SEQUENCE: 1965
ggaagagaaa ggguaggaag                                                 20

<210> SEQ ID NO 1966
<211> LENGTH: 20
<212> TYPE: RNA
<213> ORGANISM: Artificial Sequence
<220> FEATURE:
<223> OTHER INFORMATION: synthesized

<400> SEQUENCE: 1966
ggaagagaua ggguaggaag                                                 20

<210> SEQ ID NO 1967
<211> LENGTH: 20
<212> TYPE: RNA
<213> ORGANISM: Artificial Sequence
<220> FEATURE:
<223> OTHER INFORMATION: synthesized

<400> SEQUENCE: 1967
uacccuaucu cuuccagaua                                                 20

<210> SEQ ID NO 1968
<211> LENGTH: 20
<212> TYPE: RNA
<213> ORGANISM: Artificial Sequence
<220> FEATURE:
<223> OTHER INFORMATION: synthesized

<400> SEQUENCE: 1968
uacccuuucu cuuccagaua                                                 20

<210> SEQ ID NO 1969
<211> LENGTH: 20
<212> TYPE: RNA
<213> ORGANISM: Artificial Sequence
<220> FEATURE:
<223> OTHER INFORMATION: synthesized

<400> SEQUENCE: 1969
uaggguagga agaaaugggg                                                 20

<210> SEQ ID NO 1970
<211> LENGTH: 20
<212> TYPE: RNA
<213> ORGANISM: Artificial Sequence
<220> FEATURE:
<223> OTHER INFORMATION: synthesized

<400> SEQUENCE: 1970
uaucucuucc agauaaguug                                                 20

<210> SEQ ID NO 1971
<211> LENGTH: 20
<212> TYPE: RNA
<213> ORGANISM: Artificial Sequence
<220> FEATURE:
<223> OTHER INFORMATION: synthesized
```

```
<400> SEQUENCE: 1971
uccuacccua ucucuuccag                                                    20

<210> SEQ ID NO 1972
<211> LENGTH: 20
<212> TYPE: RNA
<213> ORGANISM: Artificial Sequence
<220> FEATURE:
<223> OTHER INFORMATION: synthesized

<400> SEQUENCE: 1972
uccuacccuu ucucuuccag                                                    20

<210> SEQ ID NO 1973
<211> LENGTH: 20
<212> TYPE: RNA
<213> ORGANISM: Artificial Sequence
<220> FEATURE:
<223> OTHER INFORMATION: synthesized

<400> SEQUENCE: 1973
ucuggaagag aaaggguagg                                                    20

<210> SEQ ID NO 1974
<211> LENGTH: 20
<212> TYPE: RNA
<213> ORGANISM: Artificial Sequence
<220> FEATURE:
<223> OTHER INFORMATION: synthesized

<400> SEQUENCE: 1974
ucuggaagag auaggguagg                                                    20

<210> SEQ ID NO 1975
<211> LENGTH: 20
<212> TYPE: RNA
<213> ORGANISM: Artificial Sequence
<220> FEATURE:
<223> OTHER INFORMATION: synthesized

<400> SEQUENCE: 1975
ucuuccuacc cuaucucuuc                                                    20

<210> SEQ ID NO 1976
<211> LENGTH: 20
<212> TYPE: RNA
<213> ORGANISM: Artificial Sequence
<220> FEATURE:
<223> OTHER INFORMATION: synthesized

<400> SEQUENCE: 1976
ucuuccuacc cuuucucuuc                                                    20

<210> SEQ ID NO 1977
<211> LENGTH: 20
<212> TYPE: RNA
<213> ORGANISM: Artificial Sequence
<220> FEATURE:
<223> OTHER INFORMATION: synthesized

<400> SEQUENCE: 1977
uggaagagaa aggguaggaa                                                    20

<210> SEQ ID NO 1978
<211> LENGTH: 20
```

```
<212> TYPE: RNA
<213> ORGANISM: Artificial Sequence
<220> FEATURE:
<223> OTHER INFORMATION: synthesized

<400> SEQUENCE: 1978
uggaagagau aggguaggaa                                              20

<210> SEQ ID NO 1979
<211> LENGTH: 20
<212> TYPE: RNA
<213> ORGANISM: Artificial Sequence
<220> FEATURE:
<223> OTHER INFORMATION: synthesized

<400> SEQUENCE: 1979
uuccuacccu aucucuucca                                              20

<210> SEQ ID NO 1980
<211> LENGTH: 20
<212> TYPE: RNA
<213> ORGANISM: Artificial Sequence
<220> FEATURE:
<223> OTHER INFORMATION: synthesized

<400> SEQUENCE: 1980
uuccuacccu uucucuucca                                              20

<210> SEQ ID NO 1981
<211> LENGTH: 20
<212> TYPE: RNA
<213> ORGANISM: Artificial Sequence
<220> FEATURE:
<223> OTHER INFORMATION: synthesized

<400> SEQUENCE: 1981
uucucuucca gauaaguugg                                              20

<210> SEQ ID NO 1982
<211> LENGTH: 20
<212> TYPE: RNA
<213> ORGANISM: Artificial Sequence
<220> FEATURE:
<223> OTHER INFORMATION: synthesized

<400> SEQUENCE: 1982
uuucucuucc agauaaguug                                              20

<210> SEQ ID NO 1983
<211> LENGTH: 20
<212> TYPE: RNA
<213> ORGANISM: Artificial Sequence
<220> FEATURE:
<223> OTHER INFORMATION: synthesized

<400> SEQUENCE: 1983
uuucuuccua cccuaucucu                                              20

<210> SEQ ID NO 1984
<211> LENGTH: 20
<212> TYPE: RNA
<213> ORGANISM: Artificial Sequence
<220> FEATURE:
<223> OTHER INFORMATION: synthesized

<400> SEQUENCE: 1984
``` uucuuccua cccuuucucu                              20

<210> SEQ ID NO 1985
<211> LENGTH: 20
<212> TYPE: RNA
<213> ORGANISM: Artificial Sequence
<220> FEATURE:
<223> OTHER INFORMATION: synthesized

<400> SEQUENCE: 1985
uuccacugag ggugcucgau                              20

<210> SEQ ID NO 1986
<211> LENGTH: 20
<212> TYPE: RNA
<213> ORGANISM: Artificial Sequence
<220> FEATURE:
<223> OTHER INFORMATION: synthesized

<400> SEQUENCE: 1986
ugccuaucga gcacccucag                              20

<210> SEQ ID NO 1987
<211> LENGTH: 20
<212> TYPE: RNA
<213> ORGANISM: Artificial Sequence
<220> FEATURE:
<223> OTHER INFORMATION: synthesized

<400> SEQUENCE: 1987
aaggaaaugc aaggggccau                              20

<210> SEQ ID NO 1988
<211> LENGTH: 20
<212> TYPE: RNA
<213> ORGANISM: Artificial Sequence
<220> FEATURE:
<223> OTHER INFORMATION: synthesized

<400> SEQUENCE: 1988
agucauggcu cuguacuguu                              20

<210> SEQ ID NO 1989
<211> LENGTH: 20
<212> TYPE: RNA
<213> ORGANISM: Artificial Sequence
<220> FEATURE:
<223> OTHER INFORMATION: synthesized

<400> SEQUENCE: 1989
uuaacuuagu cuaggggac                               20

<210> SEQ ID NO 1990
<211> LENGTH: 20
<212> TYPE: RNA
<213> ORGANISM: Artificial Sequence
<220> FEATURE:
<223> OTHER INFORMATION: synthesized

<400> SEQUENCE: 1990
cguguaacag agaguuaaga                              20

<210> SEQ ID NO 1991
<211> LENGTH: 22
<212> TYPE: DNA
<213> ORGANISM: Artificial Sequence

```
<220> FEATURE:
<223> OTHER INFORMATION: synthesized

<400> SEQUENCE: 1991
tgatgctctg attgagggtt cc                                          22

<210> SEQ ID NO 1992
<211> LENGTH: 20
<212> TYPE: DNA
<213> ORGANISM: Artificial Sequence
<220> FEATURE:
<223> OTHER INFORMATION: synthesized

<400> SEQUENCE: 1992
aggtgctgaa ctgcatgttg                                             20

<210> SEQ ID NO 1993
<211> LENGTH: 20
<212> TYPE: DNA
<213> ORGANISM: Artificial Sequence
<220> FEATURE:
<223> OTHER INFORMATION: synthesized

<400> SEQUENCE: 1993
acatgccgca gatgagaatg                                             20

<210> SEQ ID NO 1994
<211> LENGTH: 21
<212> TYPE: DNA
<213> ORGANISM: Artificial Sequence
<220> FEATURE:
<223> OTHER INFORMATION: synthesized

<400> SEQUENCE: 1994
tttccgtctc tgatccggtt c                                           21

<210> SEQ ID NO 1995
<211> LENGTH: 22
<212> TYPE: DNA
<213> ORGANISM: Artificial Sequence
<220> FEATURE:
<223> OTHER INFORMATION: synthesized

<400> SEQUENCE: 1995
cacacacatg cacttacctg tg                                          22

<210> SEQ ID NO 1996
<211> LENGTH: 19
<212> TYPE: DNA
<213> ORGANISM: Artificial Sequence
<220> FEATURE:
<223> OTHER INFORMATION: synthesized

<400> SEQUENCE: 1996
atttgccaag ttgccgtcc                                              19
```